(12) United States Patent
Bae et al.

(10) Patent No.: US 11,254,676 B2
(45) Date of Patent: Feb. 22, 2022

(54) PYRAZOLE DERIVATIVE COMPOUND AND USE THEREOF

(71) Applicant: HANMI PHARM. CO., LTD., Hwaseong-si (KR)

(72) Inventors: In Hwan Bae, Hwaseong-si (KR); Ji Sook Kim, Hwaseong-si (KR); Won Jeoung Kim, Hwaseong-si (KR); Chang Hee Park, Hwaseong-si (KR); Ji Young Song, Hwaseong-si (KR); Young Gil Ahn, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 16/646,883

(22) PCT Filed: Sep. 13, 2018

(86) PCT No.: PCT/KR2018/010741
§ 371 (c)(1),
(2) Date: Mar. 12, 2020

(87) PCT Pub. No.: WO2019/054766
PCT Pub. Date: Mar. 21, 2019

(65) Prior Publication Data
US 2021/0009591 A1 Jan. 14, 2021

(30) Foreign Application Priority Data
Sep. 13, 2017 (KR) .................. 10-2017-0117226

(51) Int. Cl.
*C07D 401/06* (2006.01)
*A61K 31/454* (2006.01)
*C07D 471/10* (2006.01)
*C07D 401/14* (2006.01)
*C07D 403/06* (2006.01)
*C07D 405/14* (2006.01)
*C07D 417/14* (2006.01)
*C07D 471/04* (2006.01)
*C07D 471/08* (2006.01)
*A61K 45/06* (2006.01)

(52) U.S. Cl.
CPC ......... *C07D 471/10* (2013.01); *C07D 401/06* (2013.01); *C07D 401/14* (2013.01); *C07D 403/06* (2013.01); *C07D 405/14* (2013.01); *C07D 417/14* (2013.01); *C07D 471/04* (2013.01); *C07D 471/08* (2013.01); *A61K 45/06* (2013.01)

(58) Field of Classification Search
CPC .. C07D 401/06; C07D 231/14; A61K 31/454; A61K 31/415; A61P 35/00

USPC .............. 546/211; 514/326, 406; 548/374.1
See application file for complete search history.

(56) References Cited

U.S. PATENT DOCUMENTS

| 5,134,142 | A | 7/1992 | Matsuo et al. |
| 7,393,842 | B2 * | 7/2008 | Makriyannis ........... A61P 25/06 514/210.2 |
| 7,872,006 | B2 * | 1/2011 | Moritani ............... C07D 401/12 514/236.5 |
| 8,084,467 | B2 | 12/2011 | Makriyannis et al. |
| 9,133,128 | B2 | 9/2015 | Fulp et al. |
| 2004/0192667 | A1 | 9/2004 | Makriyannis et al. |
| 2007/0219210 | A1 | 9/2007 | Kanaya et al. |
| 2014/0107157 | A1 | 4/2014 | Fulp et al. |
| 2016/0009720 | A1 | 1/2016 | Wu et al. |
| 2018/0354960 | A1 | 12/2018 | Yamashita et al. |

FOREIGN PATENT DOCUMENTS

| AU | 2004200420 A1 | 9/2004 |
| WO | 2006/133926 A1 | 12/2006 |
| WO | 2007/046550 A1 | 4/2007 |
| WO | 2012/135113 A2 | 10/2012 |
| WO | 2015/089192 A1 | 6/2015 |
| WO | 2016/004105 A1 | 1/2016 |
| WO | 2016/007722 A1 | 1/2016 |
| WO | 2017/090756 A1 | 6/2017 |

OTHER PUBLICATIONS

Sasmal, P. et al.: Novel pyrazole-3-carboxamide derivatives as cannabinoid-1 (CB1) antagonists: journey6 from non-polar to polar amides. Bioorganic & Med. Chem. Lett., vol. 21, pp. 562-568, 2011.*
Daniel P. Mould et al., "Development of 5-hydroxypyrazole derivatives as reversible inhibitors of lysine specific demethylase 1", Bioorganic & Medicinal Chemistry Letters, 2017, pp. 3190-3195, vol. 27.
Yujiang Shi et al., "Histone Demethylation Mediated by the Nuclear Amine Oxidase Homolog LSD1", Cell, Dec. 29, 2004, pp. 941-953, vol. 119.
International Search Report for PCT/KR2018/010741 dated Dec. 18, 2018. [PCT/ISA/210].
Written Opinion for PCT/KR2018/010741 dated Dec. 18, 2018. [PCT/ISA/237].
Sasmal et al., "Structure-activity relationship studies of novel pyrazole and imidazole carboxamides as cannabinoid-1 (CB1) antagonists", Bioorganic & Medicinal Chemistry Letters, 2011, vol. 21, pp. 4913-4918 (6 pages total).

* cited by examiner

*Primary Examiner* — Charanjit Aulakh
(74) *Attorney, Agent, or Firm* — Sughrue Mion, PLLC

(57) ABSTRACT

Provided is a compound represented by Formula 1 having an inhibitory activity on lysine-specific demethylase-1 (LSD1), an optical isomer, a solvate, a tautomer, or a pharmaceutically acceptable salt thereof, which is effective in preventing or treating a disease caused by abnormal activation of LSD1.

6 Claims, No Drawings

PYRAZOLE DERIVATIVE COMPOUND AND USE THEREOF

CROSS REFERENCE TO RELATED APPLICATIONS

This application is a National Stage of International Application No. PCT/KR2018/010741 filed Sep. 13, 2018, claiming priority based on Korean Patent Application No. 10-2017-0117226 filed Sep. 13, 2017.

TECHNICAL FIELD

The present disclosure relates to a pyrazole derivative compound and a use thereof, and more particularly to a pyrazole derivative compound having an inhibitory activity on lysine-specific histone demethylase-1 (LSD1) and a pharmaceutical composition including the pyrazole derivative compound.

BACKGROUND ART

Cancer stem cells or cancer-initiating cells have some pluripotent stem cell characteristics that contribute to the heterogeneity of cancer cells. This characteristic can make cancer cells more resistant to traditional therapies, such as chemotherapy or radiation therapy, and then cause recurrence after treatment. Therefore, efforts to develop anticancer drugs that are more advanced than conventional chemotherapy or radiation therapy are continuing.

Epigenetics is a study of a phenomenon that genetic expression pattern and activity are altered, and the genetic expression pattern and activity are succeeded to the next generation without altering the DNA sequence. These epigenetic studies are focused on mechanisms such as DNA methylation, histone modification, and chromatin remodeling. Epigenetic modification has been found to be a major cause of outbreaks of various diseases. It was found that the onset and maintenance of epigenetic modification involve DNA methylation, histone modification, and genetic modifications regarding non-coding RNA (ncRNA), and many epigenetic regulatory genes are often mutated, or the expression of the epigenetic regulatory genes is abnormal in many cancers.

Lysine-specific histone demethylase-1 (LSD1, also known as KDM1A) may remove a methyl group, thus regulating genetic expressions that are important in terms of development of cancer and cell proliferation (Shi, Y., et al., Histone demethylation mediated by the nuclear amine oxidase homolog LSD1. Cell, 2004. 119(7): p. 941-53).

The LSD1 inhibitors studied so far do not exhibit sufficient selective inhibitory activity on LSD1 or have side effects such as showing resistance to drugs or showing toxicity to normal cells, and thus, they cannot be effectively used for the treatment of cancer and neoplastic diseases.

PRIOR ART DOCUMENT

Patent Document (Patent Document 1) WO 2016/007722
(Patent Document 2) WO 2012/135113

Non-Patent Document (Non-patent Document 1) Cell, 2004. 119(7): p. 941-53

DISCLOSURE

Technical Problem

An aspect of the present disclosure provides a novel compound having a sufficient inhibitory activity on lysine-specific histone demethylase-1 (LSD1).

Another aspect of the present disclosure provides a pharmaceutical use of the novel compound for preventing or treating a disease caused by abnormal activation of LSD1.

Technical Solution

An aspect of the present disclosure provides a compound represented by Formula 1, an optical isomer, a solvate, or a tautomer, or a pharmaceutically acceptable salt thereof:

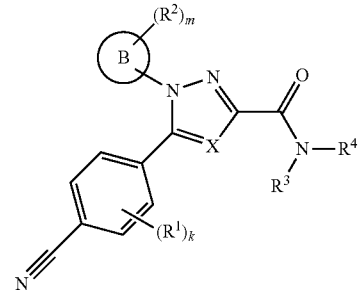

Formula 1

Another aspect of the present disclosure provides a pharmaceutical composition for preventing or treating a disease caused by abnormal activation of lysine-specific demethylase-1 (LSD1), the pharmaceutical composition including: the compound represented by Formula 1, an optical isomer, a solvate, a tautomer, or a pharmaceutically acceptable salt thereof as an active ingredient, and a pharmaceutically acceptable carrier.

Still another aspect of the present disclosure provides a method of treating a disease caused by abnormal activation of LSD1, the method including administering to a subject a therapeutically effective amount of the compound represented by Formula 1, an optical isomer, a solvate, or a tautomer, or a pharmaceutically acceptable salt thereof.

Advantageous Effects

As apparent from the foregoing description, the compound represented by Formula 1 according to an aspect of the present disclosure, an optical isomer, a solvate, or a tautomer, or a pharmaceutically acceptable salt thereof may suppress activity of LSD1.

MODE FOR INVENTION

The present disclosure will be described in further detail.
Unless otherwise defined, all terms (including technical and scientific terms) used herein have the same meaning as commonly understood by one of ordinary skill in the art to which this invention belongs. Although exemplary methods or materials are listed herein, other similar or equivalent ones are also within the scope of the present invention. Also, the numerical values set forth herein are considered to include the meaning of "about" unless explicitly stated. All publications disclosed as references herein are incorporated in their entirety by reference.

The term "alkyl" as used herein refers to, for example, a straight-chained or branched hydrocarbon having 1 to 20 carbon atoms ($C_1$-$C_{20}$). Examples of the alkyl include methyl, ethyl, n-propyl, i-propyl, n-butyl, i-butyl, and t-butyl, but embodiments are not limited thereto. The term "alkoxy" as used herein refers to —O-alkyl. The term "alkylthio" as used herein refers to —S— alkyl.

The term "alkenyl" as used herein refers to a straight-chained or branched $C_2$-$C_{20}$ hydrocarbon having at least one C=C double bond and 2 to 20 carbon atoms. Examples of the alkenyl include vinyl, 2-propenyl, and 2-butenyl, but embodiments are not limited thereto.

The term "alkynyl" as used herein refers to a straight-chained or branched $C_2$-$C_{20}$ hydrocarbon having at least one C≡C triple bond and 2 to 20 carbon atoms. Examples of the alkynyl include ethynyl, 2-propynyl, and 2-butynyl, but embodiments are not limited thereto.

The term "halogen" as used herein refers to fluorine, chlorine, bromine, or iodine.

The term "amine" or "amino" as used herein refers to an unsubstituted or substituent —$NH_2$, respectively. The term "alkylamino" as used herein refers to amino bound to moiety of a mother molecule via alkyl. The alkylamino include groups of compounds in which nitrogen of —$NH_2$ is bound to at least one alkyl, e.g., a $C_1$-$C_{15}$ alkyl having 1 to 15 carbon atoms. Examples of the alkylamino include benzylamino, methylamino, ethylamino, and phenethylamino.

The term "dialkylamino" as used herein refers to groups in which nitrogen of —$NH_2$ is bound to at least two additional alkyls. Examples of the dialkylamino include dimethylamino and diethylamino.

The term "$C_1$-$C_4$ alkylhydroxy" as used herein refers to $C_1$ to $C_4$ hydroxy alkyl.

The terms "carbocyclic group", "carbocycle", "carbocyclyl", and "carbocyclic ring" may be used interchangeably. The term "$C_3$-$C_{30}$ carbocyclic group" as used herein refers to a monocyclic group, a bicyclic group, or a polycyclic group having carbon atoms only as ring-forming atoms and 3 to 30 carbon atoms. The $C_3$-$C_{30}$ carbocyclic group may be an aromatic carbocyclic group or a non-aromatic carbocyclic group. The $C_3$-$C_{30}$ carbocyclic group may be a ring such as benzene, a monovalent group such as phenyl, or a divalent group such as phenylene. Also, depending on the number of substituents connected to the $C_3$-$C_{30}$ carbocyclic group, the $C_3$-$C_{30}$ carbocyclic group may be a trivalent group or a quadrivalent group. In some embodiments, the $C_3$-$C_{20}$ carbocyclic group may be an aromatic or non-aromatic, saturated or unsaturated $C_2$ to $C_{20}$ hydrocarbon. Examples of the carbocyclic group include cyclopropane, cyclobutane, cyclopentane, cyclopentene, cyclohexane, cyclohexene, bicyclo[2.1.1]hexane, bicyclo[2.2.1]heptane, bicyclo[2.2.1]heptene, bicyclo[3.1.1]heptane, bicyclo[3.1.1]heptyl, bicyclo[2.2.2]octane, adamantane, benzene, pyridine, pyridazine, pyrimidine, pyrazine, pyrrole, pyrazole, indole, pyrazolopyridine, pyrrolopyridine, benzimidazole, benzopyrazole, benzothiophene, quinoline, benzothiazole, indazole, benzofuran, benzodioxin, benzopyran, indane, naphthalene, and anthracene. These carbocyclic groups may each independently be substituted with at least one substituent described herein.

The terms "heterocyclic group", "heterocycle", "heterocyclyl", and "heterocyclic ring" may be used interchangeably. The term "$C_1$-$C_{30}$ heterocyclic group" as used herein refers to a group having substantially the same structure as the $C_3$-$C_{30}$ carbocyclic group, except that at least one heteroatom selected from N, O, P, and S is used as a ring-forming atom, in addition to carbon atoms (e.g., 1 to 30 carbon atoms). Examples thereof include pyridinyl, pyridazinyl, pyrimidinyl, pyrazinyl, pyrrolyl, pyrazolyl, indolyl, pyrazolopyridinyl, benzimidazolyl, benzopyrazolyl, benzothiophenyl, benzofuranyl, benzodioxinyl, benzopyranyl, pyrrolopyridinyl, quinolinyl, benzothiazolyl, and indazolyl.

Examples of the monocyclic heterocyclic group include piperidinyl, pyrrolidinyl, piperazinyl, azepinyl, pyrrolyl, pyrazolyl, oxetanyl, pyrazolinyl, imidazolyl, imidazolinyl, imidazolidinyl, triazolyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, 2-oxopiperazinyl, 2-oxopiperidinyl, 2-oxopyrrolodinyl, 2-oxoazepinyl, 4-piperidonyl, pyridyl, pyridyl N-oxide, pyrazinyl, pyrimidinyl, pyridazinyl, tetrahydropyranyl, morpholinyl, thiamorpholinyl, thiamorpholinyl sulfoxide, and thiamorpholinyl sulfone.

Examples of the bicyclic heterocyclic group include diazaspiro-nonanyl (e.g., diazaspiro[3.5]nonanyl), diazaspiro-decanyl) (e.g., diazaspiro[4.5]decanyl), azabicyclo-heptanyl, azabicyclo-octanyl, diazabicyclo-nonanyl (e.g., diazabicyclo[3.3.1]nonanyl), diazabicyclo-decanyl, octahydro-1H-pyrrolo[2,3-c]pyridinyl, indolyl, dihydroindolyl, benzothiazolyl, benzoxazinyl, benzoxazolyl, benzothienyl, benzothiazinyl, quinuclidinyl, quinolinyl, tetrahydroquinolinyl, decahydroquinolinyl, isoquinolinyl, tetrahydroisoquinolinyl, decahydroisoquinolinyl, benzimidazolyl, benzopyranyl, indolizinyl, benzofuryl, chromonyl, coumarinyl, benzopyranyl, cinnolynyl, quinoxalinyl, indazolyl, pyrrolopyridyl, furopyridinyl, dihydroisoindolyl, dihydroquinazolinyl, and phthalazinyl.

Examples of the tricyclic heterocyclic group include carbazolyl, dibenzoazepinyl, dithienoazepinyl, benzindolyl, phenanthrolinyl, acridinyl, phenanthridinyl, phenoxazinyl, phenothiazinyl, xanthenyl, and carbolynyl. The term "cycloalkyl" as used herein refers to a monovalent saturated hydrocarbon ring system having 3 to 20 carbon atoms (e.g., $C_3$-$C_{12}$). Examples of the cycloalkyl include cyclopropyl, cyclobutyl, cyclopentyl, cyclohexyl, cycloheptyl, and cyclooctyl. The term "cycloalkoxy" as used herein refers to —O-cycloalkyl.

The term "cycloalkenyl" as used herein refers to a monovalent non-aromatic hydrocarbon ring system having 3 to 20 carbon atoms (for example, $C_3$-$C_{12}$) and at least one double bond. For example, the cycloalkenyl include cyclopentenyl, cyclohexenyl, and cycloheptenyl.

The term "heterocycloalkyl" as used herein refers to a 3- to 20-membered monovalent unsaturated hydrocarbon ring system having at least one heteroatom (e.g., O, N, or S). For example, the heterocycloalkyl may be a 5- to 8-membered monocyclic system, an 8- to 12-membered dicyclic system, or an 11- to 14-membered tricyclic system. Examples of the heterocycloalkyl group include piperazinyl, a pyrrolidinyl, dioxanyl, morpholinyl, and tetrahydrofuranyl, but embodiments are not limited thereto.

The term "heterocycloalkenyl" as used herein refers to a 3- to 20-membered monovalent unsaturated hydrocarbon ring system having at least one heteroatom (e.g., O, N, or S) and at least one double bond. For example, the heterocycloalkenyl may be a non-aromatic 5- to 8-membered monocyclic system, a non-aromatic 8- to 12-membered dicyclic system, or a non-aromatic 11- to 14-membered tricyclic system.

The term "aryl" as used herein refers to, for example, a $C_6$-$C_{20}$ monovalent aromatic hydrocarbon having 6 to 20 carbon atoms derived by removing one hydrogen atom attached to one carbon atom in a mother aromatic ring system. The aryl may include a dicyclic radical including an aromatic ring fused with a partially unsaturated ring or saturated ring. Examples of the aryl include a radical derived from benzene (phenyl), substituted benzene, naphthalene, anthracene, biphenyl, indenyl, indanyl, 1,2-dihydronaphthalene, and 1,2,3,4-tetrahydronaphthyl. The term "aryloxy" as used herein refers to —O— aryl. The term "arylthio" as used herein refers to —S— aryl.

The term "heteroaryl" refers to, for example, a monovalent aromatic hydrocarbon having 5 to 30 atoms including at least one heteroatom selected from N, O, and S and at least one carbon atom (for example, $C_1$-$C_{20}$). The term "heteroaryloxy" as used herein refers to —O—. The term "heteroarylthio" as used herein refers to S-heteroaryl. The heteroaryl may include a fused ring system of, e.g., 5-, 6-, or 7-membered ring (at least one of which is aromatic). Examples of the heteroaryl include monocyclic or bicyclic aryl, e.g., pyrrolyl, pyrazolyl, imidazolyl, triazolyl, oxazolyl, isoxazolyl, thiazolyl, tetrazole, isothiazolyl, furyl, thienyl, 2-pyridyl, 3-pyridyl, 4-pyridyl, pyridyl N-oxide, pyrazinyl, pyrimidinyl, pyridazinyl, indolyl, benzothiazolyl, benzoxazolyl, benzothienyl, quinolinyl, isoquinolinyl, benzimidazolyl, and benzofuryl. The "carbocyclic, heterocyclic, alkyl, alkoxy, alkenyl, alkynyl, cycloalkyl, cycloalkoxy, cycloalkenyl, heterocycloalkyl, heterocycloalkenyl, aryl, aryloxy, arylthio, heteroaryl, heteroaryloxy, heteroarylthio, and amine" may each independently substituted with at least one substituent described herein.

Also, regarding the expression $C_A$, "A" indicates the number of carbon atoms in a substituted or unsubstituted hydrocarbon or the number of carbon atoms of a substituent in a substituted hydrocarbon. For example, the number of carbon atoms including the substituted substituents of the substituted $C_3$-$C_{20}$ carbocyclic group, the substituted $C_1$-$C_{20}$ heterocyclic group, the substituted $C_1$-$C_{20}$ alkyl, the substituted $C_1$-$C_{20}$ alkoxy, the substituted $C_2$-$C_{20}$ alkenyl, substituted $C_2$-$C_{20}$ alkynyl, the substituted $C_3$-$C_{20}$ cycloalkyl, the substituted $C_3$-$C_{20}$ cycloalkoxy, the substituted $C_3$-$C_{20}$ cycloalkenyl, the substituted $C_1$-$C_{20}$ heterocycloalkyl, the substituted $C_1$-$C_{20}$ heterocycloalkenyl, the substituted $C_6$-$C_{20}$ aryl, the substituted $C_6$-$C_{20}$ aryloxy, the $C_6$-$C_{20}$ arylthio, the $C_1$-$C_{20}$ heteroaryl, the $C_1$-$C_{20}$ heteroaryloxy, or the $C_1$-$C_{20}$ heteroarylthio is 20 or less.

For example, the substituent may be selected from halogen, a cyano group, a hydroxyl group, a thiol group, a nitro group, an amino group, an oxo group, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_3$-$C_{10}$ carbocyclic group, a substituted or unsubstituted $C_1$-$C_{10}$ heterocyclic group, a substituted or unsubstituted $C_1$-$C_{10}$ alkoxy group, a substituted or unsubstituted $C_3$-$C_{10}$ cycloalkoxy group, a substituted or unsubstituted $C_1$-$C_{10}$ alkylthio group, a substituted or unsubstituted $C_6$-$C_{10}$ aryloxy group, a substituted or unsubstituted $C_6$-$C_{10}$ arylthio group, a substituted or unsubstituted $C_1$-$C_{10}$ heteroaryloxy group, a substituted or unsubstituted $C_1$-$C_{10}$ heteroarylthio group, a substituted or unsubstituted $C_6$-$C_{10}$ aryl group, a substituted or unsubstituted $C_1$-$C_{10}$ heteroaryl group, —N($Q_3$)($Q_4$), —C(=O)($Q_3$), —N—C(=O)($Q_3$), —N—C(=O)—N($Q_3$)($Q_4$), —O—C(=O)($Q_3$), —S(=O)($Q_3$), —S(=O)$_2$($Q_3$), —P(=O)($Q_3$)($Q_4$), and —N—C(=NH)—N($Q_3$)($Q_4$).

A substituent of the substituted $C_1$-$C_{10}$ alkyl group, the substituted $C_2$-$C_{10}$ alkenyl group, the substituted $C_2$-$C_{10}$ alkynyl group, the substituted $C_3$-$C_{10}$ carbocyclic group, the substituted $C_1$-$C_{10}$ heterocyclic group, the substituted $C_1$-$C_{10}$ alkoxy group, the substituted $C_3$-$C_{10}$ cycloalkoxy group, the substituted $C_1$-$C_{10}$ alkylthio group, the substituted $C_6$-$C_{10}$ aryloxy group, the substituted $C_6$-$C_{10}$ arylthio group, the substituted $C_1$-$C_{10}$ heteroaryloxy group, the substituted $C_1$-$C_{10}$ heteroarylthio group, the substituted $C_6$-$C_{10}$ aryl group, or the substituted $C_1$-$C_{10}$ heteroaryl group may be at least one selected from:

halogen, a cyano group, a hydroxyl group, a thiol group, a nitro group, an oxo group, a $C_1$-$C_{10}$ alkyl group, a $C_2$-$C_{10}$ alkenyl group, a $C_2$-$C_{10}$ alkynyl group, a $C_3$-$C_{10}$ cycloalkyl group, a $C_1$-$C_{10}$ heterocycloalkyl group, a $C_1$-$C_{10}$ alkoxy group, a $C_3$-$C_{10}$ cycloalkoxy group, a $C_1$-$C_{10}$ alkylthio group, a $C_6$-$C_{10}$ aryloxy group, a $C_6$-$C_{10}$ arylthio group, a $C_1$-$C_{10}$ heteroaryloxy group, a $C_1$-$C_{10}$ heteroarylthio group, —N($Q_5$)($Q_6$), —C(=O)($Q_5$), —N—C(=O)($Q_5$), —N—C(=O)—N($Q_5$)($Q_6$), —O—C(=O)($Q_5$), —S(=O)($Q_5$), —S(=O)$_2$($Q_5$), —P(=O)($Q_5$)($Q_6$), and —N—C(=NH)—N($Q_5$)($Q_6$), wherein $Q_3$ to $Q_6$ may each independently be selected from hydrogen, halogen, a cyano group, a hydroxyl group, a thiol group, a nitro group, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_3$-$C_{10}$ carbocyclic group, a substituted or unsubstituted $C_1$-$C_{10}$ heterocyclic group, a substituted or unsubstituted $C_1$-$C_{10}$ alkoxy group, a substituted or unsubstituted $C_3$-$C_{10}$ cycloalkoxy group, a substituted or unsubstituted $C_1$-$C_{10}$ alkylthio group, a substituted or unsubstituted $C_6$-$C_{10}$ aryloxy group, a substituted or unsubstituted $C_6$-$C_{10}$ arylthio group, a substituted or unsubstituted $C_1$-$C_{10}$ heteroaryloxy group, a substituted or unsubstituted $C_1$-$C_{10}$ heteroarylthio group, a substituted or unsubstituted $C_1$-$C_{10}$ alkylamino group, a substituted or unsubstituted $C_1$-$C_{10}$ dialkylamino group, a substituted or unsubstituted $C_6$-$C_{10}$ aryl group, and a $C_1$-$C_{10}$ heteroaryl group.

A substituent of the substituted $C_1$-$C_{10}$ alkyl group, the substituted $C_2$-$C_{10}$ alkenyl group, the substituted $C_2$-$C_{10}$ alkynyl group, the substituted $C_3$-$C_{10}$ carbocyclic group, the substituted $C_1$-$C_{10}$ heterocyclic group, the substituted $C_1$-$C_{10}$ alkoxy group, the substituted $C_3$-$C_{10}$ cycloalkoxy group, the substituted $C_1$-$C_{10}$ alkylthio group, the substituted $C_6$-$C_{10}$ aryloxy group, the substituted $C_6$-$C_{10}$ arylthio group, the substituted $C_1$-$C_{10}$ heteroaryloxy group, the substituted $C_1$-$C_{10}$ heteroarylthio group, the substituted $C_1$-$C_{10}$ alkylamino group, the substituted $C_1$-$C_{10}$ dialkylamino group, the substituted $C_6$-$C_{10}$ aryl group, and the substituted $C_1$-$C_{10}$ heteroaryl group may be at least one selected from:

halogen, a cyano group, a hydroxyl group, a thiol group, a nitro group, a $C_1$-$C_{10}$ alkyl group, a $C_2$-$C_{10}$ alkenyl group, a $C_2$-$C_{10}$ alkynyl group, a $C_3$-$C_{10}$ carbocyclic group, a $C_1$-$C_{10}$ heterocyclic group, a $C_1$-$C_{10}$ alkoxy group, a $C_3$-$C_{10}$ cycloalkoxy group, a $C_1$-$C_{10}$ alkylthio group, a $C_6$-$C_{10}$ aryloxy group, a $C_6$-$C_{10}$ arylthio group, a $C_1$-$C_{10}$ heteroaryloxy group, a $C_1$-$C_{10}$ heteroarylthio group, a $C_1$-$C_{10}$ alkylamino group, a $C_1$-$C_{10}$ dialkylamino group, a $C_6$-$C_{10}$ aryl group, and a $C_1$-$C_{10}$ heteroaryl group.

The present inventors have made intensive efforts to develop a new anticancer drug by using lysine-specific demethylase-1 (LSD1) as a key target for cancer therapy. As a result, a novel pyrazole derivative compound was developed, which is capable of sufficiently suppressing LSD1 involved in the transcription of various genes important for cancer progression and cell proliferation from a viewpoint of epigenetics.

An aspect of the present disclosure provides a compound represented by Formula 1, an optical isomer, a solvate, or a tautomer, or a pharmaceutically acceptable salt thereof:

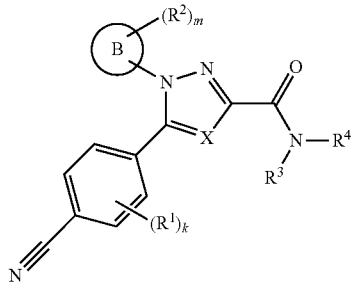

Formula 1 wherein, in Formula 1,

may be a $C_3$-$C_{30}$ carbocyclic group or a $C_1$-$C_{30}$ heterocyclic group, X may be $C(R^5)$ or N, $R^1(s)$ to $R^5$ may each independently be a monovalent radical selected from hydrogen, halogen, a cyano group, a hydroxyl group, a thiol group, a nitro group, a substituted or unsubstituted $C_1$-$C_{20}$ alkyl group, a substituted or unsubstituted $C_2$-$C_{20}$ alkenyl group, a substituted or unsubstituted $C_2$-$C_{20}$ alkynyl group, a substituted or unsubstituted $C_3$-$C_{20}$ carbocyclic group, a substituted or unsubstituted $C_1$-$C_{20}$ heterocyclic group, a substituted or unsubstituted $C_1$-$C_{20}$ alkoxy group, a substituted or unsubstituted $C_3$-$C_{20}$ cycloalkoxy group, a substituted or unsubstituted $C_1$-$C_{20}$ alkylthio group, a substituted or unsubstituted $C_6$-$C_{20}$ aryloxy group, a substituted or unsubstituted $C_6$-$C_{20}$ arylthio group, a substituted or unsubstituted $C_1$-$C_{20}$ heteroaryloxy group, a substituted or unsubstituted $C_1$-$C_{20}$ heteroarylthio group, a $C_1$-$C_{20}$ alkylamino group, a substituted or unsubstituted $C_6$-$C_{20}$ aryl group, a substituted or unsubstituted $C_1$-$C_{20}$ heteroaryl group, —$N(Q_1)(Q_2)$, —$C(=O)(Q_1)$, —N—C(=O)($Q_1$), —N—C(=O)—$N(Q_1)(Q_2)$, —O—C(=O)($Q_1$), —S(=O)($Q_1$), —S(=O)$_2$($Q_1$), —P(=O)($Q_1$)($Q_2$), and —N—C(=NH)—$N(Q_1)(Q_2)$, when $R^1(s)$ or $R^2(s)$ is optionally two or greater, two of $R^1(s)$ or $R^2(s)$ are adjacently substituted at two ring atoms that are consecutively connected in a corresponding ring, adjacently substituted two $R^1(s)$ or $R^2(s)$ may be connected to each other to form a substituted or unsubstituted $C_3$-$C_{30}$ carbocyclic group or a substituted or unsubstituted $C_1$-$C_{30}$ heterocyclic group, thus forming a fused ring with the corresponding ring, $R^3$ and $R^4$ may optionally be bound to form a substituted or unsubstituted $C_1$-$C_{30}$ heterocyclic group with an amide nitrogen of Formula 1, k may be an integer from 0 to 4; when k is 2 or greater, at least two $R^1(s)$ may be identical to or different from each other, and m may be an integer from 0 to 7; when m is 2 or greater, at least two $R^2(s)$ may be identical to or different from each other, wherein $Q_1$ and $Q_2$ may each independently be one selected from hydrogen, halogen, a hydroxyl group, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_1$-$C_{10}$ alkoxy group, a substituted or unsubstituted $C_3$-$C_{10}$ cycloalkoxy group, a substituted or unsubstituted $C_1$-$C_{10}$ alkylthio group, a substituted or unsubstituted $C_6$-$C_{10}$ aryloxy group, a substituted or unsubstituted $C_6$-$C_{10}$ arylthio group, a substituted or unsubstituted $C_1$-$C_0$ heteroaryloxy group, a substituted or unsubstituted $C_1$-$C_{10}$ heteroarylthio group, a substituted or unsubstituted $C_1$-$C_{10}$ alkylamino group, a substituted or unsubstituted $C_6$-$C_{10}$ aryl group, and a substituted or unsubstituted $C_1$-$C_{10}$ heteroaryl group.

In an example embodiment, in Formula 1,

may be a $C_3$-$C_{30}$ carbocyclic group or a $C_1$-$C_{30}$ heterocyclic group. In some embodiments,

may be one selected from a phenyl group, a pyridinyl group, a pyridazinyl group, a pyrimidinyl group, a pyrazinyl group, a pyrrolyl group, a pyrazolyl group, an indolyl group, a pyrazolopyridinyl group, a pyrrolopyridinyl group, a benzimidazolyl group, a benzopyrazolyl group, a benzothiophenyl group, a quinolinyl group, a benzothiazolyl group, an indazolyl group, a benzofuranyl group, a benzodioxanyl group, a benzopyranyl group, an indanyl group, and a naphthyl group.

In an example embodiment, in Formula 1, $R^2(s)$ may be one selected from hydrogen, halogen, a cyano group, a hydroxyl group, a thiol group, a nitro group, a substituted or unsubstituted $C_1$-$C_{15}$ alkyl group, a substituted or unsubstituted $C_2$-$C_{15}$ alkenyl group, a substituted or unsubstituted $C_2$-$C_{15}$ alkynyl group, a substituted or unsubstituted $C_3$-$C_{15}$ carbocyclic group, a substituted or unsubstituted $C_1$-$C_{15}$ heterocyclic group, a substituted or unsubstituted $C_1$-$C_{15}$ alkoxy group, a substituted or unsubstituted $C_3$-$C_{15}$ cycloalkoxy group, a substituted or unsubstituted $C_1$-$C_{15}$ alkylthio group, a substituted or unsubstituted $C_6$-$C_{15}$ aryloxy group, a substituted or unsubstituted $C_6$-$C_{15}$ arylthio group, a substituted or unsubstituted $C_1$-$C_{15}$ heteroaryloxy group, a substituted or unsubstituted $C_1$-$C_{15}$ heteroarylthio group, a $C_1$-$C_{15}$ alkylamino group, —$N(Q_3)(Q_4)$, —C(=O)($Q_3$), —N—C(=O)($Q_3$), —N—C(=O)—$N(Q_3)(Q_4)$, —O—C(=O)($Q_3$), —S(=O)($Q_3$), —S(=O)$_2$($Q_3$), —P(=O)($Q_3$)($Q_4$), and —N—C(=NH)—$N(Q_3)(Q_4)$, wherein $Q_3$ and $Q_4$ may each independently be one selected from hydrogen, halogen, a hydroxyl group, a substituted or unsubstituted $C_1$-$C_6$ alkyl group, a substituted or unsubstituted $C_2$-$C_6$ alkenyl group, a substituted or unsubstituted $C_2$-$C_6$ alkynyl group, a substituted or unsubstituted $C_3$-$C_6$ cycloalkyl group, a substituted or unsubstituted $C_1$-$C_6$ heterocycloalkyl group, a substituted or unsubstituted $C_1$-$C_6$ alkoxy group, a substituted or unsubstituted $C_3$-$C_6$ cycloalkoxy group, a substituted or unsubstituted $C_1$-$C_6$ alkylthio group, a substituted or unsubstituted $C_6$-$C_9$ aryloxy group, a substituted or unsubstituted $C_6$-$C_9$ arylthio group, a substituted or unsubstituted $C_1$-$C_6$ heteroaryloxy group, a substituted or unsubstituted $C_1$-$C_6$ heteroarylthio group, a substituted or unsubstituted $C_1$-$C_6$ alkylamino group, a substituted or unsubstituted $C_6$-$C_9$ aryl group, and a substituted or unsubstituted $C_1$-$C_6$ heteroaryl group. In some embodiments, $R^2$ may be one selected from a substituted or unsubstituted $C_3$-$C_{15}$ cycloalkyl group and a substituted or unsubstituted $C_1$-$C_{15}$ heterocycloalkyl group.

In an example embodiment, in Formula 1, $R^3$ and $R^4$ may each independently be one selected from hydrogen, halogen, a substituted or unsubstituted $C_1$-$C_{15}$ alkyl group, a substituted or unsubstituted $C_3$-$C_{15}$ carbocyclic group, a substituted or unsubstituted $C_1$-$C_{15}$ heterocyclic group, a substituted or unsubstituted $C_1$-$C_{15}$ alkoxy group, a substituted or unsubstituted $C_3$-$C_{15}$ cycloalkoxy group, a substituted or unsubstituted $C_1$-$C_{15}$ alkylthio group, a substituted or unsubstituted $C_6$-$C_{15}$ aryloxy group, a substituted or unsubstituted $C_6$-$C_{15}$ arylthio group, a substituted or unsubstituted $C_1$-$C_{15}$ heteroaryloxy group, a substituted or unsubstituted $C_1$-$C_{15}$ heteroarylthio group, a substituted or unsubstituted $C_6$-$C_{15}$ aryl group, and a substituted or unsubstituted $C_1$-$C_{15}$ heteroaryl group.

In an example embodiment, $R^3$ and $R^4$ may be bound to each other to form a substituted or unsubstituted $C_1$-$C_{30}$ heterocyclic group with amide nitrogen of Formula 1, and for example, the substituted or unsubstituted $C_1$-$C_{30}$ heterocyclic group may be one selected from a piperidinyl group, a pyrrolidinyl group, a piperazinyl group, an azepinyl group, a diazaspiro-nonanyl group, a diazaspiro-decanyl group, an azabicyclo-heptanyl group, an azabicyclo-octanyl group, a diazabicyclo-nonanyl group, and a diazabicyclo-decanyl group.

In an example embodiment, at least one substituent of the substituted or unsubstituted $C_1$-$C_{30}$ heterocyclic group formed by binding of $R^3$ and $R^4$ with the amide nitrogen of Formula 1 may be selected from:

halogen, a cyano group, a hydroxyl group, a thiol group, a nitro group, a substituted or unsubstituted $C_1$-$C_{15}$ alkyl group, a substituted or unsubstituted $C_2$-$C_{15}$ alkenyl group, a substituted or unsubstituted $C_2$-$C_{15}$ alkynyl group, a substituted or unsubstituted $C_3$-$C_{20}$ carbocyclic group, a substituted or unsubstituted $C_1$-$C_{15}$ heterocyclic group, a substituted or unsubstituted $C_1$-$C_{20}$ alkoxy group, a substituted or unsubstituted $C_3$-$C_{20}$ cycloalkoxy group, a substituted or unsubstituted $C_1$-$C_{20}$ alkylthio group, —N($Q_5$)($Q_6$), —C(=O)($Q_5$), —N—C(=O)($Q_5$), —N—C(=O)—N($Q_5$)($Q_6$), —O—C(=O)($Q_5$), —S(=O)($Q_5$), —S(=O)$_2$($Q_5$), —P(=O)($Q_5$)($Q_6$), and —N—C(=NH)—N($Q_5$)($Q_6$), wherein $Q_5$ and $Q_6$ may each independently be one selected from hydrogen, halogen, a hydroxyl group, a substituted or unsubstituted $C_1$-$C_6$ alkyl group, a substituted or unsubstituted $C_2$-$C_6$ alkenyl group, a substituted or unsubstituted $C_2$-$C_6$ alkynyl group, a substituted or unsubstituted $C_3$-$C_6$ cycloalkyl group, a substituted or unsubstituted $C_1$-$C_6$ heterocycloalkyl group, a substituted or unsubstituted $C_1$-$C_6$ alkoxy group, a substituted or unsubstituted $C_3$-$C_6$ cycloalkoxy group, a substituted or unsubstituted $C_1$-$C_6$ alkylthio group, a substituted or unsubstituted $C_6$-$C_9$ aryloxy group, a substituted or unsubstituted $C_6$-$C_9$ arylthio group, a substituted or unsubstituted $C_1$-$C_6$ heteroaryloxy group, a substituted or unsubstituted $C_1$-$C_6$ heteroarylthio group, a substituted or unsubstituted $C_1$-$C_6$ alkylamino group, a substituted or unsubstituted $C_6$-$C_9$ aryl group, and a substituted or unsubstituted $C_1$-$C_6$ heteroaryl group.

In an example embodiment,

may be one selected from a phenyl group, a pyridinyl group, a quinolinyl group, a benzothiazolyl group, an indazolyl group, a benzodioxinyl group, an indanyl group, and a naphthyl group, X may be C($R^5$), wherein $R^5$ may be one selected from hydrogen, halogen, a hydroxyl group, a substituted or unsubstituted $C_1$-$C_4$ alkyl group, and a substituted or unsubstituted $C_1$-$C_4$ alkoxy group, $R^2$(s) may be one selected from hydrogen, halogen, a cyano group, a hydroxyl group, a thiol group, a nitro group, a substituted or unsubstituted $C_1$-$C_{15}$ alkyl group, a substituted or unsubstituted $C_2$-$C_{15}$ alkenyl group, a substituted or unsubstituted $C_2$-$C_{15}$ alkynyl group, a substituted or unsubstituted $C_3$-$C_{15}$ cycloalkyl group, a substituted or unsubstituted $C_3$-$C_{15}$ cycloalkenyl group, a substituted or unsubstituted $C_1$-$C_{15}$ heterocycloalkyl group, a substituted or unsubstituted $C_1$-$C_{15}$ heterocycloalkenyl group, a substituted or unsubstituted $C_1$-$C_{15}$ alkoxy group, a substituted or unsubstituted $C_3$-$C_{15}$ cycloalkoxy group, a substituted or unsubstituted $C_1$-$C_{15}$ alkylthio group, a substituted or unsubstituted $C_6$-$C_{15}$ aryloxy group, a substituted or unsubstituted $C_6$-$C_{15}$ arylthio group, a substituted or unsubstituted $C_1$-$C_{15}$ heteroaryloxy group, a substituted or unsubstituted $C_1$-$C_{15}$ heteroarylthio group, a $C_1$-$C_{20}$ alkylamino group, —N($Q_7$)($Q_8$), —C(=O)($Q_7$), —N—C(=O)($Q_7$), —N—C(=O)—N($Q_7$)($Q_8$), —O—C(=O)($Q_7$), —S(=O)($Q_7$), —S(=O)$_2$($Q_7$), —P(=O)($Q_7$)($Q_8$), and —N—C(=NH)—N($Q_7$)($Q_8$), $R^3$ and $R^4$ may be bound to form one selected from a substituted or unsubstituted piperidinyl group, a substituted or unsubstituted pyrrolidinyl group, a substituted or unsubstituted piperazinyl group, a substituted or unsubstituted azepinyl group, a substituted or unsubstituted diazaspiro-nonanyl group, a substituted or unsubstituted diazaspiro-decanyl group, a substituted or unsubstituted azabicyclo-heptanyl group, a substituted or unsubstituted azabicyclo-octanyl group, a substituted or unsubstituted diazabicyclo-nonanyl group, a substituted or unsubstituted diazabicyclo-decanyl group, and a substituted or unsubstituted octahydro-1H-pyrrolo[2,3-c]pyridyl group, with amide nitrogen of Formula 1, at least one substituent of the substituted piperidinyl group, the substituted pyrrolidinyl group, the substituted piperazinyl group, the substituted azepinyl group, the substituted diazaspiro-nonanyl group, the substituted diazaspiro-decanyl group, the substituted azabicyclo-heptanyl group, the substituted azabicyclo-octanyl group, the substituted diazabicyclo-nonanyl group, the substituted diazabicyclo-decanyl group, and the substituted octahydro-1H-pyrrolo[2,3-c]pyridyl group may be selected from:

a substituted or unsubstituted $C_1$-$C_{15}$ alkyl group, a substituted or unsubstituted $C_2$-$C_{15}$ alkenyl group, a substituted or unsubstituted $C_2$-$C_{15}$ alkynyl group, a substituted or unsubstituted $C_3$-$C_{15}$ cycloalkyl group, a substituted or unsubstituted $C_1$-$C_{15}$ heterocycloalkyl group, a substituted or unsubstituted $C_1$-$C_{15}$ alkoxy group, a substituted or unsubstituted $C_3$-$C_{15}$ cycloalkoxy group, a substituted or unsubstituted $C_1$-$C_{15}$ alkylthio group, a substituted or unsubstituted $C_1$-$C_{15}$ alkylamino group, —N($Q_5$)($Q_{10}$), —C(=O)($Q_9$), —N—C(=O)($Q_9$), —N—C(=O)—N($Q_9$)($Q_{10}$), —O—C(=O)(Q$_9$), —S(=O)(Q$_9$), —S(=O)$_2$(Q$_9$), —P(=O)(Q$_9$)(Q$_{10}$), and —N—C(=NH)—N(Q$_9$)(Q$_{10}$), wherein Q$_7$ to Q$_{10}$ may each independently be one selected from hydrogen, halogen, a hydroxyl group, a substituted or unsubstituted C$_1$-C$_6$ alkyl group, a substituted or unsubstituted C$_2$-C$_6$ alkenyl group, a substituted or unsubstituted C$_2$-C$_6$ alkynyl group, a substituted or unsubstituted C$_3$-C$_6$ cycloalkyl group, a substituted or unsubstituted C$_1$-C$_6$ heterocycloalkyl group, a substituted or unsubstituted C$_1$-C$_6$ alkoxy group, a substituted or unsubstituted C$_3$-C$_6$ cycloalkoxy group, a substituted or unsubstituted C$_1$-C$_6$ alkylthio group, a substituted or unsubstituted C$_6$-C$_9$ aryl group, a substituted or unsubstituted C$_6$-C$_9$ aryloxy group, a substituted or unsubstituted C$_6$-C$_9$ arylthio group, a substituted or unsubstituted C$_1$-C$_6$ heteroaryl group, a substituted or unsubstituted C$_1$-C$_6$ heteroaryloxy group, and a substituted or unsubstituted C$_1$-C$_6$ heteroarylthio group, k may be 0, and m may be an integer from 0 to 2.

In some embodiments, in Formula 1, when (B)

is a phenyl group or a pyridinyl group, and m is an integer from 1 to 5, at least one selected from R$^2$(s) may be selected from a hydroxyl group, a thiol group, a substituted or unsubstituted C$_2$-C$_{10}$ alkenyl group, a substituted or unsubstituted C$_2$-C$_{10}$ alkynyl group, a substituted or unsubstituted C$_3$-C$_{10}$ carbocyclic group, a substituted or unsubstituted C$_1$-C$_{10}$ heterocyclic group, a substituted or unsubstituted C$_3$-C$_{10}$ cycloalkoxy group, a substituted or unsubstituted C$_6$-C$_{10}$ aryloxy group, a substituted or unsubstituted C$_6$-C$_{10}$ arylthio group, a substituted or unsubstituted C$_1$-C$_{10}$ heteroaryloxy group, a substituted or unsubstituted C$_1$-C$_{10}$ heteroarylthio group, a substituted or unsubstituted C$_6$-C$_{10}$ aryl group, a substituted or unsubstituted C$_1$-C$_{10}$ heteroaryl group, —N(Q$_3$)(Q$_4$), —C(=O)(Q$_3$), —N—C(=O)(Q$_3$), —N—C(=O)—N(Q$_3$)(Q$_4$), —O—C(=O)(Q$_3$), —S(=O)(Q$_3$), —S(=O)$_2$(Q$_3$), —P(=O)(Q$_3$)(Q$_4$), and —N—C(=NH)—N(Q$_3$)(Q$_4$), R$^3$ and R$^4$ may be bound to form a substituted or unsubstituted C$_1$-C$_{15}$ heterocyclic group, and at least one substituent of the substituted C$_1$-C$_{15}$ heterocyclic group may be selected from a cyano group, a thiol group, a nitro group, a substituted or unsubstituted C$_2$-C$_{10}$ alkenyl group, a substituted or unsubstituted C$_2$-C$_{10}$ alkynyl group, a substituted or unsubstituted C$_3$-C$_{10}$ carbocyclic group, a substituted or unsubstituted C$_1$-C$_1$ heterocyclic group, a substituted or unsubstituted C$_3$-C$_{10}$ cycloalkoxy group, a substituted or unsubstituted C$_1$-C$_{10}$ alkylthio group, a substituted or unsubstituted C$_6$-C$_{10}$ aryloxy group, a substituted or unsubstituted C$_6$-C$_{10}$ arylthio group, a substituted or unsubstituted C$_1$-C$_{10}$ heteroaryloxy group, a substituted or unsubstituted C$_1$-C$_{20}$ heteroarylthio group, a substituted or unsubstituted C$_6$-C$_{20}$ aryl group, a substituted or unsubstituted C$_1$-C$_{20}$ heteroaryl group, —N(Q$_5$)(Q$_6$), —C(=O)(Q$_5$), —N—C(=O)(Q$_5$), —N—C(=O)—N(Q$_5$)(Q$_6$), —O—C(=O)(Q$_5$), —S(=O)(Q$_5$), —S(=O)$_2$(Q$_5$), —P(=O)(Q$_5$)(Q$_6$), and —N—C(=NH)—N(Q$_5$)(Q$_6$).

Also, at least one substituent of the substituted C$_2$-C$_{10}$ alkenyl group, the substituted C$_2$-C$_{10}$ alkynyl group, the substituted C$_3$-C$_{10}$ carbocyclic group, the substituted C$_1$-C$_{10}$ heterocyclic group, the substituted C$_3$-C$_{10}$ cycloalkoxy group, the substituted C$_1$-C$_{10}$ alkylthio group, the substituted C$_6$-C$_{10}$ aryloxy group, the substituted C$_6$-C$_{10}$ arylthio group, the substituted C$_1$-C$_{10}$ heteroaryloxy group, the substituted C$_1$-C$_{10}$ heteroarylthio group, the substituted C$_6$-C$_{10}$ aryl group, and the substituted C$_1$-C$_{10}$ heteroaryl group may be selected from: a C$_2$-C$_{10}$ alkenyl group, a C$_2$-C$_{10}$ alkynyl group, a C$_3$-C$_{10}$ cycloalkyl group, a C$_1$-C$_{10}$ heterocycloalkyl group, a C$_3$-C$_{10}$ cycloalkoxy group, a C$_6$-C$_{10}$ aryloxy group, a C$_6$-C$_{10}$ arylthio group, a C$_1$-C$_{10}$ heteroaryloxy group, a C$_1$-C$_{10}$ heteroarylthio group, a C$_6$-C$_{10}$ aryl group, a C$_1$-C$_{10}$ heteroaryl group, and a C$_1$-C$_{10}$ alkylamino group.

In an example embodiment, in Formula 1, (B)

may be a phenyl group or a pyridinyl group,

X may be C(R$^a$), wherein R$^a$ may be hydrogen or a C$_1$-C$_4$ alkyl group,

R$^1$(s) may be hydrogen or fluorine,

R$^2$(s) may each independently be selected from halogen, a C$_1$-C$_6$ alkyl group, a C$_1$-C$_6$ alkoxy group, a C$_1$-C$_6$ alkylamino group, a C$_1$-C$_6$ alkylthio group, a substituted or unsubstituted C$_3$-C$_6$ cycloalkyl group, a substituted or unsubstituted N-linked pyrrolidinyl group, a substituted or unsubstituted N-linked piperidinyl group, and a substituted or unsubstituted N-linked azetidinyl group, at least one substituent of the substituted C$_3$-C$_6$ cycloalkyl group, the substituted N-linked pyrrolidinyl group, the substituted or unsubstituted N-linked piperidinyl group, and the substituted or unsubstituted N-linked azetidinyl group may be selected from:

halogen, a hydroxy group, a C$_1$-C$_4$ alkyl group, a C$_1$-C$_4$ alkoxy group, a C$_1$-C$_4$ alkylhydroxy group, and a C$_1$-C$_6$ heterocyclic group, when R$^2$(s) is two or more, two R$^2$(s) may be bound to each other and fused to (B)

to form a substituted or unsubstituted C$_3$-C$_{12}$ carbocyclic group or a substituted or unsubstituted C$_6$-C$_{12}$ heterocyclic group, R$^3$ and R$^4$ may be bound to form a substituted or unsubstituted piperidinyl group, a substituted or unsubstituted azepanyl group, or a substituted or unsubstituted azabicyclooctanyl group, with the amide nitrogen of Formula 1, and at least one substituent of the substituted piperidinyl group, the substituted azepanyl group, or the substituted azabicyclooctanyl group may be selected from an amino group, a C$_1$-C$_4$ alkylamino group, and N(Q$_a$)(Q$_b$), wherein Q$_a$ and Q$_b$ may each independently be selected from hydrogen and a C$_1$-C$_6$ alkyl group.

In an example embodiment, in Formula 1, R$^2$(s) may each independently be selected from halogen, a C$_1$-C$_6$ alkyl group, a C$_1$-C$_6$ alkoxy group, a C$_1$-C$_6$ alkylamino group, a C$_1$-C$_6$ alkylthio group, a substituted or unsubstituted C$_3$-C$_6$ cycloalkyl group, a substituted or unsubstituted N-linked pyrrolidinyl group, a substituted or unsubstituted N-linked piperidinyl group, and a substituted or unsubstituted N-linked azetidinyl group, at least one substituent of the substituted $C_3$-$C_6$ cycloalkyl group, or the substituted N-linked azetidinyl group may be selected from halogen and a hydroxy group, at least one substituent of the substituted N-linked substituted pyrrolidinyl group or the substituted N-linked piperidinyl group may be selected from halogen, a hydroxy group, a $C_1$-$C_4$ alkyl group, a $C_1$-$C_4$ alkoxy group, a $C_1$-$C_4$ alkylhydroxy group, and a piperidine group, and when $R^2$(s) is two or more, two $R^2$(s) may be bound and fused with

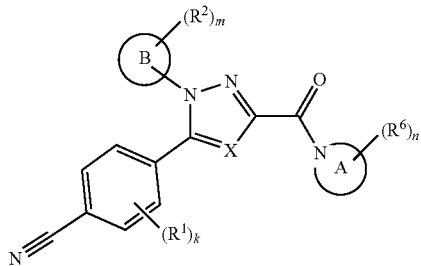

to form a heterocyclic group or a carbocyclic group selected from an indazole group, a benzothiazole group, an indane group, a dihydrobenzodioxin group, a quinoline group, and a pyrrolopyridine group, wherein the heterocyclic group or a carbocyclic group are unsubstituted or substituted with a $C_1$-$C_3$ alkyl group.

In an example embodiment, $R^3$ and $R^4$ in the compound represented by Formula 1 may be bound to form a compound represented by Formula 2.

Formula 2 wherein, in Formula 2, may be a $C_1$-$C_{30}$ heterocyclic group including a nitrogen atom, for example, the $C_1$-$C_{30}$ heterocyclic group including a nitrogen atom may be one selected from a piperidinyl group, a pyrrolidinyl group, a piperazinyl group, an azepinyl group, diazaspiro-nonanyl group, a diazaspiro-decanyl group, an azabicyclo heptanyl group, an azabicyclo-octanyl group, a diazabicyclo-nonanyl group, and a diazabicyclo-decanyl group, each unsubstituted or substituted with at least one substituent described herein.

In Formula 2, $R^1$, $R^2$, k, and m may be defined the same as those in Formula 1. In Formula 2, n may be an integer from 0 to 6; when n is 2 or greater, at least two $R^6$(s) may be identical to or different from each other, and $R^6$(s) may each independently be selected from hydrogen, halogen, a cyano group, a hydroxyl group, a thiol group, a nitro group, a substituted or unsubstituted $C_1$-$C_{15}$ alkyl group, a substituted or unsubstituted $C_2$-$C_{15}$ alkenyl group, a substituted or unsubstituted $C_2$-$C_{15}$ alkynyl group, a substituted or unsubstituted $C_3$-$C_{15}$ carbocyclic group, a substituted or unsubstituted $C_1$-$C_{15}$ heterocyclic group, a substituted or unsubstituted $C_1$-$C_{20}$ alkoxy group, a substituted or unsubstituted $C_3$-$C_{20}$ cycloalkoxy group, a substituted or unsubstituted $C_1$-$C_{20}$ alkylthio group, —N($Q_{25}$)($Q_{26}$), —C(=O)($Q_{25}$), —N—C(=O)($Q_{25}$), —N—C(=O)—N($Q_{25}$)($Q_{26}$), —O—C(=O)($Q_{25}$), —S(=O)($Q_{25}$), —S(=O)$_2$($Q_{25}$), —P(=O)($Q_{25}$)($Q_{26}$), and —N—C(=NH)—N($Q_{25}$)($Q_{26}$), wherein at least one substituent of the substituted $C_1$-$C_{15}$ alkyl group, the substituted $C_2$-$C_{15}$ alkenyl group, the substituted $C_2$-$C_{15}$ alkynyl group, the substituted $C_3$-$C_{15}$ carbocyclic group, the substituted $C_1$-$C_{15}$ heterocyclic group, the substituted $C_1$-$C_{15}$ alkoxy group, the substituted $C_3$-$C_{15}$ cycloalkoxy group, the substituted $C_1$-$C_{15}$ alkylthio group, and the substituted $C_1$-$C_{15}$ alkylamino group may be selected from halogen, a cyano group, a hydroxyl group, a thiol group, a nitro group, a $C_1$-$C_{15}$ alkyl group, a $C_2$-$C_{15}$ alkenyl group, a $C_2$-$C_{15}$ alkynyl group, a $C_3$-$C_{15}$ carbocyclic group, a $C_1$-$C_{15}$ heterocyclic group, a $C_1$-$C_{15}$ alkoxy group, a $C_3$-$C_{15}$ cycloalkoxy group, a $C_1$-$C_{15}$ alkylthio group, —N($Q_{27}$)($Q_{28}$), —C(=O)($Q_{27}$), —N—C(=O)($Q_{27}$), —N—C(=O)—N($Q_{27}$)($Q_{28}$), —O—C(=O)($Q_{27}$), —S(=O)($Q_{27}$), —S(=O)$_2$($Q_{27}$), —P(=O)($Q_{27}$)($Q_{28}$), and —N—C(=NH)—N($Q_{27}$)($Q_{28}$), and $Q_{25}$ to $Q_{28}$ may each independently be selected from hydrogen, halogen, a cyano group, a hydroxyl group, a thiol group, a nitro group, a substituted or unsubstituted $C_1$-$C_{15}$ alkyl group, a substituted or unsubstituted $C_2$-$C_{15}$ alkenyl group, a substituted or unsubstituted $C_2$-$C_{15}$ alkynyl group, a substituted or unsubstituted $C_3$-$C_{15}$ cycloalkyl group, a substituted or unsubstituted $C_1$-$C_{15}$ heterocycloalkyl group, a substituted or unsubstituted $C_1$-$C_{15}$ alkoxy group, a substituted or unsubstituted $C_3$-$C_{15}$ cycloalkoxy group, and a substituted or unsubstituted $C_1$-$C_{15}$ alkylthio group.

At least one substituent of the substituted $C_1$-$C_{15}$ alkyl group, the substituted $C_2$-$C_{15}$ alkenyl group, the substituted $C_2$-$C_{15}$ alkynyl group, the substituted $C_3$-$C_{15}$ cycloalkyl group, the substituted $C_1$-$C_{15}$ heterocycloalkyl group, the substituted $C_1$-$C_{15}$ alkoxy group, the substituted $C_3$-$C_{15}$ cycloalkoxy group, the substituted $C_1$-$C_{15}$ alkylthio group, the substituted $C_6$-$C_{15}$ aryloxy group, and the substituted $C_6$-$C_{15}$ arylthio group may be selected from halogen, a cyano group, a hydroxyl group, a thiol group, a nitro group, a $C_1$-$C_{15}$ alkyl group, a $C_2$-$C_{15}$ alkenyl group, a $C_2$-$C_{15}$ alkynyl group, a $C_3$-$C_{15}$ cycloalkyl group, a $C_1$-$C_{15}$ heterocycloalkyl group, a $C_1$-$C_{15}$ alkoxy group, a $C_3$-$C_{15}$ cycloalkoxy group, and a $C_1$-$C_{15}$ alkylthio group.

In an example embodiment, in Formula 1, at least one substituent of the substituted or unsubstituted $C_1$-$C_{30}$ heterocyclic group formed by binding of $R^3$ and $R^4$ with the amide nitrogen of Formula 1 or at least one substituent of the compound represented by Formula 2 may be selected from —N($Q_{29}$)($Q_{30}$), —N—C(=O)($Q_{29}$), —N—C(=O)—N($Q_{29}$)($Q_{30}$), and —N—C(=NH)—N($Q_{29}$)($Q_{30}$), wherein $Q_{29}$ and $Q_{30}$ may each independently be one selected from hydrogen, halogen, a hydroxyl group, a $C_1$-$C_{15}$ alkyl group unsubstituted or substituted with F, Cl, Br, or I, a $C_3$-$C_{15}$ cycloalkyl group unsubstituted or substituted with F, Cl, Br, or I, a $C_2$-$C_{15}$ cycloalkenyl group unsubstituted or substituted with F, Cl, Br, or I, a $C_1$-$C_{20}$ alkoxy group unsubstituted or substituted with F, Cl, Br, or I, a $C_3$-$C_{15}$ cycloalkoxy group unsubstituted or substituted with F, Cl, Br, or I, and a $C_1$-$C_{15}$ alkylamino group unsubstituted or substituted with F, Cl, Br, or I.

In an example embodiment, (A)

of the compound represented by Formula 2 may be substituted with at least one substituent to form a compound represented by Formula 3.

Formula 3

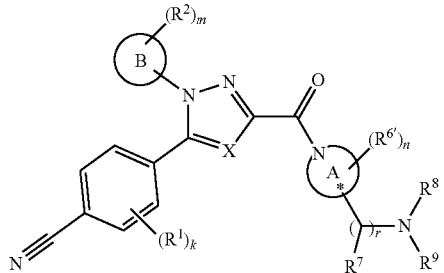

wherein, in Formula 3, (B), $R^1$, $R^2$, k, and m may each be defined the same as those in Formula 1, and (A)

and n may each be defined the same as those in Formula 2.

In Formula 3, r may be an integer from 0 to 6; when r is 2 or greater, at least two $R^{6'}$(s) may be identical to or different from each other, and $R^{6'}$(s) may be defined the same as $R^6$(s) in Formula 2.

In Formula 3, $R^7$ may each independently be selected from hydrogen, halogen, a hydroxyl group, a substituted or unsubstituted $C_1$-$C_{15}$ alkyl group, a substituted or unsubstituted $C_1$-$C_{15}$ alkoxy group, a substituted or unsubstituted $C_3$-$C_{15}$ carbocyclic group, and a substituted or unsubstituted $C_1$-$C_{15}$ heterocyclic group, $R^8$ and $R^9$ may each independently be selected from hydrogen, halogen, a substituted or unsubstituted $C_1$-$C_{15}$ alkyl group, a substituted or unsubstituted $C_1$-$C_{15}$ alkoxy group, a substituted or unsubstituted $C_3$-$C_{15}$ carbocyclic group, and a substituted or unsubstituted $C_1$-$C_{15}$ heterocyclic group.

In an example embodiment, in Formula 1, (B)

may be one selected from a phenyl group, a pyridinyl group, a quinolinyl group, a benzothiazolyl group, an indazolyl group, a benzodioxinyl group, an indanyl group, and a naphthyl group, X may be $C(R^5)$, $R^5$ may be selected from hydrogen, halogen, a hydroxyl group, a substituted or unsubstituted $C_1$-$C_4$ alkyl group, and a substituted or unsubstituted $C_1$-$C_4$ alkoxy group, $R^2$(s) may be one selected from hydrogen, halogen, a cyano group, a hydroxyl group, a thiol group, a nitro group, a substituted or unsubstituted $C_1$-$C_{15}$ alkyl group, a substituted or unsubstituted $C_2$-$C_{15}$ alkenyl group, a substituted or unsubstituted $C_2$-$C_{15}$ alkynyl group, a substituted or unsubstituted $C_3$-$C_{15}$ carbocyclic group, a substituted or unsubstituted $C_1$-$C_{15}$ heterocyclic group, a substituted or unsubstituted $C_1$-$C_{15}$ alkoxy group, a substituted or unsubstituted $C_3$-$C_{15}$ cycloalkoxy group, a substituted or unsubstituted $C_1$-$C_{15}$ alkylthio group, a substituted or unsubstituted $C_6$-$C_{15}$ aryloxy group, a substituted or unsubstituted $C_6$-$C_{15}$ arylthio group, a substituted or unsubstituted $C_1$-$C_{15}$ heteroaryloxy group, a substituted or unsubstituted $C_1$-$C_{15}$ heteroarylthio group, $-N(Q_3)(Q_4)$, $-C(=O)(Q_3)$, $-N-C(=O)(Q_3)$, $-N-C(=O)-N(Q_3)(Q_4)$, $-O-C(=O)(Q_3)$, $-S(=O)(Q_3)$, $-S(=O)_2(Q_3)$, $-P(=O)(Q_3)(Q_4)$, and $-N-C(=NH)-N(Q_3)(Q_4)$, (A)

may be a substituted or unsubstituted $C_1$-$C_{30}$ heterocyclic group one selected from a piperidinyl group, a pyrrolidinyl group, a piperazinyl group, an azepinyl group, a diazaspirononanyl group, a diazaspirodecanyl group, an azabicyclo-heptanyl group, an azabicyclo-octanyl group, a diazabicyclo-nonanyl group, and a diazabicyclo-decanyl group, at least one substituent of the substituted $C_1$-$C_{30}$ heterocyclic group may be selected from $-N(Q_5)(Q_6)$, $-N-C(=O)(Q_5)$, $-N-C(=O)-N(Q_5)(Q_6)$, and $-N-C(=NH)-N(Q_5)(Q_6)$; and a $C_1$-$C_{15}$ alkyl group, a $C_2$-$C_{15}$ alkenyl group, a $C_2$-$C_{15}$ alkynyl group, a $C_3$-$C_{15}$ carbocyclic group, a $C_1$-$C_{15}$ heterocyclic group, a $C_1$-$C_{15}$ alkoxy group, a $C_3$-$C_{15}$ cycloalkoxy group, a $C_1$-$C_{15}$ alkylthio group, and a $C_1$-$C_{15}$ alkylamino group, each substituted with at least one selected from $-N(Q_5)(Q_6)$, $-N-C(=O)(Q_5)$, $-N-C(=O)-N(Q_5)(Q_6)$, and $-N-C(=NH)-N(Q_5)(Q_6)$, k may be 0, and m may be an integer from 0 to 2.

In an example embodiment, the compound represented by Formula 1 may be a compound represented by Formula 4, an optical isomer, a solvate, or a tautomer, or a pharmaceutically acceptable salt thereof:

Formula 4

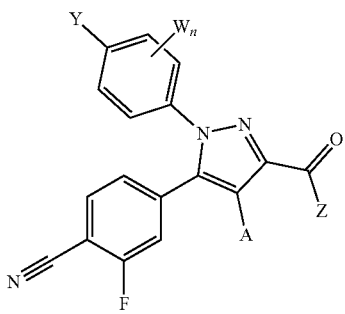

wherein, in Formula 4,

A may be hydrogen or a $C_1$-$C_4$ alkyl group,

W(s) may each independently be halogen, n may be a natural number from 1 to 4,

Y may be a substituted or unsubstituted $C_3$-$C_6$ cycloalkyl group, a substituted or unsubstituted N-linked pyrrolidinyl group, or a substituted or unsubstituted N-linked piperidinyl group, wherein the substituted $C_3$-$C_6$ cycloalkyl group may be a $C_3$-$C_6$ cycloalkyl group in which at least one hydrogen is substituted with a functional group each independently selected from halogen and a hydroxy group, and the substituted N-linked pyrrolidinyl group and the substituted N-linked piperidinyl group may each be a N-linked pyrrolidinyl group and a N-linked piperidinyl group, respectively, in which at least one ring hydrogen atom is substituted with a functional group each independently selected from a $C_1$-$C_4$ alkyl group, halogen, a $C_1$-$C_4$ alkoxy group, a hydroxy group, and a $C_1$-$C_{10}$ heterocyclic group, and Z may be a substituted or unsubstituted N-linked pyrrolidinyl group, a substituted or unsubstituted N-linked piperidinyl group, or a substituted or unsubstituted N-linked azepanyl group, wherein at least one substituent of the substituted N-linked pyrrolidinyl group, the substituted N-linked piperidinyl group, or the substituted N-linked azepanyl group may be selected from an amino group, a $C_1$-$C_4$ alkylamino group, a $C_1$-$C_4$ alkyl group, halogen, a $C_1$-$C_4$ alkoxy group, and a $C_1$-$C_{10}$ heterocyclic group.

In an example embodiment, in the compound represented by Formula 4,

A may be hydrogen,

W(s) may be fluorine, n may be a natural number of 1,

Y may be a substituted or unsubstituted N-linked pyrrolidinyl group or a substituted or unsubstituted N-linked piperidinyl group, wherein the substituted N-linked pyrrolidinyl group and the substituted N-linked piperidinyl group may each be a N-linked pyrrolidinyl group and a N-linked piperidinyl group, respectively, in which at least one ring hydrogen atom is substituted with a functional group each independently selected from a $C_1$-$C_4$ alkyl group, halogen, a $C_1$-$C_4$ alkoxy group, and a hydroxy group, and Z may be a substituted N-linked piperidinyl group or a unsubstituted piperidinyl group in which at least one substituent is substituted with a functional group selected from an amino group, a $C_1$-$C_4$ alkylamino group, a $C_1$-$C_4$ alkyl group, halogen, and a $C_1$-$C_4$ alkoxy group.

In an example embodiment of the present disclosure, examples of the compound represented by Formula 1 are described below. Also, the scope of the present disclosure may include an isomer e.g., an optical isomer or a tautomer, a solvate, or a pharmaceutically acceptable salt of the following compounds:

1) (R)-4-(3-(3-aminopiperidine-1-carbonyl)-1-(4-cyclopropylphenyl)-1H-pyrazole-5-yl)benzonitrile
2) (R)-4-(1-(4-cyclopropylphenyl)-3-(3-methylaminopiperidine-1-carbonyl)-1H-pyrazole-5-yl)benzonitrile
3) (R)-4-(3-(3-aminopiperidine-1-carbonyl)-1-(4-cyclopropyl-2-fluorophenyl)-1H-pyrazole-5-yl)benzonitrile
4) (R)-4-(1-(4-cyclopropyl-2-fluorophenyl)-3-(3-(methylamino)piperidine-1-carbonyl)-1H-pyrazole-5-yl)benzonitrile
5) (R)-4-(3-(3-aminopiperidine-1-carbonyl)-1-(4-cyclopropyl-2-fluorophenyl)-1H-pyrazole-5-yl)-2-fluorobenzonitrile
6) (R)-4-(1-(4-cyclopropyl-2-fluorophenyl)-3-(3-(methylamino)piperidine-1-carbonyl)-1H-pyrazole-5-yl)benzonitrile
7) (R)-4-(3-(3-aminoazepane-1-carbonyl)-1-(4-(cyclopropylphenyl)-1H-pyrazole-5-yl)benzonitrile
8) (R)-4-(3-(3-aminoazepane-1-carbonyl)-1-(4-cyclopropyl-2-fluorophenyl)-1H-pyrazole-5-yl)-2-fluorobenzonitrile
9) 4-(3-((3R,5R)-3-amino-5-methylpiperidine-1-carbonyl)-1-(4-cyclopropyl-2-fluorophenyl)-1H-pyrazole-5-yl)-2-fluorobenzonitrile
10) (R)-4-(3-(3-aminopiperidine-1-carbonyl)-1-(4-cyclopropyl-2,6-difluorophenyl)-1H-pyrazole-5-yl)-2-fluorobenzonitrile
11) (R)-4-(3-(3-aminoazepane-1-carbonyl)-1-(4-cyclopropyl-2,6-difluorophenyl)-1H-pyrazole-5-yl)-2-fluorobenzonitrile
12) (R)-4-(3-(3-aminopiperidine-1-carbonyl)-1-(2-chloro-4-cyclopropylphenyl)-1H-pyrazole-5-yl)-2-fluorobenzonitrile
13) (R)-4-(3-(3-aminoazepane-1-carbonyl)-1-(2-chloro-4-cyclopropylphenyl)-1H-pyrazole-5-yl)-2-fluorobenzonitrile
14) (R)-4-(3-(3-aminopiperidine-1-carbonyl)-1-phenyl-1H-pyrazole-5-yl)benzonitrile
15) (R)-4-(3-(3-aminopiperidine-1-carbonyl)-1-(pyridine-2-yl)-1H-pyrazole-5-yl)benzonitrile
16) (R)-4-(3-(3-aminopiperidine-1-carbonyl)-1-(4-fluorophenyl)-1H-pyrazole-5-yl)benzonitrile
17) (R)-4-(3-(3-aminopiperidine-1-carbonyl)-1-(4-chlorophenyl)-1H-pyrazole-5-yl)benzonitrile
18) (R)-4-(1-(4-chlorophenyl)-3-(3-methylaminopiperidine-1-carbonyl)-1H-pyrazole-5-yl)benzonitrile
19) (R)-4-(3-(3-aminopiperidine-1-carbonyl)-1-(3-chlorophenyl)-1H-pyrazole-5-yl)benzonitrile
20) (R)-4-(3-(3-aminopiperidine-1-carbonyl)-1-(4-bromophenyl)-1H-pyrazole-5-yl)benzonitrile
21) (R)-4-(1-(4-bromophenyl)-3-(3-(methylamino)piperidine-1-carbonyl)-1H-pyrazole-5-yl)benzonitrile
22) (S)-4-(3-(3-aminopyrrolidine-1-carbonyl)-1-(p-tolyl)-1H-pyrazole-5-yl)benzonitrile
23) (S)-4-(3-(3-(methylamino)pyrrolidine-1-carbonyl)-1-(p-tolyl)-1H-pyrazole-5-yl)benzonitrile
24) (S)-4-(3-(3-(dimethylamino)pyrrolidine-1-carbonyl)-1-(p-tolyl)-1H-pyrazole-5-yl)benzonitrile
25) (R)-4-(3-(3-(dimethylamino)pyrrolidine-1-carbonyl)-1-(p-tolyl)-1H-pyrazole-5-yl)benzonitrile
26) (R)-4-(3-(3-(methylamino)pyrrolidine-1-carbonyl)-1-(p-tolyl)-1H-pyrazole-5-yl)benzonitrile
27) (R)-4-(3-(3-aminopyrrolidine-1-carbonyl)-1-(p-tolyl)-1H-pyrazole-5-yl)benzonitrile
28) (R)-4-(3-(3-aminopiperidine-1-carbonyl)-1-(p-tolyl)-1H-pyrazole-5-yl)benzonitrile
29) (R)-4-(3-(3-(methylamino)piperidine-1-carbonyl)-1-(p-tolyl)-1H-pyrazole-5-yl)benzonitrile 30) (R)-4-(3-(3-(dimethylamino)piperidine-1-carbonyl)-1-(p-tolyl)-1H-pyrazole-5-yl)benzonitrile
31) (R)-4-(3-(3-aminopiperidine-1-carbonyl)-1-(m-tolyl)-1H-pyrazole-5-yl)benzonitrile
32) (R)-4-(3-(3-aminopiperidine-1-carbonyl)-1-(o-tolyl)-1H-pyrazole-5-yl)benzonitrile
33) (R)-4-(3-(3-aminopiperidine-1-carbonyl)-1-(4-ethylphenyl)-1H-pyrazole-5-yl)benzonitrile
34) (R)-4-(1-(4-ethylphenyl)-3-(3-(methylamino)piperidine-1-carbonyl)-1H-pyrazole-5-yl)benzonitrile
35) (R)-4-(3-(3-aminopiperidine-1-carbonyl)-1-(4-isopropylphenyl)-1H-pyrazole-5-yl)benzonitrile
36) (R)-4-(1-(4-isopropylphenyl)-3-(3-(methylamino)piperidine-1-carbonyl)-1H-pyrazole-5-yl) benzonitrile
37) (R)-4-(3-(3-aminoa piperidine-1-carbonyl)-1-(2-fluoro-4-isopropylphenyl)-1H-pyrazole-5-yl)benzonitrile
38) (R)-4-(3-(3-aminopiperidine-1-carbonyl)-1-(2-fluoro-4-isopropylphenyl)-1H-pyrazole-5-yl)-2-fluorobenzonitrile
39) (R)-4-(3-(3-aminoazepane-1-carbonyl)-1-(2-cyclopropyl-2,6-difluorophenyl)-1H-pyrazole-5-yl)-2-fluorobenzonitrile
40) (R)-4-(3-(3-aminopiperidine-1-carbonyl)-1-(4-(tert-butyl)phenyl)-1H-pyrazole-5-yl)benzonitrile
41) (R)-4-(1-(4-(tert-butyl)phenyl-3-(3-methylaminopiperidine-1-carbonyl)-1H-pyrazole-5-yl)benzonitrile
42) (R)-4-(3-(3-aminopiperidine-1-carbonyl)-1-(4-(tert-butyl)-2-fluorophenyl)-1H-pyrazole-5-yl)benzonitrile
43) (R)-4-(3-(3-aminopiperidine-1-carbonyl)-1-(4-(tert-butyl-2-fluorophenyl)-1H-pyrazole-5-yl)-2-fluorobenzonitrile
44) (R)-4-(3-(3-aminoazepane-1-carbonyl)-1-(4-(tert-butyl-2-fluorophenyl)-1H-pyrazole-5-yl)-2-fluorobenzonitrile
45) (R)-4-(3-(3-aminopiperidine-1-carbonyl)-1-(4-(trifluoromethoxy)phenyl)-1H-pyrazole-5-yl) benzonitrile
46) (R)-4-(3-(3-aminopiperidine-1-carbonyl)-1-(4-(methylsulfonyl)phenyl)-1H-pyrazole-5-yl)benzonitrile
47) (R)-4-(3-(3-aminopiperidine-1-carbonyl)-1-(4-(trifluoromethyl)phenyl)-1H-pyrazole-5-yl)benzonitrile
48) (R)-4-(3-(3-aminopiperidine-1-carbonyl)-1-(2-fluoro-4-methylphenyl)-1H-pyrazole-5-yl)benzonitrile
49) (R)-4-(3-(3-aminopiperidine-1-carbonyl)-1-(3-fluoro-4-methoxyphenyl)-1H-pyrazole-5-yl) benzonitrile
50) (R)-4,4'-(3-(3-aminopiperidine-1-carbonyl)-1H-pyrazole-1,5-diyl)dibenzonitrile
51) (R)-4-(1-(4-(dimethylamino)phenyl)-3-(3-(methylamino)piperidine-1-carbonyl)-1H-pyrazole-5-yl)benzonitrile
52) (R)-4-(3-(3-aminopiperidine-1-carbonyl)-1-(4-((2-(dimethylamino)ethyl)(methyl)amino)phenyl)-1H-pyrazole-5-yl)benzonitrile
53) ((R)-4-(3-(3-aminopiperidine-1-carbonyl)-1-(4-(dimethylamino)phenyl)-1H-pyrazole-5-yl) benzonitrile
54) (R)-4-(3-(3-aminopiperidine-1-carbonyl)-1-(4-(dimethylamino)-2-fluorophenyl)-1H-pyrazole-5-yl)benzonitrile
55) (R)-4-(3-(3-aminopiperidine-1-carbonyl)-1-(4-(diethylamino)-2-fluorophenyl)-1H-pyrazole-5-yl)benzonitrile
56) (R)-4-(3-(3-aminopiperidine-1-carbonyl)-1-(4-(azetidine-1-yl)-2-fluorophenyl)-1H-pyrazole-5-yl)benzonitrile
57) (R)-4-(3-(3-aminopiperidine-1-carbonyl)-1-(2-fluoro-4-(pyrrolidine-1-yl)phenyl)-1H-pyrazole-5-yl)benzonitrile
58) (R)-4-(3-(3-aminopiperidine-1-carbonyl)-1-(2-fluoro-4-(pyrrolidine-1-yl)phenyl)-1H-pyrazole-5-yl)-2-fluorobenzonitrile
59) (R)-2-fluoro-4-(1-(2-fluoro-4-(pyrrolidine-1-yl)phenyl)-3-(3-(methylamino)piperidine-1-carbonyl)-1H-pyrazole-5-yl)benzonitrile
60) (R)-4-(3-(3-aminoazepane-1-carbonyl)-1-(2-fluoro-4-(pyrrolidine-1-yl)phenyl)-1H-pyrazole-5-yl)-2-fluorobenzonitrile
61) 4-(3-((R)-3-aminopiperidine-1-carbonyl)-1-(2-fluoro-4-((R)-3-fluoropyrrolidine-1-yl)phenyl)-1H-pyrazole-5-yl)-2-fluorobenzonitrile
62) 4-(3-((R)-3-aminopiperidine-1-carbonyl)-1-(2-fluoro-4-((S)-3-fluoropyrrolidine-1-yl)phenyl)-1H-pyrazole-5-yl)-2-fluorobenzonitrile
63) (R)-4-(3-(3-aminopiperidine-1-carbonyl)-1-(4-(3,3-difluoropyrrolidine-1-yl)-2-fluorophenyl)-1H-pyrazole-5-yl)-2-fluorobenzonitrile
64) (R)-4-(1-(4-(3,3-difluoropyrrolidine-1-yl)-2-fluorophenyl)-3-(3-(methylamino)piperidine-1-carbonyl)-1H-pyrazole-5-yl)-2-fluorobenzonitrile
65) 4-(3-((R)-3-aminopiperidine-1-carbonyl)-1-(2-fluoro-4-(3-methoxypyrrolidin-1-yl)phenyl)-1H-pyrazol-5-yl)-2-fluorobenzonitrile
66) 2-fluoro-4-(1-(2-fluoro-4-(3-methoxypyrrolidine-1-yl)phenyl)-3-((R)-3-(methylamino)piperidine-1-carbonyl)-1H-pyrazole-5-yl)benzonitrile
67) 4-(3-((R)-3-aminopiperidine-1-carbonyl)-1-(2-fluoro-4-((S)-3-methoxypyrrolidine-1-yl)phenyl)-1H-pyrazole-5-yl)-2-fluorobenzonitrile
68) 2-fluoro-4-(1-(2-fluoro-4-((S)-3-methoxypyrrolidine-1-yl)phenyl)-3-((R)-3-(methylamino)piperidine-1-carbonyl)-1H-pyrazole-5-yl)benzonitrile
69) 4-(3-((R)-3-aminopiperidine-1-carbonyl)-1-(2-fluoro-4-((R)-3-methoxypyrrolidine-1-yl)phenyl)-1H-pyrazole-5-yl)-2-fluorobenzonitrile
70) 2-fluoro-4-(1-(2-fluoro-4-((R)-3-methoxypyrrolidine-1-yl)phenyl)-3-((R)-3-(methylamino)piperidine-1-carbonyl)-1H-pyrazole-5-yl)benzonitrile
71) 2-fluoro-4-(1-(2-fluoro-4-((S)-3-ethoxypyrrolidine-1-yl)phenyl)-3-((R)-3-(methylamino)piperidine-1-carbonyl)-1H-pyrazole-5-yl)benzonitrile
72) 4-(3-((R)-3-aminopiperidine-1-carbonyl)-1-(2-fluoro-4-(3-hydroxypyrrolidine-1-yl)phenyl)-1H-pyrazole-5-yl)-2-fluorobenzonitrile
73) 2-fluoro-4-(1-(2-fluoro-4-((S)-3-chloropyrrolidine-1-yl)phenyl)-3-((R)-3-(methylamino)piperidine-1-carbonyl)-1H-pyrazole-5-yl)benzonitrile
74) (R)-4-(3-(3-aminopiperidine-1-carbonyl)-1-(2,6-difluoro-4-(pyrrolidine-1-yl)phenyl)-1H-pyrazole-5-yl)-2-fluorobenzonitrile
75) (R)-4-(3-(3-aminopiperidine-1-carbonyl)-1-(2-chloro-4-(pyrrolidine-1-yl)phenyl)-1H-pyrazole-5-yl)-2-fluorobenzonitrile
76) (R)-4-(3-(3-aminopiperidine-1-carbonyl)-1-(2-methoxy-4-(pyrrolidine-1-yl)phenyl)-1H-pyrazole-5-yl)-2-fluorobenzonitrile
77) (R)-4-(3-(3-aminopiperidine-1-carbonyl)-1-(2-fluoro-4-(piperidine-1-yl)phenyl)-1H-pyrazole-5-yl)benzonitrile
78) (R)-4-(3-(3-aminopiperidine-1-carbonyl)-1-(2-fluoro-4-(piperidine-1-yl)phenyl)-1H-pyrazole-5-yl)-2-fluorobenzonitrile
79) (R)-2-fluoro-4-(1-(2-fluoro-4-(piperidine-1-yl)phenyl)-3-(3-(methylamino)piperidine-1-car bonyl)-1H-pyrazole-5-yl)benzonitrile
80) 4-(3-((R)-3-aminopiperidine-1-carbonyl)-1-(2-fluoro-4-(3-methylpiperidine-1-yl)phenyl)-1H-pyrazole-5-yl)-2-fluorobenzonitrile
81) (R)-4-(3-(3-aminopiperidine-1-carbonyl)-1-(2-fluoro-4-(4-methylpiperidine-1-yl)phenyl)-1H-pyrazole-5-yl)-2-fluorobenzonitrile 82) 4-(3-((R)-3-aminopiperidine-1-carbonyl)-1-(4-(3,5-dimethylpiperidine-1-yl)-2-fluorophenyl)-1H-pyrazole-5-yl)-2-fluorobenzonitrile
83) (R)-4-(1-(4-([1,4'-bipiperidine]-1'-yl)-2-fluorophenyl)-3-(3-aminopiperidine-1-carbonyl)-1H-pyrazole-5-yl)-2-fluorobenzonitrile
84) (R)-4-(3-(3-aminoazepane-1-carbonyl)-1-(2-fluoro-4-(piperidine-1-yl)phenyl)-1H-pyrazole-5-yl)-2-fluorobenzonitrile
85) (R)-4-(3-(3-aminopiperidine-1-carbonyl)-1-(1-methyl-1H-indazole-6-yl)-1H-pyrazole-5-yl) benzonitrile
86) (R)-4-(3-(3-aminopiperidine-1-carbonyl)-1-(2-methylbenzo[d]thiazole-5-yl)-1H-pyrazole-5-yl)benzonitrile
87) (R)-4-(3-(3-aminopiperidine-1-carbonyl)-1-(2,3-dihydro-1H-indane-5-yl)-1H-pyrazole-5-yl)benzonitrile
88) (R)-4-(3-(3-aminopiperidine-1-carbonyl)-1-(2,3-dihydro-1H-inden-5-yl)-1H-pyrazole-5-yl)-2-fluorobenzonitrile
89) (R)-4-(1-(2,3-dihydro-1H-inden-5-yl)-3-(3-(methylamino)piperidine-1-carbonyl)-1H-pyrazole-5-yl)benzonitrile
90) (R)-4-(3-(3-aminopiperidine-1-carbonyl)-1-(2,3-dihydrobenzo[b][1,4]dioxin-6-yl)-1H-pyrazole-5-yl)benzonitrile
91) (R)-4-(3-(3-aminopiperidine-1-carbonyl)-1-(quinoline-6-yl)-1H-pyrazole-5-yl)benzonitrile
92) (R)-4-(3-(3-aminopiperidine-1-carbonyl)-1-(quinoline-3-yl)-1H-pyrazole-5-yl)benzonitrile
93) (R)-4-(3-(3-aminopiperidine-1-carbonyl)-1-(1-methyl-1H-pyrrolo[2,3-b]pyridine-5-yl)-1H-pyrazole-5-yl)benzonitrile
94) (R)-4-(3-(3-aminopiperidine-1-carbonyl)-1-(2-fluoro-4-(2-hydroxy-2-methylpropyl)phenyl)-1H-pyrazole-5-yl)-2-fluorobenzonitrile
95) 4-(3-(piperazine-1-carbonyl)-1-(p-tolyl)-1H-pyrazole-5-yl)benzonitrile
96) 4-(3-(3-(aminomethyl)piperazine-1-carbonyl)-1-(p-tolyl)-1H-pyrazole-5-yl)benzonitrile
97) (S)-5-(4-cyanophenyl)-N-(1-(methylsulfonyl)piperidine-3-yl)-1-(p-tolyl)-1H-pyrazole-3-carboxamide
98) 4-(3-(2,7-diazaspiro[3.5]nonane-7-carbonyl)-1-(p-tolyl)-1H-pyrazole-5-yl)benzonitrile
99) 4-(3-(2,8-diazaspiro[4.5]decane-8-carbonyl)-1-(p-tolyl)-1H-pyrazole-5-yl)benzonitrile
100) 4-(3-(octahydro-1H-pyrrolo[2,3-c]pyridine-6-carbonyl)-1-(p-tolyl)-1H-pyrazole-5-yl)benzonitrile
101) 4-(3-(3,7-diazabicyclo[3.3.1]nonane-3-carbonyl)-1-(2-fluoro-4-isopropylphenyl)-1H-pyrazole-5-yl)-2-fluorobenzonitrile
102) 4-(3-(3-amino-8-azabicyclo[3.2.1]octane-8-carbonyl)-1-(2-fluoro-4-isopropylphenyl)-1H-pyrazole-5-yl)-2-fluorobenzonitrile
103) 4-(3-(3-amino-8-azabicyclo[3.2.1]octane-8-carbonyl)-1-(2-fluoro-4-pyrrolidine-1-yl)phenyl)-1H-pyrazole-5-yl)-2-fluorobenzonitrile
104) 4-(3-(3,7-diazabicyclo[3.3.1]nonane-3-carbonyl)-1-(p-tolyl)-1H-pyrazole-5-yl) benzonitrile
105) 5-(4-cyanophenyl)-N-(piperidine-4-yl)-1-(p-tolyl)-1H-pyrazole-3-carboximide
106) 5-(4-cyanophenyl)-N-(1-methylpiperidine-4-yl)-1-(p-tolyl)-1H-pyrazole-3-carboximide
107) (R)-5-(4-cyanophenyl)-N-(1-methylpiperidine-3-yl)-1-(p-tolyl)-1H-pyrazole-3-carboximide
108) (S)-5-(4-cyanophenyl)-N-(1-methylpiperidine-3-yl)-1-(p-tolyl)-1H-pyrazole-3-carboximide
109) (R)-5-(4-cyanophenyl)-N-(1-methylpyrrolidine-3-yl)-1-(p-tolyl)-1H-pyrazole-3-carboximide
110) 5-(4-cyano-3-fluorophenyl)-1-(2-fluoro-4-(pyrrolidine-1-yl)phenyl)-N-methyl-N-(piperidine-3-yl)-1H-pyrazole-3-carboximide
111) (S)-5-(4-cyano-3-fluorophenyl)-1-(2-fluoro-4-(pyrrolidine-1-yl)phenyl)-N-methyl-N-(piperidine-3-yl)-1H-pyrazole-3-carboximide
112) (R)-5-(4-cyano-3-fluorophenyl)-1-(2-fluoro-4-(pyrrolidine-1-yl)phenyl)-N-methyl-N-(piperidine-3-yl)-1H-pyrazole-3-carboximide
113) (R)-4-(3-(3-aminopiperidine-1-carbonyl)-1-(4-cyclopropyl-2-fluorophenyl)-4-methyl-1H-pyrazole-5-yl)benzonitrile.

In an example embodiment, examples of the compound represented by Formula 4 include Compounds 5), 6), 8) to 13), 58) to 75), and 78) to 84) of the compound represented by Formula 1 and an optical isomer, a solvate, a tautomer, or a pharmaceutically acceptable salt thereof.

Another aspect of the present disclosure provides a pharmaceutical composition for preventing or treating a disease caused by abnormal activation of lysine-specific demethylase-1 (LSD1), the pharmaceutical composition including: the compounds represented by Formulae 1 to 4, an optical isomer, a solvate, a tautomer, or a pharmaceutically acceptable salt thereof as an active ingredient, and a pharmaceutically acceptable carrier.

The term "isomer" as used herein refers to different compounds having the same molecular formula but differing in the arrangement and coordination of atoms and includes structural isomers and stereoisomers.

The term "structural isomer" as used herein refers to a compound having the same molecular formula but having different arrangement order of atoms. The "tautomer" is one of the structural isomers, which refers to a compound that interconverts both isomers and whose structure changes.

The term "stereoisomer" as used herein refers to any of various stereoisomeric coordination which may exist for a compound of the present disclosure and includes geometric isomers and optical isomers.

The term "diastereomer" as used to refer to stereoisomers that have at least two asymmetric atoms and are not mirror images of one another.

The term "geometric isomer" as used herein refers to isomers in which a spatial position of an atom or a functional group linked to a carbon atom of a double bond in a planar structure having a double bond between carbon atoms is different. The term "optical isomer" as used herein refers to any of various stereoisomeric coordination which may exist for a compound of the present disclosure and includes geometric isomers. Since the compounds of Formulae 1 to 4 of the present disclosure may have an asymmetric carbon center (asymmetric carbon), the compounds of Formulae 1 to 4 according to an aspect of the present disclosure may be in form of an enantiomer (R or S isomer), racemate, diastereomer, or any mixture thereof. All these isomers and mixtures are included within the scope of the present disclosure.

The term "enantiomer" as used herein refers to a pair of stereoisomers that are mirror images of each other and non-superimposable. A pair of enantiomers at a mixing ratio of 1:1 is referred to as "racemic" mixture.

The term "solvate" as used herein may include a molecular complex including the compound and at least one pharmaceutically acceptable solvent molecule, e.g., ethanol or water.

The term "pharmaceutically acceptable salts" as used herein refers to a salt that retains biological effectiveness and properties of the according to the present disclosure and is not biologically or otherwise undesirable. For example, the salt may include non-toxic inorganic and organic base addition salt or acid addition salt, but embodiments are not limited thereto.

In an example embodiment, for preventing or treating a disease caused by abnormal activation of LSD1, the pharmaceutical composition may be used in combination with a pharmaceutically acceptable additional drug. In an example embodiment, the pharmaceutical composition formulated in a pharmaceutically acceptable form including a tablet, a pill, a powder, a capsule, syrup, emulsion, and microemulsion.

In the present specification, LSD1, which may be involved in histone modification that is important, is an enzyme that plays a key role from a viewpoint of epigenetics regarding transcription regulation mechanism. LSD1 includes an N-terminal SWIRM domain (Swi3p, Rsc8p, and Moira), two types of transcription variants of LSD1 may be present result from selective splicing, and LSD1 have the structural similarity and amino acids uniformity/homogeneity with polyamine oxidases and monoamine oxidase (MAO). Also, LSD1 demethylates H3K4, suppress transcription, and demethylates H3K9 for activation of gene expression of a nuclear hormone receptor complex (e.g., androgen receptor) at the same time. This suggests that LSD1 may regulate alternative gene expression in a situation-dependent manner, as the substrate specificity of LSD1 is determined by related factors.

Also, as cancer cells rapidly divide and grow, blood vessels constrict inside a solid tumor, thus causing a low oxygen environment. Expression of hypoxia induced factor-1 (HIF-1) protein, which is known as promoting cancer occurrence metastasis in such a low oxygen environment, may be regulated depending on methylation by LSD1. LSD1 may also be involved in activation of some proteins such as E2F, STAT3, Tat, and myosin phosphatase target subset 1 (MYPT1), which are not histones, such as p53 and DNMT1, which play an important role in cancer. This suggests a tumorigenesis mechanism due to LSD1 problem in regulating chromatin remodeling. In addition, LSD1 may increase activity of another epigenetic regulator, e.g. DNA methyltransferase 1 (DNMT1) and histone deacetylase (HDAC) complexes. LSD1 may also contribute to various biological processes, including cell proliferation, epithelial mesenchymal transition (EMT), and stem cell biology (embryonic stem and cancer stem cell) or self-renewal and somatic cell transformation.

Also, since LSD1 contributes to tumorigenesis by altering epigenetic markers on histone and non-histone proteins, abnormal activation of LSD1 may cause various cancers.

According to the result of Experimental Example 1 described herein, the compounds represented by Formulae 1 to 4 was found to have significant enzyme activity suppressing effects on LSD1.

Also, as described above, since LSD1 contributes to tumorigenesis by altering epigenetic markers on histone and non-histone proteins, LSD1 suppressing activity may normalize gene expression, thereby inducing differentiation program to become a mature cell type, reducing cell proliferation, and promoting apoptosis of cancer cells. Thus, the compounds represented by Formulae 1 to 4 may be used in preventing or treating various diseases caused by abnormal activation of LSD1.

In an example embodiment, the pharmaceutical composition may include a pharmaceutically acceptable excipient, carrier, or additive. The pharmaceutical composition of the present disclosure may be formulated according to a conventional method and may be formulated into various oral dosage forms such as a tablet, a pill, powder, a capsule, syrup, emulsion, and microemulsion; or parenteral dosage forms such as intramuscular, intravenous or subcutaneous administration.

When the pharmaceutical composition of the present disclosure is prepared in a form of an oral formulation, examples of an additive or a carrier to be used include cellulose, calcium silicate, maize starch, lactose, sucrose, dextrose, calcium phosphate, stearic acid, magnesium stearate, gelatin, talc, a surfactant, a suspension, an emulsifier, and a diluent. When the pharmaceutical composition of the present disclosure is prepared in a form of an injection, examples of an additive or a carrier may include water, saline solution, aqueous glucose solution, pseudosaccharide solution, alcohol, glycol, ether (e.g., polyethylene glycol 400), oil, fatty acid, fatty acid ester, glyceride, a surfactant, a suspension, and an emulsifier.

The dose of the pharmaceutical composition as an active ingredient is an effective amount for treating or preventing a subject or a patient. The compound may be administered orally or parenterally, as desired. When the compound is administered orally, the active ingredient may be administered in an amount in a range of 0.01 milligrams (mg) to 1,000 mg, more particularly, 0.1 mg to 300 mg, per kilogram (kg) of body weight per day. When the compound is administered parenterally, the active ingredient may be administered from one to several times in an amount in a range of 0.01 mg to 100 mg, more particularly, 0.1 mg to 50 mg, per kg of body weight per day. The dose for a particular subject or patient should be determined in light of the patient's weight, age, sex, health condition, diet, time of administration, method of administration, severity of disease, etc. It is to be understood that the dose may be appropriately adjusted by a practitioner. The dose is not intended to limit the scope of the present disclosure in any way.

Still another aspect of the present disclosure provides a method of treating a disease caused by abnormal activation of LSD1, the method including administering to a subject a therapeutically effective amount of the compounds represented by Formulae 1 to 4, an optical isomer, a solvate, or a tautomer, or a pharmaceutically acceptable salt thereof.

Details of the method of preventing or treating may be the same as described above with reference to the pharmaceutical composition according to an aspect of the present disclosure. Also, the dose used in the method of preventing or treating is an amount effective in treatment or prevention of a subject or a patient. The dose of the pharmaceutical composition may be applied without any change.

The term "treating" or "treatment" as used herein refers to inhibiting a disease, for example, inhibiting a disease, condition, or disorder in a subject that has experienced or exhibited pathology or a symptom of the disease, condition, or disorder. In other words, the term "treating" or "treatment" refers to preventing additional occurrence of pathology and/or symptom or improving a disease, for example, improving a disease, condition, or disorder in a subject that has experienced or exhibited pathology or a symptom of the disease, condition, or disorder. In other words, the term "treating" or "treatment" refers to relieving pathology and/or symptom, e.g. reducing disease severity.

The term "preventing" or "prevention" as used herein refers to prevention of a disease, for example, prevention of a disease, condition, or disorder in a subject that may be predisposed to the disease, condition, or disorder but has not yet experienced or exhibited pathology or a symptom of the disease.

The term "subject" or "patient" as used herein refers to any animal, including mammals, for example, mice, rats, other rodents, rabbits, dogs, cats, pigs, cows, sheep, horses, or primates and humans.

Hereinafter, a method of preparing the compounds of the present disclosure will be described in detail.

The abbreviations used in the following Preparation Examples, preparation methods, and Examples each indicate:

$P(C_6H_{11})_3$: tricyclohexyl phosphine
$Pd(OAc)_2$: palladium acetate
$K_2CO_3$: potassium carbonate
$PtO_2$: platinum oxide
$NaNO_2$: sodium nitrite
$LiOH \cdot H_2O$: lithium hydroxide
$SnCl_2$: tin (II) chloride
HATU: (2-(1H-9-azabenzotriazole-1-yl)-1,1,3,3-tetramethyluronium hexafluorophosphate)
TFA: trifluoro acetic acid
HOBt: N-hydroxy benzotriazole
EDCl: 1-ethyl-3-(3-dimethyl aminopropyl)carbodiamide
MeI: iodine methane
DIPEA: N,N-diisopropylethylamine
THF: tetrahydrofuran
DMSO: dimethyl sulfoxide
EA: ethyl acetate
1,4-dioxane: 1,4-dioxane
$CH_2Cl_2$: dichloromethane
$Na_2SO_4$: anhydrous sodium sulfate Synthesis of a pyrazole derivative according to the present disclosure may be performed using an intermediate prepared in Reaction Scheme 1 or Reaction Scheme 2 or using an intermediate commercially available in the market. Mass analysis of the obtained pyrazole derivative was performed by using MicroMass ZQ™ available from Waters.

A pharmaceutical composition including as active ingredient the compounds represented by Formulae 1 to 4 synthesized according to the preparation method, an optical isomer, a solvate, a tautomer, or a pharmaceutically acceptable salt thereof may be used in prevention and treatment of a disease that may be treated by regulation of LSD1.

A method of preparing the compounds represented by Formulae 1 to 4 may be shown as Reaction Schemes 1 and 2.

Reaction Scheme 1

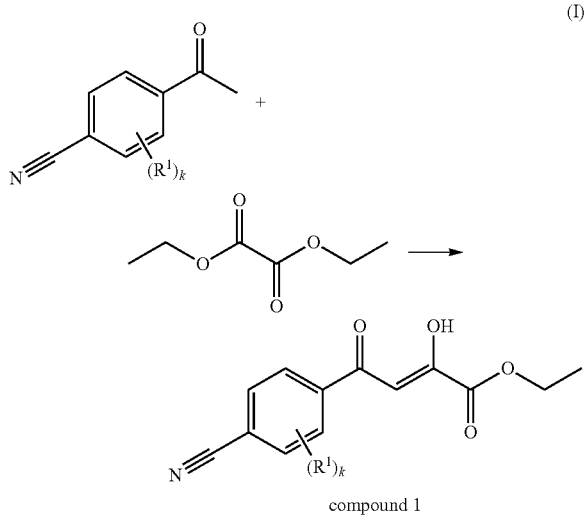

compound 1

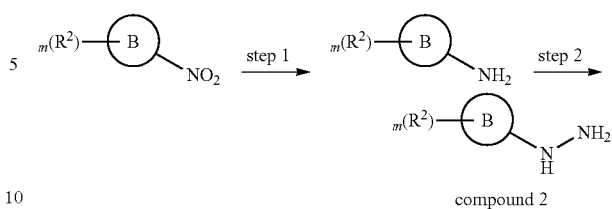

compound 2 wherein, in Reaction Scheme 1,

, $R^1$, $R^2$, k, and m may be the same as those defined in Formula 1.

The steps of the method according to an example embodiment will be described in detail.

(I)

1 to 2 equivalents of sodium ethoxide was dissolved in ethanol, and the mixture was cooled to a temperature in a range of 0° C. to 5° C. 2 to 3 equivalents of diethyl oxalate was added dropwise thereto for 30 minutes. 1 equivalent (standard equivalent) of 4-acetylbenzonitrile derivative dissolved in ethanol was added dropwise thereto at a temperature in a range of 0° C. to 5° C. The internal temperature thereof was raised to room temperature, and the mixture was stirred overnight. Once the reaction was complete, a solvent was removed therefrom under reduced pressure, and water was added thereto. The resulting mixture was titrated with an HCl aqueous solution to a pH in a range of 2 to 3, and an organic layer was extracted using ethyl acetate. The organic layer was washed with soft water, dried using anhydrous sodium sulfate, and concentrated under reduced pressure. Methyl tert-butyl ether was added to the residue, and the formed solid was filtered under reduced pressure to thereby obtain a desired compound.

(II—Step 1)

1 equivalent (standard equivalent) of nitro-substituted a compound substituted with a nitro group was dissolved in a mixture of tetrahydrofuran and ethanol at a mixing ratio of 1:1. a platinum catalyst or a palladium catalyst was added thereto, followed by stirring overnight at room temperature in a hydrogen atmosphere. Once the reaction was complete, celite filtration was performed under reduced pressure for concentration, thereby obtaining a desired compound.

(II—Step 2)

1 equivalent (standard equivalent) of the compound substituted with an amino group synthesized in II-Step 1 was dissolved in an HCl aqueous solution, and the solution was cooled to a temperature of 0° C. to 5° C. 1 to 2 equivalents of sodium nitrite aqueous solution was slowly added dropwise thereto, followed by stirring at a temperature of 0° C. to 5° C. for 1 to 3 hours, thereby forming a diazonium salt. 2 to 3 equivalents of tin (II) chloride dissolved in an HCl aqueous solution was slowly added dropwise thereto at a temperature of 0° C. to 5° C. The reaction temperature thereof was raised to room temperature, and the mixture was stirred. Once the reaction was complete, the formed solid was subjected to filtration, and the resulting product was washed with water and ether, followed by vacuum drying, thereby obtaining a desired compound.

Reaction Scheme 2

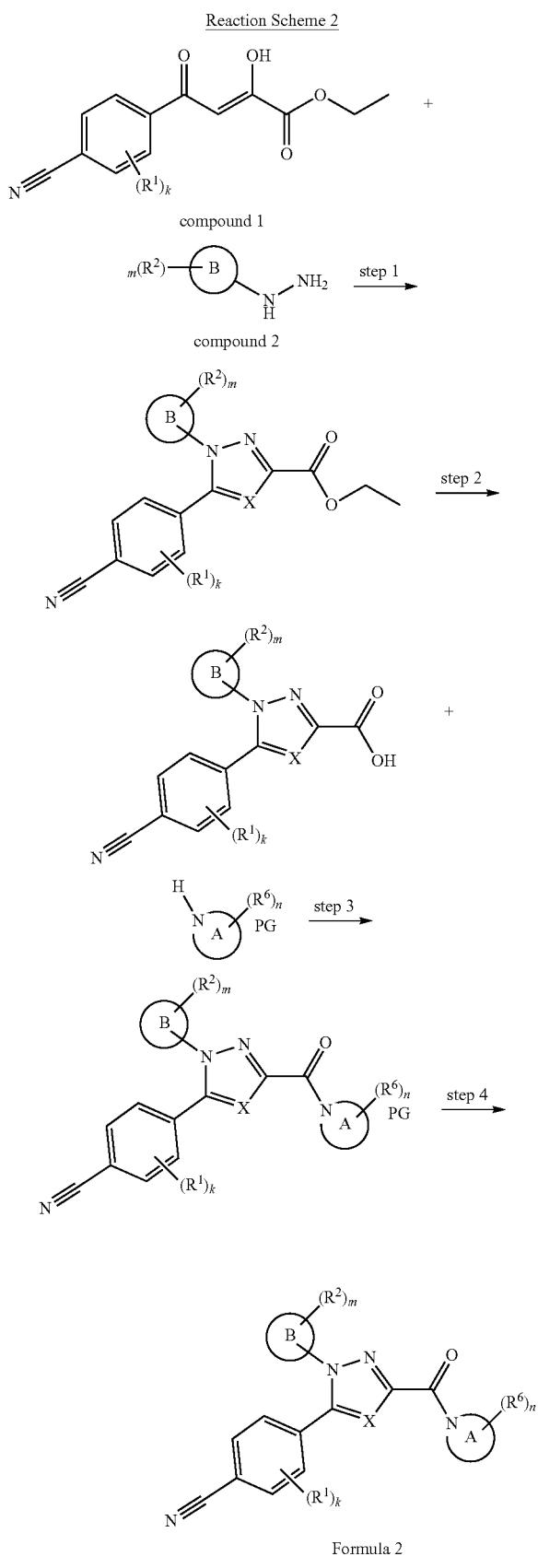

Formula 2 wherein, in Reaction Scheme 2, (A), (B),

X, $R^1$, $R^2$, $R^6$, k, m, and n are defined the same as those in Formula 1 or 2.

In Reaction Scheme 2, an amine-protecting group (PG) may be butoxycarbonyl (Boc), benzyloxycarbonyl (Cbz), 9-fluorenylmethoxycarbonyl (Fmoc), acetyl, benzoyl, or tosyl.

The steps of the method according to an example embodiment will be described in detail.

Step 1)

1 equivalent of Compound 1 and 1 equivalent (standard equivalent) of Compound 2 dissolved in ethanol. 1 equivalent of hydrochloric acid dissolved in dioxane was added thereto, and the temperature was raised to 50° C. to 70° C. Once the reaction was complete, the temperature was lowered to room temperature. The formed solid was subjected to filtration under reduced pressure and washed with cooled ethanol, thereby obtaining a desired compound.

Step 2)

1 equivalent (standard equivalent) of the compound synthesized in Step 1 was dissolved in a mixture of tetrahydrofuran and water mixed at a ratio of 1:1.3 to 5 equivalents of lithium hydroxide was added thereto, followed by stirring at room temperature. Once the reaction was complete, the mixture was titrated with an HCl aqueous solution to a pH in a range of 2 to 3, and ethanol was removed therefrom by distillation under reduced pressure. The formed solid was subjected to filtration under reduced pressure, thereby obtaining a desired compound.

Step 3)

1 equivalent (standard equivalent) of carbonic acid derivative synthesize in Step 2 was dissolved in dichloromethane, followed by addition of 2 to 3 equivalents of HATU, and 3 to 5 equivalents of DIPEA. The reaction mixture was stirred at room temperature, and 1 equivalent of amine substituted with A ring. The mixture was stirred at room temperature. Once the reaction was complete, dichloromethane and water were added to the reaction mixture. Then, an organic layer was separated therefrom. The organic layer was washed with soft water, dried using anhydrous sodium sulfate, and concentrated under reduced pressure. The residue was purified through a column chromatography, thereby obtaining a desired compound.

Step 4)

1 equivalent (standard equivalent) of PG-protected carbamate derivative synthesized in Step 3 was dissolved in dichloromethane. Trifluoroacetic acid was added thereto, followed by stirring at room temperature. Once the reaction was complete, water was added to the reaction mixture. Then, an organic layer was extracted using dichloromethane and separated therefrom. The organic layer was washed with soft water, dried using anhydrous sodium sulfate, and concentrated under reduced pressure. The residue was purified through a column chromatography, thereby obtaining a desired compound.

The compounds represented by Formulae 1, 3, and 4 were also obtained in a similar manner as the preparation of the compound represented by Formula 2. The synthetic method of the compounds represented by Formulae 1 to 4 is not limited to the method described herein. One of ordinary skill in the art of organic chemistry may prepare these compounds using various methods known in the art. Although the method has been described by way of specific examples herein, specific reaction conditions, such as an amount of a reaction solvent, a base, and a reactant to be used, are not limited to those described in the present specification, and may not be construed as limiting the scope of the present disclosure.

Hereinafter, the present disclosure will be described in more detail with reference to the following Preparation Examples and Examples. However, these Preparation Examples and Examples are intended to help understand the present disclosure, and the scope of the present disclosure is not limited thereto in any sense.

Preparation Example 1: Preparation of ethyl (Z)-4-(4-cyanophenyl)-2-hydroxy-4-oxo-2-butenoate

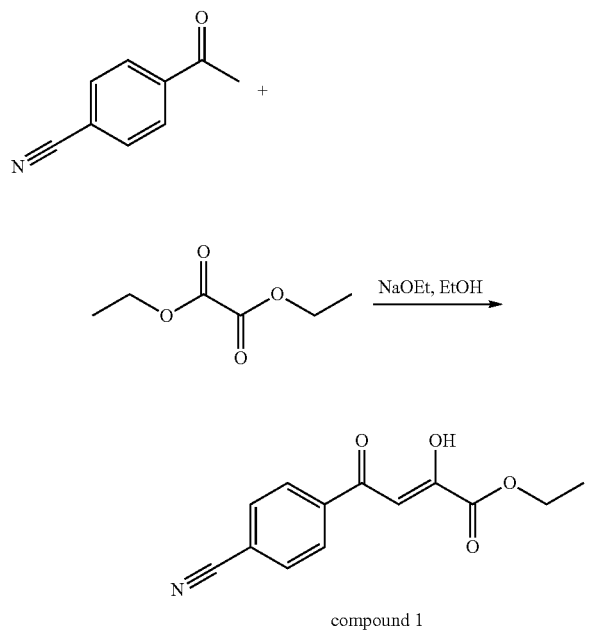

compound 1

9.4 grams (g, 137.7 millimole (mmol)) of sodium ethoxide was dissolved in 150 milliliters (mL) of ethanol, and then cooled to a temperature in a range of 0° C. to 5° C. 18.7 mL (137.7 mmol) of diethyl oxalate was added dropwise thereto for 30 minutes. 10 g (68.9 mmol) of 4-acetyl benzonitrile dissolved in 50 mL of ethanol was added dropwise thereto for 30 minutes at a temperature in a range of 0° C. to 5° C. The internal temperature thereof was raised to room temperature, and the mixture was stirred overnight. Once the reaction was complete, the solvent was removed therefrom under reduced pressure. Then, 100 mL of water was added thereto. The resulting mixture was titrated with 1N HCl aqueous solution to a pH in a range of 2 to 3, and an organic layer was extracted two times using ethyl acetate. The organic layer was washed with soft water, dried using anhydrous sodium sulfate, and concentrated under reduced pressure. 100 mL of methyl tert-butyl ether was added to the residue to form a solid. The solid was subjected to filtration under reduced pressure to obtain 9.0 g of a desired compound (yield: 53%).

$^1$H-NMR (300 MHz, CDCl$_3$): δ 8.07 (d, 2H), 7.81 (d, 2H), 7.07 (s, 1H), 4.38 (q, 2H), 1.42 (t, 3H)

Preparation Example 2: Preparation of (4-cyclopropyl phenyl)hydrazine hydrochloride

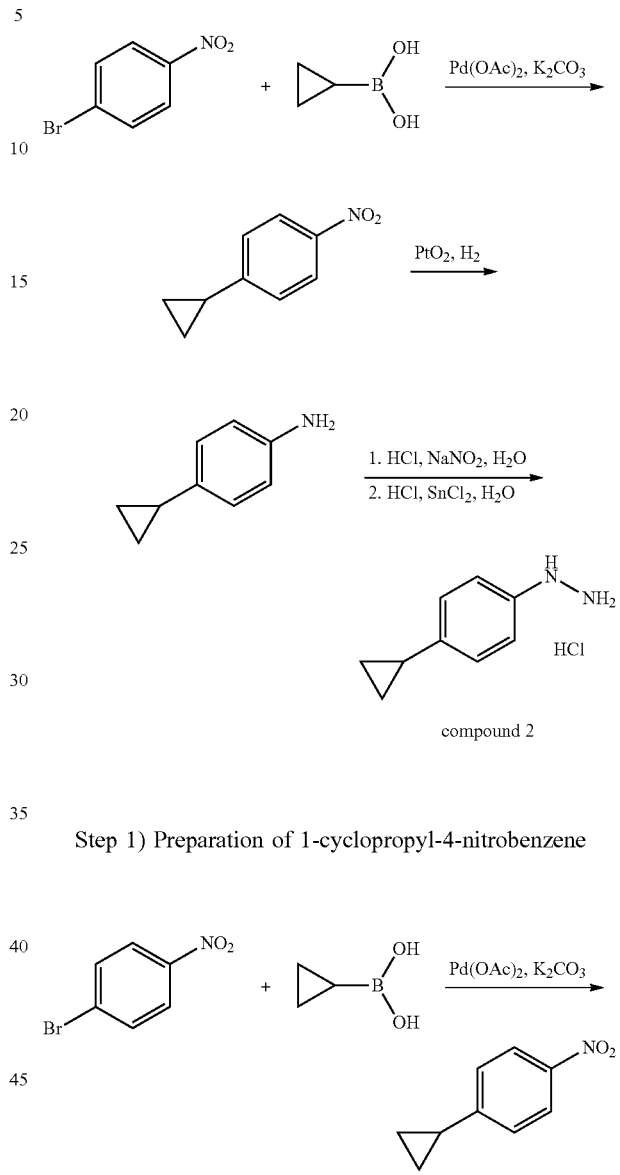

compound 2

Step 1) Preparation of 1-cyclopropyl-4-nitrobenzene 3.0 g (14.9 mmol) of 4-bromonitrobenzene and 1.7 g (19.4 mmol) of cyclopropyl boronic acid were dissolved in 40 mL of toluene and 4 mL of water. 133 mg (0.6 mmol) of palladium acetate (Pd(OAc)$_2$), 418 mg (1.49 mmol) of tricyclohexyl phosphine (P(C$_6$H$_{11}$)$_3$), and 6.8 g (49.2 mmol) of potassium carbonate (K$_2$CO$_3$) were added thereto. Purging with argon gas was performed for 30 minutes, and heating to a temperature in a range of 100° C. to 110° C., followed by reacting for three hours. Once the reaction was complete, celite filtration was performed under reduced pressure for concentration. The residue obtained through concentration was purified through column chromatography (ethylacetate:hexane=1:9 (v/v)), thereby obtaining 2.1 g of a desired compound (yield: 86%).

$^1$H-NMR (300 MHz, CDCl$_3$): δ 8.09 (d, 2H), 7.17 (d, 2H), 1.96 (m, 1H), 1.12 (m, 2H), 0.82 (m, 2H)

Step 2) Preparation of 4-cyclopropylaniline

Example 1: Preparation of (R)-4-(3-(3-aminopiperidine-1-carbonyl)-1-(4-cyclopropylphenyl)-1H-pyrazole-5-yl)benzonitrile

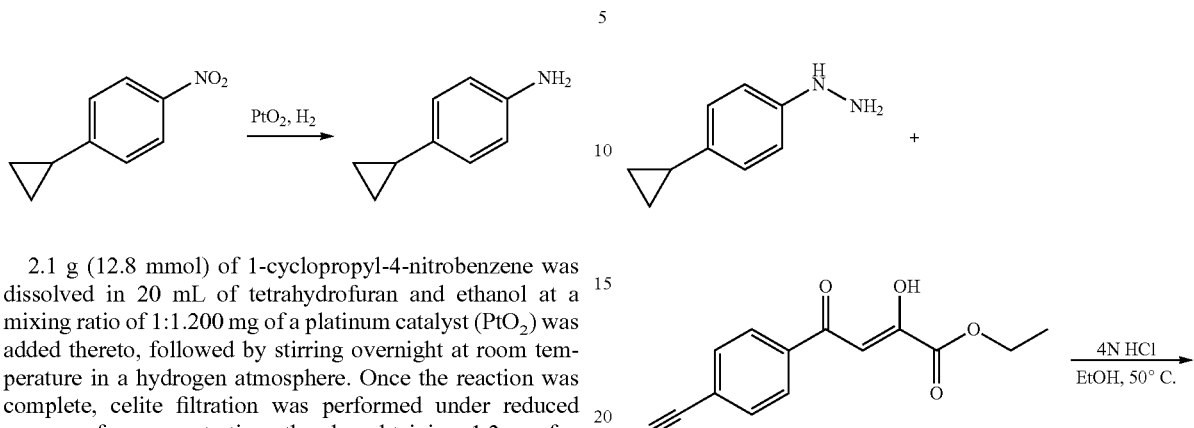

2.1 g (12.8 mmol) of 1-cyclopropyl-4-nitrobenzene was dissolved in 20 mL of tetrahydrofuran and ethanol at a mixing ratio of 1:1. 200 mg of a platinum catalyst ($PtO_2$) was added thereto, followed by stirring overnight at room temperature in a hydrogen atmosphere. Once the reaction was complete, celite filtration was performed under reduced pressure for concentration, thereby obtaining 1.3 g of a desired compound (yield: 76%).

$^1$H-NMR (300 MHz, $CDCl_3$): δ 6.97 (d, 2H), 6.57 (d, 2H), 3.52 (brs, 2H), 1.82 (m, 1H), 0.84 (m, 2H), 0.58 (m, 2H)

Step 3) Preparation of (4-cyclopropyl phenyl)hydrazine hydrochloride

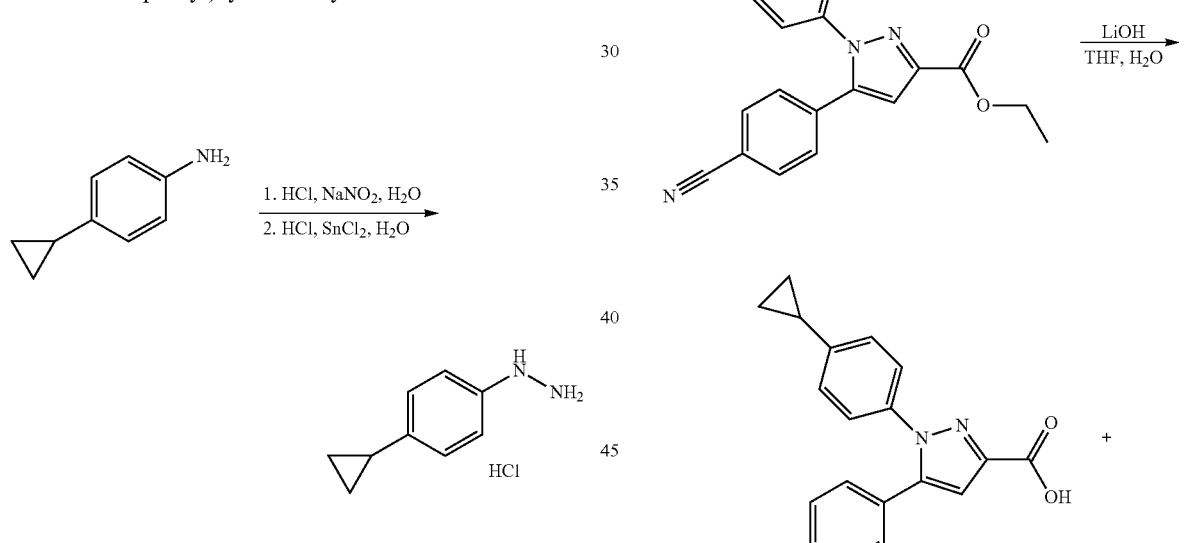

1.3 g (9.76 mmol) of 4-cyclopropylaniline was dissolved in a 6N HCl aqueous solution, followed by cooling to a temperature in a range of 0° C. to 5° C. A 6 mL aqueous solution of 673 mg (9.76 mmol) of sodium nitrite ($NaNO_2$) was slowly added dropwise thereto, followed by stirring at a temperature in a range of 0° C. to 5° C. for 1 hour, thereby forming a diazonium salt. 4.63 g (24.4 mmol) of tin (II) chloride ($SnCl_2$) dissolved in 20 mL of c-HCl was added dropwise thereto for 30 minutes at a temperature in a range of 0° C. to 5° C. The reaction temperature was raised to room temperature, followed by stirring for 5 hours. Once the reaction was complete, the formed solid was subjected to filtration, and the resulting product was washed with water and ether, followed by vacuum drying, thereby obtaining 1.1 g of a desired compound (yield: 76%).

$^1$H-NMR (300 MHz, DMSO-$d_6$): δ 10.21 (brs, 2H), 8.11 (brs, 1H), 6.99 (d, 2H), 6.89 (d, 2H), 1.82 (m, 1H), 0.86 (m, 2H), 0.58 (m, 2H)

-continued

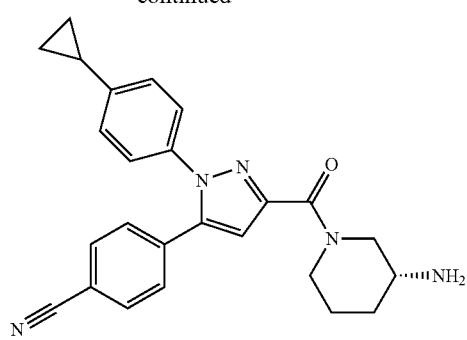

Step 1) Preparation of ethyl 5-(4-cyanophenyl)-1-(4-cyclopropylphenyl)-1H-pyrazole-3-carboxylate

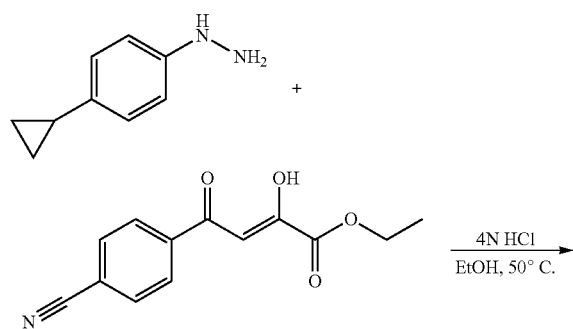

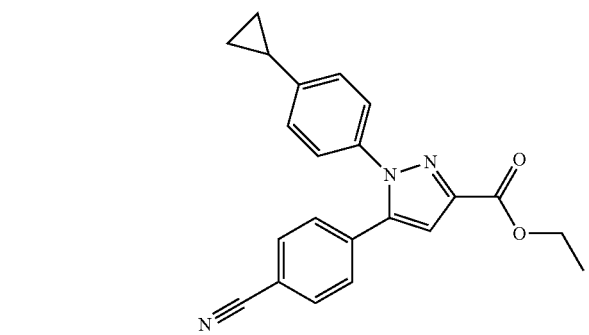

300 mg (1.22 mmol) of ethyl (Z)-4-(4-cyanophenyl)-2-hydroxy-4-oxobut-2-enolate and 181 mg (1.22 mmol) of (4-cyclopropylphenyl)hydrazine were dissolved in a solution in 10 mL of ethanol. 0.3 mL (1.22 mmol) of 4N HCl in dioxane was added thereto, and then the temperature was raised to 50° C. The mixture was stirred overnight at a temperature of 50° C. Once the reaction was complete, the temperature was lowered to room temperature. The formed solid was subjected to filtration under reduced pressure, and the resultant was washed with 10 mL of cooled ethanol, thereby obtaining 115 mg of a desired compound (yield: 26%).

$^1$H-NMR (300 MHz, CDCl$_3$): δ 7.58 (d, 2H), 7.34 (d, 2H) 7.12 (d, 2H), 7.04 (m, 3H), 4.43 (q, 2H), 1.93 (m, 1H), 1.45 (t, 3H), 0.97 (m, 2H), 0.70 (m, 2H)

Step 2) Preparation of 5-(4-cyanophenyl)-1-(4-cyclopropylphenyl)-1H-pyrazole-3-carboxylic Acid

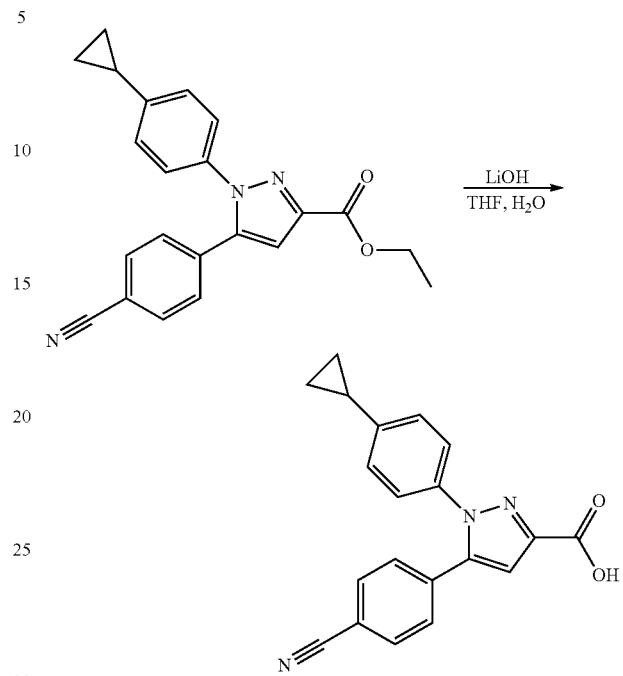

115 mg (0.32 mmol) of ethyl 5-(4-cyanophenyl)-1-(4-cyclopropylphenyl)-1H-pyrazole-3-carboxylate was dissolved in 10 mL of a mixture of tetrahydrofuran and water at a mixing ratio of 1:1.41 mg (0.97 mmol) of lithium hydroxide (LiOH.H$_2$O) was added thereto, followed by stirring at room temperature for 6 hours. Once the reaction was complete, the mixture was titrated with an 1N HCl aqueous solution to a pH of in a range of 2 to 3, and ethanol was removed therefrom by distillation under reduced pressure. The formed solid was subjected to filtration under reduced pressure, thereby obtaining 110 mg of a desired compound (yield: 97%).

$^1$H-NMR (300 MHz, CDCl$_3$): δ 7.63 (d, 2H), 7.33 (d, 2H) 7.16 (d, 2H), 7.04 (m, 3H), 1.90 (m, 1H), 1.02 (m, 2H), 0.71 (m, 2H)

Step 3) Preparation of tert-butyl (R)-(1-(5-(4-cyanophenyl)-1-(4-cyclopropylphenyl)-1H-pyrazole-3-carbonyl)piperidine-3-yl)carbamate

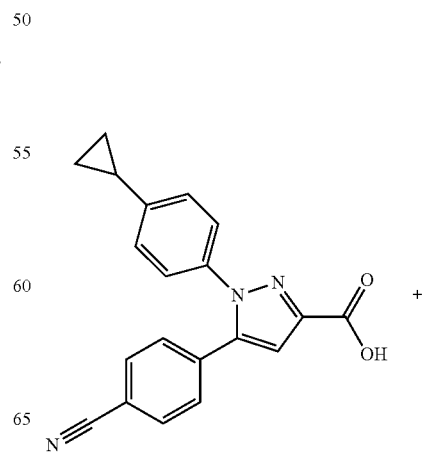

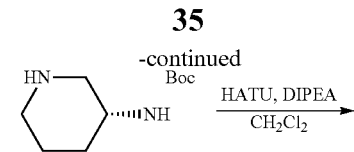

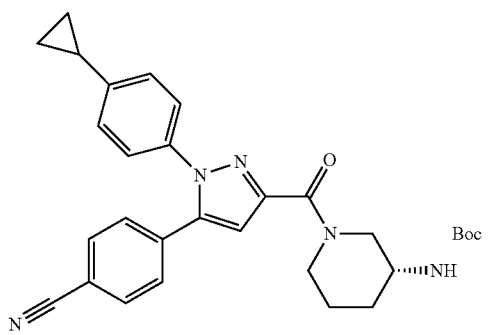

110 mg (0.35 mmol) of 5-(4-cyanophenyl)-1-(4-cyclopropylphenyl)-1H-pyrazole-3-carboxylic acid was dissolved in 2 mL of dichloromethane, followed by addition of 200 mg (0.53 mmol) of HATU and 0.18 mL (1.05 mmol) of DIPEA. The reaction mixture was stirred at room temperature for 30 minutes, followed by addition of 69 mg (0.35 mmol) of tert-butyl (R)-piperidine-3-ylcarbamate. The mixture was stirred at room temperature for 12 hours. Once the reaction was complete, dichloromethane and water were added to the reaction mixture, and then an organic layer was separated therefrom. The organic layer was washed with soft water, dried using anhydrous sodium sulfate, and concentrated under reduced pressure. The obtained residue was purified using column chromatography (dichloromethane:methanol=20:1 (v/v)), thereby obtaining 70 mg of a desired compound (yield: 89%).

$^1$H-NMR (300 MHz, DMSO-d$_6$): δ 7.61 (d, 2H), 7.33 (d, 2H), 7.16 (m, 2H), 7.00 (m, 3H), 5.45 (m, 1H), 4.99 (m, 2H), 3.69 (m, 2H), 1.84 (m, 4H), 1.59 (s, 9H), 1.50 (m, 2H), 0.94 (m, 2H), 0.72 (m, 2H)

Step 4) Preparation of (R)-4-(3-(3-aminopiperidine-1-carbonyl)-1-(4-cyclopropylphenyl)-1H-pyrazole-5-yl)benzonitrile

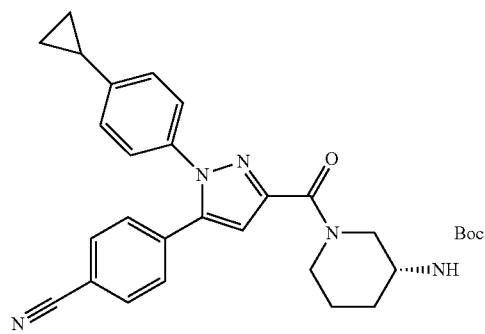 

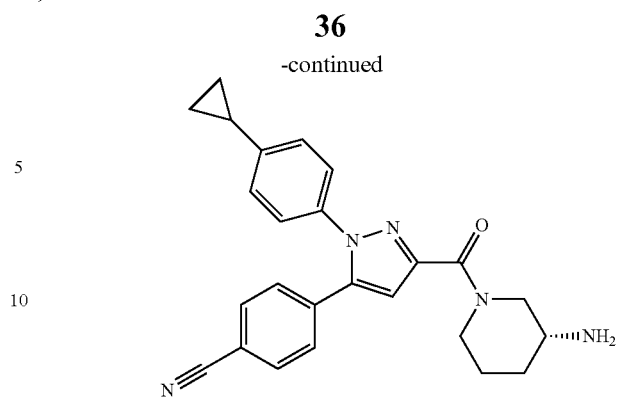

70 mg (0.25 mmol) of tert-butyl (R)-(1-(5-(4-cyanophenyl)-1-(4-cyclopropylphenyl)-1H-pyrazole-3-carbonyl)piperidine-3-yl)carbamate was dissolved in 6 mL of dichloromethane. 1 mL of trifluoroacetic acid (TFA) was added thereto, followed by stirring at room temperature for 3 hours. Once the reaction was complete, water was added to the reaction mixture. Then, an organic layer was extracted using dichloromethane and separated therefrom. The organic layer was washed with soft water, dried using anhydrous sodium sulfate, and concentrated under reduced pressure. The obtained residue was purified using column chromatography (dichloromethane:methanol=10:1 (v/v)), thereby obtaining 50 mg of a desired compound (yield: 37%).

$^1$H-NMR (300 MHz, DMSO-d$_6$): 7.82 (d, 2H), 7.41 (d, 2H) 7.13 (m, 4H), 7.04 (m, 1H), 4.27 (m, 2H), 3.13 (m, 3H), 2.74 (m, 2H), 1.94 (m, 1H), 1.89 (m, 2H), 1.70 (m, 2H), 0.99 (m, 2H), 0.68 (m, 2H)

MS (ESI$^+$): [M+H]$^+$ m/z 412.2,

Example 2: Preparation of (R)-4-(1-(4-cyclopropylphenyl)-3-(3-methylaminopiperidine-1-carbonyl)-1H-pyrazole-5-yl)benzonitrile A desired compound was obtained in substantially the same manner as in Example 1, except that tert-butyl (R)-methyl(piperidine-3-yl)carbamate was used instead of tert-butyl (R)-piperidine-3-ylcarbamate in Step 3) of Example 1.

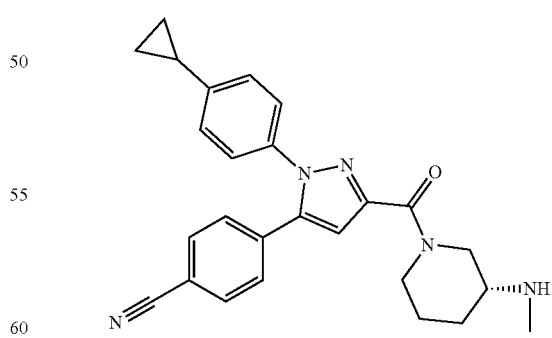

$^1$H-NMR (300 MHz, CDCl$_3$): 7.62 (d, 2H), 7.33 (d, 2H), 7.10 (m, 4H), 6.97 (d, 1H), 4.48 (m, 2H), 3.21 (m, 2H), 2.67 (m, 1H), 2.47 (d, 3H), 2.01 (m, 1H), 1.92 (m, 2H), 1.61 (m, 2H), 1.02 (m 2H), 0.73 (m, 2H).

MS (ESI$^+$): [M+H]$^+$ m/z 372.2

Example 3: Preparation of (R)-4-(3-(3-aminopiperidine-1-carbonyl)-1-(4-cyclopropyl-2-fluorophenyl)-1H-pyrazole-5-yl)benzonitrile A desired compound was obtained in substantially the same manner as in Example 1, except that (4-cyclopropyl-2-fluorophenyl)hydrazine hydrochloride was used instead of (4-cyclopropylphenyl)hydrazine hydrochloride in Step 1) of Example 1.

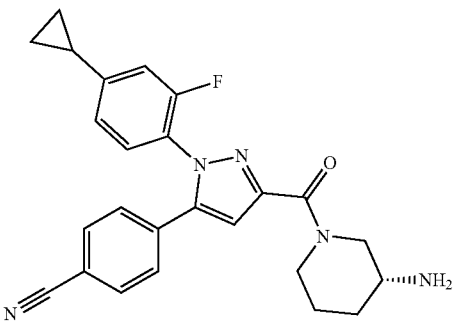 [SMILES: N#Cc1ccc(-c2cc(C(=O)N3CCC[C@@H](N)C3)nn2-c2ccc(C3CC3)cc2F)cc1]

$^1$H-NMR (300 MHz, CDCl$_3$): δ 7.59 (d, 2H), 7.32 (m, 3H), 6.96 (m, 2H), 6.77 (d, 1H), 4.43 (m, 2H), 3.21 (m, 3H), 1.90 (m, 3H), 1.42 (m, 2H), 1.07 (m, 2H), 0.75 (m, 2H)
MS (ESI$^+$): [M+H]$^+$ m/z 430.2

Example 4: Preparation of (R)-4-(1-(4-cyclopropyl-2-fluorophenyl)-3-(3-(methylamino)piperidine-1-carbonyl)-1H-pyrazole-5-yl)benzonitrile A desired compound was obtained in substantially the same manner as in Example 1, except that (4-cyclopropyl-2-fluorophenyl)hydrazine hydrochloride was used instead of (4-cyclopropylphenyl)hydrazine hydrochloride in Step 1) of Example 1, and tert-butyl (R)-methyl(piperidine-3-yl)carbamate was used instead of tert-butyl (R)-piperidine-3-ylcarbamate in Step 3) of Example 1.

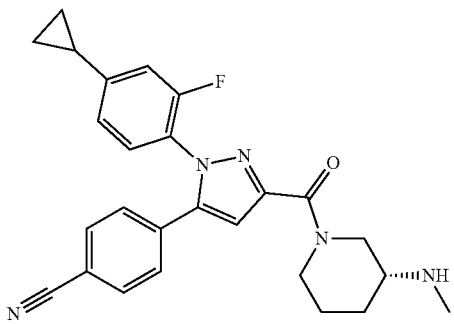 [SMILES: CN[C@@H]1CCCN(C(=O)c2cc(-c3ccc(C#N)cc3)n(-c3ccc(C4CC4)cc3F)n2)C1]

$^1$H-NMR (300 MHz, CDCl$_3$): δ 7.64 (d, 2H), 7.37 (m, 3H), 6.98 (m, 2H), 6.77 (d, 1H), 4.52 (m, 2H), 3.24 (m, 2H), 2.72 (m, 1H), 2.48 (d, 3H), 1.94 (m, 2H), 0.75 (m, 2H)
MS (ESI$^+$): [M+H]$^+$ m/z 444.2

Example 5: Preparation of (R)-4-(3-(3-aminopiperidine-1-carbonyl)-1-(4-cyclopropyl-2-fluorophenyl)-1H-pyrazole-5-yl)-2-fluorobenzonitrile A desired compound was obtained in substantially the same manner as in Example 1, except that ethyl (Z)-4-(4-cyano-3-fluorophenyl)-2-hydroxy-4-oxo-2-butenoate was used instead of ethyl (Z)-4-(4-cyanophenyl)-2-hydroxy-4-oxo-2-butenoate, and (4-cyclopropyl-2-fluorophenyl)hydrazine hydrochloride was used instead of (4-cyclopropylphenyl)hydrazine hydrochloride in Step 1) of Example 1.

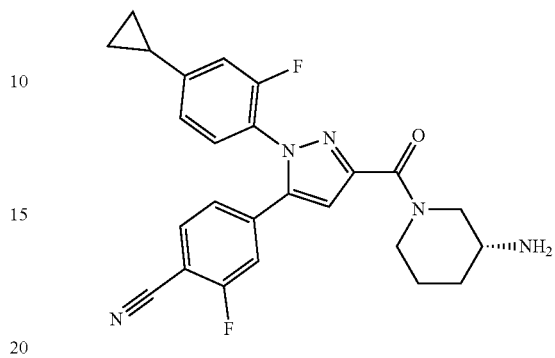

$^1$H-NMR (300 MHz, CDCl$_3$): δ 7.54 (t, 1H), 7.31 (m, 1H), 7.10 (m, 2H), 7.08 (m, 2H), 6.78 (d, 1H), 4.17 (m, 2H), 3.72 (m, 1H), 3.56 (m, 1H), 3.31 (m, 1H), 1.84 (m, 4H), 1.11 (m, 1H), 0.75 (m, 2H)
MS (ESI$^+$): [M+H]$^+$ m/z 448.2

Example 6: Preparation of (R)-4-(1-(4-cyclopropyl-2-fluorophenyl)-3-(3-(methylamino)piperidine-1-carbonyl)-1H-pyrazole-5-yl)-2-fluorobenzonitrile A desired compound was obtained in substantially the same manner as in Example 1, except that ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate, and (4-cyclopropyl-2-fluorophenyl)hydrazine hydrochloride was used instead of (4-cyclopropylphenyl)hydrazine hydrochloride in Step 1) of Example 1, and tert-butyl (R)-methyl(piperidine-3-yl)carbamate was used instead of tert-butyl (R)-piperidine-3-ylcarbamate in Step 3) of Example 1.

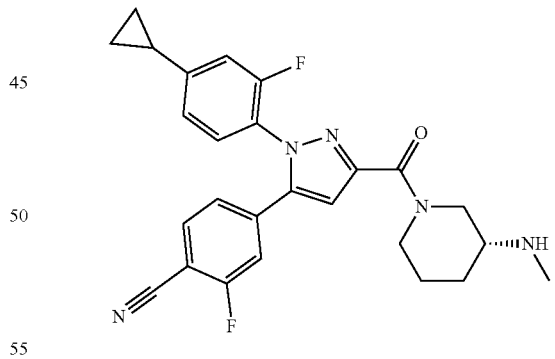

$^1$H-NMR (300 MHz, CDCl$_3$): δ 7.56 (m, 1H), 7.32 (m, 1H), 7.07 (m, 4H), 7.79 (d, 1H), 4.52 (m, 2H), 3.22 (m, 2H), 2.68 (m, 1H), 2.47 (d, 3H), 1.93 (m, 2H), 1.49 (m, 2H), 1.09 (m, 2H), 0.75 (m, 2H)
MS (ESI$^+$): [M+H]$^+$ m/z 462.2

Example 7: Preparation of (R)-4-(3-(3-aminoazepane-1-carbonyl)-1-(4-(cyclopropylphenyl)-1H-pyrazole-5-yl)benzonitrile A desired compound was obtained in substantially the same manner as in Example 1, except that tert-butyl (R)- azepane-3-ylcarbamate was used instead of tert-butyl (R)-piperidine-3-ylcarbamate in Step 3) of Example 1.

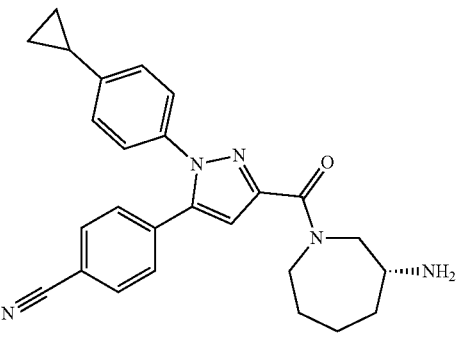 [SMILES: N#Cc1ccc(-c2cc(C(=O)N3CCCC[C@@H](N)C3)nn2-c2ccc(C3CC3)cc2)cc1]

¹H-NMR (300 MHz, CDCl₃): δ 7.60 (d, 2H), 7.33 (d, 2H), 7.09 (m, 5H), 3.46 (dd, 1H), 3.31 (dd, 1H), 2.13 (m, 5H), 1.92 (m, 4H), 1.08 (q, 2H).
MS (ESI⁺): [M+H]⁺ m/z 426.2

Example 8: Preparation of (R)-4-(3-(3-amino-azepane-1-carbonyl)-1-(4-cyclopropyl-2-fluorophenyl)-1H-pyrazole-5-yl)-2-fluorobenzonitrile A desired compound was obtained in substantially the same manner as in Example 1, except that ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate, and (4-cyclopropyl-2-fluorophenyl)hydrazine hydrochloride was used instead of 4-cyclopropylphenylhydrazine hydrochloride in Step 1) of Example 1, and tert-butyl (R)-azepane-3-yl carbamate was used instead of tert-butyl (R)-piperidine-3-ylcarbamate in Step 3) of Example 1.

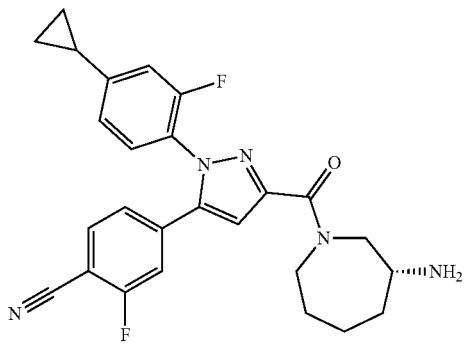 [SMILES: N#Cc1ccc(-c2cc(C(=O)N3CCCC[C@@H](N)C3)nn2-c2ccc(C3CC3)cc2F)cc1F]

¹H-NMR (300 MHz, CDCl₃): δ 7.52 (t, 1H), 7.33 (t, 1H), 7.09 (m, 3H), 6.94 (d, 1H), 6.79 (dd, 1H), 3.46 (dd, 1H), 3.31 (dd, 1H), 2.13 (m, 5H), 1.92 (m, 4H), 1.08 (q, 2H).
MS (ESI⁺): [M+H]⁺ m/z 462.2

Example 9: Preparation of 4-(3-((3R,5R)-3-amino-5-methylpiperidine-1-carbonyl)-1-(4-cyclopropyl-2-fluorophenyl)-1H-pyrazole-5-yl)-2-fluorobenzonitrile A desired compound was obtained in substantially the same manner as in Example 1, except that (4-cyclopropyl-2-fluorophenyl)hydrazine hydrochloride was used instead of (4-cyclopropylphenyl)hydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1, and tert-butyl ((3R,5R)-5-methylpiperidine-3-yl)carbamate was used instead of tert-butyl (R)-piperidine-3-ylcarbamate in Step 3) of Example 1.

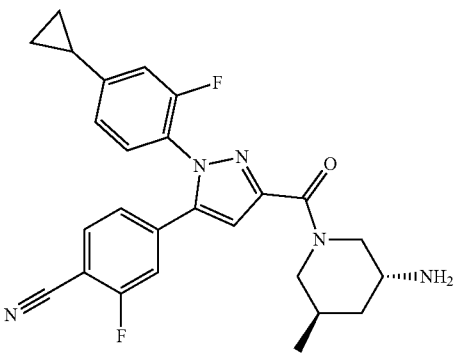 [SMILES: C[C@@H]1C[C@@H](N)CN(C(=O)c2cc(-c3ccc(C#N)c(F)c3)n(-c3ccc(C4CC4)cc3F)n2)C1]

¹H-NMR (300 MHz, CDCl₃): δ 7.56 (t, 1H), 7.28 (m, 1H), 7.08 (m, 3H), 6.97 (d, 1H), 6.80 (d, 1H), 4.32 (m, 2H), 3.49 (m, 1H), 3.26 (m, 2H), 1.94 (m, 1H), 1.74 (m, 1H), 1.32 (m, 2H), 1.09 (m, 2H), 0.94 (dd, 3H), 0.76 (m, 2H)
MS (ESI⁺): [M+H]⁺ m/z 462.2

Example 10: Preparation of (R)-4-(3-(3-aminopiperidine-1-carbonyl)-1-(4-cyclopropyl-2,6-difluorophenyl)-1H-pyrazole-5-yl)-2-fluorobenzonitrile A desired compound was obtained in substantially the same manner as in Example 1, except that (4-cyclopropyl-2,6-difluorophenyl)hydrazine hydrochloride was used instead of (4-cyclopropylphenyl)hydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1.

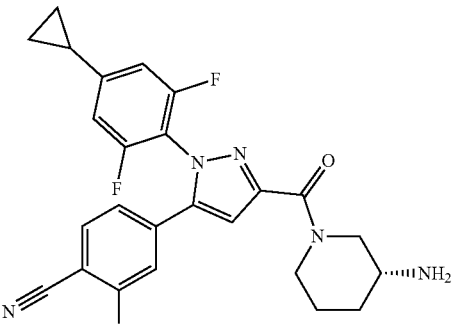

¹H-NMR (300 MHz, CDCl₃): δ 7.58 (t, 1H), 7.17 (t, 2H), 7.10 (s, 1H), 6.71 (d, 2H), 4.35 (m, 2H), 3.10 (m, 3H), 1.70 (m, 5H), 1.13 (m, 2H), 0.77 (m, 2H)
MS (ESI⁺): [M+H]⁺ m/z 466.2

Example 11: Preparation of (R)-4-(3-(3-amino-azepane-1-carbonyl)-1-(4-cyclopropyl-2,6-difluorophenyl)-1H-pyrazole-5-yl)-2-fluorobenzonitrile A desired compound was obtained in substantially the same manner as in Example 1, except that (4-cyclopropyl- 2,6-difluorophenyl)hydrazine hydrochloride was used instead of (4-cyclopropylphenyl)hydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1, and tert-butyl (R)-azepane-3-yl carbamate was used instead of tert-butyl (R)-piperidine-3-ylcarbamate in Step 3) of Example 1.

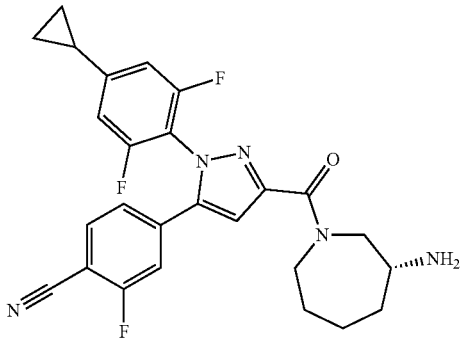 [SMILES: N#Cc1ccc(-c2cc(C(=O)N3CCCC[C@@H](N)C3)nn2-c2c(F)cc(C3CC3)cc2F)cc1F]

$^1$H-NMR (300 MHz, CDCl$_3$): δ 7.56 (t, 1H), 7.12 (m, 3H), 6.70 (d, 2H), 4.08 (m, 2H), 3.31 (m, 3H), 1.88 (m, 5H), 1.43 (m, 2H), 1.13 (m, 2H), 0.76 (m, 2H)
MS (ESI$^+$): [M+H]$^+$ m/z 480.

Example 12: Preparation of (R)-4-(3-(3-aminopiperidine-1-carbonyl)-1-(2-chloro-4-cyclopropylphenyl)-1H-pyrazole-5-yl)-2-fluorobenzonitrile A desired compound was obtained in substantially the same manner as in Example 1, except that (2-chloro-4-cyclopropylphenyl)hydrazine hydrochloride was used instead of (4-cyclopropylphenyl)hydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1.

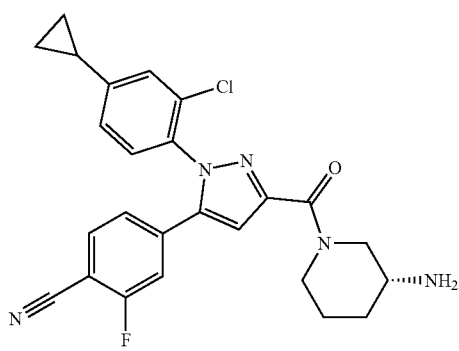 [SMILES: N#Cc1ccc(-c2cc(C(=O)N3CCC[C@@H](N)C3)nn2-c2ccc(C3CC3)cc2Cl)cc1F]

$^1$H-NMR (300 MHz, CDCl$_3$): δ 7.54 (t, 1H), 7.24 (m, 1H), 7.17 (s, 1H), 7.05 (m, 4H), 4.36 (m, 2H), 3.36 (m, 4H), 1.37 (m, 4H), 1.10 (m, 2H), 0.78 (m, 2H)
MS (ESI$^+$): [M+H]$^+$ m/z 464.2

Example 13: Preparation of (R)-4-(3-(3-aminoazepane-1-carbonyl)-1-(2-chloro-4-cyclopropylphenyl)-1H-pyrazole-5-yl)-2-fluorobenzonitrile A desired compound was obtained in substantially the same manner as in Example 1, except that (2-chloro-4-cyclopropylphenyl)hydrazine hydrochloride was used instead of (4-cyclopropylphenyl)hydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1, and tert-butyl (R)-azepane-3-ylcarbamate was used instead of tert-butyl (R)-piperidine-3-ylcarbamate in Step 3) of Example 1.

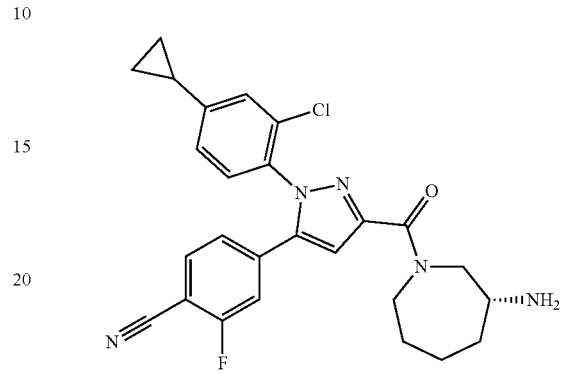

$^1$H-NMR (300 MHz, CDCl$_3$): δ 7.56 (t, 1H), 7.17 (m, 2H), 7.06 (m, 4H), 4.04 (m, 2H), 3.89 (m, 1H), 3.31 (m, 3H), 1.85 (m, 3H), 1.37 (m, 4H), 1.10 (m, 2H), 0.77 (m, 2H)
MS (ESI$^+$): [M+H]$^+$ m/z 478.2

Example 14: Preparation of (R)-4-(3-(3-aminopiperidine-1-carbonyl)-1-phenyl-1H-pyrazole-5-yl)benzonitrile A desired compound was obtained in substantially the same manner as in Example 1, except that phenylhydrazine hydrochloride was used instead of (4-cyclopropylphenyl)hydrazine hydrochloride in Step 1) of Example 1.

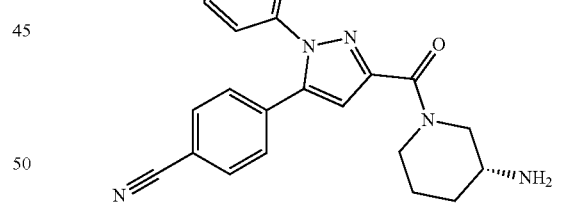

$^1$H-NMR (300 MHz, CDCl$_3$): 7.60 (d, 2H), 7.39 (t, 3H), 7.33 (d, 2H), 6.97 (s, 1H), 4.51 (m, 2H), 3.21 (m, 2H), 2.98 (m, 1H), 1.84 (m, 2H), 1.67 (m, 2H).
MS (ESI$^+$): [M+H]$^+$ m/z 372.2

Example 15: Preparation of (R)-4-(3-(3-aminopiperidine-1-carbonyl)-1-(pyridine-2-yl)-1H-pyrazole-5-yl)benzonitrile A desired compound was obtained in substantially the same manner as in Example 1, except that 2-hydrazinopyridine hydrochloride was used instead of (4-cyclopropylphenyl)hydrazine hydrochloride in Step 1) of Example 1.

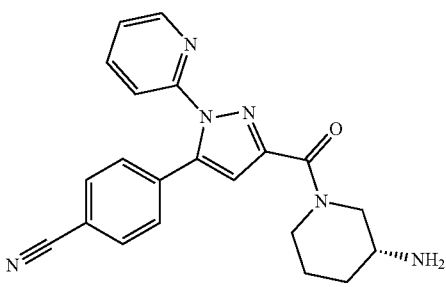 [SMILES: N#Cc1ccc(-c2cc(C(=O)N3CCC[C@@H](N)C3)nn2-c2ccccn2)cc1]

¹H-NMR (300 MHz, CDCl₃): 8.30 (m, 1H), 7.98 (t, 1H), 7.63 (m, 3H), 7.28 (m, 3H), 6.92 (m, 1H), 4.56 (m, 2H), 3.34 (m, 2H), 2.98 (m, 2H), 1.89 (m, 3H)

MS (ESI⁺): [M+H]⁺ m/z 373.2

Example 16: Preparation of (R)-4-(3-(3-aminopiperidine-1-carbonyl)-1-(4-fluorophenyl)-1H-pyrazole-5-yl)benzonitrile A desired compound was obtained in substantially the same manner as in Example 1, except that (4-fluorophenyl)hydrazine hydrochloride was used instead of (4-cyclopropylphenyl)hydrazine hydrochloride in Step 1) of Example 1.

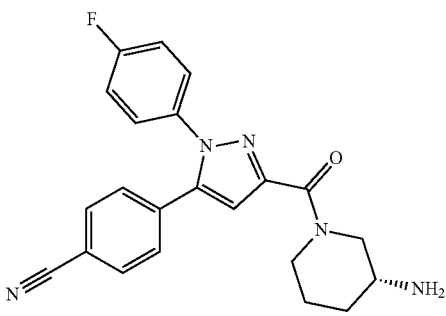 [SMILES: N#Cc1ccc(-c2cc(C(=O)N3CCC[C@@H](N)C3)nn2-c2ccc(F)cc2)cc1]

¹H-NMR (300 MHz, CDCl₃): δ 7.63 (m, 2H), 7.34 (m, 4H), 7.09 (m, 2H), 6.97 (m, 1H), 4.51 (m, 2H), 3.21 (m, 2H), 2.98 (m, 1H), 1.84 (m, 2H), 1.67 (m, 2H).

MS (ESI⁺): [M+H]⁺ m/z 390.2

Example 17: Preparation of (R)-4-(3-(3-aminopiperidine-1-carbonyl)-1-(4-chlorophenyl)-1H-pyrazole-5-yl)benzonitrile A desired compound was obtained in substantially the same manner as in Example 1, except that (4-chlorophenyl)hydrazine hydrochloride was used instead of (4-cyclopropylphenyl)hydrazine hydrochloride in Step 1) of Example 1.

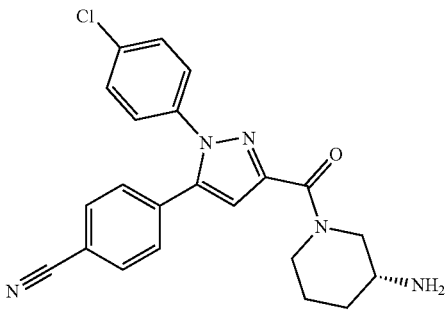 [SMILES: N#Cc1ccc(-c2cc(C(=O)N3CCC[C@@H](N)C3)nn2-c2ccc(Cl)cc2)cc1]

¹H-NMR (300 MHz, CDCl₃): δ 7.63 (d, 2H), 7.38 (t, 4H), 7.21 (d, 2H), 6.97 (d, 1H), 4.51 (m, 2H), 3.21 (m, 2H), 2.98 (m, 1H), 1.84 (m, 2H), 1.67 (m, 2H).

MS (ESI⁺): [M+H]⁺ m/z 406.1

Example 18: Preparation of (R)-4-(1-(4-chlorophenyl)-3-(3-(methylamino)piperidine-1-carbonyl)-1H-pyrazole-5-yl)benzonitrile A desired compound was obtained in substantially the same manner as in Example 1, except that (4-chlorophenyl)hydrazine hydrochloride was used instead of 4-cyclopropylphenylhydrazine hydrochloride in Step 1) of Example 1, and tert-butyl (R)-methyl(piperidine-3-yl)carbamate was used instead of tert-butyl (R)-piperidine-3-ylcarbamate in Step 3) of Example 1.

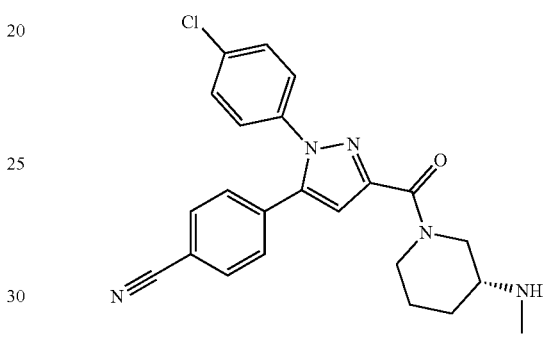

¹H-NMR (300 MHz, CDCl₃): 7.64 (d, 2H), 7.32 (m, 4H), 7.19 (d, 2H), 6.97 (d, 1H), 4.48 (m, 2H), 3.21 (m, 2H), 2.67 (m, 1H), 2.47 (d, 3H), 1.92 (m, 2H), 1.61 (m, 2H).

MS (ESI⁺): [M+H]⁺ m/z 372.2

Example 19: Preparation of (R)-4-(3-(3-aminopiperidine-1-carbonyl)-1-(3-chlorophenyl)-1H-pyrazole-5-yl)benzonitrile A desired compound was obtained in substantially the same manner as in Example 1, except that (3-chlorophenyl)hydrazine hydrochloride was used instead of (4-cyclopropylphenyl)hydrazine hydrochloride in Step 1) of Example 1.

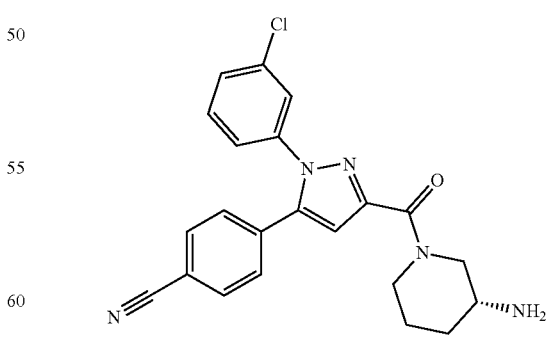

¹H-NMR (300 MHz, CDCl₃): δ 7.64 (d, 2H), 7.34 (m, 4H), 7.29 (s, 1H), 7.03 (m, 1H), 6.97 (m, 1H), 4.51 (m, 2H), 3.21 (m, 2H), 2.98 (m, 1H), 1.84 (m, 2H), 1.67 (m, 2H).

MS (ESI⁺): [M+H]⁺ m/z 406.0

Example 20: Preparation of (R)-4-(3-(3-aminopiperidine-1-carbonyl)-1-(4-bromophenyl)-1H-pyrazole-5-yl)benzonitrile A desired compound was obtained in substantially the same manner as in Example 1, except that (4-bromophenyl)hydrazine hydrochloride was used instead of (4-cyclopropylphenyl)hydrazine hydrochloride in Step 1) of Example 1.

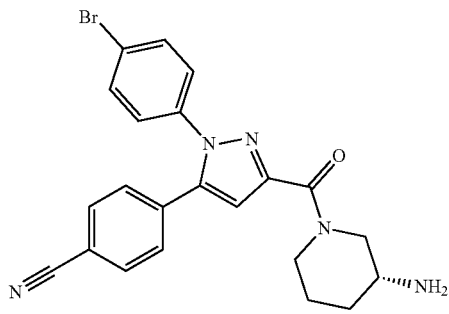 [SMILES: N#Cc1ccc(-c2cc(C(=O)N3CCC[C@@H](N)C3)nn2-c2ccc(Br)cc2)cc1]

¹H-NMR (300 MHz, DMSO-d₆): δ 8.27 (t, 1H), 7.83 (d, 2H), 7.44 (d, 2H), 7.28 (m, 4H), 7.13 (s, 1H), 3.50 (m, 12H).
MS (ESI⁺): [M+H]⁺ m/z 450.1

Example 21: Preparation of (R)-4-(1-(4-bromophenyl)-3-(3-(methylamino)piperidine-1-carbonyl)-1H-pyrazole-5-yl)benzonitrile A desired compound was obtained in substantially the same manner as in Example 1, except that (4-bromophenyl)hydrazine hydrochloride was used instead of (4-cyclopropylphenyl)hydrazine hydrochloride in Step 1) of Example 1, and tert-butyl (R)-methyl(piperidine-3-yl)carbamate was used instead of tert-butyl (R)-piperidine-3-ylcarbamate in Step 3) of Example 1.

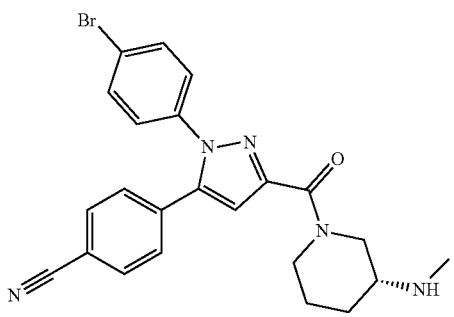 [SMILES: CN[C@@H]1CCCN(C(=O)c2cc(-c3ccc(C#N)cc3)n(-c3ccc(Br)cc3)n2)C1]

¹H-NMR (300 MHz, DMSO-d₆): δ 7.85 (d, 2H), 7.38 (d, 2H), 7.21 (d, 2H), 7.14 (d, 2H), 6.72 (m, 1H), 2.32 (s, 3H), 1.84 (m, 2H), 1.42 (m, 10H).
MS (ESI⁺): [M+H]⁺ m/z 464.1

Example 22: Preparation of (S)-4-(3-(3-aminopyrrolidine-1-carbonyl)-1-(p-tolyl)-1H-pyrazole-5-yl)benzonitrile A desired compound was obtained in substantially the same manner as in Example 1, except that p-tolylhydrazine hydrochloride was used instead of (4-cyclopropylphenyl)hydrazine hydrochloride in Step 1) of Example 1, and tert-butyl (S)-pyrrolidine-3-ylcarbamate was used instead of tert-butyl (R)-piperidine-3-ylcarbamate in Step 3) of Example 1.

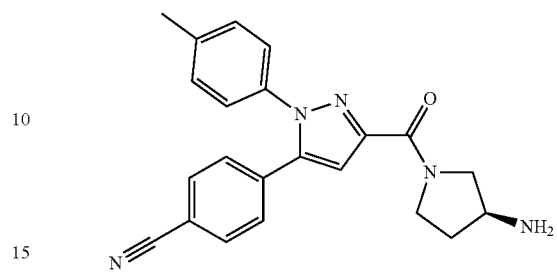

1H-NMR (300 MHz, DMSO-d₆): δ 7.83 (d, 2H), 7.44 (d, 2H), 7.23 (q, 4H), 7.12 (s, 1H), 3.94 (m, 2H), 3.48 (m, 4H), 2.34 (s, 3H), 1.94 (m, 2H), 1.57 (m, 1H)
MS (ESI⁺): [M+H]⁺ m/z 372.2

Example 23: Preparation of (S)-4-(3-(3-(methylamino)pyrrolidine-1-carbonyl)-1-(p-tolyl)-1H-pyrazole-5-yl)benzonitrile

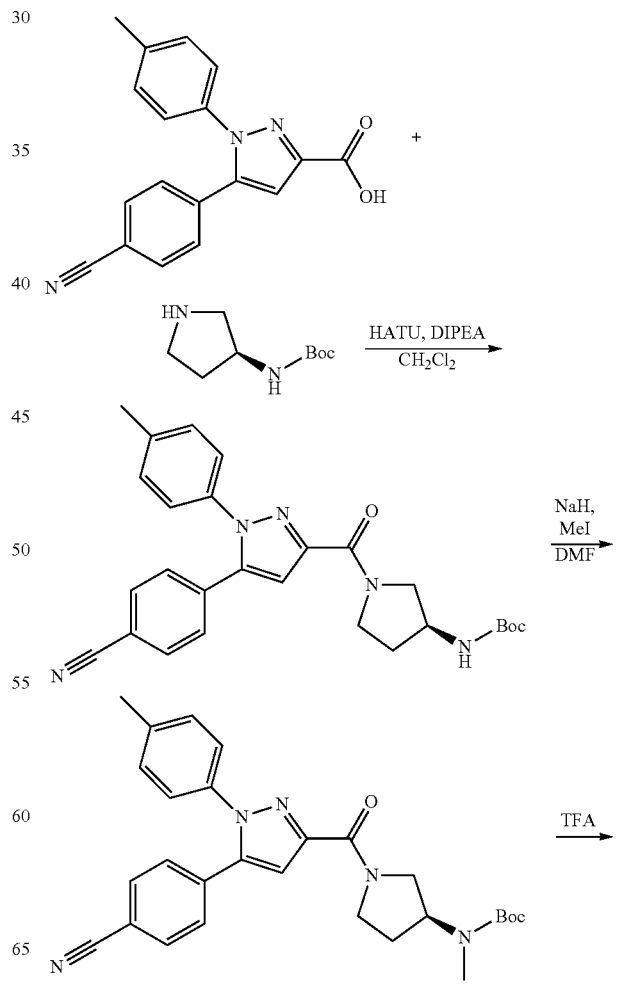

47

-continued

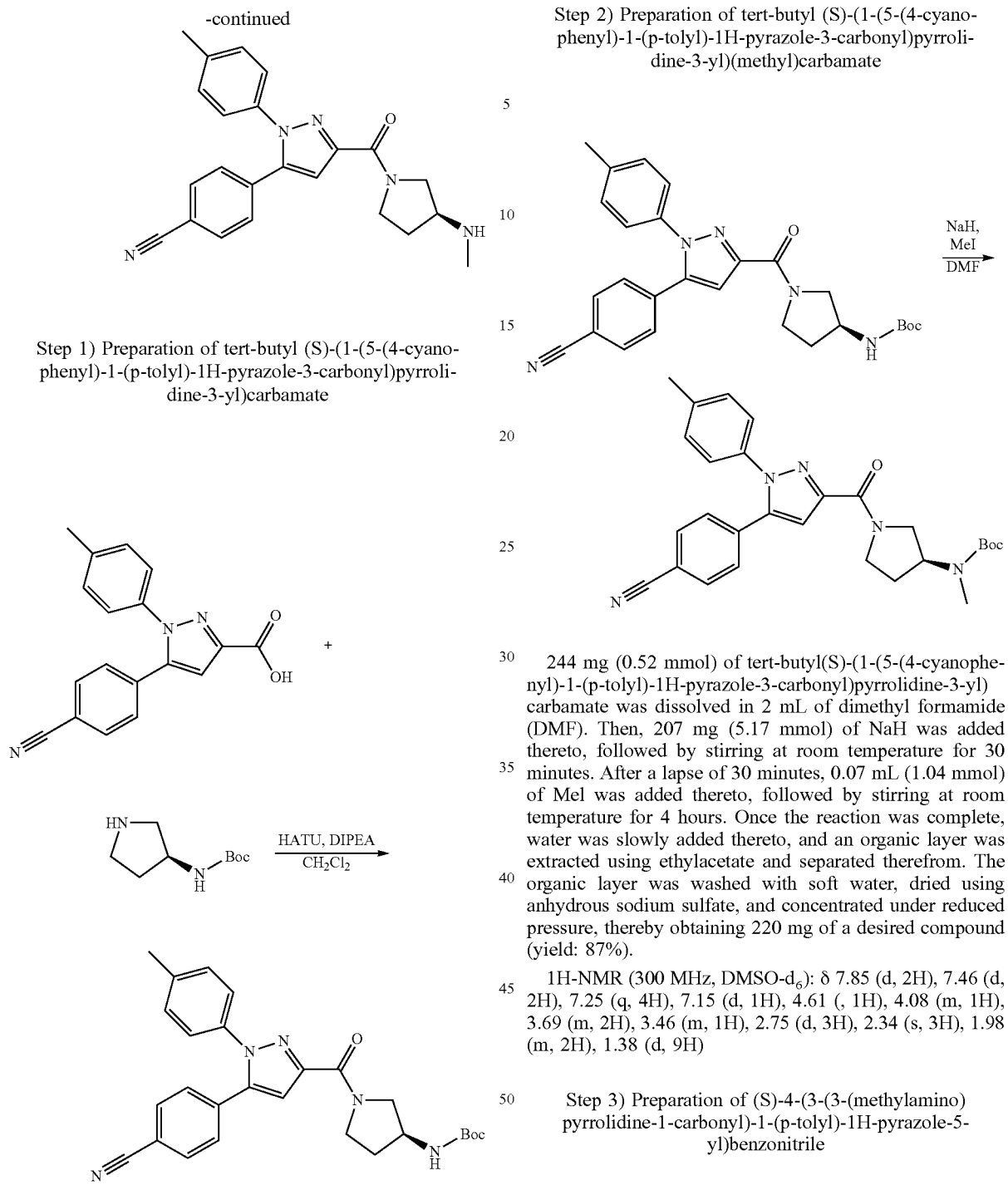

Step 1) Preparation of tert-butyl (S)-(1-(5-(4-cyano-phenyl)-1-(p-tolyl)-1H-pyrazole-3-carbonyl)pyrrolidine-3-yl)carbamate A desired compound was obtained in substantially the same manner as in Example 1, except that p-tolylhydrazine hydrochloride was used instead of (4-cyclopropylphenyl) hydrazine hydrochloride in Step 1) of Example 1, and tert-butyl (S)-pyrrolidine-3-ylcarbamate was used instead of tert-butyl (R)-piperidine-3-ylcarbamate in Step 3) of Example 1.

1H-NMR (300 MHz, DMSO-d₆): δ 7.85 (d, 2H), 7.46 (d, 2H), 7.19 (m, 5H), 7.13 (d, 1H), 3.85 (m, 2H), 3.40 (m, 2H), 3.37 (m, 1H), 2.34 (s, 3H), 1.90 (m, 1H), 1.70 (m, 1H), 1.39 (d, 9H)

48

Step 2) Preparation of tert-butyl (S)-(1-(5-(4-cyano-phenyl)-1-(p-tolyl)-1H-pyrazole-3-carbonyl)pyrrolidine-3-yl)(methyl)carbamate

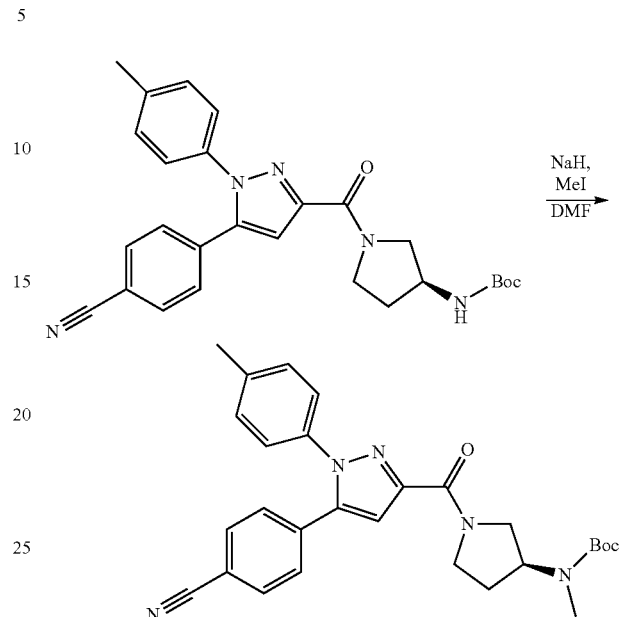

244 mg (0.52 mmol) of tert-butyl(S)-(1-(5-(4-cyanophenyl)-1-(p-tolyl)-1H-pyrazole-3-carbonyl)pyrrolidine-3-yl) carbamate was dissolved in 2 mL of dimethyl formamide (DMF). Then, 207 mg (5.17 mmol) of NaH was added thereto, followed by stirring at room temperature for 30 minutes. After a lapse of 30 minutes, 0.07 mL (1.04 mmol) of MeI was added thereto, followed by stirring at room temperature for 4 hours. Once the reaction was complete, water was slowly added thereto, and an organic layer was extracted using ethylacetate and separated therefrom. The organic layer was washed with soft water, dried using anhydrous sodium sulfate, and concentrated under reduced pressure, thereby obtaining 220 mg of a desired compound (yield: 87%).

1H-NMR (300 MHz, DMSO-d₆): δ 7.85 (d, 2H), 7.46 (d, 2H), 7.25 (q, 4H), 7.15 (d, 1H), 4.61 (, 1H), 4.08 (m, 1H), 3.69 (m, 2H), 3.46 (m, 1H), 2.75 (d, 3H), 2.34 (s, 3H), 1.98 (m, 2H), 1.38 (d, 9H)

Step 3) Preparation of (S)-4-(3-(3-(methylamino)pyrrolidine-1-carbonyl)-1-(p-tolyl)-1H-pyrazole-5-yl)benzonitrile

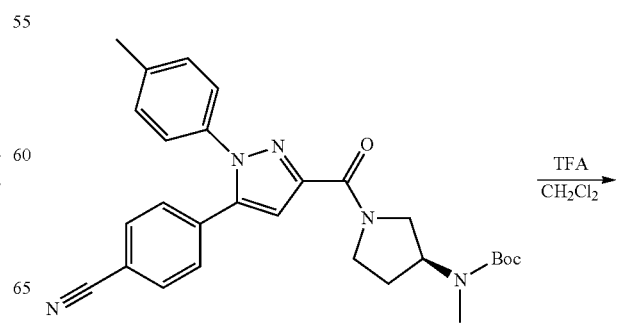

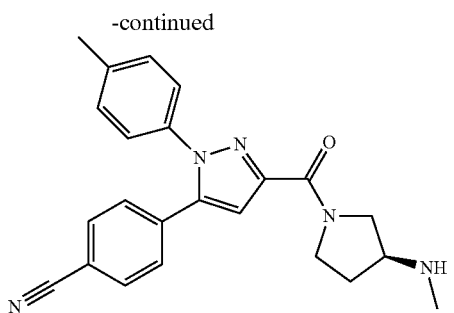

A desired compound was obtained in substantially the same manner as in Example 1, except that tert-butyl (S)-(1-(5-(4-cyanophenyl)-1-(p-tolyl)-1H-pyrazole-3-carbonyl)pyrrolidine-3-yl)carbamate was used instead of tert-butyl (R)-(1-(5-(4-cyanophenyl)-1-(4-cyclopropylphenyl)-1H-pyrazole-3-carbonyl)piperidine-3-yl)carbamate in Step 4) of Example 1.

1H-NMR (300 MHz, DMSO-d$_6$): δ 7.84 (d, 2H), 7.44 (d, 2H), 7.20 (q, 4H), 7.12 (s, 1H), 3.91 (m, 2H), 3.50 (m, 3H), 3.14 (m, 1H), 2.34 (s, 3H), 2.24 (d, 3H), 1.93 (m, 1H), 1.71 (m, 1H)

MS: [M+H]$^+$ m/z 386.2

Example 24: Preparation of (S)-4-(3-(3-(dimethylamino)pyrrolidine-1-carbonyl)-1-(p-tolyl)-1H-pyrazole-5-yl)benzonitrile

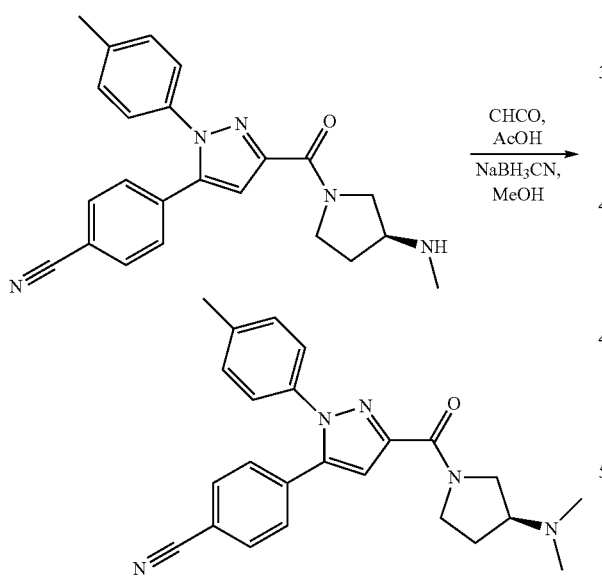

74 mg (0.19 mmol) of (S)-4-(3-(3-(methylamino)pyrrolidine-1-carbonyl)-1-(p-tolyl)-1H-pyrazole-5-yl)benzonitrile prepared in Step 3 of Example 23 was dissolved in 1 mL of methanol, and 37% 0.07 mL (0.96 mmol) of a formaldehyde solution and 0.02 mL (0.39 mmol) of an acetic acid were added dropwise thereto at room temperature. Then, the temperature was lowered to a temperature in a range of 0° C. to 5° C. 24 mg (0.39 mmol) of sodium cyanoborohydride was added thereto at a temperature in a range of 0° C. to 5° C. Then the temperature was raised to room temperature, followed by stirring for 3 hours. Once the reaction was complete, a sodium hydrogen carbonate saturated aqueous solution was slowly added thereto, and an organic layer was extracted using ethylacetate and separated therefrom. The organic layer was washed with soft water, dried using anhydrous sodium sulfate, and concentrated under reduced pressure. The obtained residue was purified using column chromatography (dichloromethane:methanol=8:1 (v/v)), thereby obtaining 48 mg of a desired compound (yield: 63%).

1H-NMR (300 MHz, DMSO-d$_6$): δ 7.84 (d, 2H), 7.44 (d, 2H), 7.24 (q, 4H), 7.14 (s, 1H), 4.12 (m, 1H), 3.74 (m, 2H), 2.70 (m, 1H), 2.34 (s, 3H), 2.17 (d, 6H), 2.07 (m, 1H), 1.73 (m, 1H), 3.23 (m, 1H).

MS: [M+H]$^+$ m/z 400.2

Example 25: Preparation of (R)-4-(3-(3-(dimethylamino)pyrrolidine-1-carbonyl)-1-(p-tolyl)-1H-pyrazole-5-yl)benzonitrile

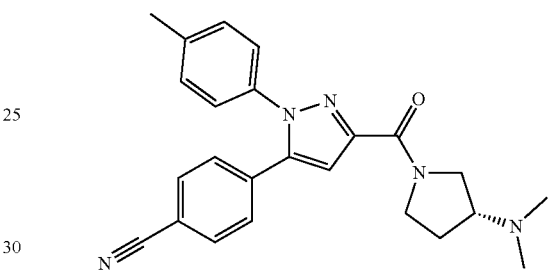

A desired compound was obtained in substantially the same manner as in Example 1, except that p-tolylhydrazine hydrochloride was used instead of (4-cyclopropylphenyl)hydrazine hydrochloride in Step 1) of Example 1, and (R)—N,N-dimethylpyrrolidine-3-amine was used instead of tert-butyl (R)-piperidine-3-ylcarbamate in Step 3) of Example 1.

$^1$H-NMR (300 MHz, DMSO-d$_6$): δ 7.84 (d, 2H), 7.44 (d, 2H), 7.24 (m, 4H), 7.14 (s, 1H), 4.15 (m, 1H), 3.80 (m, 1H), 3.44 (m 1H), 3.30 (m, 1H), 2.70 (m, 1H), 2.35 (s, 3H), 2.17 (d, 6H), 1.75 (m, 1H).

[M+H]$^+$ m/z 400.2

Example 26: Preparation of (R)-4-(3-(3-(methylamino)pyrrolidine-1-carbonyl)-1-(p-tolyl)-1H-pyrazole-5-yl)benzonitrile

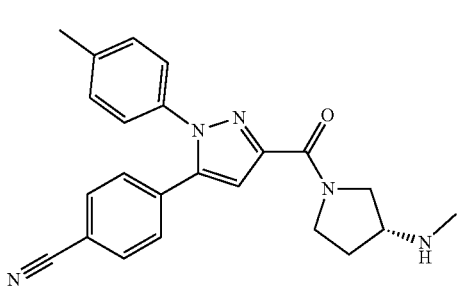 [SMILES: CN[C@@H]1CCN(C(=O)c2cc(-c3ccc(C#N)cc3)n(-c3ccc(C)cc3)n2)C1]

A desired compound was obtained in substantially the same manner as in Example 1, except that p-tolylhydrazine hydrochloride was used instead of (4-cyclopropylphenyl)hydrazine hydrochloride in Step 1) of Example 1, and tert-butyl (R)-methyl(pyrrolidine-3-yl)carbamate was used instead of tert-butyl (R)-piperidine-3-ylcarbamate in Step 3) of Example 1.

¹H-NMR (300 MHz, DMSO-d$_6$): 7.97 (d, 1H), 7.84 (d, 2H), 7.44 (d, 2H), 7.26 (s, 3H), 7.17 (s, 1H), 3.97 (m, 1H), 2.60 (m, 1H), 2.02 (m, 2H), 1.65 (m, 2H), 1.49 (m, 2H).

[M+H]$^+$ m/z 386.2

Example 27: Preparation of (R)-4-(3-(3-aminopyrrolidine-1-carbonyl)-1-(p-tolyl)-1H-pyrazole-5-yl)benzonitrile

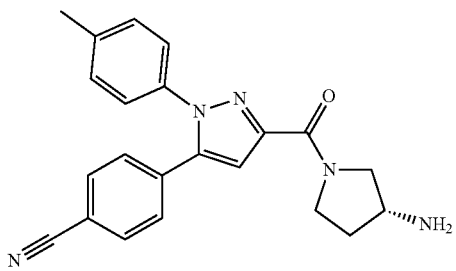 [SMILES: Cc1ccc(-n2nc(C(=O)N3CC[C@@H](N)C3)cc2-c2ccc(C#N)cc2)cc1]

A desired compound was obtained in substantially the same manner as in Example 1, except that p-tolylhydrazine hydrochloride was used instead of (4-cyclopropylphenyl)hydrazine hydrochloride in Step 1) of Example 1, and tert-butyl (R)-pyrrolidine-3-ylcarbamate was used instead of tert-butyl (R)-piperidine-3-ylcarbamate in Step 3) of Example 1.

¹H-NMR (300 MHz, DMSO-d$_6$): δ 7.84 (d, 2H), 7.45 (d, 2H), 7.25 (m, 4H), 7.12 (s, 1H), 4.02 (m, 2H), 3.66 (m, 3H), 2.35 (s, 3H), 1.99 (m, 3H), 1.67 (m, 1H)

[M+H]$^+$ m/z 372.2

Example 28: Preparation of (R)-4-(3-(3-aminopiperidine-1-carbonyl)-1-(p-tolyl)-1H-pyrazole-5-yl)benzonitrile

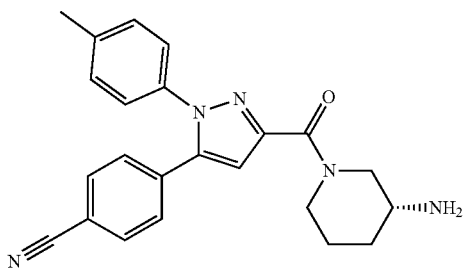 [SMILES: Cc1ccc(-n2nc(C(=O)N3CCC[C@@H](N)C3)cc2-c2ccc(C#N)cc2)cc1]

A desired compound was obtained in substantially the same manner as in Example 1, except that p-tolylhydrazine hydrochloride was used instead of (4-cyclopropylphenyl)hydrazine hydrochloride in Step 1) of Example 1.

¹H NMR spectrum (300 MHz, CDCl$_3$) δ 7.60 (d, 2H), 7.44 (d, 2H), 7.20 (m, 4H), 6.96 (s, 1H), 4.58 (m, 2H), 3.34 (m, 1H), 2.96 (m, 1H), 2.78 (m, 1H), 2.39 (s, 3H), 2.00 (m, 1H), 1.82 (m, 1H), 1.60 (m, 1H), 1.28 (m, 3H).

MS (ESI$^+$): [M+H]$^+$ m/z 386.2

Example 29: Preparation of (R)-4-(3-(3-(methylamino)piperidine-1-carbonyl)-1-(p-tolyl)-1H-pyrazole-5-yl)benzonitrile

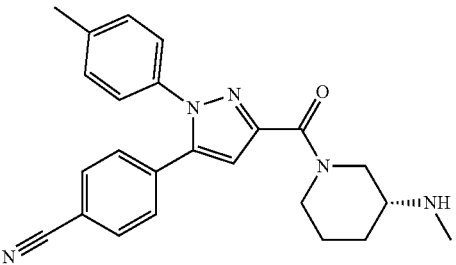 [SMILES: CN[C@@H]1CCCN(C(=O)c2cc(-c3ccc(C#N)cc3)n(-c3ccc(C)cc3)n2)C1]

A desired compound was obtained in substantially the same manner as in Example 1, except that p-tolylhydrazine hydrochloride was used instead of (4-cyclopropylphenyl)hydrazine hydrochloride in Step 1) of Example 1, and tert-butyl(R)-methyl(piperidine-3-yl)carbamate was used instead of tert-butyl (R)-piperidine-3-ylcarbamate in Step 3) of Example 1.

1H-NMR (300 MHz, DMSO-d$_6$): δ 7.85 (d, 2H), 7.44 (d, 2H), 7.24 (q, 4H), 7.05 (d, 1H), 4.50 (m, 2H), 3.08 (m, 1H), 2.81 (m, 1H), 2.34 (s, 5H), 2.20 (s, 1H), 1.94 (m, 1H), 1.70 (m, 1H), 1.41 (m, 3H).

[M+H]$^+$ m/z 400.2

Example 30: Preparation of (R)-4-(3-(3-(dimethylamino)piperidine-1-carbonyl)-1-(p-tolyl)-1H-pyrazole-5-yl)benzonitrile

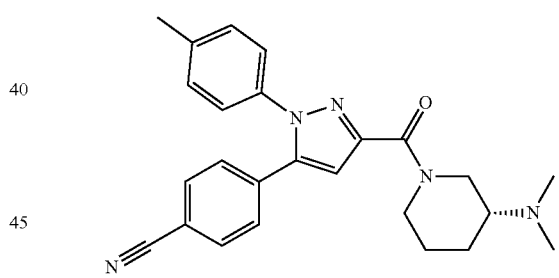

A desired compound was obtained in substantially the same manner as in Example 1, except that p-tolylhydrazine hydrochloride was used instead of (4-cyclopropylphenyl)hydrazine hydrochloride in Step 1) of Example 1, and N,N-dimethyl (R)-piperidine-3-ylcarbamate was used instead of tert-butyl (R)-piperidine-3-ylcarbamate in Step 3) of Example 1.

1H-NMR (300 MHz, DMSO-d$_6$): δ 7.84 (d, 2H), 7.44 (d, 2H), 7.24 (q, 4H), 7.05 (d, 1H), 4.76 (m, 3H), 3.16 (m, 1H), 2.80 (m, 1H), 2.34 (s, 3H), 2.25 (s, 3H), 2.14 (s, 3H), 1.90 (m, 1H), 1.80 (m, 1H), 1.49 (m, 2H).

[M+H]$^+$ m/z 414.2

Example 31: Preparation of (R)-4-(3-(3-aminopiperidine-1-carbonyl)-1-(m-tolyl)-1H-pyrazole-5-yl)benzonitrile A desired compound was obtained in substantially the same manner as in Example 1, except that m-tolylhydrazine

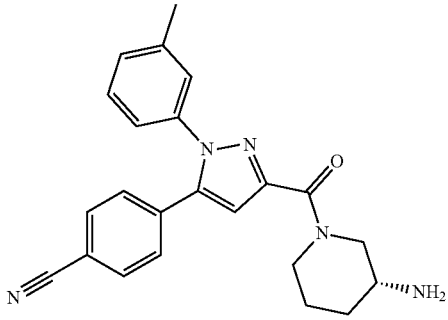 [SMILES: Cc1cccc(-n2nc(C(=O)N3CCC[C@@H](N)C3)cc2-c2ccc(C#N)cc2)c1]

¹H-NMR (300 MHz, CDCl₃): 7.61 (m, 2H), 7.58 (m, 6H), 6.96 (s, 1H), 4.52 (m, 2H), 4.26 (m, 1H), 3.47 (m, 2H), 2.97 (m, 2H), 2.77 (m, 1H), 2.35 (s, 3H), 2.03 (m, 1H), 1.83 (m, 1H)

MS (ESI⁺): [M+H]⁺ m/z 386.2

Example 32: Preparation of (R)-4-(3-(3-aminopiperidine-1-carbonyl)-1-(o-tolyl)-1H-pyrazole-5-yl)benzonitrile A desired compound was obtained in substantially the same manner as in Example 1, except that o-tolylhydrazine hydrochloride was used instead of (4-cyclopropylphenyl)hydrazine hydrochloride in Step 1) of Example 1.

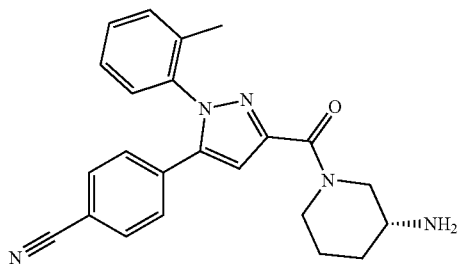 [SMILES: Cc1ccccc1-n1nc(C(=O)N2CCC[C@@H](N)C2)cc1-c1ccc(C#N)cc1]

¹H-NMR (300 MHz, CDCl₃): δ 7.55 (m, 2H), 7.41 (m, 5H), 7.20 (m 1H), 7.06 (s, 1H0, 4.55 (m, 2H), 4.28 (m, 1H), 3.47 (m, 2H), 2.99 (m, 1H), 2.82 (m, 1H), 2.01 (s, 3H), 1.96 (m, 1H), 1.81 (m, 1H).

MS (ESI⁺): [M+H]⁺ m/z 386.2

Example 33: Preparation of (R)-4-(3-(3-aminopiperidine-1-carbonyl)-1-(4-ethylphenyl)-1H-pyrazole-5-yl)benzonitrile A desired compound was obtained in substantially the same manner as in Example 1, except that (4-ethylphenyl) hydrazine hydrochloride was used instead of (4-cyclopropylphenyl)hydrazine hydrochloride in Step 1) of Example 1.

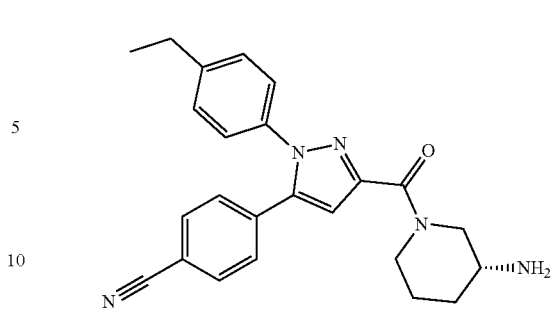

¹H-NMR (300 MHz, CDCl₃): δ 7.62 (d, 2H), 7.36 (m, 2H), 7.24 (m, 4H), 6.98 (s, 1H), 4.59 (m, 2H), 4.26 (m, 1H), 3.33 (m, 2H), 3.0 (m, 1H), 2.81 (m, 1H), 2.76 (m, 2H), 2.03 (m, 1H), 1.83 (m, 1H), 1.29 (m, 3H)

MS (ESI⁺): [M+H]⁺ m/z 400.2

Example 34: Preparation of (R)-4-(1-(4-ethylphenyl)-3-(3-(methylamino)piperidine-1-carbonyl)-1H-pyrazole-5-yl)benzonitrile A desired compound was obtained in substantially the same manner as in Example 1, except that (4-ethylphenyl) hydrazine hydrochloride was used instead of (4-cyclopropylphenyl)hydrazine hydrochloride in Step 1) of Example 1, and tert-butyl (R)-methyl(piperidine-3-yl)carbamate was used instead of tert-butyl (R)-piperidine-3-ylcarbamate in Step 3) of Example 1.

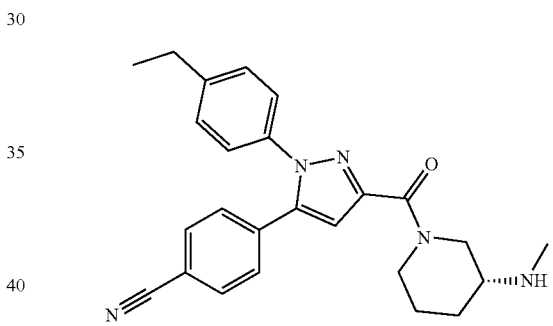

¹H-NMR (300 MHz, CDCl₃): δ 7.63 (d, 2H), 7.37 (m, 2H), 7.24 (m, 4H), 7.02 (m, 1H), 4.79 (m, 3H), 3.49 (m, 1H), 3.28 (m, 2H), 2.72 (m, 3H), 2.56 (d, 3H), 2.04 (m, 1H), 1.86 (m, 1H), 1.27 (m, 3H)

MS (ESI⁺): [M+H]⁺ m/z 414.2

Example 35: Preparation of (R)-4-(3-(3-aminopiperidine-1-carbonyl)-1-(4-isopropylphenyl)-1H-pyrazole-5-yl)benzonitrile

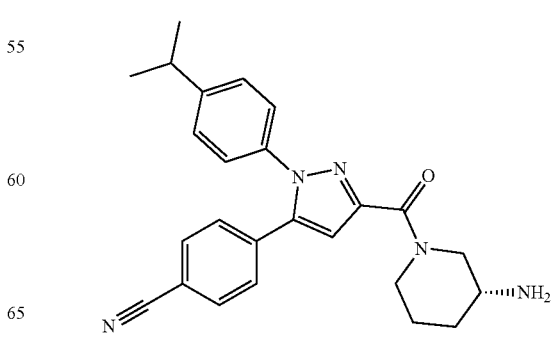

A desired compound was obtained in substantially the same manner as in Example 1, except that (4-isopropylphenyl)hydrazine hydrochloride was used instead of (4-cyclopropylphenyl)hydrazine hydrochloride in Step 1) of Example 1.

$^1$H-NMR (300 MHz, CDCl$_3$): δ 7.63 (d, 2H), 7.37 (m, 2H), 7.29 (m, 4H), 6.92 (s, 1H), 4.58 (m, 2H), 4.26 (m, 1H), 3.38 (m, 2H), 3.00 (m, 2H), 2.81 (m, 1H), 2.00 (m, 1H), 1.84 (m, 1H), 1.28 (dd, 6H)

MS (ESI$^+$): [M+H]$^+$ m/z 414.2

Example 36: Preparation of (R)-4-(1-(4-isopropylphenyl)-3-(3-(methylamino)piperidine-1-carbonyl)-1H-pyrazole-5-yl) benzonitrile A desired compound was obtained in substantially the same manner as in Example 1, except that (4-isopropylphenyl)hydrazine hydrochloride was used instead of (4-cyclopropylphenyl)hydrazine hydrochloride in Step 1) of Example 1, and tert-butyl (R)-methyl(piperidine-3-yl)carbamate was used instead of tert-butyl (R)-piperidine-3-ylcarbamate in Step 3) of Example 1.

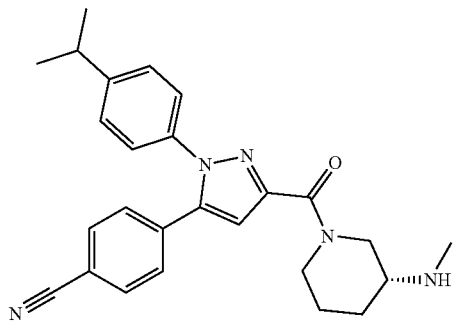 [SMILES: CN[C@@H]1CCCN(C(=O)c2cc(-c3ccc(C#N)cc3)n(-c3ccc(C(C)C)cc3)n2)C1]

$^1$H-NMR (300 MHz, CDCl$_3$): δ 7.62 (m, 2H), 7.35 (m, 6H), 7.03 (s, 1H), 4.92 (m, 1H), 4.38 (m, 2H), 3.32 (m, 1H), 3.01 (m, 4H), 2.92 (d, 3H), 2.06 (m, 1H), 1.88 (m, 1H), 1.25 (m, 6H).

MS (ESI$^+$): [M+H]$^+$ m/z 428.2

Example 37: Preparation of (R)-4-(3-(3-aminopiperidine-1-carbonyl)-1-(2-fluoro-4-isopropylphenyl)-1H-pyrazole-5-yl) benzonitrile A desired compound was obtained in substantially the same manner as in Example 1, except that (2-fluoro-4-isopropylphenyl)hydrazine hydrochloride was used instead of (4-cyclopropylphenyl)hydrazine hydrochloride in Step 1) of Example 1.

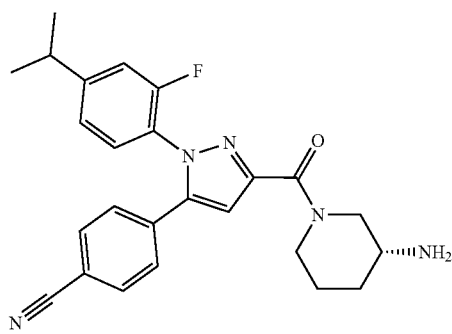 [SMILES: CC(C)c1ccc(-n2nc(C(=O)N3CCC[C@@H](N)C3)cc2-c2ccc(C#N)cc2)c(F)c1]

$^1$H-NMR (300 MHz, CDCl$_3$): δ 7.60 (m, 2H), 7.34 (m, 3H), 7.11 (m, 1H), 7.05 (s, 1H), 6.98 (m, 1H), 4.50 (m, 2H), 3.35 (m, 2H), 2.99 (m, 2H), 2.83 (m, 1H), 2.02 (m, 1H), 1.82 (m, 1H), 1.40 (m, 2H), 1.27 (dd, 6H)

MS (ESI$^+$): [M+H]$^+$ m/z 432.2

Example 38: Preparation of (R)-4-(3-(3-aminopiperidine-1-carbonyl)-1-(2-fluoro-4-isopropylphenyl)-1H-pyrazole-5-yl)-2-fluorobenzonitrile A desired compound was obtained in substantially the same manner as in Example 1, except that (2-fluoro-4-isopropylphenyl)hydrazine hydrochloride was used instead of (4-cyclopropylphenyl)hydrazine hydrochloride, and (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1.

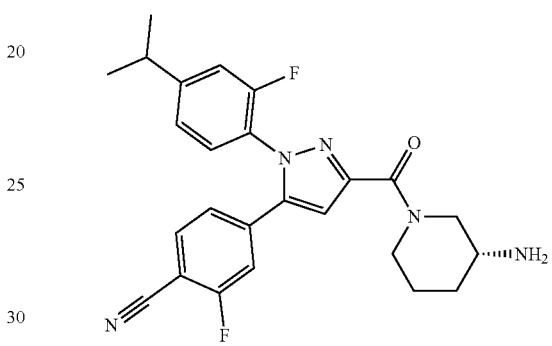

$^1$H-NMR (300 MHz, CDCl$_3$): δ 7.57 (m, 1H), 7.36 (m, 1H), 7.13 (m, 5H), 4.47 (m, 2H), 3.35 (m, 2H), 2.98 (m, 2H), 2.80 (m, 1H), 2.01 (m, 1H), 1.78 (m, 1H), 1.28 (m, 1H), 1.27 (dd, 6H)

MS (ESI$^+$): [M+H]$^+$ m/z 450.2

Example 39: Preparation of (R)-4-(3-(3-aminoazepane-1-carbonyl)-1-(2-fluoro-4-isopropylphenyl)-1H-pyrazole-5-yl)-2-fluorobenzonitrile A desired compound was obtained in substantially the same manner as in Example 1, except that (2-fluoro-4-isopropylphenyl)hydrazine hydrochloride was used instead of (4-cyclopropylphenyl)hydrazine hydrochloride, and (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1, and tert-butyl (R)-azepane-3-ylcarbamate was used instead of tert-butyl (R)-piperidine-3-ylcarbamate in Step 3) of Example 1.

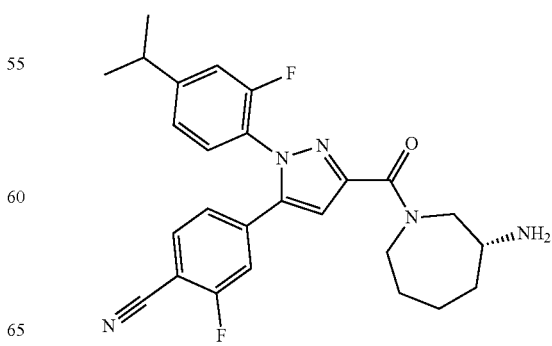

¹H-NMR (300 MHz, CDCl₃): δ 7.60 (m, 1H), 7.38 (m, 2H), 7.15 (m, 2H), 7.06 (m, 2H), 4.31 (m, 1H), 4.05 (m, 2H), 3.50 (m, 3H), 3.01 (m, 1H), 2.04 (m, 1H), 1.93 (m, 2H), 1.50 (m, 2H), 1.28 (dd, 6H)

MS (ESI⁺): [M+H]⁺ m/z 464.2

Example 40: Preparation of (R)-4-(3-(3-aminopiperidine-1-carbonyl)-1-(4-(tert-butyl)phenyl)-1H-pyrazole-5-yl)benzonitrile A desired compound was obtained in substantially the same manner as in Example 1, except that (4-(tert-butyl)phenyl)hydrazine hydrochloride was used instead of (4-cyclopropylphenyl)hydrazine hydrochloride in Step 1) of Example 1.

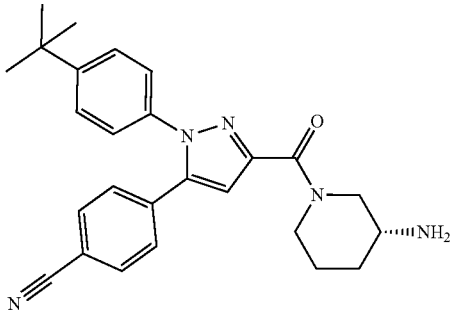 [SMILES: CC(C)(C)c1ccc(-n2nc(C(=O)N3CCC[C@@H](N)C3)cc2-c2ccc(C#N)cc2)cc1]

¹H-NMR (300 MHz, CDCl₃): 7.60 (d, 2H), 7.38 (m, 4H), 7.17 (dd, 2H), 6.97 (dd, 1H), 4.51 (m, 2H), 3.21 (m, 2H), 2.98 (m, 1H), 1.84 (m, 2H), 1.67 (m, 2H), 1.31 (s, 9H)

MS (ESI⁺): [M+H]⁺ m/z 428.2

Example 41: Preparation of (R)-4-(1-(4-(tert-butyl)phenyl-3-(3-methylaminopiperidine-1-carbonyl)-1H-pyrazole-5-yl)benzonitrile A desired compound was obtained in substantially the same manner as in Example 1, except that (4-(tert-butyl)phenyl)hydrazine hydrochloride was used instead of 4-cyclopropylphenylhydrazine hydrochloride in Step 1) of Example 1, and tert-butyl (R)-methyl(piperidine-3-yl)carbamate was used instead of tert-butyl (R)-piperidine-3-ylcarbamate in Step 3) of Example 1.

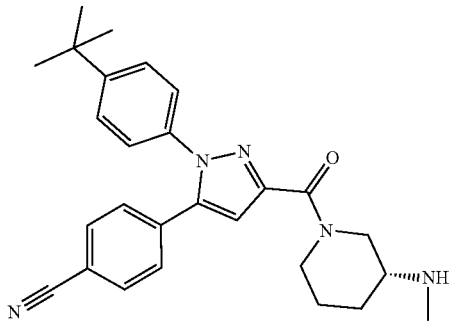 [SMILES: CN[C@@H]1CCCN(C(=O)c2cc(-c3ccc(C#N)cc3)n(-c3ccc(C(C)(C)C)cc3)n2)C1]

¹H-NMR (300 MHz, CDCl₃): 7.61 (d, 2H), 7.37 (m, 4H), 7.17 (dd, 2H), 6.97 (dd, 1H), 4.48 (m, 2H), 3.21 (m, 2H), 2.67 (m, 1H), 2.47 (d, 3H), 1.92 (m, 2H), 1.61 (m, 2H), 1.31 (s, 9H)

MS (ESI⁺): [M+H]⁺ m/z 442.3

Example 42: Preparation of (R)-4-(3-(3-aminopiperidine-1-carbonyl)-1-(4-(tert-butyl)-2-fluorophenyl)-1H-pyrazole-5-yl)benzonitrile A desired compound was obtained in substantially the same manner as in Example 1, except that (4-(tert-butyl)-2-fluorophenyl)hydrazine hydrochloride was used instead of (4-cyclopropylphenyl)hydrazine hydrochloride in Step 1) of Example 1.

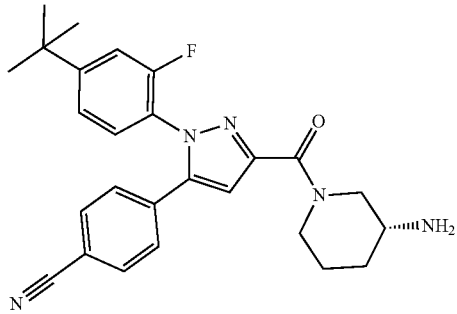 [SMILES: CC(C)(C)c1ccc(-n2nc(C(=O)N3CCC[C@@H](N)C3)cc2-c2ccc(C#N)cc2)c(F)c1]

¹H-NMR (300 MHz, CDCl₃): δ 7.58 (d, 2H), 7.33 (m, 3H), 7.22 (m, 1H), 7.09 (dd, 1H), 6.96 (s, 1H), 4.51 (m, 2H), 3.21 (m, 2H), 2.98 (m, 1H), 1.84 (m, 2H), 1.67 (m, 2H), 1.31 (s, 9H)

MS (ESI⁺): [M+H]⁺ m/z 446.2

Example 43: Preparation of (R)-4-(3-(3-aminopiperidine-1-carbonyl)-1-(4-(tert-butyl-2-fluorophenyl)-1H-pyrazole-5-yl)-2-fluorobenzonitrile A desired compound was obtained in substantially the same manner as in Example 1, except that (4-(tert-butyl-2-fluorophenyl)hydrazine hydrochloride was used instead of 4-cyclopropylphenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxo-2-butenoate in Step 1) of Example 1.

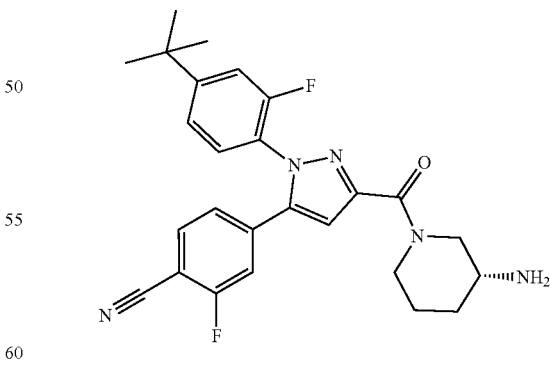

¹H-NMR (300 MHz, CDCl₃): δ 7.56 (t, 1H), 7.38 (q, 1H), 7.30 (t, 1H), 7.15 (m, 2H), 7.03 (m, 1H), 7.01 (s, 1H) 4.51 (m, 2H), 3.21 (m, 2H), 2.98 (m, 1H), 1.84 (m, 2H), 1.67 (m, 2H), 1.31 (s, 9H)

MS (ESI⁺): [M+H]⁺ m/z 464.2

Example 44: Preparation of (R)-4-(3-(3-amino-azepane-1-carbonyl)-1-(4-(tert-butyl-2-fluorophenyl)-1H-pyrazole-5-yl)-2-fluorobenzonitrile A desired compound was obtained in substantially the same manner as in Example 1, except that (4-(tert-butyl-2-fluorophenyl)hydrazine hydrochloride was used instead of 4-cyclopropylphenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxo-2-butenoate in Step 1) of Example 1, and tert-butyl (R)-azepane-3-yl carbamate was used instead of tert-butyl (R)-piperidine-3-ylcarbamate in Step 3) of Example 1.

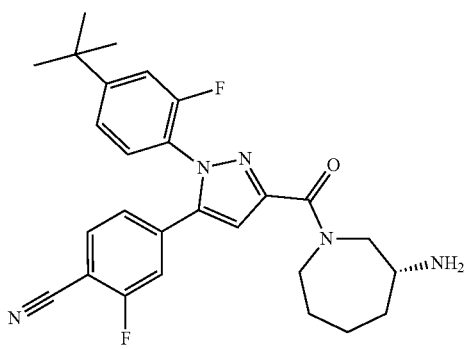 [SMILES: CC(C)(C)c1ccc(-n2nc(C(=O)N3CCCC[C@@H](N)C3)cc2-c2ccc(C#N)c(F)c2)c(F)c1]

$^1$H-NMR (300 MHz, CDCl$_3$): δ 7.55 (t, 1H), 7.34 (q, 1H), 7.28 (t, 2H), 7.15 (m, 3H) 3.34 (m, 2H), 1.91 (m, 6H)), 1.46 (m, 2H), 1.34 (s, 9H)
MS (ESI$^+$): [M+H]$^+$ m/z 478.2

Example 45: Preparation of (R)-4-(3-(3-aminopiperidine-1-carbonyl)-1-(4-(trifluoromethoxy)phenyl)-1H-pyrazole-5-yl) benzonitrile A desired compound was obtained in substantially the same manner as in Example 1, except that (4-(trifluoromethoxy)phenyl)hydrazine hydrochloride was used instead of (4-cyclopropylphenyl)hydrazine hydrochloride in Step 1) of Example 1.

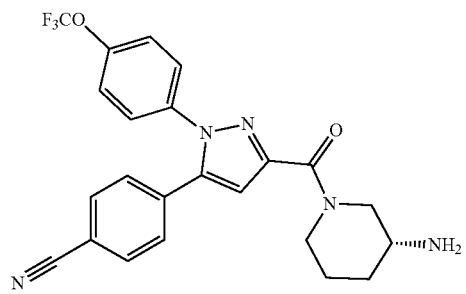 [SMILES: N#Cc1ccc(-c2cc(C(=O)N3CCC[C@@H](N)C3)nn2-c2ccc(OC(F)(F)F)cc2)cc1]

$^1$H-NMR (300 MHz, CDCl$_3$): δ 7.64 (d, 2H), 7.29 (m, 6H), 6.97 (s, 1H), 4.34 (m, 2H), 3.19 (m, 3H), 2.49 (br, 2H), 2.05 (m, 1H), 1.95 (m, 1H), 1.57 (m, 2H).
MS (ESI$^+$): [M+H]$^+$ m/z 456.2

Example 46: Preparation of (R)-4-(3-(3-aminopiperidine-1-carbonyl)-1-(4-(methylsulfonyl)phenyl)-1H-pyrazole-5-yl)benzonitrile A desired compound was obtained in substantially the same manner as in Example 1, except that (4-(methylsulfonyl)phenyl)hydrazine hydrochloride was used instead of (4-cyclopropylphenyl)hydrazine hydrochloride in Step 1) of Example 1.

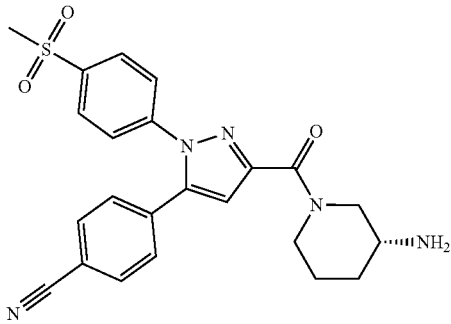 [SMILES: CS(=O)(=O)c1ccc(-n2nc(C(=O)N3CCC[C@@H](N)C3)cc2-c2ccc(C#N)cc2)cc1]

$^1$H-NMR (300 MHz, CDCl$_3$): δ 7.97 (d, 2H), 7.68 (d, 2H), 7.49 (d, 2H), 7.37 (d, 2H), 6.99 (s, 1H), 4.40 (m, 2H), 3.24 (m, 2H), 3.10 (s, 3H), 3.00 (m, 1H), 1.95 (m, 2H), 1.56 (m, 2H).
MS (ESI$^+$): [M+H]$^+$ m/z 450.2

Example 47: Preparation of (R)-4-(3-(3-aminopiperidine-1-carbonyl)-1-(4-(trifluoromethyl)phenyl)-1H-pyrazole-5-yl)benzonitrile A desired compound was obtained in substantially the same manner as in Example 1, except that (4-(trifluoromethyl)phenyl)hydrazine hydrochloride was used instead of (4-cyclopropylphenyl)hydrazine hydrochloride in Step 1) of Example 1.

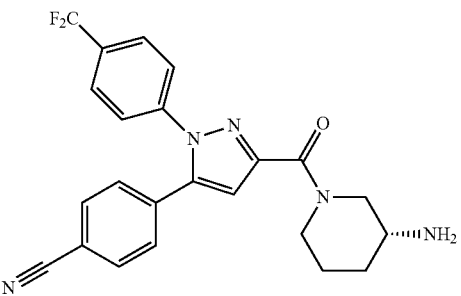

$^1$H-NMR (300 MHz, CDCl$_3$): δ 7.67 (m, 4H), 7.37 (m, 4H), 6.99 (s, 1H), 4.50 (m, 2H), 3.21 (m, 2H), 2.89 (m, 2H), 2.04 (m, 1H), 1.65 (m, 1H), 1.50 (m, 3H).
MS (ESI$^+$): [M+H]$^+$ m/z 440.2

Example 48: Preparation of (R)-4-(3-(3-aminopiperidine-1-carbonyl)-1-(2-fluoro-4-methylphenyl)-1H-pyrazole-5-yl)benzonitrile A desired compound was obtained in substantially the same manner as in Example 1, except that 2-fluoro-4-methylphenyl)hydrazine hydrochloride was used instead of (4-cyclopropylphenyl)hydrazine hydrochloride in Step 1) of Example 1.

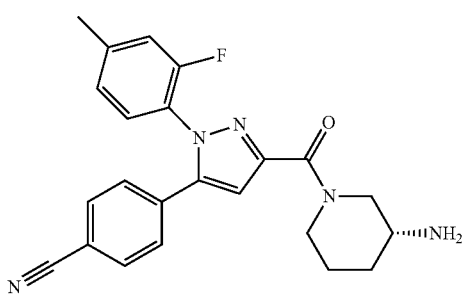 [SMILES: Cc1ccc(-n2nc(C(=O)N3CCC[C@@H](N)C3)cc2-c2ccc(C#N)cc2)c(F)c1]

$^1$H-NMR (300 MHz, CDCl$_3$): δ 7.58 (d, 2H), 7.32 (m, 3H), 7.04 (d, 1H), 6.98 (s, 1H), 6.92 (d, 1H), 4.32 (m, 2H), 3.31 (m, 3H), 2.70 (br, 2H), 2.40 (s, 3H), 2.00 (m, 1H), 1.82 (m, 1H), 1.56 (m, 2H).

MS (ESI$^+$): [M+H]$^+$ m/z 404.2

Example 49: Preparation of (R)-4-(3-(3-aminopiperidine-1-carbonyl)-1-(3-fluoro-4-methoxyphenyl)-1H-pyrazole-5-yl) benzonitrile A desired compound was obtained in substantially the same manner as in Example 1, except that (3-fluoro-4-methoxyphenyl)hydrazine hydrochloride was used instead of (4-cyclopropylphenyl)hydrazine hydrochloride in Step 1) of Example 1.

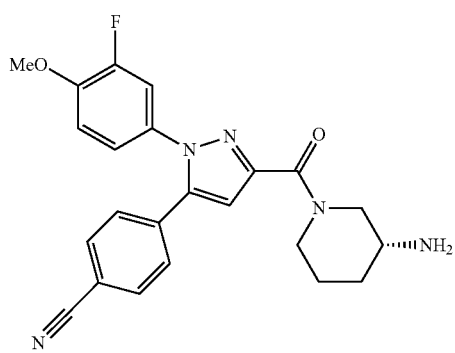 [SMILES: COc1ccc(-n2nc(C(=O)N3CCC[C@@H](N)C3)cc2-c2ccc(C#N)cc2)cc1F]

$^1$H-NMR (300 MHz, CDCl$_3$): δ 7.61 (m, 2H), 7.33 (m, 2H), 7.10 (m, 1H), 6.93 (m, 3H), 4.52 (m, 2H), 3.93 (s, 3H), 3.29 (m, 2H), 2.97 (m, 1H), 1.84 (m, 2H), 1.58 (m, 2H).

MS (ESI$^+$): [M+H]$^+$ m/z 420.2

Example 50: Preparation of (R)-4,4'-(3-(3-aminopiperidine-1-carbonyl)-1H-pyrazole-1,5-diyl)dibenzonitrile A desired compound was obtained in substantially the same manner as in Example 1, except that (4-hydrazinylbenzonitrile)hydrazine hydrochloride was used instead of (4-cyclopropylphenyl)hydrazine hydrochloride in Step 1) of Example 1.

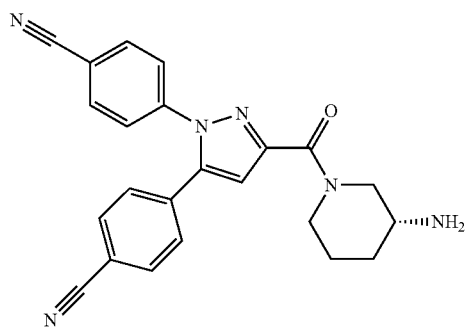 [SMILES: N#Cc1ccc(-c2cc(C(=O)N3CCC[C@@H](N)C3)nn2-c2ccc(C#N)cc2)cc1]

$^1$H-NMR (300 MHz, CDCl$_3$): δ 7.70 (q, 4H), 7.40 (m, 4H), 7.99 (d, 1H), 4.51 (m, 2H), 3.21 (m, 2H), 2.98 (m, 1H), 1.84 (m, 2H), 1.67 (m, 2H).

MS (ESI$^+$): [M+H]$^+$ m/z 397.2

Example 51: Preparation of (R)-4-(1-(4-(dimethylamino)phenyl)-3-(3-(methylamino)piperidine-1-carbonyl)-1H-pyrazole-5-yl)benzonitrile Step 1) Preparation of ethyl 5-(4-cyanophenyl)-1-(4-iodophenyl)-1H-pyrazole-3-carboxylate

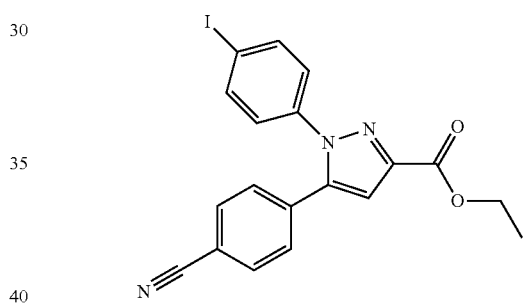

A desired compound was obtained in substantially the same manner as in Step 1) of Example 1, except that 4-iodophenylhydrazine hydrochloride was used instead of (4-cyclopropylphenyl)hydrazine hydrochloride in Step 1) of Example 1.

$^1$H-NMR (300 MHz, CDCl$_3$): δ 7.60 (m, 2H), 7.41 (m, 2H), 7.10 (m, 3H), 6.45 (m, 2H), 4.45 (q, 2H), 1.42 (t, 3H).

Step 2) Preparation of ethyl 5-(4-cyanophenyl)-1-(4-(dimethylamino)phenyl)-1H-pyrazole-3-carboxylate

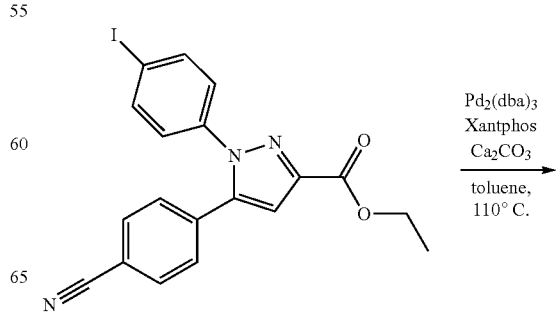

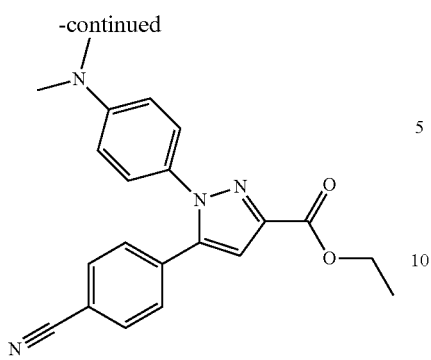

200 mg (0.45 mmol) of ethyl 5-(4-cyanophenyl)-1-(4-iodophenyl)-1H-pyrazole-3-carboxylate, 41 mg (0.045 mmol) of Pd$_2$(dba)$_3$, 294 mg (0.90 mmol) of Cs$_2$CO$_3$, 52 mg (0.09 mmol) of Xantphos, and 44 mg (0.54 mmol) of dimethylamine hydrochloride were dissolved in 1,4-dioxane. This reaction mixture was stirred at a temperature of 100° C. for 12 hours. The mixture was cooled to room temperature, followed by celite filtration and concentration under reduced pressure. The obtained residue was purified using column chromatography (dichloromethane:methanol=10:1 (v/v)), thereby obtaining 110 mg of a desired compound (yield: 67%).

$^1$H-NMR (300 MHz, CDCl$_3$): δ 7.80 (m, 2H), 7.42 (m, 2H), 6.98 (m, 3H), 6.68 (m, 2H), 4.34 (q, 2H), 2.92 (s, 6H), 1.42 (t, 3H).

Step 3) Preparation of (R)-4-(1-(4-(dimethylamino)phenyl)-3-(3-(methylamino)piperidine-1-carbonyl)-1H-pyrazole-5-yl)benzonitrile

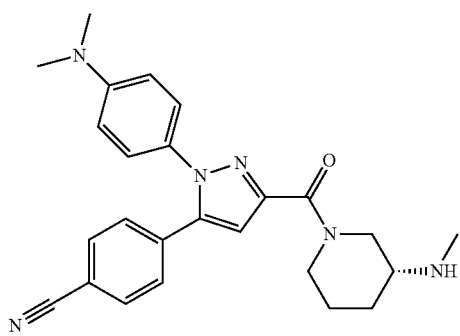 [SMILES: CN[C@@H]1CCCN(C(=O)c2cc(-c3ccc(C#N)cc3)n(-c3ccc(N(C)C)cc3)n2)C1]

A desired compound was obtained in substantially the same manner as in Example 1, except that, using ethyl 5-(4-cyanophenyl)-1-(4-(dimethylamino)phenyl)-1H-pyrazole-3-carboxylate prepared in Step 2), tert-butyl (R)-methyl(piperidine-3-yl)carbamate was used instead of tert-butyl (R)-piperidine-3-ylcarbamate in Step 3) of Example 1.

$^1$H-NMR (300 MHz, CDCl$_3$): δ 7.60 (m, 2H), 7.36 (m, 2H), 7.10 (m, 2H), 6.98 (s, 1H), 6.65 (m, 2H), 4.48 (m, 2H), 3.21 (m, 2H), 2.99 (s, 6H), 2.75 (m, 1H), 2.56 (d, 3H), 2.07 (m, 1H), 1.82 (m, 1H), 1.40 (m, 2H)

MS (ESI$^+$): [M+H]$^+$ m/z 429.2

Example 52: Preparation of (R)-4-(3-(3-aminopiperidine-1-carbonyl)-1-(4-((2-(dimethylamino)ethyl)(methyl)amino)phenyl)-1H-pyrazole-5-yl)benzonitrile A desired compound was obtained in substantially the same manner as in Example 51, except that N1,N1,N2-trimethylethane-1,2-diamine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

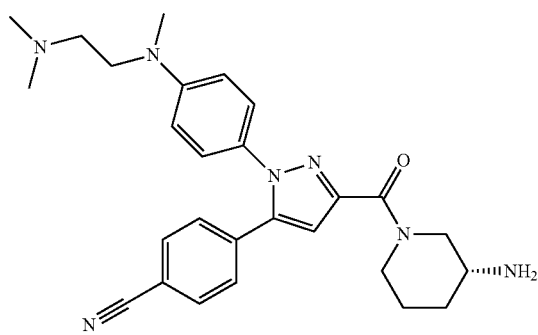 [SMILES: CN(C)CCN(C)c1ccc(-n2nc(C(=O)N3CCC[C@@H](N)C3)cc2-c2ccc(C#N)cc2)cc1]

$^1$H-NMR (300 MHz, CDCl$_3$): δ 7.61 (m, 2H), 7.38 (m, 2H), 7.10 (m, 2H), 7.07 (s, 1H), 6.65 (m, 2H), 4.49 (m, 2H), 3.51 (m, 2H), 3.22 (m, 2H), 3.00 (s, 3H), 2.75 (m, 1H), 2.52 (m, 2H), 2.31 (s, 6H), 2.05 (m, 1H), 1.82 (m, 1H), 1.42 (m, 2H)

MS (ESI$^+$): [M+H]$^+$ m/z 472.3

Example 53: Preparation of ((R)-4-(3-(3-aminopiperidine-1-carbonyl)-1-(4-(dimethylamino)phenyl)-1H-pyrazole-5-yl) benzonitrile A desired compound was obtained in substantially the same manner as in Example 46, except that tert-butyl (R)-piperidine-3-ylcarbamate was used instead of tert-butyl (R)-methyl(piperidine-3-yl)carbamate in Step 3) of Example 51.

$^1$H-NMR (300 MHz, DMSO-d$_6$): δ 7.83 (d, 2H), 7.42 (d, 2H), 7.10 (m, 3H), 6.68 (m, 2H), 4.44 (m, 2H), 3.39 (m, 3H), 2.48 (s, 6H), 1.94 (m, 2H), 1.69 (m, 2H), 1.23 (m, 2H).

MS (ESI$^+$): [M+H]$^+$ m/z 415.2

Example 54: Preparation of (R)-4-(3-(3-aminopiperidine-1-carbonyl)-1-(4-(dimethylamino)-2-fluorophenyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride in Step 1) of Example 51, and tert-butyl (R)-piperidine-3-ylcarbamate was used instead of tert-butyl (R)-methyl(piperidine-3-yl)carbamate in Step 3 of Example 51.

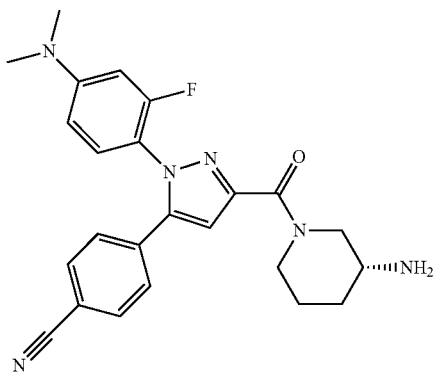 [SMILES: CN(C)c1ccc(-n2nc(C(=O)N3CCC[C@@H](N)C3)cc2-c2ccc(C#N)cc2)c(F)c1]

$^1$H-NMR (300 MHz, CDCl$_3$): δ 7.60 (m, 2H), 7.38 (m, 2H), 7.22 (m, 1H), 7.00 (s, 1H), 6.97 (m, 1H), 6.35 (m, 1H), 4.48 (m, 2H), 3.33 (m, 2H), 3.07 (m, 1H), 3.00 (s, 6H), 2.85 (m, 1H), 2.00 (m, 1H), 1.62 (m, 1H), 1.46 (m, 1H)
MS (ESI$^+$): [M+H]$^+$ m/z 433.2

Example 55: Preparation of (R)-4-(3-(3-aminopiperidine-1-carbonyl)-1-(4-(diethylamino)-2-fluorophenyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride in Step 1) of Example 51, diethylamine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3 of Example 51.

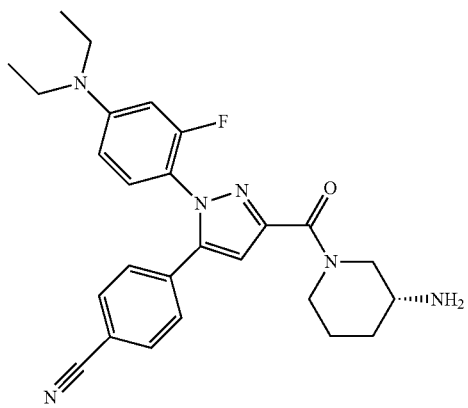 [SMILES: CCN(CC)c1ccc(-n2nc(C(=O)N3CCC[C@@H](N)C3)cc2-c2ccc(C#N)cc2)c(F)c1]

$^1$H-NMR (300 MHz, CDCl$_3$): δ 7.61 (m, 2H), 7.37 (m, 2H), 7.27 (m, 1H), 7.01 (m, 1H), 6.43 (m, 1H), 6.31 (m, 1H), 4.50 (m, 2H), 3.47 (m, 4H), 3.27 (m, 2H), 2.98 (m, 1H), 2.00 (m, 1H), 1.82 (m, 1H), 1.44 (m, 2H), 1.21 (m, 6H)
MS (ESI$^+$): [M+H]$^+$ m/z 461.2

Example 56: Preparation of (R)-4-(3-(3-aminopiperidine-1-carbonyl)-1-(4-(azetidine-1-yl)-2-fluorophenyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride in Step 1) of Example 51, azetidine was used instead of dimethylamine hydrochloride in Step 2) of Example 51, and tert-butyl (R)-piperidine-3-ylcarbamate was used instead of tert-butyl (R)-methyl (piperidine-3-yl)carbamate in Step 3) of Example 51.

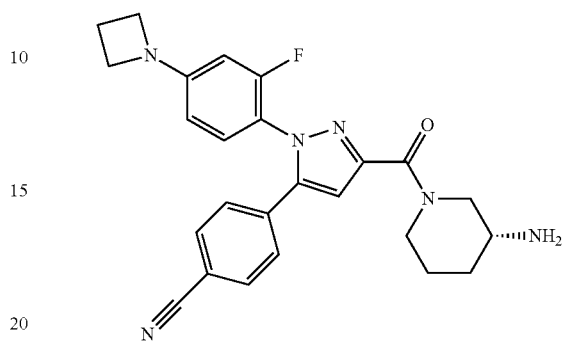

$^1$H-NMR (300 MHz, DMSO-d$_6$): δ 7.84 (d, 2H), 7.46 (d, 2H), 7.32 (m, 1H), 7.09 (m, 1H), 6.28 (m, 2H), 4.37 (m, 2H), 3.84 (m, 3H), 3.05 (m, 2H), 2.36 (m, 5H), 1.88 (m, 5H)
MS (ESI$^+$): [M+H]$^+$ m/z 445.2

Example 57: Preparation of (R)-4-(3-(3-aminopiperidine-1-carbonyl)-1-(2-fluoro-4-(pyrrolidine-1-yl)phenyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride in Step 1) of Example 51, pyrrolidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

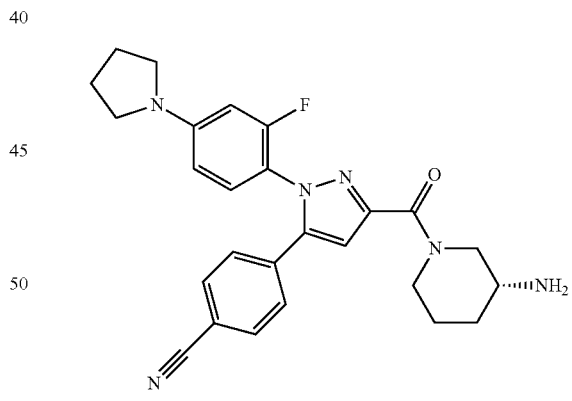

$^1$H-NMR (300 MHz, DMSO-d$_6$): δ 7.84 (d, 2H), 7.47 (d, 2H), 7.37 (m, 1H), 7.03 (m, 1H), 6.39 (m, 2H), 4.37 (m, 1H), 4.21 (m, 1H), 3.23 (m, 5H), 3.00 (m, 3H), 1.94 (m, 4H), 1.87 (m, 1H), 1.68 (m, 1H), 1.41 (m, 1H), 1.21 (m, 2H).
MS (ESI$^+$): [M+H]$^+$ m/z 459.2

Example 58: Preparation of (R)-4-(3-(3-aminopiperidine-1-carbonyl)-1-(2-fluoro-4-(pyrrolidine-1-yl)phenyl)-1H-pyrazole-5-yl)-2-fluorobenzonitrile A desired compound was obtained in substantially the same manner as in Example 51, except that (2-fluoro-4- iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, pyrrolidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

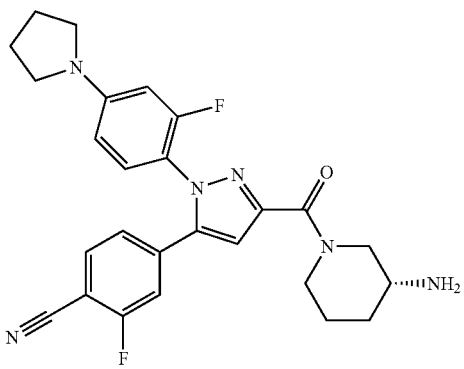 [SMILES: N#Cc1ccc(-c2cc(C(=O)N3CCC[C@@H](N)C3)nn2-c2ccc(N3CCCC3)cc2F)cc1F]

$^1$H-NMR (300 MHz, CDCl$_3$): 7.56 (m, 1H), 7.25 (m, 3H), 6.99 (s, 1H), 6.34 (m, 1H), 6.21 (m, 1H), 4.44 (m, 2H), 3.31 (m, 6H), 2.91 (m, 2H), 2.07 (m, 5H), 1.60 (m, 1H), 1.48 (m, 1H)

MS (ESI$^+$): [M+H]$^+$ m/z 477.2

Example 59: Preparation of (R)-2-fluoro-4-(1-(2-fluoro-4-(pyrrolidine-1-yl)phenyl)-3-(3-(methylamino)piperidine-1-carbonyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and pyrrolidine was used instead of dimethylamine hydrochloride in Step 2) of Example 51.

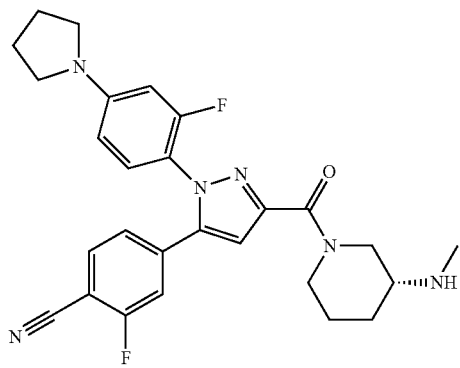 [SMILES: CN[C@@H]1CCCN(C(=O)c2cc(-c3ccc(C#N)c(F)c3)n(-c3ccc(N4CCCC4)cc3F)n2)C1]

$^1$H-NMR (300 MHz, CDCl$_3$): δ 7.55 (m, 1H), 7.17 (m, 2H), 7.10 (m, 1H), 7.02 (m, 1H), 6.32 (m, 1H), 6.19 (m, 1H), 4.75 (m, 2H), 3.52 (m, 6H), 2.81 (m, 1H), 2.58 (m, 4H), 2.08 (m, 4H), 1.61 (m, 3H), 0.86 (m, 1H)

MS (ESI$^+$): [M+H]$^+$ m/z 491.2

Example 60: Preparation of (R)-4-(3-(3-aminoazepane-1-carbonyl)-1-(2-fluoro-4-(pyrrolidine-1-yl)phenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, pyrrolidine was used instead of dimethylamine hydrochloride in Step 2) of Example 51, and tert-butyl (R)-azepane-3-ylcabamateyl was used instead of tert-butyl (R)-methyl(piperidine-3-yl)carbamate in Step 3) of Example 51.

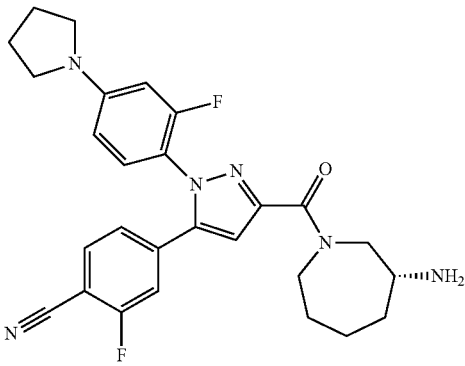 [SMILES: N#Cc1ccc(-c2cc(C(=O)N3CCCC[C@@H](N)C3)nn2-c2ccc(N3CCCC3)cc2F)cc1F]

$^1$H-NMR (300 MHz, CDCl$_3$): δ 7.57 (m, 1H), 7.25 (m, 4H), 6.33 (m, 1H), 6.21 (m, 1H), 4.47 (m, 1H), 4.27 (m, 1H), 3.94 (m, 4H), 3.29 (m, 3H), 2.16 (m, 1H), 2.04 (m, 4H), 1.86 (m, 2H), 1.44 (m, 2H)

MS (ESI$^+$): [M+H]$^+$ m/z 491.2

Example 61: Preparation of 4-(3-((R)-3-aminopiperidine-1-carbonyl)-1-(2-fluoro-4-((R)-3-fluoropyrrolidine-1-yl)phenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, (R)-3-fluoropyrrolidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

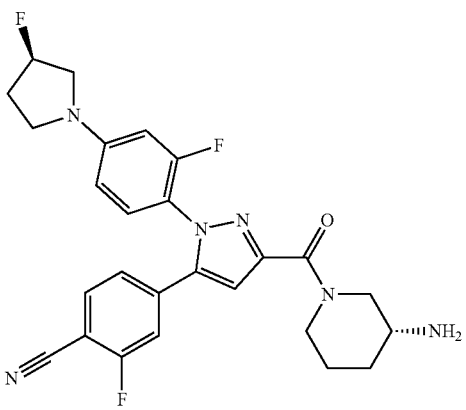

¹H-NMR (300 MHz, CDCl₃): δ 7.56 (m, 1H), 7.12 (m, 3H), 6.67 (s, 1H), 6.35 (m, 1H), 6.19 (m, 1H), 4.41 (m, 2H), 3.49 (m, 5H), 3.35 (m, 2H), 2.96 (m, 2H), 2.42 (m, 1H), 2.35 (m, 1H), 2.09 (m, 2H), 1.77 (m, 2H), 1.24 (m, 1H).

MS (ESI⁺): [M+H]⁺ m/z 495.2

Example 62: Preparation of 4-(3-((R)-3-aminopiperidine-1-carbonyl)-1-(2-fluoro-4-((S)-3-fluoropyrrolidine-1-yl)phenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, (S)-3-fluoropyrrolidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

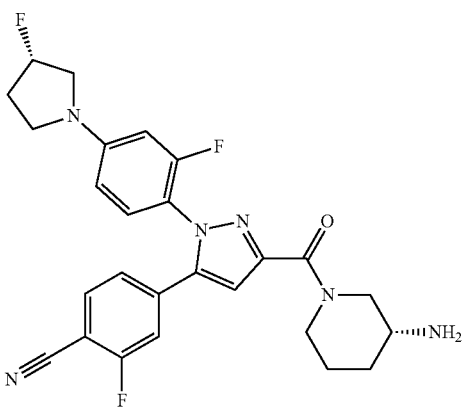 [SMILES: N#Cc1ccc(-c2cc(C(=O)N3CCC[C@@H](N)C3)nn2-c2ccc(N3CC[C@H](F)C3)cc2F)cc1F]

¹H-NMR (300 MHz, CDCl₃): δ 7.57 (m, 1H), 7.14 (m, 4H), 6.36 (m, 1H), 6.19 (m, 1H), 4.46 (m, 2H), 3.51 (m, 4H), 3.24 (m, 2H), 2.94 (m, 1H), 2.41 (m, 2H), 2.03 (m, 1H), 1.96 (m, 2H), 1.76 (m, 1H), 1.24 (m, 1H).

MS (ESI⁺): [M+H]⁺ m/z 495.2

Example 63: Preparation of (R)-4-(3-(3-aminopiperidine-1-carbonyl)-1-(4-(3,3-difluoropyrrolidine-1-yl)-2-fluorophenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, 3,3-difluoropyrrolidine hydrochloride was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

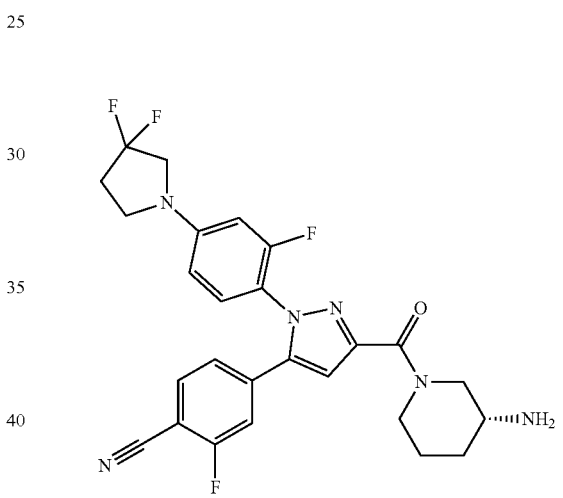

¹H-NMR (300 MHz, CDCl₃): δ 7.60 (m, 1H), 7.12 (m, 2H), 7.00 (s, 1H), 6.37 (m, 1H), 6.26 (m, 1H), 3.75 (m, 4H), 3.24 (m, 1H), 2.97 (m, 1H), 2.60 (m, 2H), 2.49 (m, 1H), 2.00 (m, 1H), 1.82 (m, 5H)

MS (ESI⁺): [M+H]⁺ m/z 513.2

Example 64: Preparation of (R)-4-(1-(4-(3,3-difluoropyrrolidine-1-yl)-2-fluorophenyl)-3-(3-(methylamino)piperidine-1-carbonyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and 3,3,-difluoropyrrolidine was used instead of dimethylamine hydrochloride in Step 2) of Example 51.

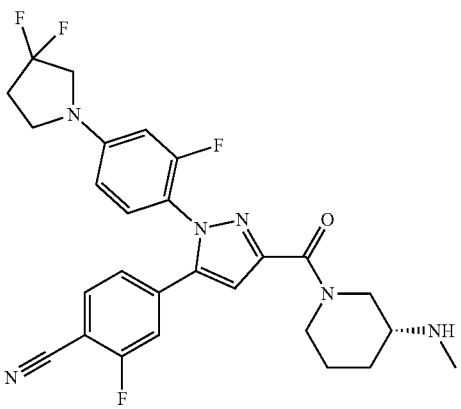 [SMILES: CN[C@@H]1CCCN(C(=O)c2cc(-c3ccc(C#N)c(F)c3)n(-c3ccc(N4CCC(F)(F)C4)cc3F)n2)C1]

¹H-NMR (300 MHz, CDCl₃): δ 7.56 (t, 1H), 7.15 (d, 1H), 7.09 (d, 1H), 7.00 (m, 1H), 6.35 (m, 1H), 6.22 (d, 1H), 4.47 (m, 2H), 3.69 (t, 2H), 3.56 (t, 3H), 3.15 (m, 2H), 2.67 (m, 2H), 2.54 (s, 3H), 1.99 (m, 1H), 1.82 (m, 2H), 1.54 (m, 2H)

MS (ESI⁺): [M+H]⁺ m/z 527.2

Example 65: Preparation of 4-(3-((R)-3-aminopiperidine-1-carbonyl)-1-(2-fluoro-4-(3-methoxypyrrolidin-1-yl)phenyl)-1H-pyrazol-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, methoxypyrrolidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

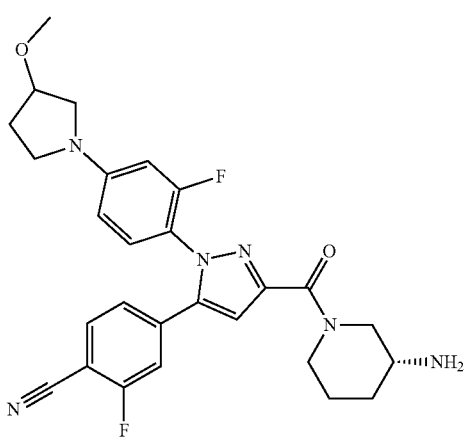

¹H-NMR (300 MHz, CDCl₃): δ 7.59 (m, 1H), 7.25 (m, 3H), 7.01 (s, 1H), 6.37 (m, 1H), 6.24 (m, 1H), 4.47 (s, 2H), 4.24 (m, 1H), 4.14 (s, 1H) 3.52 (m, 7H), 3.32 (m, 1H), 3.01 (s, 1H), 2.91 (m, 1H), 2.21 (m, 2H), 2.02 (s, 1H), 1.60 (m, 2H), 1.49 (s, 1H)

MS (ESI⁺): [M+H]⁺ m/z 507.2

Example 66: Preparation of 2-fluoro-4-(1-(2-fluoro-4-(3-methoxypyrrolidine-1-yl)phenyl)-3-((R)-3-(methylamino)piperidine-1-carbonyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and methoxypyrrolidine was used instead of dimethylamine hydrochloride in Step 2) of Example 51.

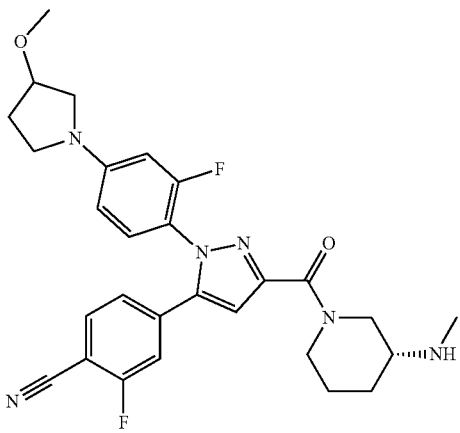

¹H-NMR (300 MHz, CDCl₃): δ 7.59 (m, 1H), 7.21 (m, 3H), 7.03 (m, 1H), 6.35 (m, 1H), 6.23 (m, 1H), 4.43 (m, 2H), 4.14 (s, 1H), 3.51 (m, 8H), 3.28 (m, 1H), 2.77 (s, 1H), 2.58 (s, 3H), 2.22 (m, 3H), 1.83 (s, 1H), 1.59 (m, 2H)

MS (ESI⁺): [M+H]⁺ m/z 521.2

Example 67: Preparation of 4-(3-((R)-3-aminopiperidine-1-carbonyl)-1-(2-fluoro-4-((S)-3-methoxypyrrolidine-1-yl)phenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, (S)-3-methoxypyrrolidine hydrochloride was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

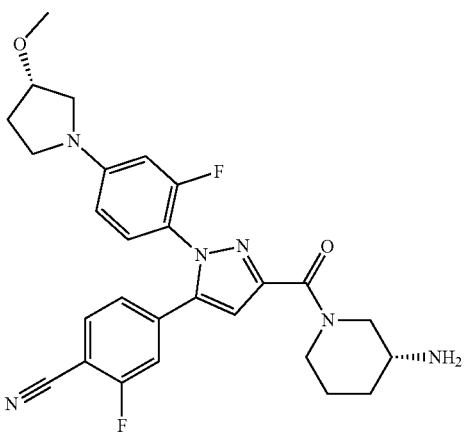 [SMILES: CO[C@H]1CCN(c2ccc(-n3nc(C(=O)N4CCC[C@@H](N)C4)cc3-c3ccc(C#N)c(F)c3)c(F)c2)C1]

¹H-NMR (300 MHz, CDCl₃): δ 7.59 (m, 1H), 7.25 (m, 3H), 7.01 (s, 1H), 6.37 (m, 1H), 6.24 (m, 1H), 4.47 (s, 2H), 4.24 (m, 1H), 4.14 (s, 1H) 3.52 (m, 7H), 3.32 (m, 1H), 3.01 (s, 1H), 2.91 (m, 1H), 2.21 (m, 2H), 2.02 (s, 1H), 1.63 (m, 2H), 1.49 (s, 1H)

(ESI⁺): [M+H]⁺ m/z 507.2

Example 68: Preparation of 2-fluoro-4-(1-(2-fluoro-4-((S)-3-methoxypyrrolidine-1-yl)phenyl)-3-((R)-3-(methylamino)piperidine-1-carbonyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and (S)-3-methoxypyrrolidine hydrochloride was used instead of dimethylamine hydrochloride in Step 2) of Example 51.

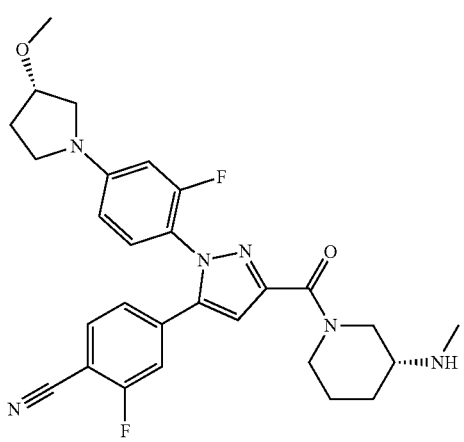 [SMILES: CN[C@@H]1CCCN(C(=O)c2cc(-c3ccc(C#N)c(F)c3)n(-c3ccc(N4CC[C@H](OC)C4)cc3F)n2)C1]

¹H-NMR (300 MHz, CDCl₃): δ 7.59 (m, 1H), 7.21 (m, 3H), 7.03 (m, 1H), 6.35 (m, 1H), 6.23 (m, 1H), 4.43 (m, 2H), 4.14 (s, 1H), 3.51 (m, 8H), 3.28 (m, 1H), 2.77 (s, 1H), 2.58 (s, 3H), 2.22 (m, 3H), 1.83 (s, 1H), 1.59 (m, 2H)

MS (ESI⁺): [M+H]⁺ m/z 521.2

Example 69: Preparation of 4-(3-((R)-3-aminopiperidine-1-carbonyl)-1-(2-fluoro-4-((R)-3-methoxypyrrolidine-1-yl)phenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, (R)-3-methoxypyrrolidine hydrochloride was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

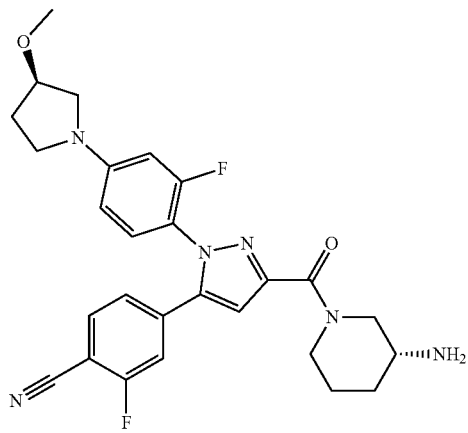 [SMILES: CO[C@@H]1CCN(c2ccc(-n3nc(C(=O)N4CCC[C@@H](N)C4)cc3-c3ccc(C#N)c(F)c3)c(F)c2)C1]

¹H-NMR (300 MHz, DMSO-d₆): δ 7.95 (t, 1H), 7.53 (d, 1H), 7.42 (m, 1H), 7.25 (d, 1H), 7.15 (m, 1H), 6.47 (m, 2H), 4.35 (m, 3H), 3.43 (m, 5H), 2.08 (m, 2H), 2.06 (m, 4H), 1.23 (m, 1H), 1.11 (m, 1H)

MS (ESI⁺): [M+H]⁺ m/z 507.2

Example 70: Preparation of 2-fluoro-4-(1-(2-fluoro-4-((R)-3-methoxypyrrolidine-1-yl)phenyl)-3-((R)-3-(methylamino)piperidine-1-carbonyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and (R)-3-methoxypyrrolidine hydrochloride was used instead of dimethylamine hydrochloride in Step 2) of Example 51.

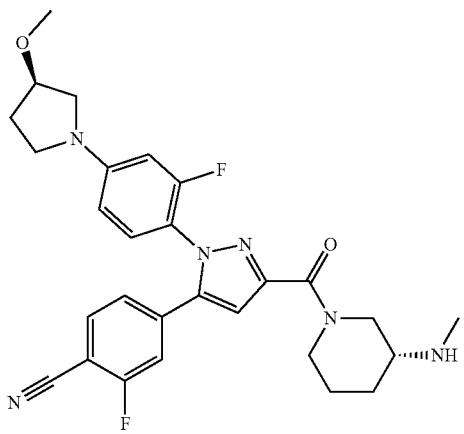 [SMILES: CN[C@@H]1CCCN(C(=O)c2cc(-c3ccc(C#N)c(F)c3)n(-c3ccc(N4CC[C@@H](OC)C4)cc3F)n2)C1]

$^1$H-NMR (300 MHz, DMSO-d$_6$): δ 7.95 (t, 1H), 7.56 (d, 1H), 7.41 (m, 1H), 7.35 (d, 1H), 7.25 (s, 1H), 6.46 (m, 2H), 4.35 (m, 3H), 3.43 (m, 2H), 2.88 (m, 1H), 2.33 (m, 3H), 2.10 (m, 2H), 1.90-1.85 (m, 2H), 1.35 (m, 2H)

MS (ESI$^+$): [M+H]$^+$ m/z 521.2

Example 71: Preparation of 2-fluoro-4-(1-(2-fluoro-4-((S)-3-ethoxypyrrolidine-1-yl)phenyl)-3-((R)-3-(methylamino)piperidine-1-carbonyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and (S)-3-ethoxypyrrolidine hydrochloride was used instead of dimethylamine hydrochloride in Step 2) of Example 51.

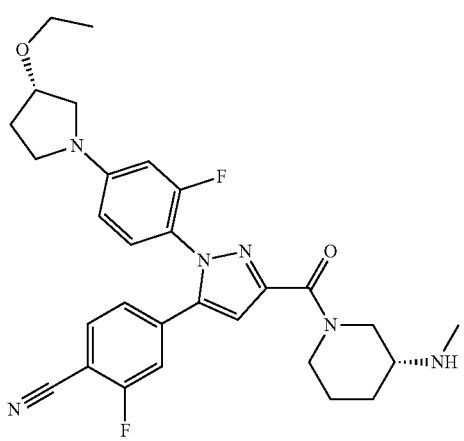 [SMILES: CCO[C@H]1CCN(c2ccc(-n3nc(C(=O)N4CCC[C@@H](NC)C4)cc3-c3ccc(C#N)c(F)c3)c(F)c2)C1]

$^1$H-NMR (300 MHz, CDCl$_3$): δ 7.58 (m, 1H), 7.16 (m, 4H), 6.33 (d, 1H), 6.21 (dd, 1H), 4.32 (m, 2H), 3.62 (m, 4H), 3.40 (m, 2H), 3.18 (s, 1H), 2.74 (m, 3H), 2.22 (m, 3H), 1.89 (m, 2H), 1.66 (m, 4H), 1.25 (t, 3H)

MS (ESI$^+$): [M+H]$^+$ m/z 535.2

Example 72: Preparation of 4-(3-((R)-3-aminopiperidine-1-carbonyl)-1-(2-fluoro-4-(3-hydroxypyrrolidine-1-yl)phenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, 3-hydroxypyrrolidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

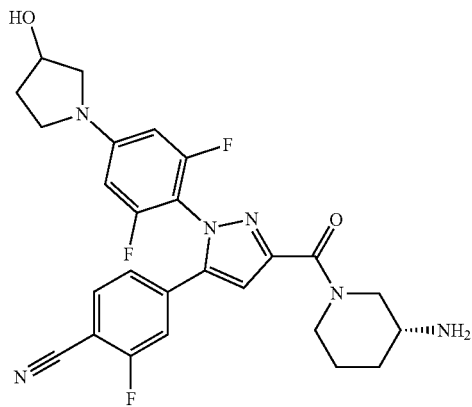 [SMILES: N#Cc1ccc(-c2cc(C(=O)N3CCC[C@@H](N)C3)nn2-c2c(F)cc(N3CCC(O)C3)cc2F)cc1F]

$^1$H-NMR (300 MHz, CDCl$_3$): δ 7.47 (t, 1H), 7.07 (m, 3H), 6.87 (s, 1H), 6.25 (d, 1H), 6.11 (d, 1H), 4.46 (m, 1H), 4.30 (m, 2H), 3.50 (m, 2H), 3.26 (m, 2H), 3.00 (m, 3H), 2.02 (m, 3H), 1.53 (m, 3H)

MS (ESI$^+$): [M+H]$^+$ m/z 493.2

Example 73: Preparation of 2-fluoro-4-(1-(2-fluoro-4-((S)-3-chloropyrrolidine-1-yl)phenyl)-3-((R)-3-(methylamino)piperidine-1-carbonyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and (S)-3-chloropyrrolidine hydrochloride was used instead of dimethylamine hydrochloride in Step 2) of Example 51.

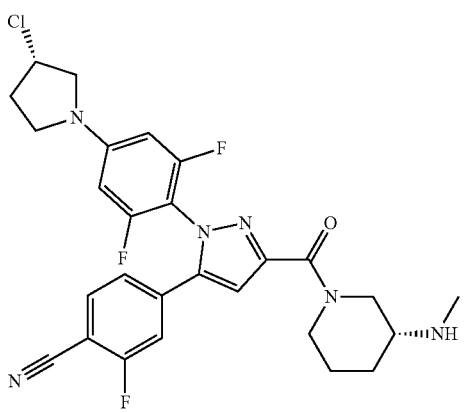 [SMILES: CN[C@@H]1CCCN(C(=O)c2cc(-c3ccc(C#N)c(F)c3)n(-c3c(F)cc(N4CC[C@H](Cl)C4)cc3F)n2)C1]

¹H-NMR (300 MHz, CDCl₃): δ 7.58 (t, 1H), 7.22 (m, 3H), 7.03 (s, 1H), 6.35 (d, 1H), 6.24 (dd, 1H), 4.68 (m, 1H), 4.32 (s, 1H), 3.81 (m, 6H), 2.94 (s, 1H), 2.64 (s, 1H), 2.64 (m, 3H), 2.47 (m, 2H), 2.04 (s, 1H), 1.88 (s, 1H), 1.65 (s, 2H)

MS (ESI⁺): [M+H]⁺ m/z 526.2

Example 74: Preparation of (R)-4-(3-(3-aminopiperidine-1-carbonyl)-1-(2,6-difluoro-4-(pyrrolidine-1-yl)phenyl)-1H-pyrazole-5-yl)-2-fluorobenzonitrile A desired compound was obtained in substantially the same manner as in Example 51, except that (2,6-difluoro-4-iodophenyl)hydrazine hydrochloride was used instead of 4-iodophenylhydrazine hydrochloride, ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, pyrrolidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

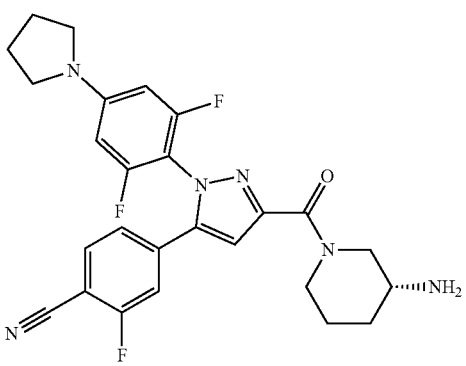 [SMILES: N#Cc1ccc(-c2cc(C(=O)N3CCC[C@@H](N)C3)nn2-c2c(F)cc(N3CCCC3)cc2F)cc1F]

¹H-NMR (300 MHz, CDCl₃): δ 7.58 (t, 1H), 7.21 (d, 1H), 7.15 (d, 1H), 7.00 (m, 1H), 6.07 (d, 2H), 4.34 (m, 2H), 3.28 (m, 4H), 2.97 (m, 2H), 2.06 (m, 4H), 2.06 (m, 4H)

MS (ESI⁺): [M+H]⁺ m/z 495.2

Example 75: Preparation of (R)-4-(3-(3-aminopiperidine-1-carbonyl)-1-(2-chloro-4-(pyrrolidine-1-yl)phenyl)-1H-pyrazole-5-yl)-2-fluorobenzonitrile

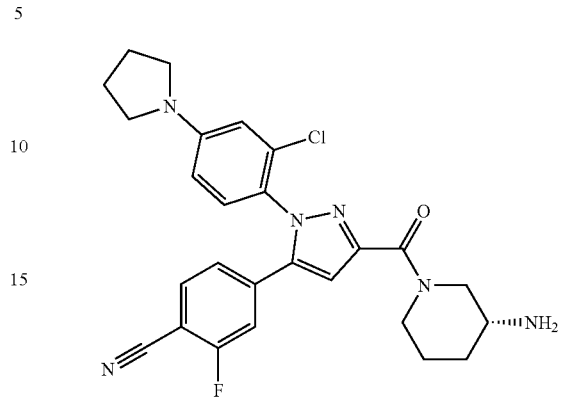

A desired compound was obtained in substantially the same manner as in Example 51, except that (2-chloro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, pyrrolidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

¹H-NMR (300 MHz, CDCl₃): δ 7.85 (d, 2H), 7.38 (d, 2H), 7.21 (d, 2H), 7.14 (d, 2H), 6.72 (m, 1H), 2.32 (s, 3H), 1.84 (m, 2H), 1.42-1.29 (m, 10H).

MS (ESI⁺): [M+H]⁺ m/z 493.2

Example 76: Preparation of (R)-4-(3-(3-aminopiperidine-1-carbonyl)-1-(2-methoxy-4-(pyrrolidine-1-yl)phenyl)-1H-pyrazole-5-yl)-2-fluorobenzonitrile A desired compound was obtained in substantially the same manner as in Example 51, except that (4-bromo-2-methoxyphenyl)hydrazine hydrochloride was used instead of 4-iodophenylhydrazine hydrochloride, ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, pyrrolidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

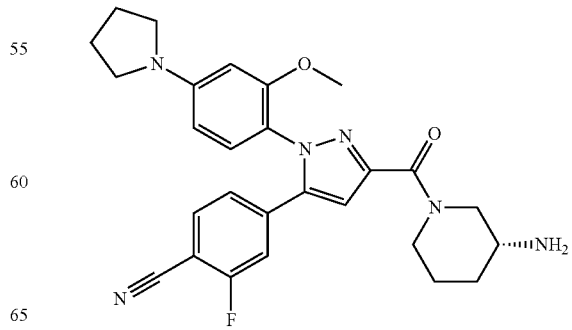

$^1$H-NMR (300 MHz, CDCl$_3$): δ 7.50 (t, 1H), 7.13 (m, 3H), 6.98 (s, 1H), 6.16 (d, 1H), 5.97 (d, 1H), 4.43 (m, 2H), 3.49 (s, 3H), 3.32 (m, 4H), 3.00 (m, 2H), 2.04 (m, 4H), 1.48 (m, 5H)

MS (ESI$^+$): [M+H]$^+$ m/z 489.2

Example 77: Preparation of (R)-4-(3-(3-aminopiperidine-1-carbonyl)-1-(2-fluoro-4-(piperidine-1-yl)phenyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride in Step 1) of Example 51, piperidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

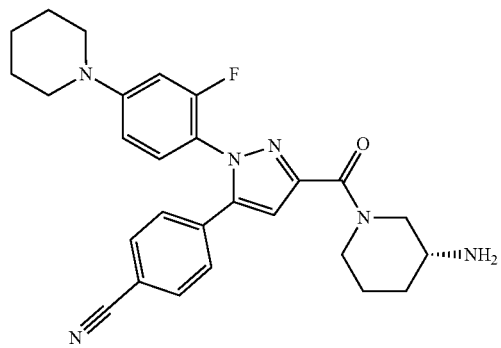 [SMILES: N#Cc1ccc(-c2cc(C(=O)N3CCC[C@@H](N)C3)nn2-c2ccc(N3CCCCC3)cc2F)cc1]

$^1$H-NMR (300 MHz, DMSO-d$_6$): δ 7.84 (d, 2H), 7.47 (d, 2H), 7.44 (m, 1H), 7.05 (m, 1H), 6.82 (m, 2H), 4.37 (m, 1H), 4.20 (m, 1H), 3.37 (m, 5H), 3.14 (m, 5H), 1.94 (m, 2H), 1.55 (m, 5H), 1.21 (m, 2H).

MS (ESI$^+$): [M+H]$^+$ m/z 473.2

Example 78: Preparation of (R)-4-(3-(3-aminopiperidine-1-carbonyl)-1-(2-fluoro-4-(piperidine-1-yl)phenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, piperidine was used instead of dimethylamine hydrochloride in Step 2) of Example 51, and tert-butyl (R)-piperidine-3-ylcarbamate was used instead of tert-butyl (R)-methyl(piperidine-3-yl)carbamate in Step 3) of Example 51.

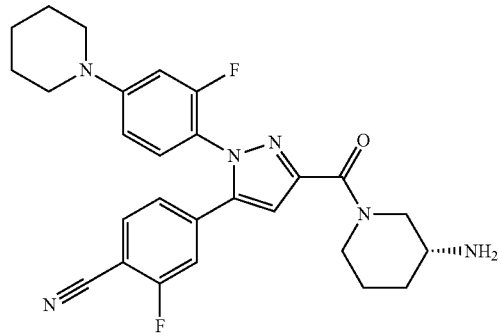 [SMILES: N#Cc1ccc(-c2cc(C(=O)N3CCC[C@@H](N)C3)nn2-c2ccc(N3CCCCC3)cc2F)cc1F]

$^1$H-NMR (300 MHz, CDCl$_3$): δ 7.59 (m, 1H), 7.24 (m, 3H), 7.02 (m, 1H), 6.73 (m, 1H), 6.59 (m, 1H), 4.46 (m, 2H), 3.42 (m, 5H), 3.00 (m, 2H), 2.16 (m, 1H), 2.04 (m, 4H), 1.86 (m, 2H), 1.44 (m, 2H)

MS (ESI$^+$): [M+H]$^+$ m/z 491.2

Example 79: Preparation of (R)-2-fluoro-4-(1-(2-fluoro-4-(piperidine-1-yl)phenyl)-3-(3-(methylamino)piperidine-1-carbonyl)-1H-pyrazole-5-yl)benzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and piperidine was used instead of dimethylamine hydrochloride in Step 2) of Example 51.

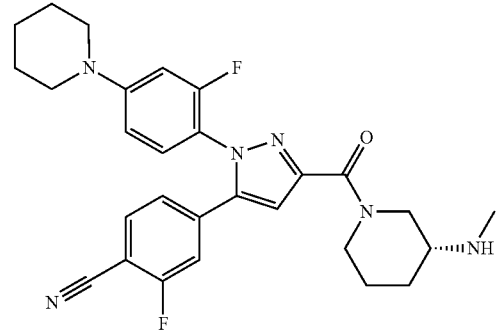 [SMILES: CN[C@@H]1CCCN(C(=O)c2cc(-c3ccc(C#N)c(F)c3)n(-c3ccc(N4CCCCC4)cc3F)n2)C1]

$^1$H-NMR (300 MHz, CDCl$_3$): δ 7.59 (m, 1H), 7.21 (m, 3H), 6.69 (m, 1H), 7.05 (m, 1H), 6.63 (m, 1H), 4.77 (m, 1H), 4.40 (m, 1H), 3.27 (m, 4H), 3.09 (m, 1H), 2.76 (m, 2H), 2.45 (m, 2H), 2.18 (m, 1H), 1.83 (m, 6H), 1.67 (m, 4H).

MS (ESI$^+$): [M+H]$^+$ m/z 422.2

Example 80: Preparation of 4-(3-((R)-3-aminopiperidine-1-carbonyl)-1-(2-fluoro-4-(3-methylpiperidine-1-yl)phenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and 3-methylpiperidine was used instead of dimethylamine hydrochloride in Step 2) of Example 51.

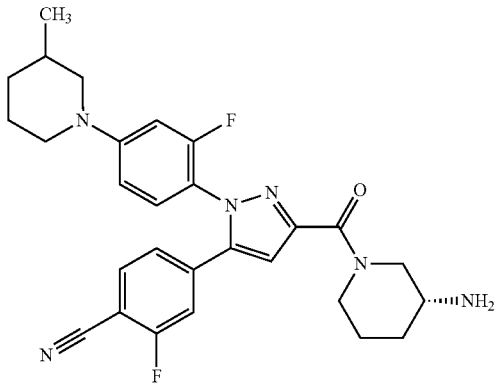 [SMILES: CC1CCCN(c2ccc(-n3nc(C(=O)N4CCC[C@@H](N)C4)cc3-c3ccc(C#N)c(F)c3)c(F)c2)C1]

¹H-NMR (300 MHz, CDCl₃): δ 7.54 (t, 1H), 7.16 (m, 4H), 6.69 (d, 1H), 6.51 (d, 1H), 4.43 (m, 2H), 3.63 (m, 2H), 3.17 (m, 7H), 2.45 (m, 1H), 1.71 (m, 7H), 1.21 (m, 1H), 0.96 (d, 3H).

MS (ESI⁺): [M+H]⁺ m/z 505.2

Example 81: Preparation of (R)-4-(3-(3-aminopiperidine-1-carbonyl)-1-(2-fluoro-4-(4-methylpiperidine-1-yl)phenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and 4-methylpiperidine was used instead of dimethylamine hydrochloride in Step 2) of Example 51.

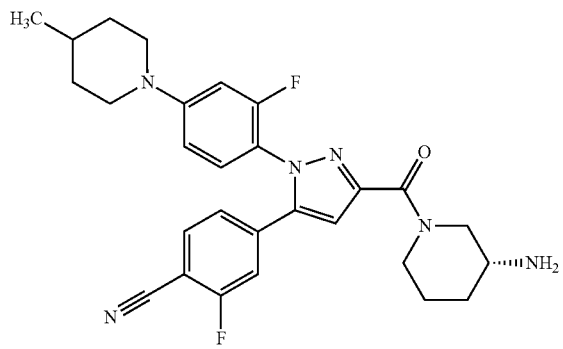 [SMILES: CC1CCN(c2ccc(-n3nc(C(=O)N4CCC[C@@H](N)C4)cc3-c3ccc(C#N)c(F)c3)c(F)c2)CC1]

¹H-NMR (300 MHz, CDCl₃): 7.68 (m, 1H), 7.27 (m, 4H), 6.79 (d, 1H), 6.64 (d, 1H), 4.52 (m, 1H), 3.84 (m, 2H), 3.42 (m, 2H) 3.05 (m, 2H), 2.89 (m, 2H), 1.82 (m, 9H), 1.47 (m, 2H), 1.16 (d, 3H)

MS (ESI⁺): [M+H]⁺ m/z 505.2

Example 82: Preparation of 4-(3-((R)-3-aminopiperidine-1-carbonyl)-1-(4-(3,5-dimethylpiperidine-1-yl)-2-fluorophenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and 3,5-dimethylpiperidine was used instead of dimethylamine hydrochloride in Step 2) of Example 51.

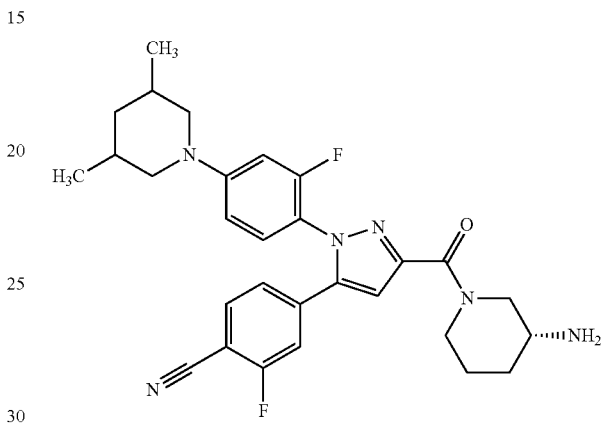

¹H-NMR (300 MHz, CDCl₃): δ 7.94 (d, 2H), 7.48 (m, 3H), 7.22 (m, 2H), 6.82 (br, 2H), 4.16 (m, 3H), 3.77 (m, 2H), 2.87 (m, 2H), 2.32 (m, 2H), 1.67 (m, 4H), 1.40 (m, 4H), 1.50 (d, 6H)

MS (ESI⁺): [M+H]⁺ m/z 519.3

Example 83: Preparation of (R)-4-(1-(4-([1,4'-bipiperidine]-1'-yl)-2-fluorophenyl)-3-(3-aminopiperidine-1-carbonyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, and 1,4-bipiperidine was used instead of dimethylamine hydrochloride in Step 2) of Example 51.

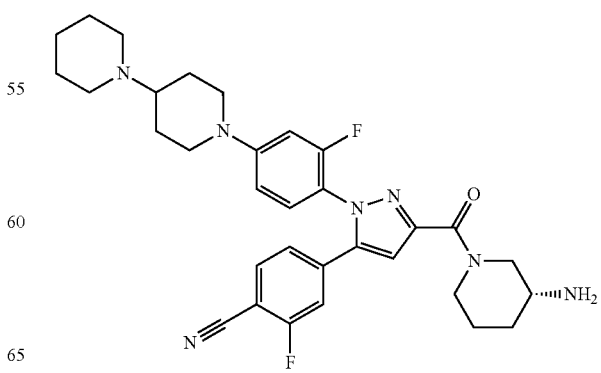

¹H-NMR (300 MHz, CDCl₃): δ 7.94 (m, 1H), 7.51 (m, 2H), 7.25 (m, 2H), 6.82 (m, 2H), 4.34 (m, 4H), 3.83 (m, 4H), 3.31 (m, 6H), 2.75 (m, 4H), 1.86 (m, 4H), 1.36 (m, 6H)
MS (ESI⁺): [M+H]⁺ m/z 574.2

Example 84: Preparation of (R)-4-(3-(3-amino-azepane-1-carbonyl)-1-(2-fluoro-4-(piperidine-1-yl)phenyl)-1H-pyrazole-5-yl)-2-fluorobenzonitrile A desired compound was obtained in substantially the same manner as in Example 51, except that (2-fluoro-4-iodophenyl)hydrazine hydrochloride was used instead of 4-iodophenylhydrazine hydrochloride, ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, piperidine was used instead of dimethylamine hydrochloride in Step 2) of Example 51, and tert-butyl (R)-azepane-3-ylcarbamate was used instead of tert-butyl (R)-methyl(piperidine-3-yl)carbamate in Step 3) of Example 51.

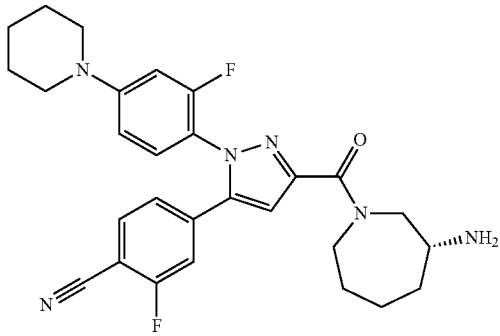 [SMILES: N#Cc1ccc(-c2cc(C(=O)N3CCCC[C@@H](N)C3)nn2-c2ccc(N3CCCCC3)cc2F)cc1F]

¹H-NMR (300 MHz, CDCl₃): δ 7.59 (m, 1H), 7.27 (m, 4H), 6.72 (m, 1H), 6.69 (m, 1H), 4.32 (m, 1H), 4.29 (m, 1H), 3.86 (m, 4H), 3.49 (m, 1H), 3.29 (m, 5H), 3.01 (m, 1H), 1.95 (m, 3H), 1.71 (m, 3H)
MS (ESI⁺): [M+H]⁺ m/z 505.3

Example 85: Preparation of (R)-4-(3-(3-aminopiperidine-1-carbonyl)-1-(1-methyl-1H-indazole-6-yl)-1H-pyrazole-5-yl) benzonitrile A desired compound was obtained in substantially the same manner as in Example 1, except that 6-hydrazinyl-1-methyl-1H-indazole hydrochloride was used instead of (4-cyclopropylphenyl)hydrazine hydrochloride in Step 1) of Example 1.

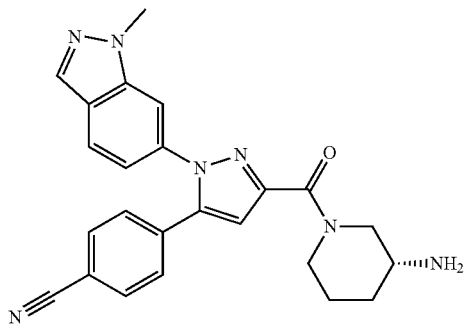 [SMILES: Cn1ncc2ccc(-n3nc(C(=O)N4CCC[C@@H](N)C4)cc3-c3ccc(C#N)cc3)cc21]

¹H-NMR (300 MHz, CDCl₃): δ 8.29 (s, 2H), 7.79 (m, 3H), 7.39 (m, 3H), 7.08 (m, 1H), 4.29 (m, 2H), 4.06 (s, 3H), 3.05 (m, 2H), 1.84 (m, 3H), 1.61 (m, 2H)
MS (ESI⁺): [M+H]⁺ m/z 426.2

Example 86: Preparation of (R)-4-(3-(3-aminopiperidine-1-carbonyl)-1-(2-methylbenzo[d]thiazole-5-yl)-1H-pyrazole-5-yl)benzonitrile A desired compound was obtained in substantially the same manner as in Example 1, except that 5-hydrazinyl-2-methylbenzo[d]thiazole hydrochloride was used instead of (4-cyclopropylphenyl)hydrazine hydrochloride in Step 1) of Example 1.

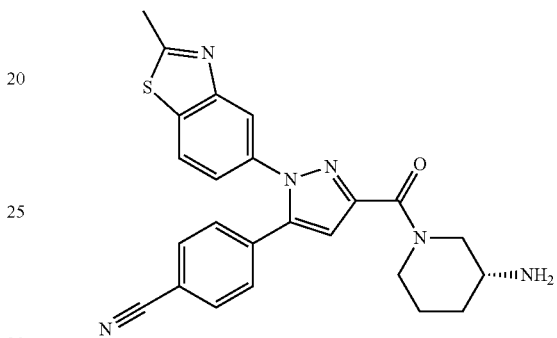

¹H-NMR (300 MHz, CDCl₃): δ 7.84 (m, 2H), 7.56 (m, 2H), 7.36 (m, 3H), 7.01 (s, 1H), 4.29 (m, 2H), 4.12 (s, 2H), 3.23 (m, 2H), 2.23 (s, 3H), 1.61 (m, 2H), 1.56 (m, 1H).
MS (ESI⁺): [M+H]⁺ m/z 373.2

Example 87: Preparation of (R)-4-(3-(3-aminopiperidine-1-carbonyl)-1-(2,3-dihydro-1H-indane-5-yl)-1H-pyrazole-5-yl)benzonitrile A desired compound was obtained in substantially the same manner as in Example 1, except that (2,3,-dihydro-1H-indane-5-yl)hydrazine hydrochloride was used instead of (4-cyclopropylphenyl)hydrazine hydrochloride in Step 1) of Example 1.

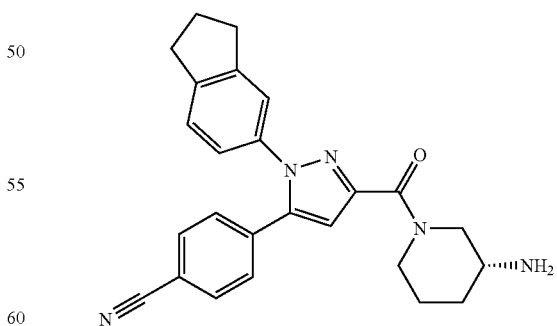

1H-NMR (300 MHz, DMSO-d₆): δ 7.85 (d, 2H), 7.45 (d, 2H), 7.26 (d, 2H), 6.99 (m, 2H), 4.16 (m, 2H), 3.09 (m, 2H), 2.88 (q, 4H), 2.63 (m, 2H), 2.04 (m, 2H), 1.87 (m, 2H), 1.70 (m, 1H), 1.35 (m, 1H), 1.28 (m, 1H).
MS (ESI⁺): [M+H]⁺ m/z 412.2

Example 88: Preparation of (R)-4-(3-(3-aminopiperidine-1-carbonyl)-1-(2,3-dihydro-1H-inden-5-yl)-1H-pyrazole-5-yl)-2-fluorobenzonitrile A desired compound was obtained in substantially the same manner as in Example 1, except that (2,3-dihydro-1H-inden-5-yl)hydrazine hydrochloride was used instead of (4-cyclopropylphenyl)hydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1.

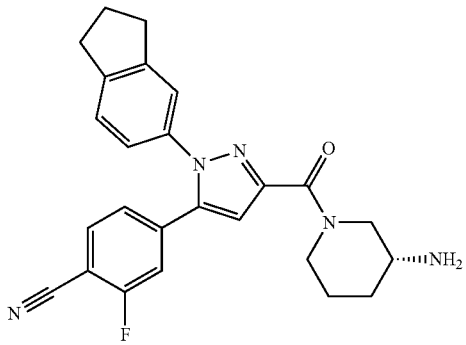 [SMILES: N#Cc1ccc(-c2cc(C(=O)N3CCC[C@@H](N)C3)nn2-c2ccc3c(c2)CCC3)cc1F]

1H-NMR (300 MHz, CDCl$_3$): δ 7.54 (t, 1H), 7.13 (m, 4H), 6.93 (m, 2H), 4.43 (m, 2H), 4.16 (m, 3H), 3.99 (m, 1H), 3.32 (m, 1H), 2.95 (m, 4H), 2.18 (m, 4H), 1.87 (m, 2H).

MS (ESI$^+$): [M+H]$^+$ m/z 430.2

Example 89: Preparation of (R)-4-(1-(2,3-dihydro-1H-inden-5-yl)-3-(3-(methylamino)piperidine-1-carbonyl)-1H-pyrazole-5-yl)benzonitrile A desired compound was obtained in substantially the same manner as in Example 1, except that (2,3-dihydro-1H-inden-5-yl)hydrazine hydrochloride was used instead of (4-cyclopropylphenyl)hydrazine hydrochloride in Step 1) of Example 1, and tert-butyl (R)-methyl(piperidine-3-yl)carbamate was used instead of tert-butyl (R)-piperidine-3-ylcarbamate in Step 3) of Example 1.

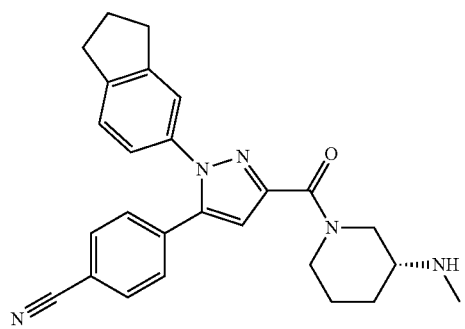 [SMILES: CN[C@@H]1CCCN(C(=O)c2cc(-c3ccc(C#N)cc3)n(-c3ccc4c(c3)CCC4)n2)C1]

1H-NMR (300 MHz, DMSO-d$_6$): δ 7.84 (d, 2H), 7.46 (d, 2H), 7.25 (d, 2H), 7.04 (s, 1H), 6.97 (d, 1H), 4.07 (m, 2H), 2.98 (m, 2H), 2.88 (q, 4H), 2.77 (m, 1H), 2.43 (m, 1H), 2.20 (d, 3H), 2.04 (m, 2H), 1.90 (m, 1H), 1.73 (m, 1H), 1.31 (m, 2H).

MS (ESI$^+$): [M+H]$^+$ m/z 426.2

Example 90: Preparation of (R)-4-(3-(3-aminopiperidine-1-carbonyl)-1-(2,3-dihydrobenzo[b][1,4]dioxin-6-yl)-1H-pyrazole-5-yl)benzonitrile A desired compound was obtained in substantially the same manner as in Example 1, except that (2,3-dihydrobenzo[b][1,4]dioxin-6-yl)hydrazine hydrochloride was used instead of (4-cyclopropylphenyl)hydrazine hydrochloride in Step 1) of Example 1.

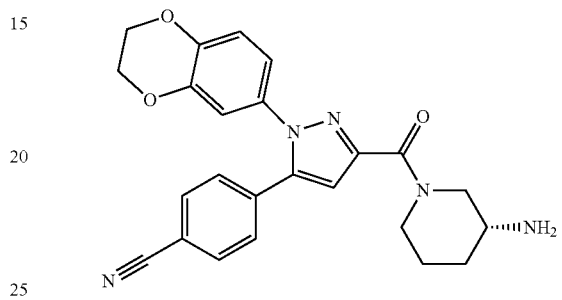

1H-NMR (300 MHz, CDCl$_3$): δ 7.61 (d, 2H), 7.36 (d, 2H), 6.95 (d, 1H), 6.83 (m, 2H), 6.87 (d, 1H), 4.44 (m, 2H), 4.28 (s, 4H), 3.28 (m, 2H), 2.98 (m, 1H), 1.91 (m, 2H), 1.34 (m, 2H).

MS (ESI$^+$): [M+H]$^+$ m/z 430.2

Example 91: Preparation of (R)-4-(3-(3-aminopiperidine-1-carbonyl)-1-(quinoline-6-yl)-1H-pyrazole-5-yl)benzonitrile A desired compound was obtained in substantially the same manner as in Example 1, except that 6-hydrazinylquinoline hydrochloride was used instead of in Step 1) of Example 1 (4-cyclopropylphenyl)hydrazine hydrochloride.

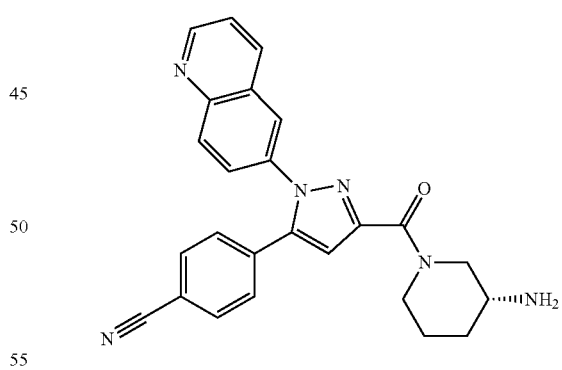

1H-NMR (300 MHz, CDCl$_3$): δ 8.99 (d, 1H), 8.11 (t, 2H), 7.75 (s, 1H), 7.60 (d, 3H), 7.48 (m, 1H), 7.37 (d, 2H), 7.03 (d, 1H), 4.51 (m, 2H), 3.21 (m, 2H), 2.98 (m, 1H), 1.84 (m, 2H), 1.67 (m, 2H).

MS (ESI$^+$): [M+H]$^+$ m/z 423.2

Example 92: Preparation of (R)-4-(3-(3-aminopiperidine-1-carbonyl)-1-(quinoline-3-yl)-1H-pyrazole-5-yl)benzonitrile A desired compound was obtained in substantially the same manner as in Example 1, except that 3-hydrazinylquinoline hydrochloride was used instead of in Step 1) of Example 1 (4-cyclopropylphenyl)hydrazine hydrochloride.

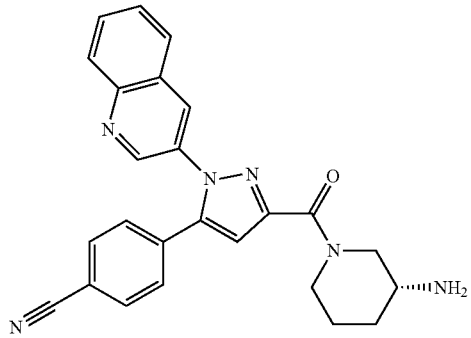 [SMILES: N#Cc1ccc(-c2cc(C(=O)N3CCC[C@@H](N)C3)nn2-c2cnc3ccccc3c2)cc1]

¹H-NMR (300 MHz, CDCl₃): δ 8.82 (s, 1H), 8.15 (d, 1H), 8.09 (s, 1H), 7.81 (t, 2H), 7.64 (t, 3H), 7.38 (d, 2H), 7.06 (s, 1H), 4.51 (m, 2H), 3.21 (m, 2H), 2.98 (m, 1H), 1.84 (m, 2H), 1.67 (m, 2H).

MS (ESI⁺): [M+H]⁺ m/z 423.2

Example 93: Preparation of (R)-4-(3-(3-aminopiperidine-1-carbonyl)-1-(1-methyl-1H-pyrrolo[2,3-b]pyridine-5-yl)-1H-pyrazole-5-yl)benzonitrile A desired compound was obtained in substantially the same manner as in Example 1, except that 5-hydrazinyl-1-methyl-1H-pyrrolo[2,3-b]pyridine hydrochloride was used instead of (4-cyclopropylphenyl)hydrazine hydrochloride in Step 1) of Example 1.

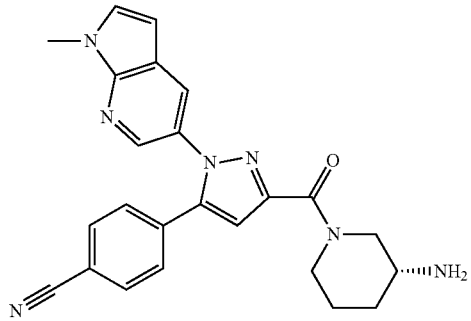 [SMILES: Cn1ccc2cc(-n3nc(C(=O)N4CCC[C@@H](N)C4)cc3-c3ccc(C#N)cc3)cnc21]

¹H-NMR (300 MHz, CDCl₃): δ 8.19 (d, 1H), 7.83 (s, 2H), 7.54 (d, 2H), 7.30 (m, 3H), 7.01 (s, 1H), 6.47 (s, 1H), 4.51 (m, 2H), 3.21 (m, 2H), 2.98 (m, 1H), 1.84 (m, 2H), 1.67 (m, 2H).

MS (ESI⁺): [M+H]⁺ m/z 426.2

Example 94: (R)-4-(3-(3-aminopiperidine-1-carbonyl)-1-(2-fluoro-4-(2-hydroxy-2-methylpropyl)phenyl)-1H-pyrazole-5-yl)-2-fluorobenzonitrile A desired compound was obtained in substantially the same manner as in Example 1, except that 1-(3-fluoro-4-hydrazinylphenol)-2-methylpropane-2-ol hydrochloride was used instead of (4-cyclopropylphenyl)hydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1.

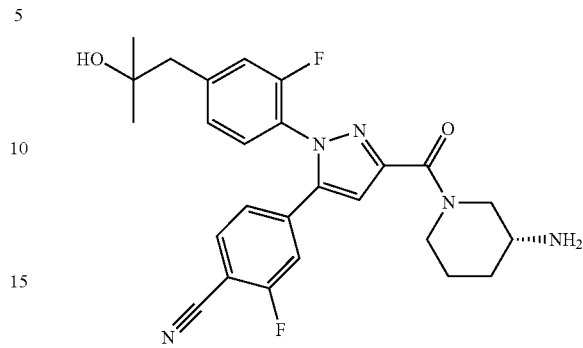

¹H-NMR (300 MHz, CDCl₃): δ 7.62 (t, 1H), 7.41 (t, 1H), 7.19 (m, 2H), 7.10 (m, 1H), 7.05 (m, 2H), 4.42 (m, 2H), 3.49 (m, 2H), 3.21 (m, 2H), 2.11 (m, 1H), 1.87 (m, 4H), 1.37 (s, 6H).

MS (ESI⁺): [M+H]⁺ m/z 480.2

Example 95: Preparation of 4-(3-(piperazine-1-carbonyl)-1-(p-tolyl)-1H-pyrazole-5-yl)benzonitrile A desired compound was obtained in substantially the same manner as in Example 1, except that (4-methylphenyl)hydrazine hydrochloride was used instead of (4-cyclopropylphenyl)hydrazine hydrochloride in Step 1) of Example 1, and tert-butyl piperazine-1-carboxylate was used instead of (R)-piperidine-3-ylcarbamate in Step 3) of Example 1.

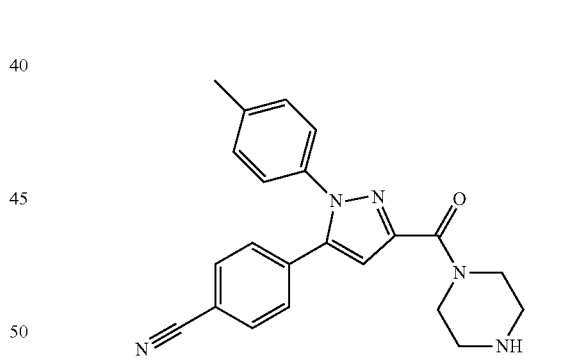

¹H-NMR (300 MHz, DMSO-d₆): 7.84 (d, 2H), 7.44 (d, 2H), 7.27 (m, 4H), 7.04 (s, 1H), 3.83 (m, 2H), 3.56 (m, 2H), 2.72 (m, 4H), 2.33 (s, 1H).

MS (ESI⁺): [M+H]⁺ m/z 372.2

Example 96: Preparation of 4-(3-(3-(aminomethyl)piperidine-1-carbonyl)-1-(p-tolyl)-1H-pyrazole-5-yl)benzonitrile A desired compound was obtained in substantially the same manner as in Example 1, except that (4-methylphenyl)hydrazine hydrochloride was used instead of (4-cyclopropylphenyl)hydrazine hydrochloride in Step 1) of Example 1, and tert-butyl (a piperidine-3-ylmethyl)carbamate was used instead of (R)-piperidine-3-ylcarbamate in Step 3) of Example 1.

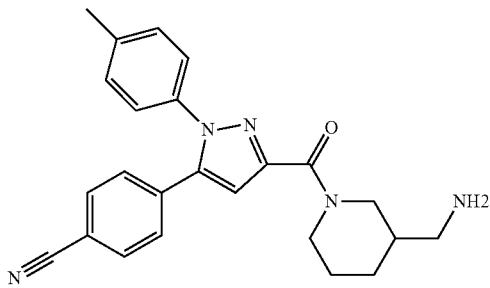 [SMILES: Cc1ccc(-n2nc(C(=O)N3CCCC(CN)C3)cc2-c2ccc(C#N)cc2)cc1]

¹H-NMR (300 MHz, DMSO-d₆): δ 7.84 (d, 2H), 7.44 (d, 2H), 7.27 (m, 4H), 7.02 (s, 1H), 4.49 (m, 2H), 3.21 (m, 1H), 3.00 (m, 1H), 2.69 (m, 1H), 2.41 (m, 1H), 2.35 (s, 3H), 1.83 (m, 4H), 1.45 (m, 2H), 1.34 (m, 1H).

MS (ESI⁺): [M+H]⁺ m/z 400.2

Example 97: Preparation of (S)-5-(4-cyanophenyl)-N-(1-(methylsulfonyl)piperidine-3-yl)-1-(p-tolyl)-1H-pyrazole-3-carboxamide A desired compound was obtained in substantially the same manner as in Example 1, except that (S)-1-(methylsulfonyl)piperidine-3-amine was used instead of tert-butyl (R)-piperidine-3-ylcarbamate in Step 3) of Example 1.

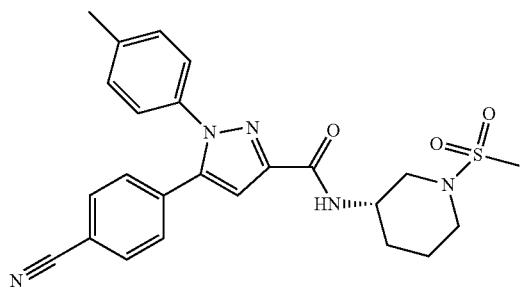 [SMILES: Cc1ccc(-n2nc(C(=O)N[C@H]3CCCN(S(C)(=O)=O)C3)cc2-c2ccc(C#N)cc2)cc1]

¹H-NMR (300 MHz, CDCl₃): δ 7.60 (d, 2H), 7.32 (d, 2H), 7.19 (m, 4H), 7.10 (s, 1H), 4.35 (m, 1H), 3.49 (m, 1H), 3.22 (m, 3H), 2.82 (s, 3H), 2.41 (s, 3H), 1.84 (m, 4H).

MS (ESI⁺): [M+H]⁺ m/z 464.2

Example 98: Preparation of 4-(3-(2,7-diazaspiro[3.5]nonane-7-carbonyl)-1-(p-tolyl)-1H-pyrazole-5-yl)benzonitrile A desired compound was obtained in substantially the same manner as in Example 1, except that tert-butyl 2,7-diazaspiro[3.5]nonane-2-carboxylate was used instead of tert-butyl (R)-piperidine-3-ylcarbamate in Step 3) of Example 1.

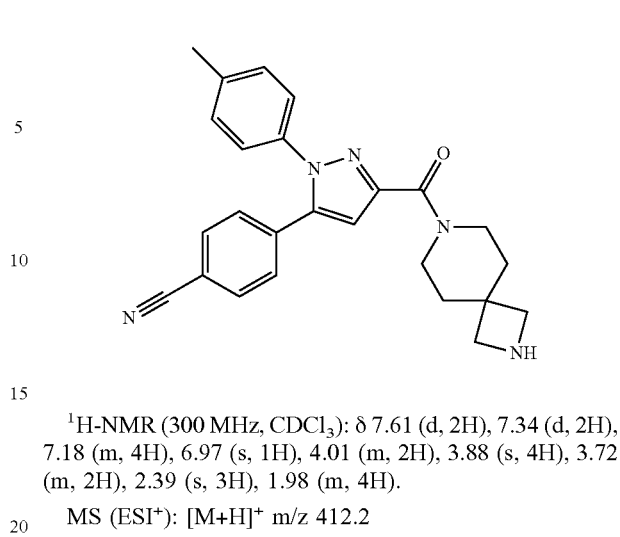

¹H-NMR (300 MHz, CDCl₃): δ 7.61 (d, 2H), 7.34 (d, 2H), 7.18 (m, 4H), 6.97 (s, 1H), 4.01 (m, 2H), 3.88 (s, 4H), 3.72 (m, 2H), 2.39 (s, 3H), 1.98 (m, 4H).

MS (ESI⁺): [M+H]⁺ m/z 412.2

Example 99: Preparation of 4-(3-(2,8-diazaspiro[4.5]decane-8-carbonyl)-1-(p-tolyl)-1H-pyrazole-5-yl)benzonitrile A desired compound was obtained in substantially the same manner as in Example 1, except that tert-butyl 2,8-diazaspiro[4.5]decane-2-carboxylate was used instead of tert-butyl (R)-piperidine-3-ylcarbamate in Step 3) of Example 1.

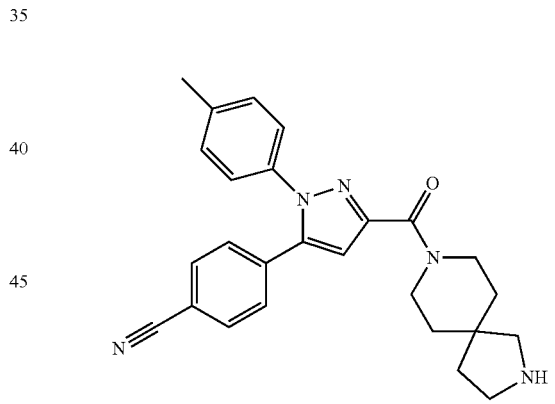

¹H-NMR (300 MHz, CDCl₃): δ 7.60 (d, 2H), 7.34 (d, 2H), 7.16 (m, 4H), 6.98 (s, 1H), 3.91 (m, 6H), 3.35 (m, 4H), 2.38 (s, 3H), 1.98 (m, 4H).

MS (ESI⁺): [M+H]⁺ m/z 426.2

Example 100: Preparation of 4-(3-(octahydro-1H-pyrrolo[2,3-c]pyridine-6-carbonyl)-1-(p-tolyl)-1H-pyrazole-5-yl)benzonitrile A desired compound was obtained in substantially the same manner as in Example 1, except that tert-butyl octahydro-1H-pyrrolo[2,3-c]pyridine-1-carboxylate was used instead of tert-butyl (R)-piperidine-3-ylcarbamate in Step 3) of Example 1.

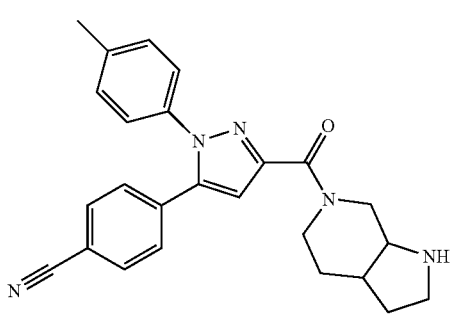 [SMILES: Cc1ccc(-n2nc(C(=O)N3CCC4CCNC4C3)cc2-c2ccc(C#N)cc2)cc1]

¹H-NMR (300 MHz, CDCl₃): δ 7.61 (t, 2H), 7.32 (t, 2H), 7.18 (m, 4H), 7.00 (s, 1H), 4.24 (m, 1H), 3.82 (m, 2H), 3.77 (m 2H), 3.49 (m, 3H), 2.4 (s, 3H) 1.84 (m, 5H)
MS (ESI⁺): [M+H]⁺ m/z 412.2

Example 101: Preparation of 4-(3-(3,7-diazabicyclo [3.3.1]nonane-3-carbonyl)-1-(2-fluoro-4-isopropylphenyl)-1H-pyrazole-5-yl)-2-fluorobenzonitrile A desired compound was obtained in substantially the same manner as in Example 1, except that (2-fluoro-4-isopropylphenyl)hydrazine hydrochloride was used instead of (4-cyclopropylphenyl)hydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1, and tert-butyl 3,7-diazabicyclo[3.3.1]nonane-3-carboxylate was used instead of tert-butyl (R)-piperidine-3-ylcarbamate in Step 3) of Example 1.

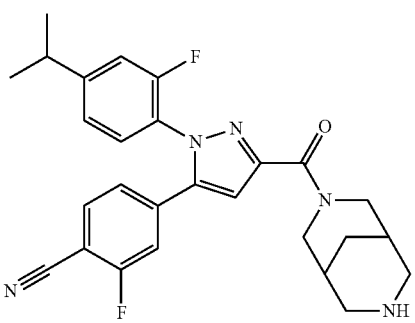 [SMILES: CC(C)c1ccc(-n2nc(C(=O)N3CC4CNCC(C4)C3)cc2-c2ccc(C#N)c(F)c2)c(F)c1]

¹H-NMR (300 MHz, CDCl₃): δ 7.59 (t, 1H), 7.37 (t, 1H), 7.15 (m, 1H), 7.06 (m, 2H), 6.99 (m, 2H), 4.80 (m, 2H), 3.35 (m, 4H), 3.02 (m, 2H), 2.93 (m, 1H), 2.05 (m, 2H), 1.85 (d, 2H), 1.29 (d, 6H).
MS (ESI⁺): [M+H]⁺ m/z 476.2

Example 102: Preparation of 4-(3-(3-amino-8-azabicyclo[3.2.1]octane-8-carbonyl)-1-(2-fluoro-4-isopropylphenyl)-1H-pyrazole-5-yl)-2-fluorobenzonitrile A desired compound was obtained in substantially the same manner as in Example 1, except that (2-fluoro-4-isopropylphenyl)hydrazine hydrochloride was used instead of (4-cyclopropylphenyl)hydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 1, and tert-butyl(8-azabicyclo[3.2.1]octane-3-yl)carbamate was used instead of tert-butyl (R)-piperidine-3-ylcarbamate in Step 3) of Example 1.

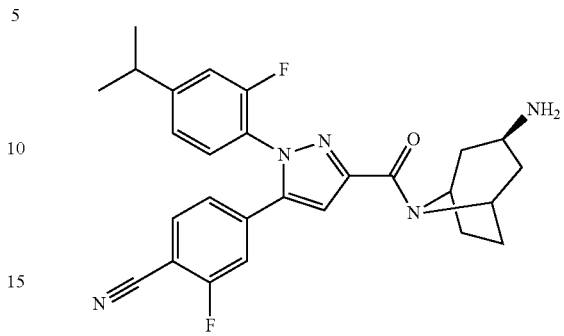

¹H-NMR (300 MHz, CDCl₃): δ 7.57 (t, 1H), 7.38 (t, 1H), 7.15 (m, 3H), 7.04 (m, 2H), 5.20 (m, 1H), 4.87 (m, 1H), 3.47 (m, 1H), 2.98 (m, 1H), 2.36 (m, 6H), 2.05 (m, 4H), 1.27 (d, 6H).
MS (ESI⁺): [M+H]⁺ m/z 476.2

Example 103: Preparation of 4-(3-(3-amino-8-azabicyclo[3.2.1]octane-8-carbonyl)-1-(2-fluoro-4-pyrrolidine-1-yl)phenyl)-1H-pyrazole-5-yl)-2-fluorobenzonitrile

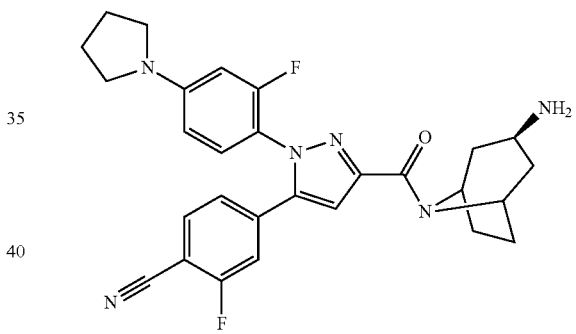

A desired compound was obtained in substantially the same manner as in Example 1, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, pyrrolidine was used instead of dimethylamine hydrochloride in Step 2) of Example 1, and tert-butyl(8-azabicyclo[3.2.1]octane-3-yl) carbamate was used instead of tert-butyl (R)-piperidine-3-ylcarbamate in Step 3) of Example 1.
¹H-NMR (300 MHz, CDCl₃): δ 7.57 (t, 1H), 7.12 (m, 3H), 7.01 (m, 1H), 6.21 (m, 1H), 6.17 (d, 1H), 4.85 (m, 1H), 4.46 (m, 2H), 3.31 (m, 4H), 2.87 (m, 1H), 2.43 (m, 3H), 2.05 (m, 6H), 1.57 (m, 2H).
MS (ESI⁺): [M+H]⁺ m/z 503.2

Example 104: Preparation of 4-(3-(3,7-diazabicyclo [3.3.1]nonane-3-carbonyl)-1-(p-tolyl)-1H-pyrazole-5-yl) benzonitrile A desired compound was obtained in substantially the same manner as in Example 1, except that tert-butylcyclo

[3.3.1]nonane-3-diazabi-carboxylate was used instead of tert-butyl (R)-piperidine-3-ylcarbamate in Step 3) of Example 1.

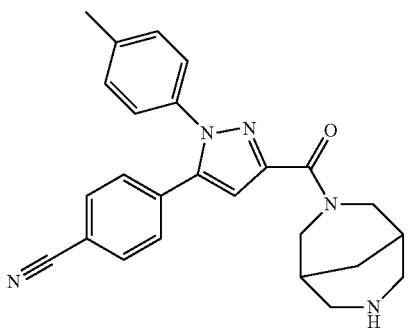 [SMILES: Cc1ccc(-n2nc(C(=O)N3CC4CNCC(C4)C3)cc2-c2ccc(C#N)cc2)cc1]

¹H-NMR (300 MHz, CDCl₃): δ 7.63 (d, 2H), 7.35 (t, 3H), 7.21 (m, 2H), 7.16 (m, 3H), 7.03 (s, 1H), 4.85 (d, 2H), 3.46 (m, 2H), 3.30 (m, 4H), 2.40 (s, 3H), 2.03 (m, 2H), 1.61 (m, 2H).
MS (ESI⁺): [M+H]⁺ m/z 412.2

Example 105: Preparation of 5-(4-cyanophenyl)-N-(piperidine-4-yl)-1-(p-tolyl)-1H-pyrazole-3-carboximide A desired compound was obtained in substantially the same manner as in Example 1, except that p-tolylhydrazine hydrochloride was used instead of (4-cyclopropylphenyl) hydrazine hydrochloride in Step 1) of Example 1, and tert-butyl 4-aminopiperidine-1-carboxylate was used instead of tert-butyl (R)-piperidine-3-ylcarbamate in Step 3) of Example 1.

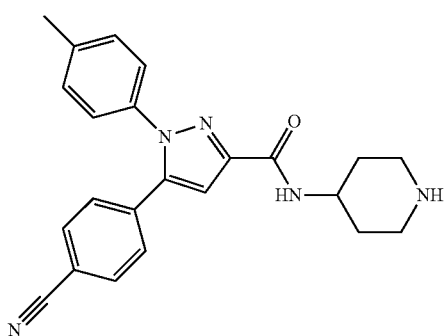 [SMILES: Cc1ccc(-n2nc(C(=O)NC3CCNCC3)cc2-c2ccc(C#N)cc2)cc1]

1H-NMR (300 MHz, DMSO-d₆): δ 8.44 (d, 1H), 7.84 (d, 2H), 7.43 (d, 2H), 7.26 (q, 4H), 7.18 (s, 1H), 4.05 (m, 1H), 3.26 (m, 2H), 2.94 (m, 2H), 2.35 (s, 3H), 1.90 (m, 2H), 1.73 (m, 2H), 1.23 (m, 1H).
MS (ESI⁺): [M+H]⁺ m/z 386.2

Example 106: Preparation of 5-(4-cyanophenyl)-N-(1-methylpiperidine-4-yl)-1-(p-tolyl)-1H-pyrazole-3-carboximide A desired compound was obtained in substantially the same manner as in Example 1, except that p-tolylhydrazine hydrochloride was used instead of (4-cyclopropylphenyl) hydrazine hydrochloride in Step 1) of Example 1, and 1-methylpiperidine-4-amine was used instead of tert-butyl (R)-piperidine-3-ylcarbamate in Step 3) of Example 1.

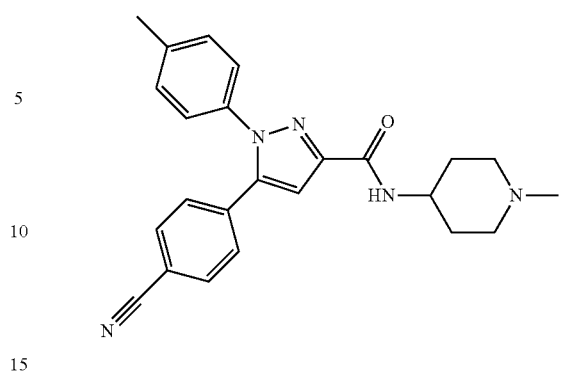

1H-NMR (300 MHz, DMSO-d₆): δ 7.97 (d, 1H), 7.84 (d, 2H), 7.44 (d, 2H), 7.25 (q, 4H), 7.16 (s, 1H), 3.97 (m, 1H), 2.60 (m, 2H), 2.35 (s, 3H), 2.15 (s, 3H), 2.00 (m, 2H), 1.63 (m, 2H), 1.42 (m, 2H).
MS (ESI⁺): [M+H]⁺ m/z 400.2

Example 107: Preparation of (R)-5-(4-cyanophenyl)-N-(1-methylpiperidine-3-yl)-1-(p-tolyl)-1H-pyrazole-3-carboximide

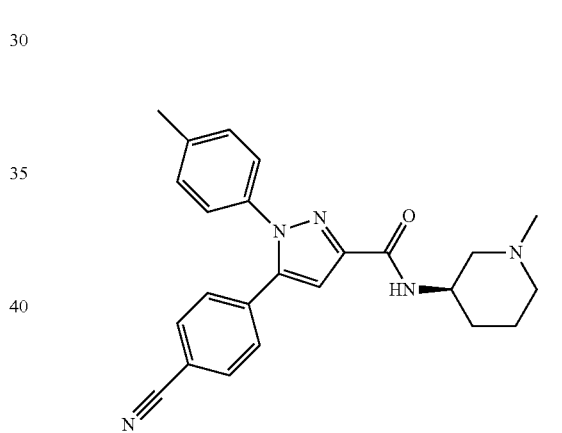

A desired compound was obtained in substantially the same manner as in Example 1, except that p-tolylhydrazine hydrochloride was used instead of (4-cyclopropylphenyl) hydrazine hydrochloride in Step 1) of Example 1, and (R)-1-methylpiperidine-3-amine was used instead of tert-butyl (R)-piperidine-3-ylcarbamate in Step 3) of Example 1.

1H-NMR (300 MHz, DMSO-d₆): δ 7.84 (d, 2H), 7.45 (d, 2H), 7.24 (q, 4H), 7.13 (s, 1H), 3.93 (m, 2H), 3.72 (m, 2H), 3.36 (m, 2H), 3.17 (m, 2H), 2.39 (s, 3H), 2.32 (d, 3H), 1.96 (m, 2H), 1.72 (m, 1H).
[M+H]⁺ m/z 400.2

Example 108: Preparation of (S)-5-(4-cyanophenyl)-N-(1-methylpiperidine-3-yl)-1-(p-tolyl)-1H-pyrazole-3-carboximide A desired compound was obtained in substantially the same manner as in Example 1, except that p-tolylhydrazine hydrochloride was used instead of (4-cyclopropylphenyl) hydrazine hydrochloride in Step 1) of Example 1, and (S)-1-methylpiperidine-3-amine was used instead of tert-butyl (R)-piperidine-3-ylcarbamate in Step 3) of Example 1.

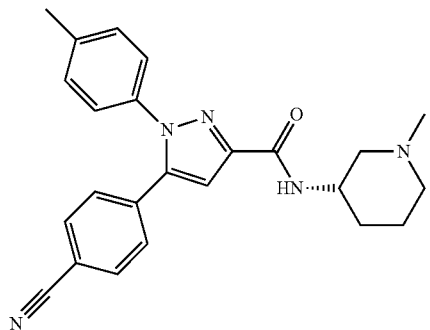

1H-NMR (300 MHz, DMSO-d₆): δ 8.14 (d, 1H), 7.84 (d, 2H), 7.43 (d, 2H), 7.26 (q, 4H), 7.15 (s, 1H), 3.68 (m, 1H), 2.73 (d, 2H), 2.34 (s, 3H), 2.15 (s, 3H), 1.94 (t, 2H), 1.60 (m, 4H).

MS (ESI⁺): [M+H]⁺ m/z 400.2

Example 109: Preparation of (R)-5-(4-cyanophenyl)-N-(1-methylpyrrolidine-3-yl)-1-(p-tolyl)-1H-pyrazole-3-carboximide A desired compound was obtained in substantially the same manner as in Example 1, except that p-tolylhydrazine hydrochloride was used instead of (4-cyclopropylphenyl) hydrazine hydrochloride in Step 1) of Example 1, and (R)-1-methylpyrrolidine-3-amine was used instead of tert-butyl (R)-piperidine-3-ylcarbamate in Step 3) of Example 1.

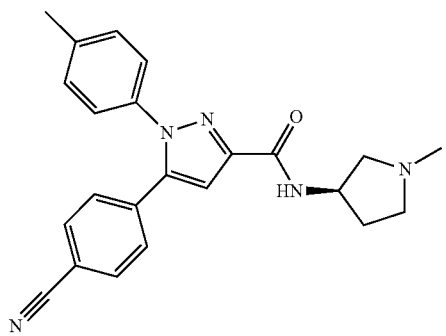 [SMILES: Cc1ccc(-n2nc(C(=O)N[C@@H]3CCN(C)C3)cc2-c2ccc(C#N)cc2)cc1]

1H-NMR (300 MHz, DMSO-d₆): 8.19 (d, 1H), 7.84 (d, 2H), 7.44 (d, 2H), 7.26 (q, 4H), 7.16 (s, 1H), 4.39 (m, 1H), 2.59 (m, 2H), 2.37 (m, 2H), 2.34 (s, 3H), 2.24 (s, 3H), 2.13 (m, 1H), 1.75 (m, 1H).

MS (ESI⁺): [M+H]⁺ m/z 386.2

Example 110: Preparation of 5-(4-cyano-3-fluorophenyl)-1-(2-fluoro-4-(pyrrolidine-1-yl)phenyl)-N-methyl-N-(piperidine-3-yl)-1H-pyrazole-3-carboximide

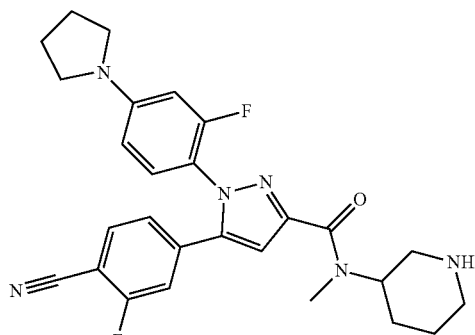

A desired compound was obtained in substantially the same manner as in Example 1, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, pyrrolidine was used instead of dimethylamine hydrochloride in Step 2) of Example 51, and tert-butyl 3-(methylamino)piperidine-1-carboxylate was used instead of tert-butyl (R)-piperidine-3-ylcarbamate in Step 3) of Example 51.

¹H-NMR (300 MHz, CDCl₃): δ 7.57 (m, 1H), 7.12 (m, 3H), 6.95 (m, 1H), 6.33 (m, 1H), 6.16 (m, 1H), 4.59 (m, 1H), 3.29 (m, 6H), 3.17 (m, 2H), 2.86 (m, 3H), 2.04 (m, 4H), 1.60 (m, 4H).

MS (ESI⁺): [M+H]⁺ m/z 491.2

Example 111: Preparation of (S)-5-(4-cyano-3-fluorophenyl)-1-(2-fluoro-4-(pyrrolidine-1-yl)phenyl)-N-methyl-N-(piperidine-3-yl)-1H-pyrazole-3-carboximide A desired compound was obtained in substantially the same manner as in Example 1, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, pyrrolidine was used instead of dimethylamine hydrochloride in Step 2) of Example 51, and tert-butyl (S)-3-(methylamino)piperidine-1-carboxylate was used instead of tert-butyl (R)-piperidine-3-ylcarbamate in Step 3) of Example 51.

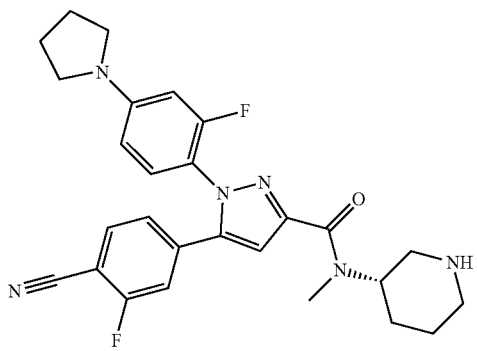 [SMILES: CN(C(=O)c1cc(-c2ccc(C#N)c(F)c2)n(-c2ccc(N3CCCC3)cc2F)n1)[C@H]1CCCNC1]

¹H-NMR (300 MHz, CDCl₃): δ 7.57 (m, 1H), 7.18 (m, 4H), 6.30 (m, 1H), 6.16 (m, 1H), 4.56 (m, 1H), 3.29 (m, 6H), 2.85 (m, 4H), 2.54 (m, 1H), 2.04 (m, 4H), 1.77 (m, 3H), 1.57 (m, 1H).
MS (ESI⁺): [M+H]⁺ m/z 491.2

Example 112: Preparation of (R)-5-(4-cyano-3-fluorophenyl)-1-(2-fluoro-4-(pyrrolidine-1-yl)phenyl)-N-methyl-N-(piperidine-3-yl)-1H-pyrazole-3-carboximide

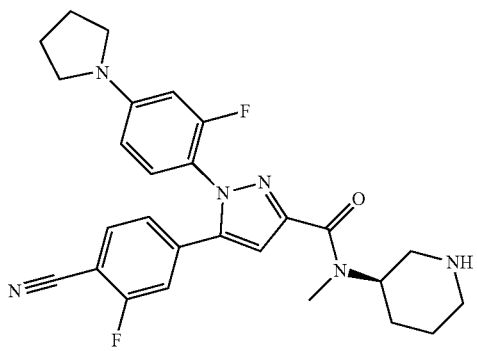 [SMILES: CN(C(=O)c1cc(-c2ccc(C#N)c(F)c2)n(-c2ccc(N3CCCC3)cc2F)n1)[C@@H]1CCCNC1]

A desired compound was obtained in substantially the same manner as in Example 1, except that (2-fluoro-4-iodophenyl)hydrazine hydrochloride was used instead of 4-iodophenylhydrazine hydrochloride, and ethyl (Z)-4-(4-cyano-3-fluorophenyl)-2-hydroxy-4-oxobut-2-enolate was used instead of ethyl (Z)-4-(4-cyanophenyl)-2-hydroxy-4-oxobut-2-enolate in Step 1) of Example 51, pyrrolidine was used instead of dimethylamine hydrochloride in Step 2) of Example 51, and tert-butyl (R)-3-(methylamino)piperidine-1-carboxylate was used instead of tert-butyl (R)-piperidine-3-ylcarbamate in Step 3) of Example 51.

¹H-NMR (300 MHz, CDCl₃): δ 7.45 (m, 1H), 7.08 (m, 4H), 6.11 (m, 1H), 6.07 (m, 1H), 4.78 (m, 1H), 3.50 (m, 8H), 2.19 (s, 3H), 1.60 (m, 8H).
MS (ESI⁺): [M+H]⁺ m/z 491.2

Example 113: Preparation of (R)-4-(3-(3-aminopiperidine-1-carbonyl)-1-(4-cyclopropyl-2-fluorophenyl)-4-methyl-1H-pyrazole-5-yl)benzonitrile A desired compound was obtained in substantially the same manner as in Example 1, except that (4-cyclo-2-fluorophenyl)hydrazine hydrochloride was used instead of 4-cyclopropylphenylhydrazine hydrochloride, and ethyl (Z)-4-(4-cyanophenyl)-2-hydroxy-3-methyl-4-oxobut-2-enolate was used instead of ethyl (Z)-4-(4-cyanophenyl)-2-hydroxy-4-oxobut-2-enolate in Step 1) of Example 1.

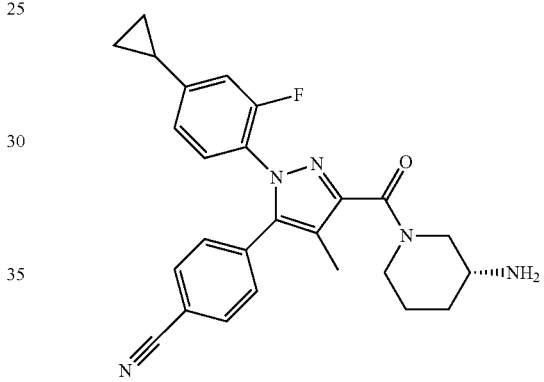

¹H-NMR (300 MHz, CDCl₃): δ 7.63 (t, 2H), 7.29 (t, 2H), 7.22 (m, 3H), 6.91 (d, 1H), 6.71 (d, 1H), 4.53 (m, 1H), 4.12 (d, 1H), 3.01 (m, 1H), 2.22 (s, 3H), 2.01 (m, 1H), 1.86 (m, 2H), 1.06 (m, 2H), 0.72 (m, 2H).
MS (ESI⁺): [M+H]⁺ m/z 444.2

The structure of each compound obtained in Examples 1 to 113 are shown in Table 1.

TABLE 1

| Example | Name | Structure |
|---|---|---|
| 1 | (R)-4-(3-(3-aminopiperidine-1-carbonyl)-1-(4-cyclopropylphenyl)-1H-pyrazole-5-yl)benzonitrile | 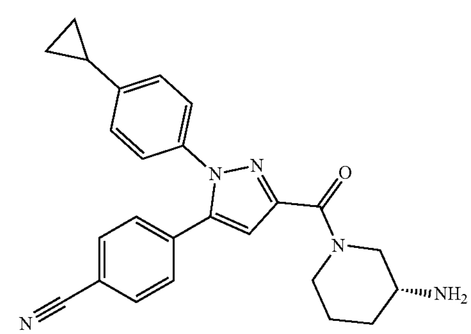 [SMILES: N#Cc1ccc(-c2cc(C(=O)N3CCC[C@@H](N)C3)nn2-c2ccc(C3CC3)cc2)cc1] |

TABLE 1-continued

| Example | Name | Structure |
|---------|------|-----------|
| 2 | (R)-4-(1-(4-cyclopropylphenyl)-3-(3-methylaminopiperidine-1-carbonyl)-1H-pyrazole-5-yl)benzonitrile | 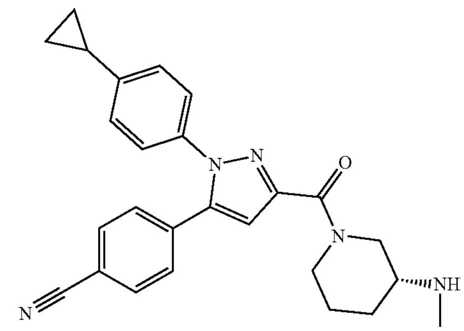 [SMILES: CN[C@@H]1CCCN(C(=O)c2cc(-c3ccc(C#N)cc3)n(-c3ccc(C4CC4)cc3)n2)C1] |
| 3 | (R)-4-(3-(3-aminopiperidine-1-carbonyl)-1-(4-cyclopropyl-2-fluorophenyl)-1H-pyrazole-5-yl)benzonitrile | 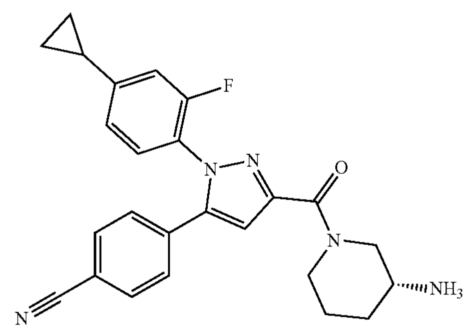 [SMILES: N#Cc1ccc(-c2cc(C(=O)N3CCC[C@@H](N)C3)nn2-c2ccc(C3CC3)cc2F)cc1] |
| 4 | (R)-4-(1-(4-cyclopropyl-2-fluorophenyl)-3-(3-(methylamino)piperidine-1-carbonyl)-1H-pyrazole-5-yl)benzonitrile | 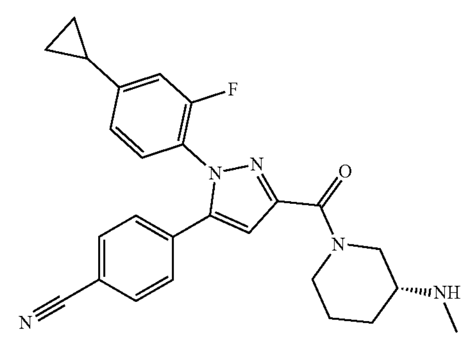 [SMILES: CN[C@@H]1CCCN(C(=O)c2cc(-c3ccc(C#N)cc3)n(-c3ccc(C4CC4)cc3F)n2)C1] |
| 5 | (R)-4-(3-(3-aminopiperidine-1-carbonyl)-1-(4-cyclopropyl-2-fluorophenyl)-1H-pyrazole-5-yl)-2-fluorobenzonitrile | 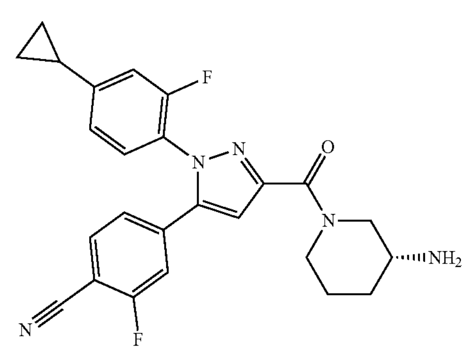 [SMILES: N#Cc1ccc(-c2cc(C(=O)N3CCC[C@@H](N)C3)nn2-c2ccc(C3CC3)cc2F)cc1F] |

TABLE 1-continued

| Example | Name | Structure |
|---|---|---|
| 6 | (R)-4-(1-(4-cyclopropyl-2-fluorophenyl)-3-(3-(methylamino)piperidine-1-carbonyl)-1H-pyrazole-5-yl)-2-fluorobenzonitrile | 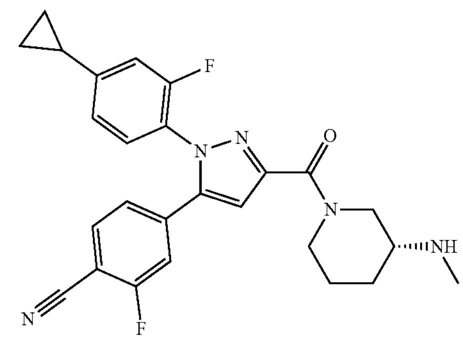 [SMILES: CN[C@@H]1CCCN(C(=O)c2cc(-c3ccc(C#N)c(F)c3)n(-c3ccc(C4CC4)cc3F)n2)C1] |
| 7 | (R)-4-(3-(3-aminoazepane-1-carbonyl)-1-(4-(cyclopropylphenyl)-1H-pyrazole-5-yl)benzonitrile | 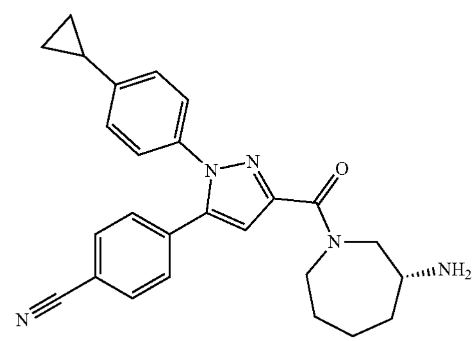 [SMILES: N#Cc1ccc(-c2cc(C(=O)N3CCCC[C@@H](N)C3)nn2-c2ccc(C3CC3)cc2)cc1] |
| 8 | (R)-4-(3-(3-aminoazepane-1-carbonyl)-1-(4-cyclopropyl-2-fluorophenyl)-1H-pyrazole-5-yl)-2-fluorobenzonitrile | 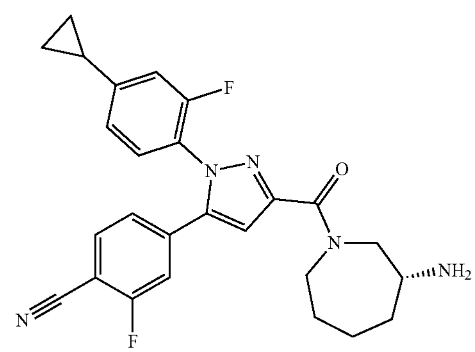 [SMILES: N#Cc1ccc(-c2cc(C(=O)N3CCCC[C@@H](N)C3)nn2-c2ccc(C3CC3)cc2F)cc1F] |
| 9 | 4-(3-((3R,5R)-3-amino-5-methylpiperidine-1-carbonyl)-1-(4-cyclopropyl-2-fluorophenyl)-1H-pyrazole-5-yl)-2-fluorobenzonitrile | 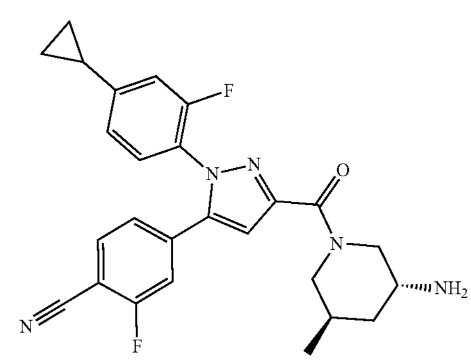 [SMILES: C[C@@H]1C[C@@H](N)CN(C(=O)c2cc(-c3ccc(C#N)c(F)c3)n(-c3ccc(C4CC4)cc3F)n2)C1] |

TABLE 1-continued

| Example | Name | Structure |
|---|---|---|
| 10 | (R)-4-(3-(3-aminopiperidine-1-carbonyl)-1-(4-cyclopropyl-2,6-difluorophenyl)-1H-pyrazole-5-yl)-2-fluorobenzonitrile | 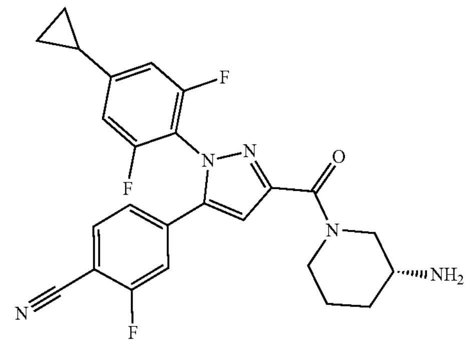 [SMILES: N#Cc1ccc(-c2cc(C(=O)N3CCC[C@@H](N)C3)nn2-c2c(F)cc(C3CC3)cc2F)cc1F] |
| 11 | (R)-4-(3-(3-aminoazepane-1-carbonyl)-1-(4-cyclopropyl-2,6-difluorophenyl)-1H-pyrazole-5-yl)-2-fluorobenzonitrile | 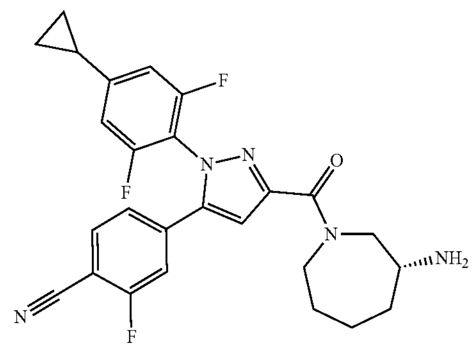 [SMILES: N#Cc1ccc(-c2cc(C(=O)N3CCCC[C@@H](N)C3)nn2-c2c(F)cc(C3CC3)cc2F)cc1F] |
| 12 | (R)-4-(3-(3-aminopiperidine-1-carbonyl)-1-(2-chloro-4-cyclopropylphenyl)-1H-pyrazole-5-yl)-2-fluorobenzonitrile | 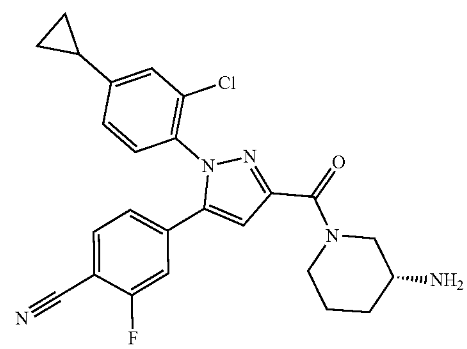 [SMILES: N#Cc1ccc(-c2cc(C(=O)N3CCC[C@@H](N)C3)nn2-c2ccc(C3CC3)cc2Cl)cc1F] |
| 13 | (R)-4-(3-(3-aminoazepane-1-carbonyl)-1-(2-chloro-4-cyclopropylphenyl)-1H-pyrazole-5-yl)-2-fluorobenzonitrile | 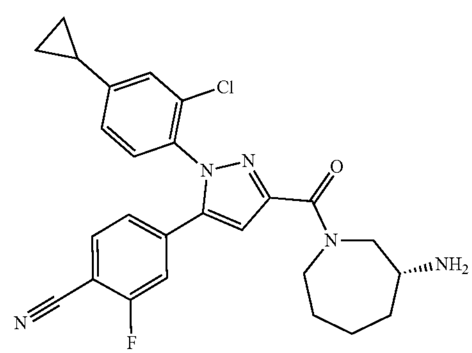 [SMILES: N#Cc1ccc(-c2cc(C(=O)N3CCCC[C@@H](N)C3)nn2-c2ccc(C3CC3)cc2Cl)cc1F] |

TABLE 1-continued

| Example | Name | Structure |
|---|---|---|
| 14 | (R)-4-(3-(3-aminopiperidine-1-carbonyl)-1-phenyl-1H-pyrazole-5-yl)benzonitrile | 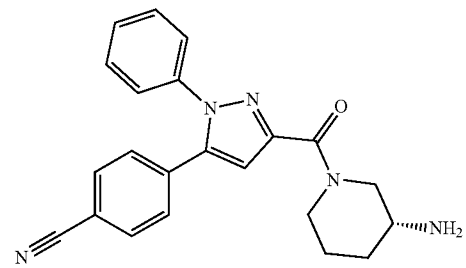 [SMILES: N#Cc1ccc(-c2cc(C(=O)N3CCC[C@@H](N)C3)nn2-c2ccccc2)cc1] |
| 15 | (R)-4-(3-(3-aminopiperidine-1-carbonyl)-1-(pyridine-2-yl)-1H-pyrazole-5-yl)benzonitrile | 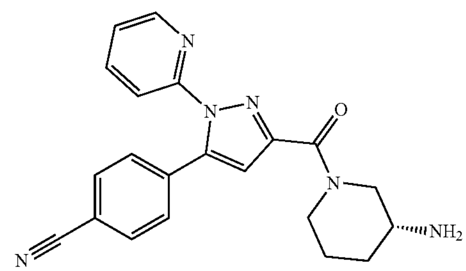 [SMILES: N#Cc1ccc(-c2cc(C(=O)N3CCC[C@@H](N)C3)nn2-c2ccccn2)cc1] |
| 16 | (R)-4-(3-(3-aminopiperidine-1-carbonyl)-1-(4-fluorophenyl)-1H-pyrazole-5-yl)benzonitrile | 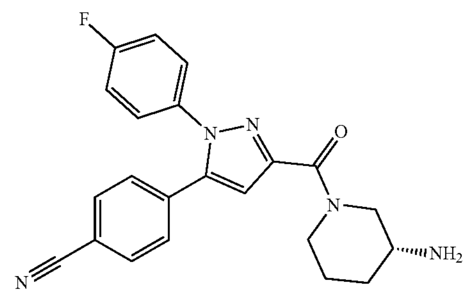 [SMILES: N#Cc1ccc(-c2cc(C(=O)N3CCC[C@@H](N)C3)nn2-c2ccc(F)cc2)cc1] |
| 17 | (R)-4-(3-(3-aminopiperidine-1-carbonyl)-1-(4-chlorophenyl)-1H-pyrazole-5-yl)benzonitrile | 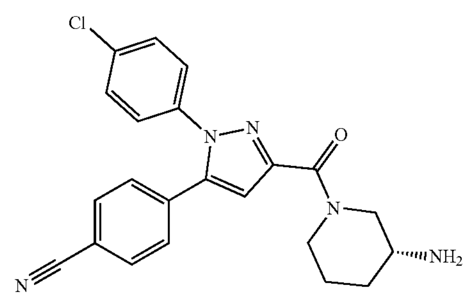 [SMILES: N#Cc1ccc(-c2cc(C(=O)N3CCC[C@@H](N)C3)nn2-c2ccc(Cl)cc2)cc1] |
| 18 | (R)-4-(1-(4-chlorophenyl)-3-(3-(methylamino)piperidine-1-carbonyl)-1H-pyrazole-5-yl)benzonitrile | 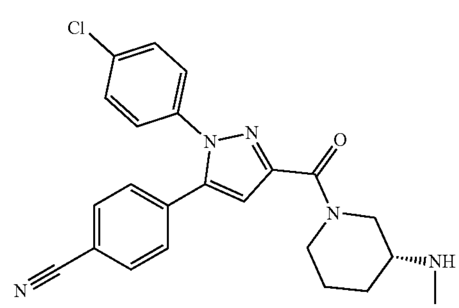 [SMILES: CN[C@@H]1CCCN(C(=O)c2cc(-c3ccc(C#N)cc3)n(-c3ccc(Cl)cc3)n2)C1] |

TABLE 1-continued

| Example | Name | Structure |
|---|---|---|
| 19 | (R)-4-(3-(3-aminopiperidine-1-carbonyl)-1-(3-chlorophenyl)-1H-pyrazole-5-yl)benzonitrile | 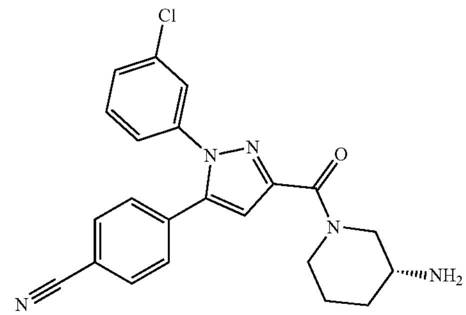 [SMILES: N#Cc1ccc(-c2cc(C(=O)N3CCC[C@@H](N)C3)nn2-c2cccc(Cl)c2)cc1] |
| 20 | (R)-4-(3-(3-aminopiperidine-1-carbonyl)-1-(4-bromophenyl)-1H-pyrazole-5-yl)benzonitrile | 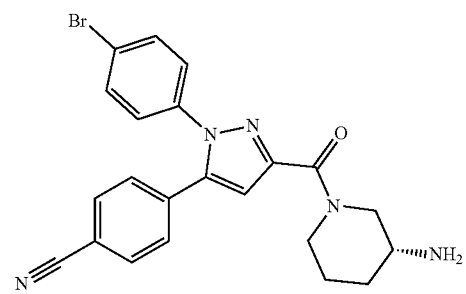 |
| 21 | (R)-4-(1-(4-bromophenyl)-3-(3-(methylamino)piperidine-1-carbonyl)-1H-pyrazole-5-yl)benzonitrile | 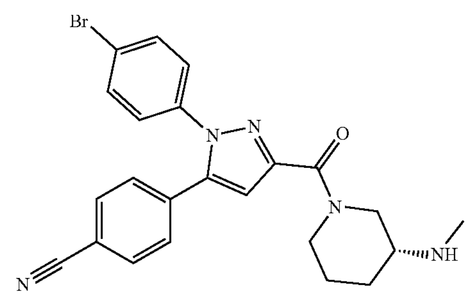 [SMILES: CN[C@@H]1CCCN(C(=O)c2cc(-c3ccc(C#N)cc3)n(-c3ccc(Br)cc3)n2)C1] |
| 22 | (S)-4-(3-(3-aminopyrrolidine-1-carbonyl)-1-(p-tolyl)-1H-pyrazole-5-yl)benzonitrile | 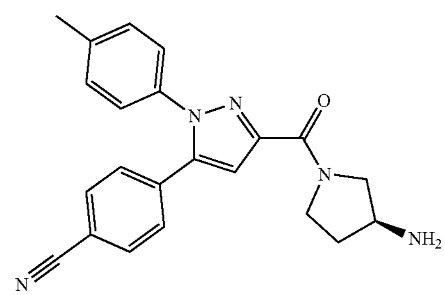 [SMILES: Cc1ccc(-n2nc(C(=O)N3CC[C@H](N)C3)cc2-c2ccc(C#N)cc2)cc1] |
| 23 | (S)-4-(3-(3-(methylamino)pyrrolidine-1-carbonyl)-1-(p-tolyl)-1H-pyrazole-5-yl)benzonitrile | 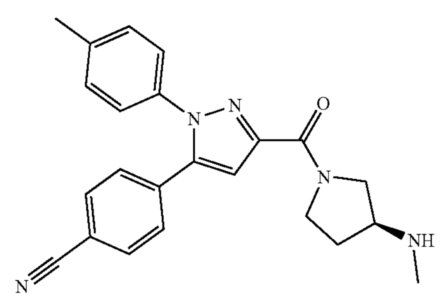 [SMILES: CN[C@H]1CCN(C(=O)c2cc(-c3ccc(C#N)cc3)n(-c3ccc(C)cc3)n2)C1] |

TABLE 1-continued

| Example | Name | Structure |
|---|---|---|
| 24 | (S)-4-(3-(3-(dimethylamino)pyrrolidine-1-carbonyl)-1-(p-tolyl)-1H-pyrazole-5-yl)benzonitrile | 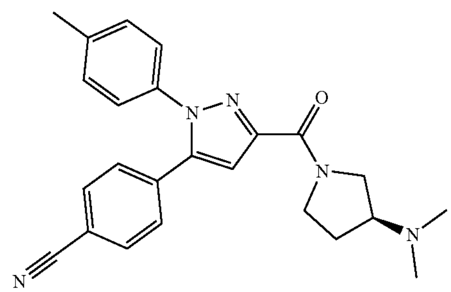 [SMILES: Cc1ccc(-n2nc(C(=O)N3CC[C@H](N(C)C)C3)cc2-c2ccc(C#N)cc2)cc1] |
| 25 | (R)-4-(3-(3-(dimethylamino)pyrrolidine-1-carbonyl)-1-(p-tolyl)-1H-pyrazole-5-yl)benzonitrile | 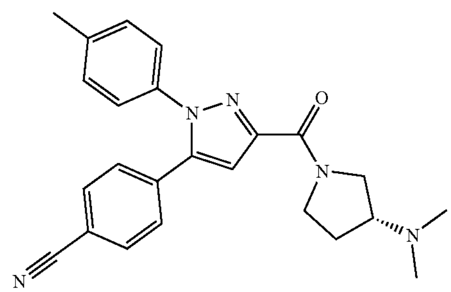 [SMILES: Cc1ccc(-n2nc(C(=O)N3CC[C@@H](N(C)C)C3)cc2-c2ccc(C#N)cc2)cc1] |
| 26 | (R)-4-(3-(3-(methylamino)pyrrolidine-1-carbonyl)-1-(p-tolyl)-1H-pyrazole-5-yl)benzonitrile | 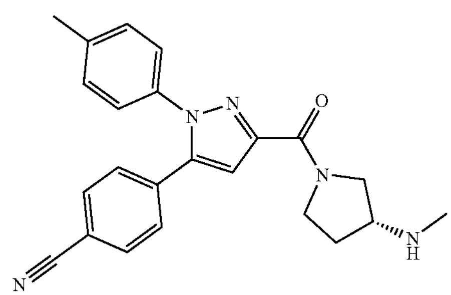 [SMILES: CN[C@@H]1CCN(C(=O)c2cc(-c3ccc(C#N)cc3)n(-c3ccc(C)cc3)n2)C1] |
| 27 | (R)-4-(3-(3-aminopyrrolidine-1-carbonyl)-1-(p-tolyl)-1H-pyrazole-5-yl)benzonitrile | 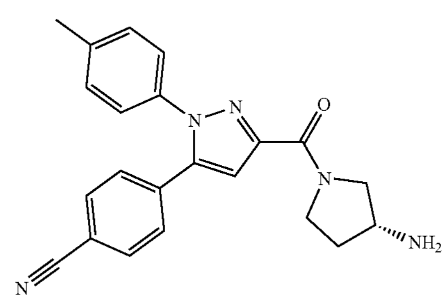 [SMILES: Cc1ccc(-n2nc(C(=O)N3CC[C@@H](N)C3)cc2-c2ccc(C#N)cc2)cc1] |
| 28 | (R)-4-(3-(3-aminopiperidine-1-carbonyl)-1-(p-tolyl)-1H-pyrazole-5-yl)benzonitrile | 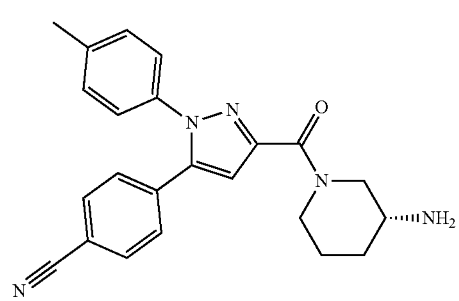 [SMILES: Cc1ccc(-n2nc(C(=O)N3CCC[C@@H](N)C3)cc2-c2ccc(C#N)cc2)cc1] |

TABLE 1-continued

| Example | Name | Structure |
|---|---|---|
| 29 | (R)-4-(3-(3-(methylamino)piperidine-1-carbonyl)-1-(p-tolyl)-1H-pyrazole-5-yl)benzonitrile | 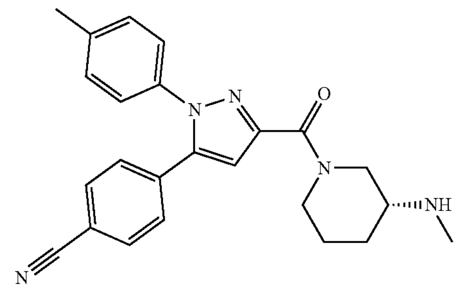 [SMILES: CN[C@@H]1CCCN(C(=O)c2cc(-c3ccc(C#N)cc3)n(-c3ccc(C)cc3)n2)C1] |
| 30 | (R)-4-(3-(3-(dimethylamino)piperidine-1-carbonyl)-1-(p-tolyl)-1H-pyrazole-5-yl)benzonitrile | 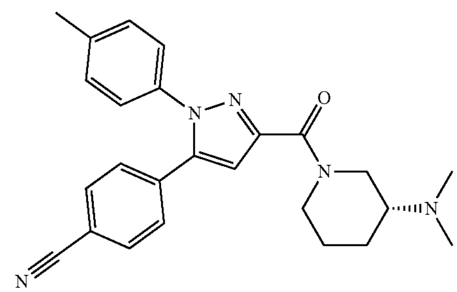 [SMILES: Cc1ccc(-n2nc(C(=O)N3CCC[C@@H](N(C)C)C3)cc2-c2ccc(C#N)cc2)cc1] |
| 31 | (R)-4-(3-(3-aminopiperidine-1-carbonyl)-1-(m-tolyl)-1H-pyrazole-5-yl)benzonitrile | 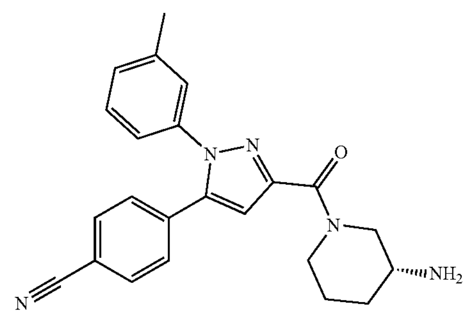 [SMILES: Cc1cccc(-n2nc(C(=O)N3CCC[C@@H](N)C3)cc2-c2ccc(C#N)cc2)c1] |
| 32 | (R)-4-(3-(3-aminopiperidine-1-carbonyl)-1-(o-tolyl)-1H-pyrazole-5-yl)benzonitrile | 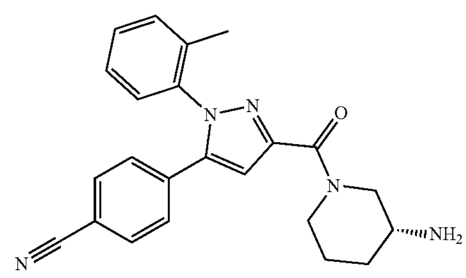 [SMILES: Cc1ccccc1-n1nc(C(=O)N2CCC[C@@H](N)C2)cc1-c1ccc(C#N)cc1] |
| 33 | (R)-4-(3-(3-aminopiperidine-1-carbonyl)-1-(4-ethylphenyl)-1H-pyrazole-5-yl)benzonitrile | 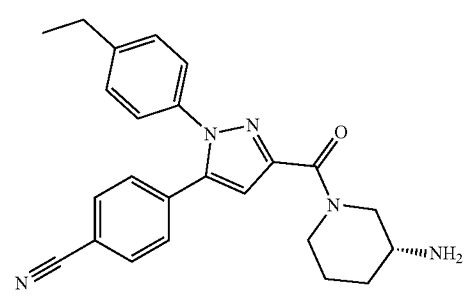 [SMILES: CCc1ccc(-n2nc(C(=O)N3CCC[C@@H](N)C3)cc2-c2ccc(C#N)cc2)cc1] |

TABLE 1-continued

| Example | Name | Structure |
|---|---|---|
| 34 | (R)-4-(1-(4-ethylphenyl)-3-(3-(methyl-amino)piperidine-1-carbonyl)-1H-pyrazole-5-yl)benzonitrile | 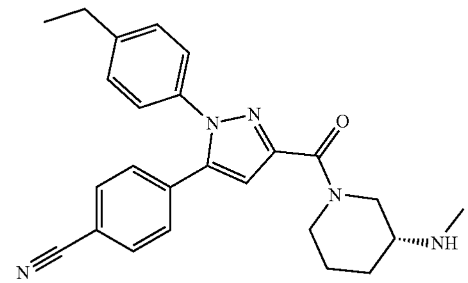 [SMILES: CCc1ccc(-n2nc(C(=O)N3CCC[C@@H](NC)C3)cc2-c2ccc(C#N)cc2)cc1] |
| 35 | (R)-4-(3-(3-aminopiperidine-1-carbonyl)-1-(4-isopropylphenyl)-1H-pyrazole-5-yl)benzonitrile | 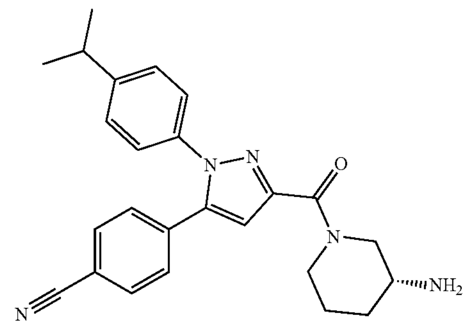 [SMILES: CC(C)c1ccc(-n2nc(C(=O)N3CCC[C@@H](N)C3)cc2-c2ccc(C#N)cc2)cc1] |
| 36 | (R)-4-(1-(4-isopropylphenyl)-3-(3-(methylamino)piperidine-1-carbonyl)-1H-pyrazole-5-yl)benzonitrile | 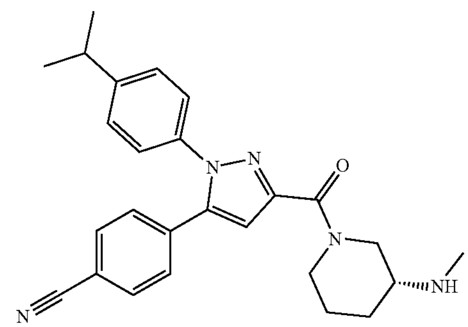 [SMILES: CN[C@@H]1CCCN(C(=O)c2cc(-c3ccc(C#N)cc3)n(-c3ccc(C(C)C)cc3)n2)C1] |
| 37 | (R)-4-(3-(3-aminopiperidine-1-carbonyl)-1-(2-fluoro-4-isopropylphenyl)-1H-pyrazole-5-yl)benzonitrile | 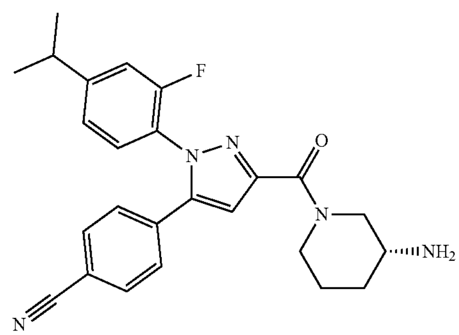 [SMILES: CC(C)c1ccc(-n2nc(C(=O)N3CCC[C@@H](N)C3)cc2-c2ccc(C#N)cc2)c(F)c1] |
| 38 | (R)-4-(3-(3-aminopiperidine-1-carbonyl)-1-(2-fluoro-4-isopropylphenyl)-1H-pyrazole-5-yl)-2-fluorobenzonitrile | 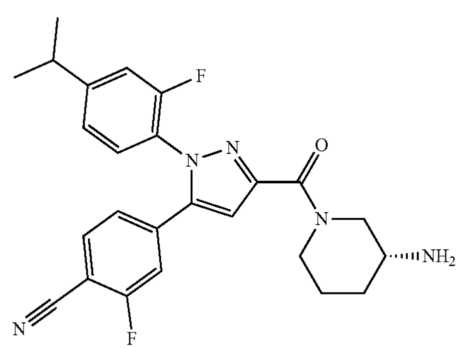 [SMILES: CC(C)c1ccc(-n2nc(C(=O)N3CCC[C@@H](N)C3)cc2-c2ccc(C#N)c(F)c2)c(F)c1] |

TABLE 1-continued

| Example | Name | Structure |
|---|---|---|
| 39 | (R)-4-(3-(3-aminoazepane-1-carbonyl)-1-(2-fluoro-4-isopropylphenyl)-1H-pyrazole-5-yl)-2-fluorobenzonitrile | 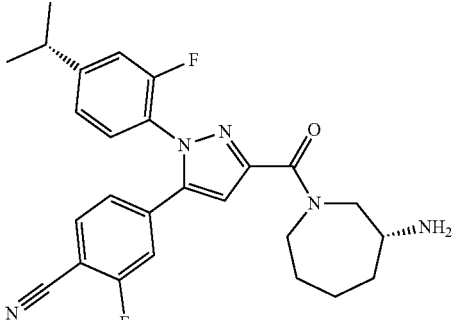 |
| 40 | (R)-4-(3-(3-aminopiperidine-1-carbonyl)-1-(4-(tert-butyl)phenyl)-1H-pyrazole-5-yl)benzonitrile | 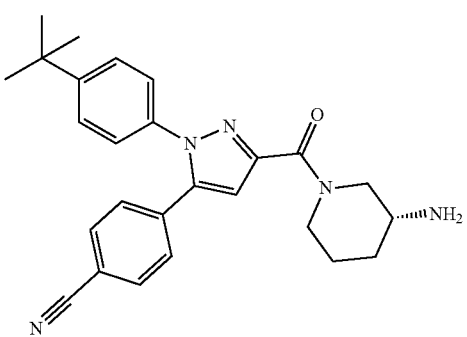 [SMILES: CC(C)(C)c1ccc(-n2nc(C(=O)N3CCC[C@@H](N)C3)cc2-c2ccc(C#N)cc2)cc1] |
| 41 | (R)-4-(1-(4-(tert-butyl)phenyl-3-(3-methyl-aminopiperidine-1-carbonyl)-1H-pyrazole-5-yl)benzonitrile | 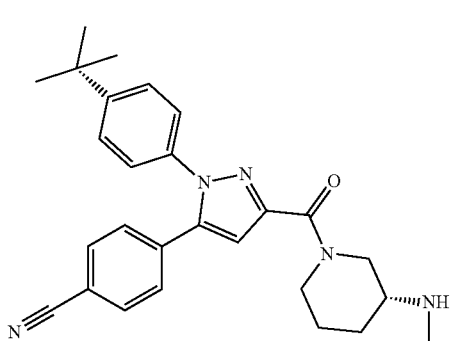 |
| 42 | (R)-4-(3-(3-aminopiperidine-1-carbonyl)-1-(4-(tert-butyl)-2-fluorophenyl)-1H-pyrazole-5-yl)benzonitrile | 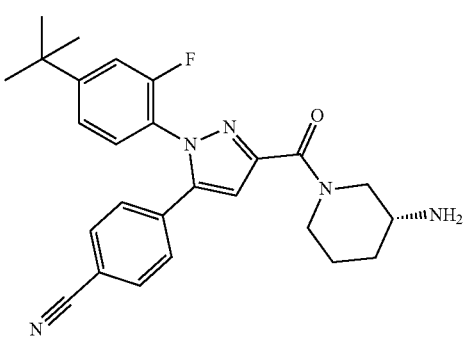 [SMILES: CC(C)(C)c1ccc(-n2nc(C(=O)N3CCC[C@@H](N)C3)cc2-c2ccc(C#N)cc2)c(F)c1] |

TABLE 1-continued

| Example | Name | Structure |
|---|---|---|
| 43 | (R)-4-(3-(3-aminopiperidine-1-carbonyl)-1-(4-(tert-butyl-2-fluorophenyl)-1H-pyrazole-5-yl)-2-fluorobenzonitrile | 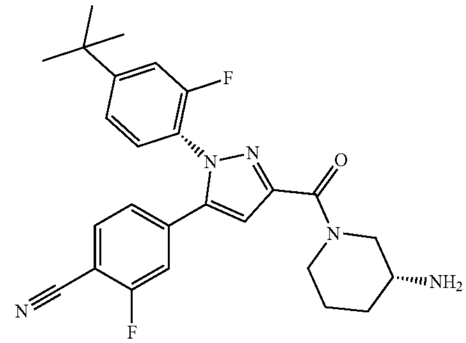 |
| 44 | (R)-4-(3-(3-aminoazepane-1-carbonyl)-1-(4-(tert-butyl-2-fluorophenyl)-1H-pyrazole-5-yl)-2-fluorobenzonitrile | 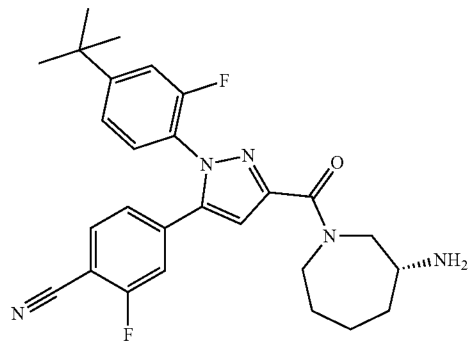 [SMILES: CC(C)(C)c1ccc(-n2nc(C(=O)N3CCCC[C@@H](N)C3)cc2-c2ccc(C#N)c(F)c2)c(F)c1] |
| 45 | (R)-4-(3-(3-aminopiperidine-1-carbonyl)-1-(4-(trifluoromethoxy)phenyl)-1H-pyrazole-5-yl)benzonitrile | 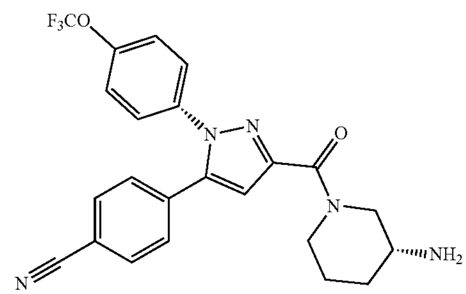 |
| 46 | (R)-4-(3-(3-aminopiperidine-1-carbonyl)-1-(4-(methylsulfonyl)phenyl)-1H-pyrazole-5-yl)benzonitrile | 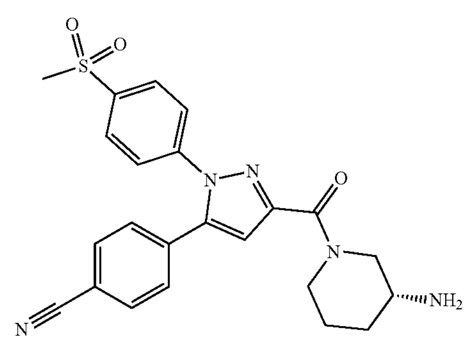 [SMILES: CS(=O)(=O)c1ccc(-n2nc(C(=O)N3CCC[C@@H](N)C3)cc2-c2ccc(C#N)cc2)cc1] |
| 47 | (R)-4-(3-(3-aminopiperidine-1-carbonyl)-1-(4-(trifluoromethyl)phenyl)-1H-pyrazole-5-yl)benzonitrile | 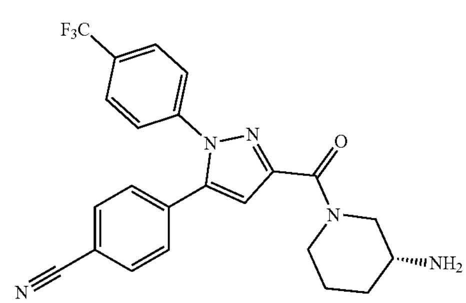 [SMILES: N#Cc1ccc(-c2cc(C(=O)N3CCC[C@@H](N)C3)nn2-c2ccc(C(F)(F)F)cc2)cc1] |

TABLE 1-continued

| Example | Name | Structure |
|---|---|---|
| 48 | (R)-4-(3-(3-aminopiperidine-1-carbonyl)-1-(2-fluoro-4-methylphenyl)-1H-pyrazole-5-yl)benzonitrile | 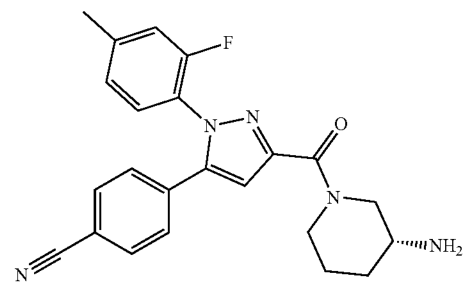 [SMILES: Cc1ccc(-n2nc(C(=O)N3CCC[C@@H](N)C3)cc2-c2ccc(C#N)cc2)c(F)c1] |
| 49 | (R)-4-(3-(3-aminopiperidine-1-carbonyl)-1-(3-fluoro-4-methoxyphenyl)-1H-pyrazole-5-yl)benzonitrile | 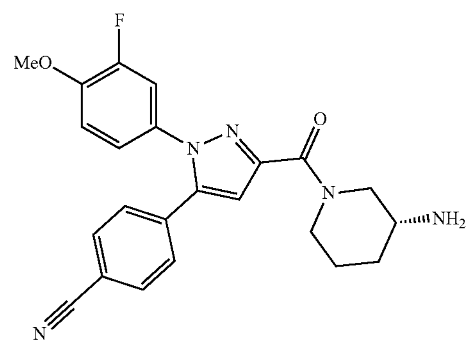 [SMILES: COc1ccc(-n2nc(C(=O)N3CCC[C@@H](N)C3)cc2-c2ccc(C#N)cc2)cc1F] |
| 50 | (R)-4,4'-(3-(3-aminopiperidine-1-carbonyl)-1H-pyrazole-1,5-diyl)dibenzonitrile | 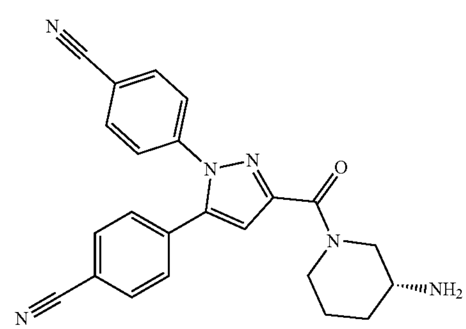 [SMILES: N#Cc1ccc(-c2cc(C(=O)N3CCC[C@@H](N)C3)nn2-c2ccc(C#N)cc2)cc1] |
| 51 | (R)-4-(1-(4-(dimethylamino)phenyl)-3-(3-(methylamino)piperidine-1-carbonyl)-1H-pyrazole-5-yl)benzonitrile | 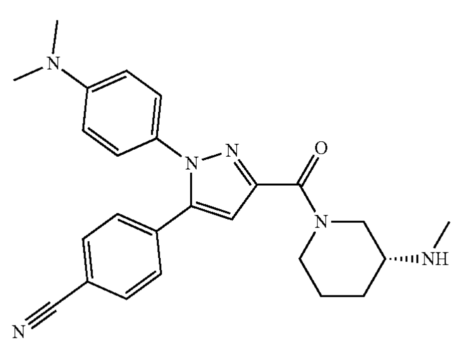 |

TABLE 1-continued

| Example | Name | Structure |
|---|---|---|
| 52 | (R)-4-(3-(3-aminopiperidine-1-carbonyl)-1-(4-((2-(dimethylamino)ethyl)(methyl)amino)phenyl)-1H-pyrazole-5-yl)benzonitrile | 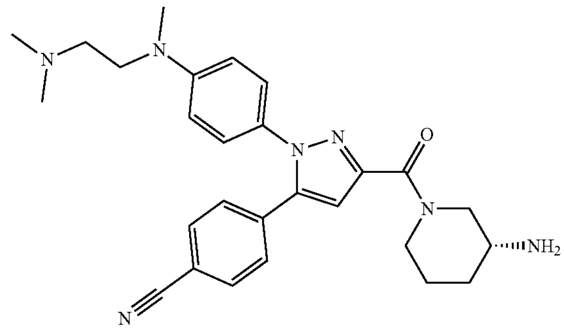 [SMILES: CN(C)CCN(C)c1ccc(-n2nc(C(=O)N3CCC[C@@H](N)C3)cc2-c2ccc(C#N)cc2)cc1] |
| 53 | ((R)-4-(3-(3-aminopiperidine-1-carbonyl)-1-(4-(dimethylamino)phenyl)-1H-pyrazole-5-yl)benzonitrile | 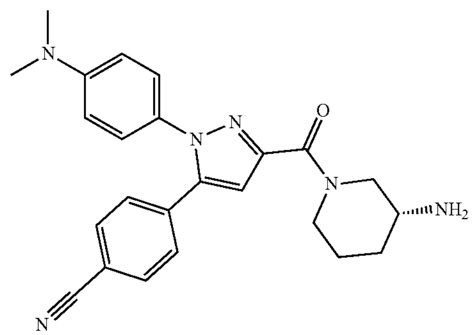 [SMILES: CN(C)c1ccc(-n2nc(C(=O)N3CCC[C@@H](N)C3)cc2-c2ccc(C#N)cc2)cc1] |
| 54 | (R)-4-(3-(3-aminopiperidine-1-carbonyl)-1-(4-(dimethylamino)-2-fluorophenyl)-1H-pyrazole-5-yl)benzonitrile | 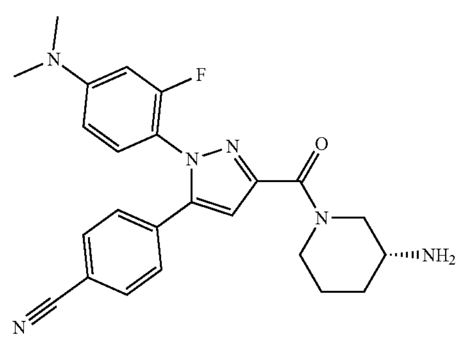 [SMILES: CN(C)c1ccc(-n2nc(C(=O)N3CCC[C@@H](N)C3)cc2-c2ccc(C#N)cc2)c(F)c1] |
| 55 | (R)-4-(3-(3-aminopiperidine-1-carbonyl)-1-(4-(diethylamino)-2-fluorophenyl)-1H-pyrazole-5-yl)benzonitrile | 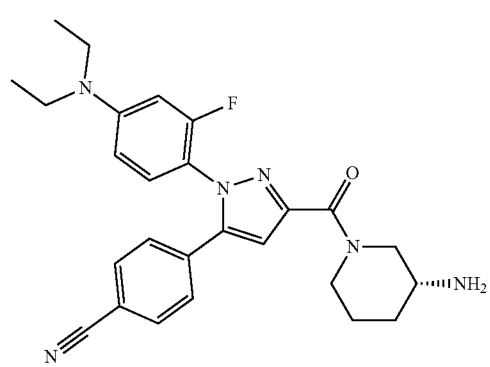 [SMILES: CCN(CC)c1ccc(-n2nc(C(=O)N3CCC[C@@H](N)C3)cc2-c2ccc(C#N)cc2)c(F)c1] |

TABLE 1-continued

| Example | Name | Structure |
|---|---|---|
| 56 | (R)-4-(3-(3-aminopiperidine-1-carbonyl)-1-(4-(azetidine-1-yl)-2-fluorophenyl)-1H-pyrazole-5-yl)benzonitrile | 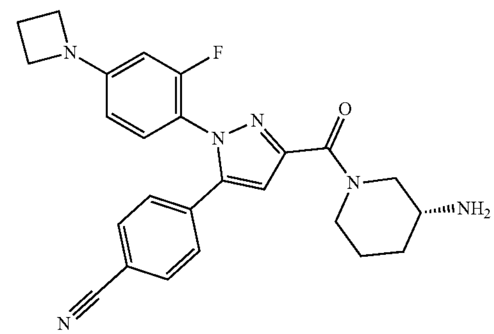 [SMILES: N#Cc1ccc(-c2cc(C(=O)N3CCC[C@@H](N)C3)nn2-c2ccc(N3CCC3)cc2F)cc1] |
| 57 | (R)-4-(3-(3-aminopiperidine-1-carbonyl)-1-(2-fluoro-4-(pyrrolidine-1-yl)phenyl)-1H-pyrazole-5-yl)benzonitrile | 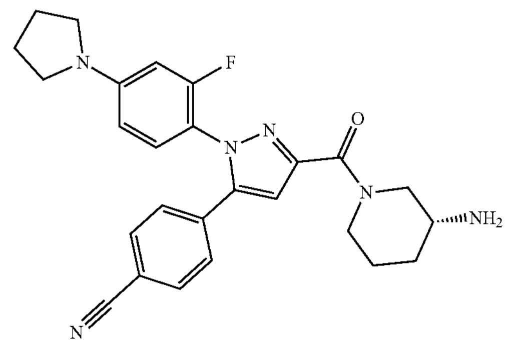 [SMILES: N#Cc1ccc(-c2cc(C(=O)N3CCC[C@@H](N)C3)nn2-c2ccc(N3CCCC3)cc2F)cc1] |
| 58 | (R)-4-(3-(3-aminopiperidine-1-carbonyl)-1-(2-fluoro-4-(pyrrolidine-1-yl)phenyl)-1H-pyrazole-5-yl)-2-fluorobenzonitrile | 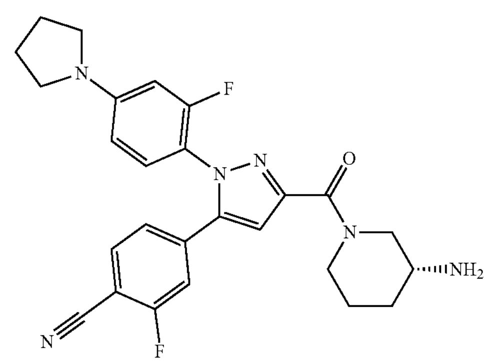 [SMILES: N#Cc1ccc(-c2cc(C(=O)N3CCC[C@@H](N)C3)nn2-c2ccc(N3CCCC3)cc2F)cc1F] |
| 59 | (R)-2-fluoro-4-(1-(2-fluoro-4-(pyrrolidine-1-yl)phenyl)-3-(3-(methylamino)piperidine-1-carbonyl)-1H-pyrazole-5-yl)benzonitrile | 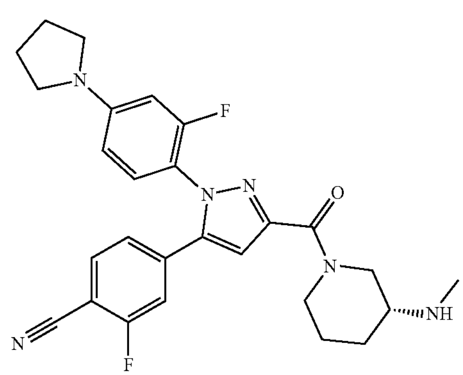 [SMILES: CN[C@@H]1CCCN(C(=O)c2cc(-c3ccc(C#N)c(F)c3)n(-c3ccc(N4CCCC4)cc3F)n2)C1] |

TABLE 1-continued

| Example | Name | Structure |
|---|---|---|
| 60 | (R)-4-(3-(3-aminoazepane-1-carbonyl)-1-(2-fluoro-4-(pyrrolidine-1-yl)phenyl)-1H-pyrazole-5-yl)-2-fluorobenzonitrile | 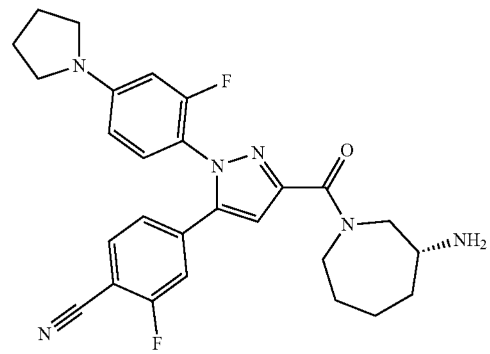 [SMILES: N#Cc1ccc(-c2cc(C(=O)N3CCCC[C@@H](N)C3)nn2-c2ccc(N3CCCC3)cc2F)cc1F] |
| 61 | 4-(3-((R)-3-aminopiperidine-1-carbonyl)-1-(2-fluoro-4-((R)-3-fluoropyrrolidine-1-yl)phenyl)-1H-pyrazole-5-yl)-2-fluorobenzonitrile | 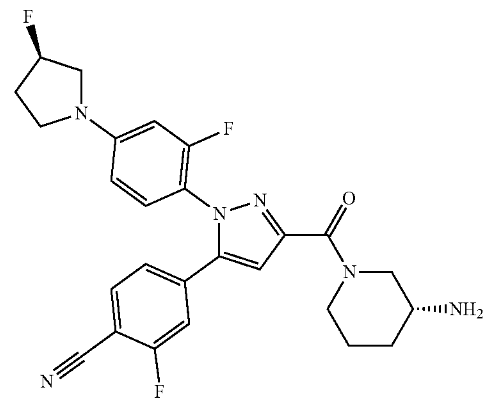 [SMILES: N#Cc1ccc(-c2cc(C(=O)N3CCC[C@@H](N)C3)nn2-c2ccc(N3CC[C@@H](F)C3)cc2F)cc1F] |
| 62 | 4-(3-((R)-3-aminopiperidine-1-carbonyl)-1-(2-fluoro-4-((S)-3-fluoropyrrolidine-1-yl)phenyl)-1H-pyrazole-5-yl)-2-fluorobenzonitrile | 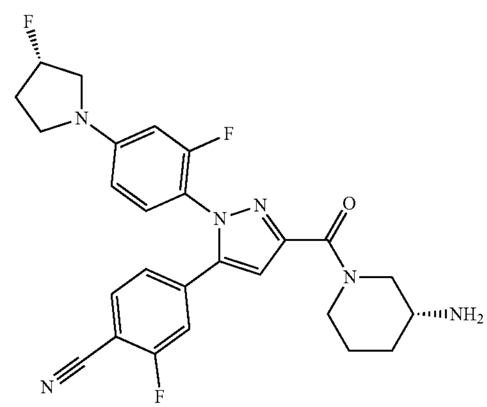 [SMILES: N#Cc1ccc(-c2cc(C(=O)N3CCC[C@@H](N)C3)nn2-c2ccc(N3CC[C@H](F)C3)cc2F)cc1F] |
| 63 | (R)-4-(3-(3-aminopiperidine-1-carbonyl)-1-(4-(3,3-difluoropyrrolidine-1-yl)-2-fluorophenyl)-1H-pyrazole-5-yl)-2-fluorobenzonitrile | 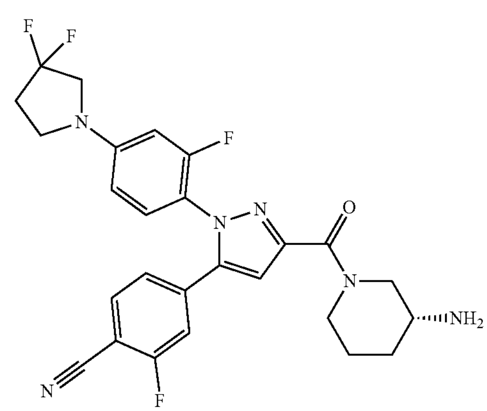 [SMILES: N#Cc1ccc(-c2cc(C(=O)N3CCC[C@@H](N)C3)nn2-c2ccc(N3CCC(F)(F)C3)cc2F)cc1F] |

TABLE 1-continued

| Example | Name | Structure |
|---|---|---|
| 64 | (R)-4-(1-(4-(3,3-difluoropyrrolidine-1-yl)-2-fluorophenyl)-3-(3-(methylamino)piperidine-1-carbonyl)-1H-pyrazole-5-yl)-2-fluorobenzonitrile | 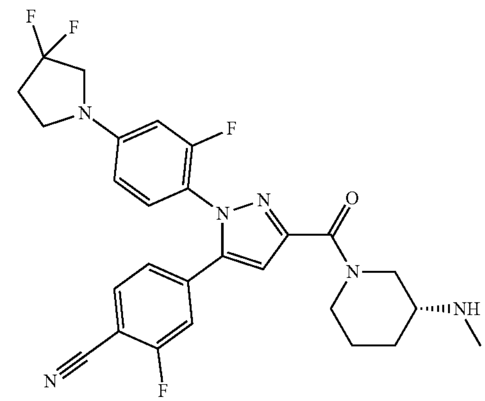 [SMILES: CN[C@@H]1CCCN(C(=O)c2cc(-c3ccc(C#N)c(F)c3)n(-c3ccc(N4CCC(F)(F)C4)cc3F)n2)C1] |
| 65 | 4-(3-((R)-3-aminopiperidine-1-carbonyl)-1-(2-fluoro-4-(3-methoxypyrrolidin-1-yl)phenyl)-1H-pyrazol-5-yl)-2-fluorobenzonitrile | 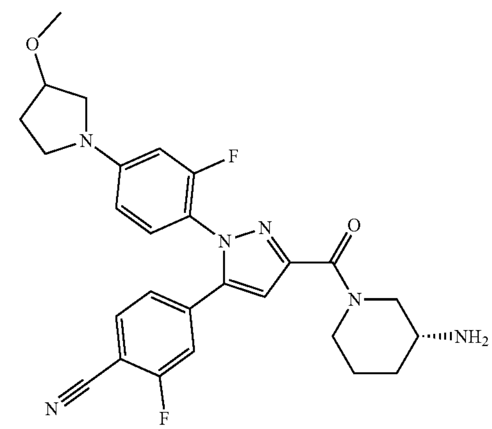 |
| 66 | 2-fluoro-4-(1-(2-fluoro-4-(3-methoxypyrrolidine-1-yl)phenyl)-3-((R)-3-(methylamino)piperidine-1-carbonyl)-1H-pyrazole-5-yl)benzonitrile | 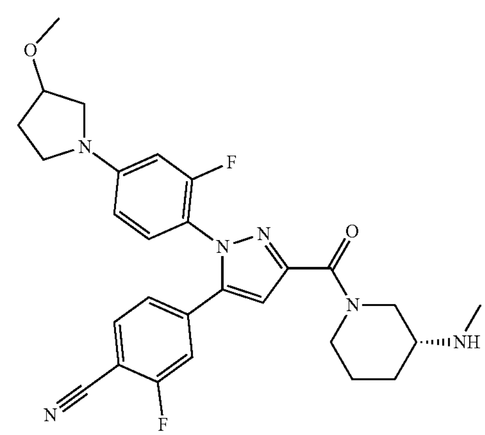 [SMILES: CN[C@@H]1CCCN(C(=O)c2cc(-c3ccc(C#N)c(F)c3)n(-c3ccc(N4CCC(OC)C4)cc3F)n2)C1] |

TABLE 1-continued

| Example | Name | Structure |
|---|---|---|
| 67 | 4-(3-((R)-3-aminopiperidine-1-carbonyl)-1-(2-fluoro-4-((S)-3-methoxypyrrolidine-1-yl)phenyl)-1H-pyrazole-5-yl)-2-fluorobenzonitrile | 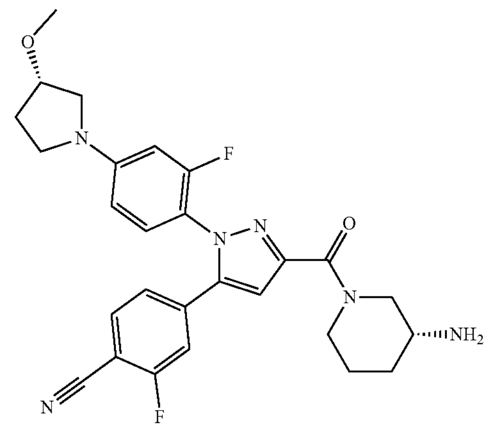 [SMILES: CO[C@H]1CCN(c2ccc(-n3nc(C(=O)N4CCC[C@@H](N)C4)cc3-c3ccc(C#N)c(F)c3)c(F)c2)C1] |
| 68 | 2-fluoro-4-(1-(2-fluoro-4-((S)-3-methoxypyrrolidine-1-yl)phenyl)-3-((R)-3-(methylamino)piperidine-1-carbonyl)-1H-pyrazole-5-yl)benzonitrile | 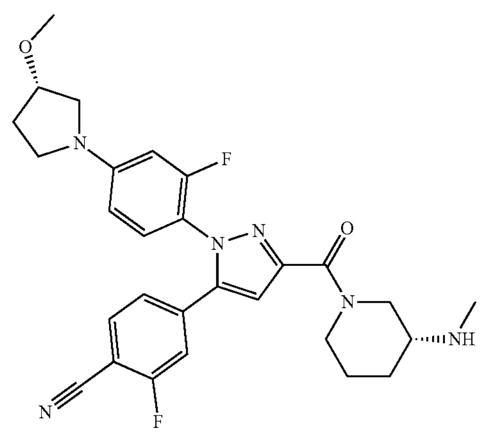 [SMILES: CN[C@@H]1CCCN(C(=O)c2cc(-c3ccc(C#N)c(F)c3)n(-c3ccc(N4CC[C@H](OC)C4)cc3F)n2)C1] |
| 69 | 4-(3-((R)-3-aminopiperidine-1-carbonyl)-1-(2-fluoro-4-((R)-3-methoxypyrrolidine-1-yl)phenyl)-1H-pyrazole-5-yl)-2-fluorobenzonitrile | 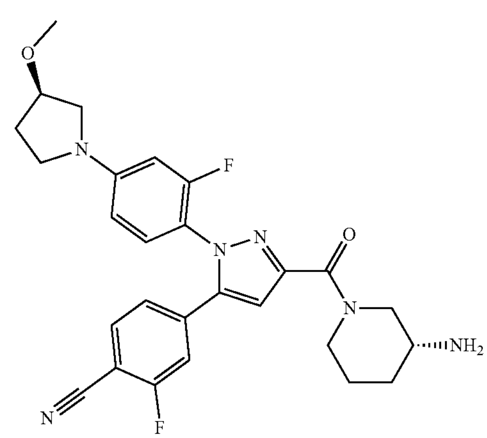 [SMILES: CO[C@@H]1CCN(c2ccc(-n3nc(C(=O)N4CCC[C@@H](N)C4)cc3-c3ccc(C#N)c(F)c3)c(F)c2)C1] |

TABLE 1-continued

| Example | Name | Structure |
|---|---|---|
| 70 | 2-fluoro-4-(1-(2-fluoro-4-((R)-3-methoxy-pyrrolidine-1-yl)phenyl)-3-((R)-3-(methyl-amino)piperidine-1-carbonyl)-1H-pyrazole-5-yl)benzonitrile | 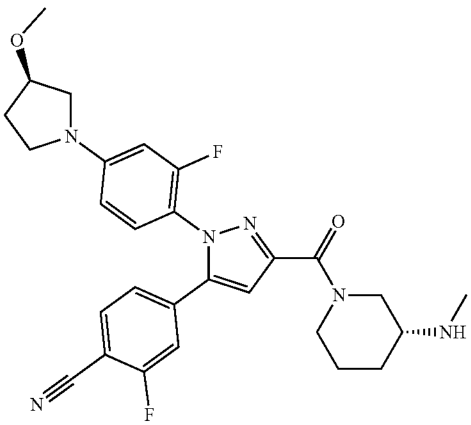 [SMILES: CN[C@@H]1CCCN(C(=O)c2cc(-c3ccc(C#N)c(F)c3)n(-c3ccc(N4CC[C@@H](OC)C4)cc3F)n2)C1] |
| 71 | 2-fluoro-4-(1-(2-fluoro-4-((S)-3-ethoxy-pyrrolidine-1-yl)phenyl)-3-((R)-3-(methyl-amino)piperidine-1-carbonyl)-1H-pyrazole-5-yl)benzonitrile | 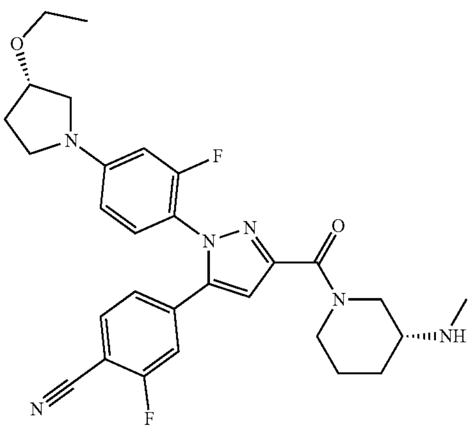 [SMILES: CCO[C@H]1CCN(c2ccc(-n3nc(C(=O)N4CCC[C@@H](NC)C4)cc3-c3ccc(C#N)c(F)c3)c(F)c2)C1] |
| 72 | 4-(3-((R)-3-aminopiperidine-1-carbonyl)-1-(2-fluoro-4-(3-hydroxypyrrolidine-1-yl)phenyl)-1H-pyrazole-5-yl)-2-fluorobenzonitrile | 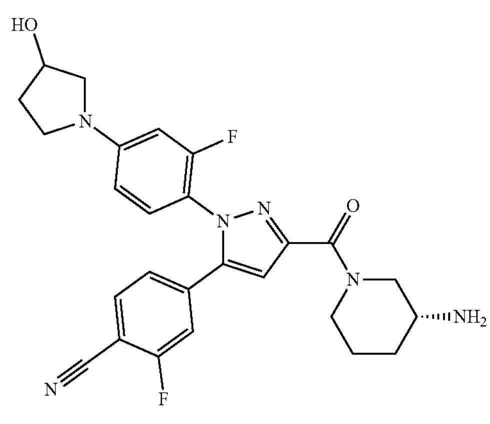 [SMILES: N#Cc1ccc(-c2cc(C(=O)N3CCC[C@@H](N)C3)nn2-c2ccc(N3CCC(O)C3)cc2F)cc1F] |

TABLE 1-continued

| Example | Name | Structure |
|---|---|---|
| 73 | 2-fluoro-4-(1-(2-fluoro-4-((S)-3-chloro-pyrrolidine-1-yl)phenyl)-3-((R)-3-(methyl-amino)piperidine-1-carbonyl)-1H-pyrazole-5-yl)benzonitrile | 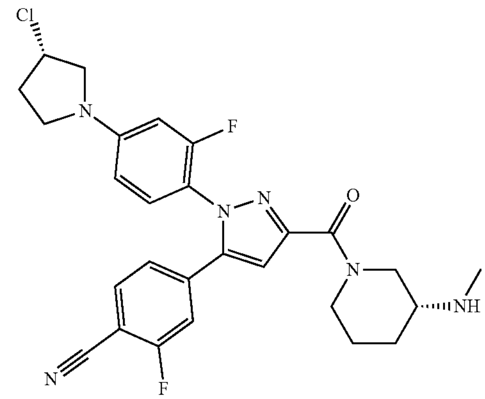 [SMILES: CN[C@@H]1CCCN(C(=O)c2cc(-c3ccc(C#N)c(F)c3)n(-c3ccc(N4CC[C@H](Cl)C4)cc3F)n2)C1] |
| 74 | (R)-4-(3-(3-aminopiperidine-1-carbonyl)-1-(2,6-difluoro-4-(pyrrolidine-1-yl)phenyl)-1H-pyrazole-5-yl)-2-fluorobenzonitrile | 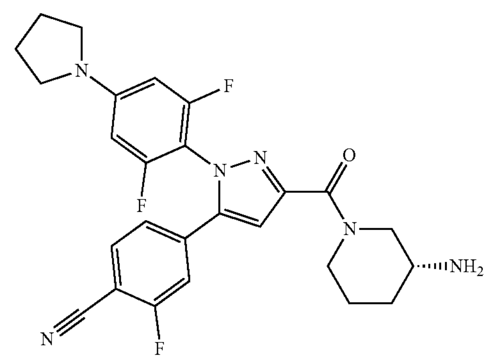 [SMILES: N#Cc1ccc(-c2cc(C(=O)N3CCC[C@@H](N)C3)nn2-c2c(F)cc(N3CCCC3)cc2F)cc1F] |
| 75 | (R)-4-(3-(3-aminopiperidine-1-carbonyl)-1-(2-chloro-4-(pyrrolidine-1-yl)phenyl)-1H-pyrazole-5-yl)-2-fluorobenzonitrile | 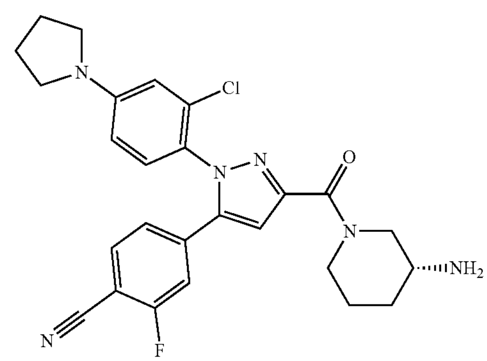 [SMILES: N#Cc1ccc(-c2cc(C(=O)N3CCC[C@@H](N)C3)nn2-c2ccc(N3CCCC3)cc2Cl)cc1F] |
| 76 | (R)-4-(3-(3-aminopiperidine-1-carbonyl)-1-(2-methoxy-4-(pyrrolidine-1-yl)phenyl)-1H-pyrazole-5-yl)-2-fluorobenzonitrile | 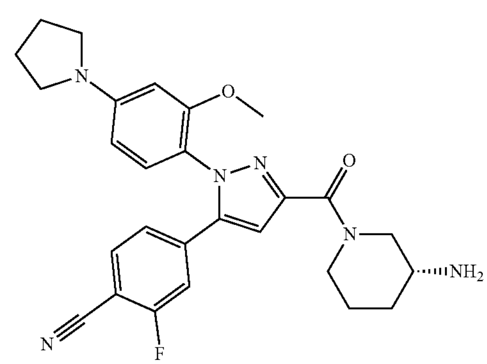 [SMILES: COc1cc(N2CCCC2)ccc1-n1nc(C(=O)N2CCC[C@@H](N)C2)cc1-c1ccc(C#N)c(F)c1] |

TABLE 1-continued

| Example | Name | Structure |
|---|---|---|
| 77 | (R)-4-(3-(3-aminopiperidine-1-carbonyl)-1-(2-fluoro-4-(piperidine-1-yl)phenyl)-1H-pyrazole-5-yl)benzonitrile | 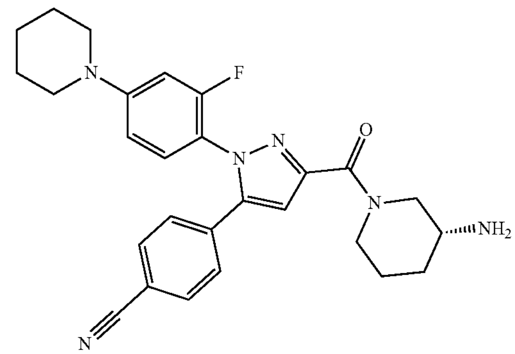 [SMILES: N#Cc1ccc(-c2cc(C(=O)N3CCC[C@@H](N)C3)nn2-c2ccc(N3CCCCC3)cc2F)cc1] |
| 78 | (R)-4-(3-(3-aminopiperidine-1-carbonyl)-1-(2-fluoro-4-(piperidine-1-yl)phenyl)-1H-pyrazole-5-yl)-2-fluorobenzonitrile | 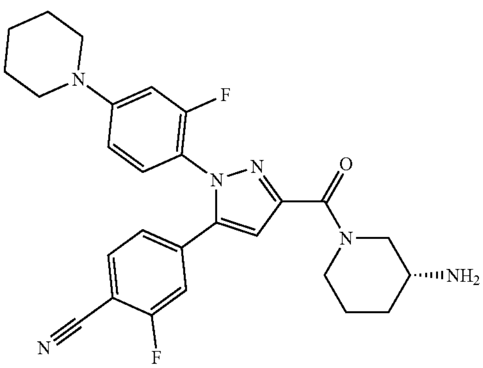 [SMILES: N#Cc1ccc(-c2cc(C(=O)N3CCC[C@@H](N)C3)nn2-c2ccc(N3CCCCC3)cc2F)cc1F] |
| 79 | (R)-2-fluoro-4-(1-(2-fluoro-4-(piperidine-1-yl)phenyl)-3-(3-(methylamino)piperidine-1-carbonyl)-1H-pyrazole-5-yl)benzonitrile | 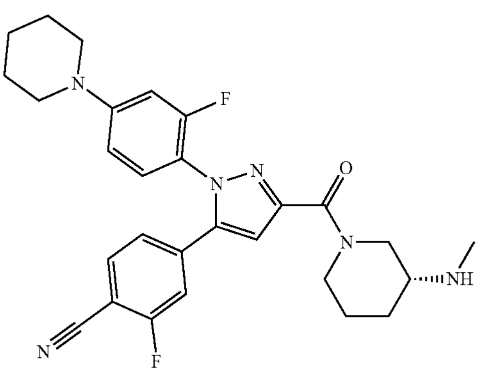 [SMILES: CN[C@@H]1CCCN(C(=O)c2cc(-c3ccc(C#N)c(F)c3)n(-c3ccc(N4CCCCC4)cc3F)n2)C1] |
| 80 | 4-(3-((R)-3-aminopiperidine-1-carbonyl)-1-(2-fluoro-4-(3-methylpiperidine-1-yl)phenyl)-1H-pyrazole-5-yl)-2-fluorobenzonitrile | 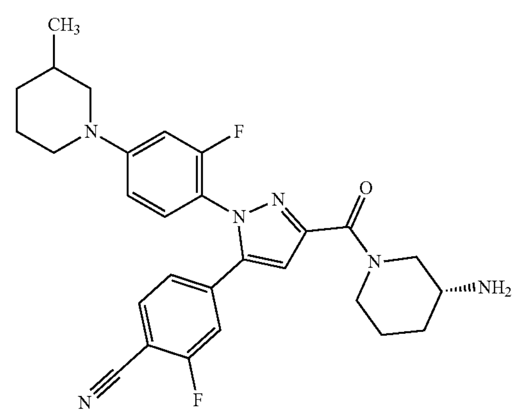 [SMILES: CC1CCCN(c2ccc(-n3nc(C(=O)N4CCC[C@@H](N)C4)cc3-c3ccc(C#N)c(F)c3)c(F)c2)C1] |

TABLE 1-continued

| Example | Name | Structure |
|---|---|---|
| 81 | (R)-4-(3-(3-aminopiperidine-1-carbonyl)-1-(2-fluoro-4-(4-methylpiperidine-1-yl)phenyl)-1H-pyrazole-5-yl)-2-fluorobenzonitrile | 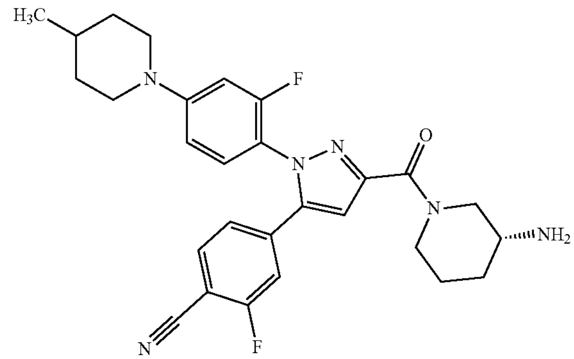 [SMILES: CC1CCN(c2ccc(-n3nc(C(=O)N4CCC[C@@H](N)C4)cc3-c3ccc(C#N)c(F)c3)c(F)c2)CC1] |
| 82 | 4-(3-((R)-3-aminopiperidine-1-carbonyl)-1-(4-(3,5-dimethylpiperidine-1-yl)-2-fluorophenyl)-1H-pyrazole-5-yl)-2-fluorobenzonitrile | 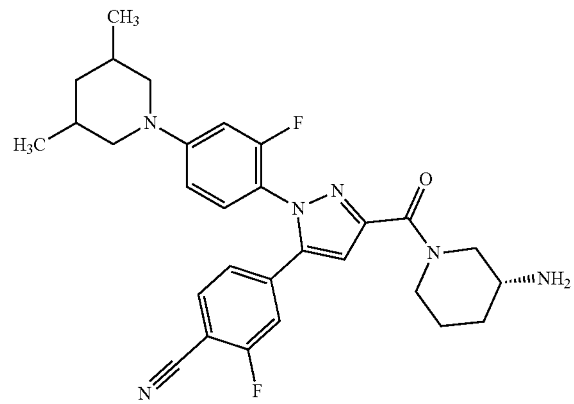 [SMILES: CC1CC(C)CN(c2ccc(-n3nc(C(=O)N4CCC[C@@H](N)C4)cc3-c3ccc(C#N)c(F)c3)c(F)c2)C1] |
| 83 | (R)-4-(1-(4-([1,4'-bipiperidine]-1'-yl)-2-fluorophenyl)-3-(3-aminopiperidine-1-carbonyl)-1H-pyrazole-5-yl)-2-fluorobenzonitrile | 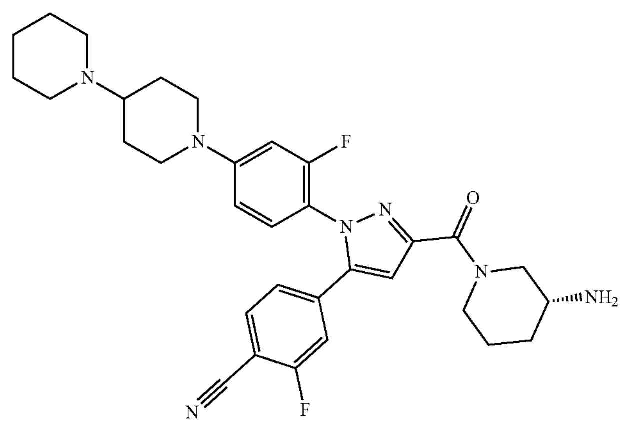 [SMILES: N#Cc1ccc(-c2cc(C(=O)N3CCC[C@@H](N)C3)nn2-c2ccc(N3CCC(N4CCCCC4)CC3)cc2F)cc1F] |
| 84 | (R)-4-(3-(3-aminoazepane-1-carbonyl)-1-(2-fluoro-4-(piperidine-1-yl)phenyl)-1H-pyrazole-5-yl)-2-fluorobenzonitrile | 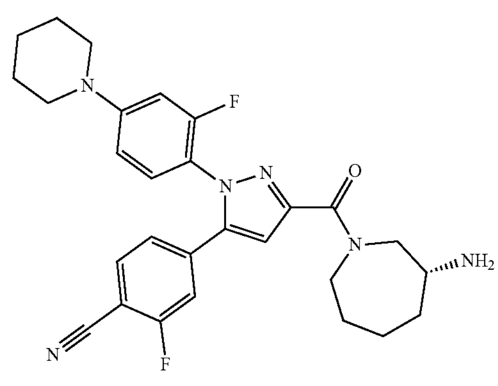 [SMILES: N#Cc1ccc(-c2cc(C(=O)N3CCCC[C@@H](N)C3)nn2-c2ccc(N3CCCCC3)cc2F)cc1F] |

TABLE 1-continued

| Example | Name | Structure |
|---|---|---|
| 85 | (R)-4-(3-(3-aminopiperidine-1-carbonyl)-1-(1-methyl-1H-indazole-6-yl)-1H-pyrazole-5-yl)benzonitrile | 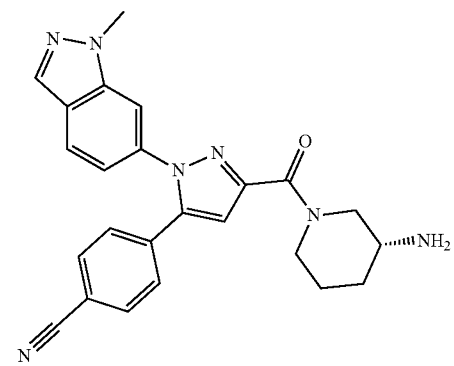 [SMILES: Cn1ncc2ccc(-n3nc(C(=O)N4CCC[C@@H](N)C4)cc3-c3ccc(C#N)cc3)cc21] |
| 86 | (R)-4-(3-(3-aminopiperidine-1-carbonyl)-1-(2-methylbenzo[d]thiazole-5-yl)-1H-pyrazole-5-yl)benzonitrile | 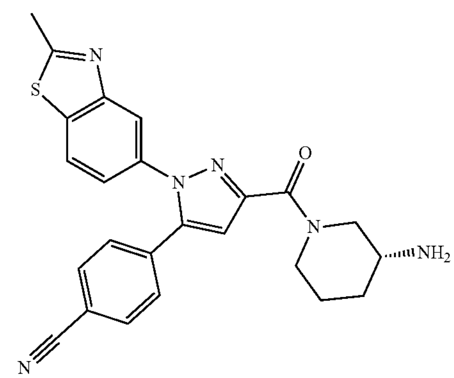 [SMILES: Cc1nc2cc(-n3nc(C(=O)N4CCC[C@@H](N)C4)cc3-c3ccc(C#N)cc3)ccc2s1] |
| 87 | (R)-4-(3-(3-aminopiperidine-1-carbonyl)-1-(2,3-dihydro-1H-indane-5-yl)-1H-pyrazole-5-yl)benzonitrile | 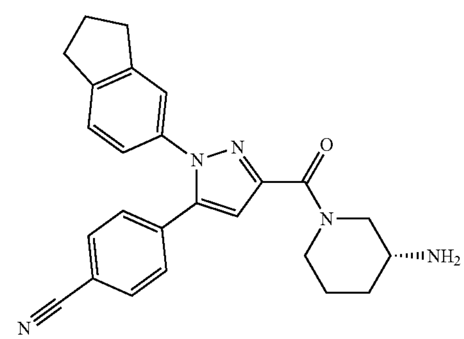 [SMILES: N#Cc1ccc(-c2cc(C(=O)N3CCC[C@@H](N)C3)nn2-c2ccc3c(c2)CCC3)cc1] |
| 88 | (R)-4-(3-(3-aminopiperidine-1-carbonyl)-1-(2,3-dihydro-1H-inden-5-yl)-1H-pyrazole-5-yl)-2-fluorobenzonitrile | 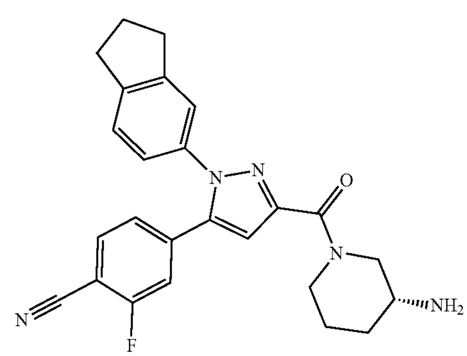 [SMILES: N#Cc1ccc(-c2cc(C(=O)N3CCC[C@@H](N)C3)nn2-c2ccc3c(c2)CCC3)cc1F] |

TABLE 1-continued

| Example | Name | Structure |
|---|---|---|
| 89 | (R)-4-(1-(2,3-dihydro-1H-inden-5-yl)-3-(3-(methylamino)piperidine-1-carbonyl)-1H-pyrazole-5-yl)benzonitrile | 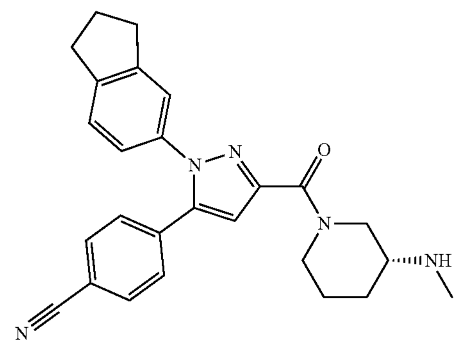 [SMILES: CN[C@@H]1CCCN(C(=O)c2cc(-c3ccc(C#N)cc3)n(-c3ccc4c(c3)CCC4)n2)C1] |
| 90 | (R)-4-(3-(3-aminopiperidine-1-carbonyl)-1-(2,3-dihydrobenzo[b][1,4]dioxin-6-yl)-1H-pyrazole-5-yl)benzonitrile | 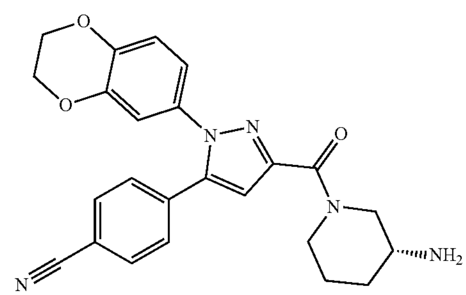 [SMILES: N#Cc1ccc(-c2cc(C(=O)N3CCC[C@@H](N)C3)nn2-c2ccc3c(c2)OCCO3)cc1] |
| 91 | (R)-4-(3-(3-aminopiperidine-1-carbonyl)-1-(quinoline-6-yl)-1H-pyrazole-5-yl)benzonitrile | 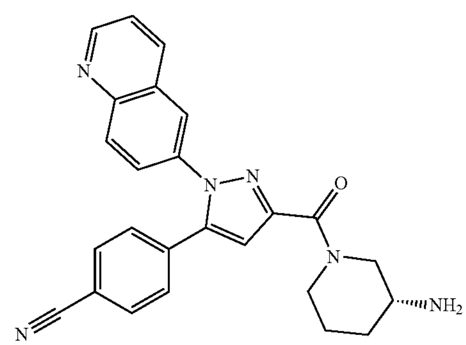 [SMILES: N#Cc1ccc(-c2cc(C(=O)N3CCC[C@@H](N)C3)nn2-c2ccc3ncccc3c2)cc1] |
| 92 | (R)-4-(3-(3-aminopiperidine-1-carbonyl)-1-(quinoline-3-yl)-1H-pyrazole-5-yl)benzonitrile | 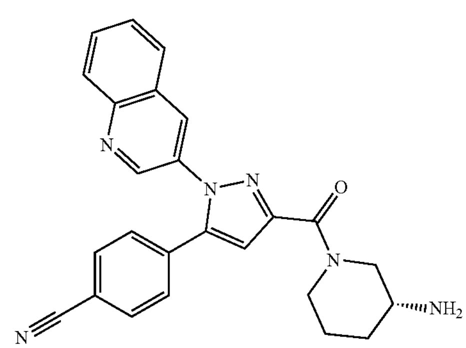 [SMILES: N#Cc1ccc(-c2cc(C(=O)N3CCC[C@@H](N)C3)nn2-c2cnc3ccccc3c2)cc1] |

TABLE 1-continued

| Example | Name | Structure |
|---|---|---|
| 93 | (R)-4-(3-(3-aminopiperidine-1-carbonyl)-1-(1-methyl-1H-pyrrolo[2,3-b]pyridine-5-yl)-1H-pyrazole-5-yl)benzonitrile | 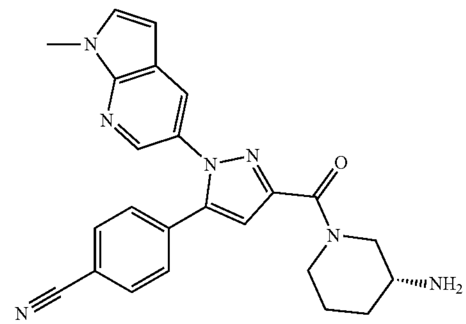 [SMILES: Cn1ccc2cc(-n3nc(C(=O)N4CCC[C@@H](N)C4)cc3-c3ccc(C#N)cc3)cnc21] |
| 94 | (R)-4-(3-(3-aminopiperidine-1-carbonyl)-1-(2-fluoro-4-(2-hydroxy-2-methylpropyl)phenyl)-1H-pyrazole-5-yl)-2-fluorobenzonitrile | 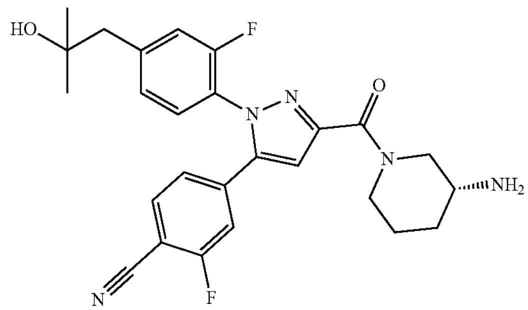 [SMILES: CC(C)(O)Cc1ccc(-n2nc(C(=O)N3CCC[C@@H](N)C3)cc2-c2ccc(C#N)c(F)c2)c(F)c1] |
| 95 | 4-(3-(piperazine-1-carbonyl)-1-(p-tolyl)-1H-pyrazole-5-yl)benzonitrile | 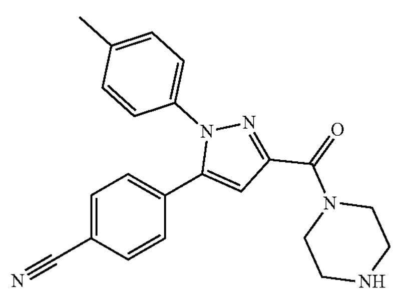 [SMILES: Cc1ccc(-n2nc(C(=O)N3CCNCC3)cc2-c2ccc(C#N)cc2)cc1] |
| 96 | 4-(3-(3-(aminomethyl)piperidine-1-carbonyl)-1-(p-tolyl)-1-H-pyrazole-5-yl)benzonitrile | 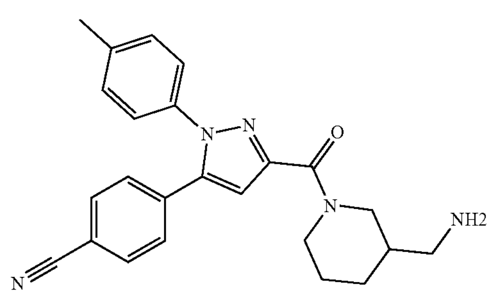 [SMILES: Cc1ccc(-n2nc(C(=O)N3CCCC(CN)C3)cc2-c2ccc(C#N)cc2)cc1] |
| 97 | (S)-5-(4-cyanophenyl)-N-(1-(methylsulfonyl)piperidine-3-yl)-1-(p-tolyl)-1H-pyrazole-3-carboxamide | 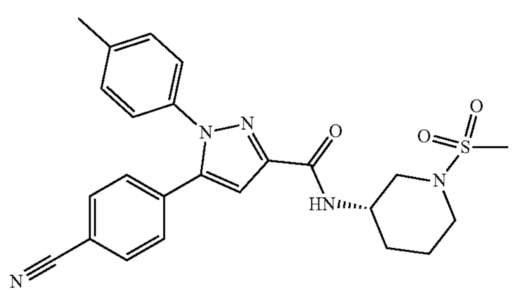 [SMILES: Cc1ccc(-n2nc(C(=O)N[C@H]3CCCN(S(C)(=O)=O)C3)cc2-c2ccc(C#N)cc2)cc1] |

TABLE 1-continued

| Example | Name | Structure |
|---|---|---|
| 98 | 4-(3-(2,7-diazaspiro[3.5]nonane-7-carbonyl)-1-(p-tolyl)-1H-pyrazole-5-yl)benzonitrile | 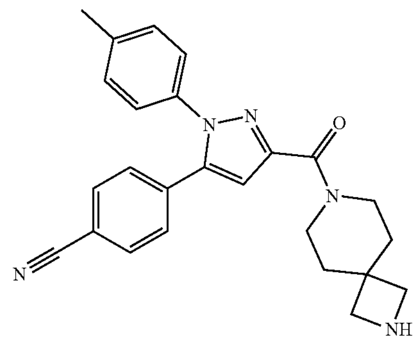 [SMILES: Cc1ccc(-n2nc(C(=O)N3CCC4(CC3)CNC4)cc2-c2ccc(C#N)cc2)cc1] |
| 99 | 4-(3-(2,8-diazaspiro[4.5]decane-8-carbonyl)-1-(p-tolyl)-1H-pyrazole-5-yl)benzonitrile | 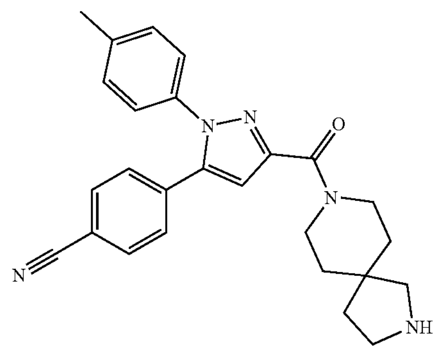 [SMILES: Cc1ccc(-n2nc(C(=O)N3CCC4(CCNC4)CC3)cc2-c2ccc(C#N)cc2)cc1] |
| 100 | 4-(3-(octahydro-1H-pyrrolo[2,3-c]pyridine-6-carbonyl)-1-(p-tolyl)-1H-pyrazole-5-yl)benzonitrile | 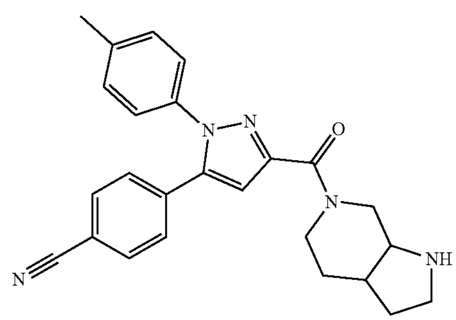 [SMILES: Cc1ccc(-n2nc(C(=O)N3CCC4CCNC4C3)cc2-c2ccc(C#N)cc2)cc1] |
| 101 | 4-(3-(3,7-diazabicyclo[3.3.1]nonane-3-carbonyl)-1-(2-fluoro-4-isopropylphenyl)-1H-pyrazole-5-yl)-2-fluorobenzonitrile | 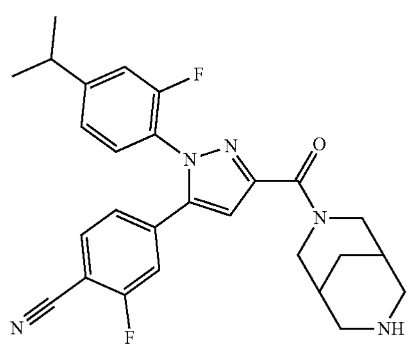 [SMILES: CC(C)c1ccc(-n2nc(C(=O)N3CC4CNCC(C4)C3)cc2-c2ccc(C#N)c(F)c2)c(F)c1] |

TABLE 1-continued

| Example | Name | Structure |
|---|---|---|
| 102 | 4-(3-(3-amino-8-azabicyclo[3.2.1]octane-8-carbonyl)-1-(2-fluoro-4-isopropylphenyl)-1H-pyrazole-5-yl)-2-fluorobenzonitrile | 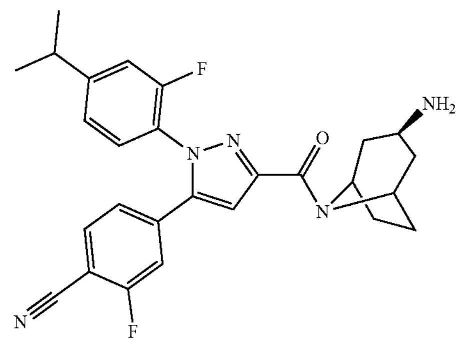 |
| 103 | 4-(3-(3-amino-8-azabicyclo[3.2.1]octane-8-carbonyl)-1-(2-fluoro-4-pyrrolidine-1-yl)phenyl)-1H-pyrazole-5-yl)-2-fluorobenzonitrile | 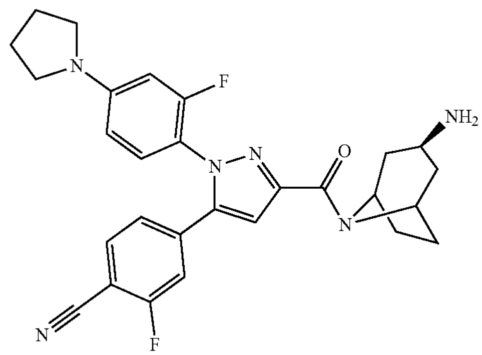 |
| 104 | 4-(3-(3,7-diazabicyclo[3.3.1]nonane-3-carbonyl)-1-(p-tolyl)-1H-pyrazole-5-yl)benzonitrile | 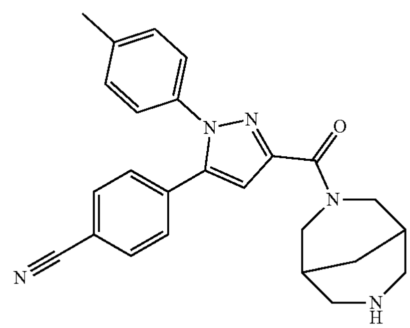 [SMILES: Cc1ccc(-n2nc(C(=O)N3CC4CNCC(C4)C3)cc2-c2ccc(C#N)cc2)cc1] |
| 105 | 5-(4-cyanophenyl)-N-(piperidine-4-yl)-1-(p-tolyl)-1H-pyrazole-3-carboximide | 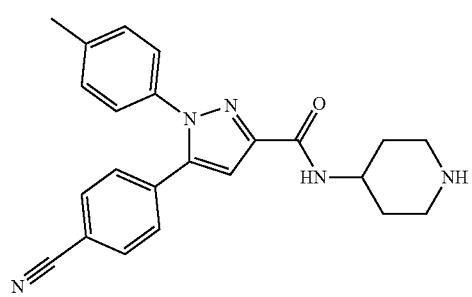 [SMILES: Cc1ccc(-n2nc(C(=O)NC3CCNCC3)cc2-c2ccc(C#N)cc2)cc1] |
| 106 | 5-(4-cyanophenyl)-N-(1-methylpiperidine-4-yl)-1-(p-tolyl)-1H-pyrazole-3-carboximide | 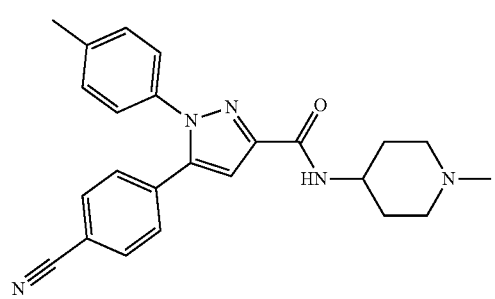 [SMILES: Cc1ccc(-n2nc(C(=O)NC3CCN(C)CC3)cc2-c2ccc(C#N)cc2)cc1] |

TABLE 1-continued
| Example | Name | Structure |
|---|---|---|
| 107 | (R)-5-(4-cyanophenyl)-N-(1-methylpiperidine-3-yl)-1-(p-tolyl)-1H-pyrazole-3-carboximide | 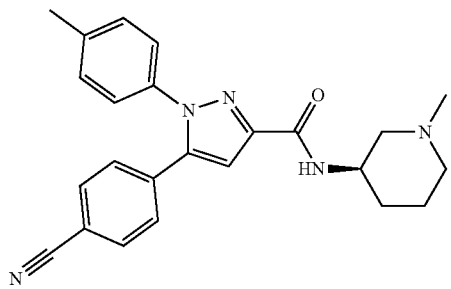 [SMILES: Cc1ccc(-n2nc(C(=O)N[C@@H]3CCCN(C)C3)cc2-c2ccc(C#N)cc2)cc1] |
| 108 | (S)-5-(4-cyanophenyl)-N-(1-methylpiperidine-3-yl)-1-(p-tolyl)-1H-pyrazole-3-carboximide | 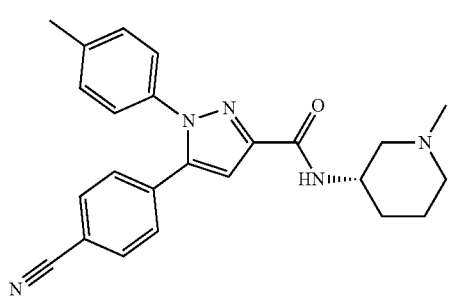 [SMILES: Cc1ccc(-n2nc(C(=O)N[C@H]3CCCN(C)C3)cc2-c2ccc(C#N)cc2)cc1] |
| 109 | (R)-5-(4-cyanophenyl)-N-(1-methylpyrrolidine-3-yl)-1-(p-tolyl)-1H-pyrazole-3-carboximide | 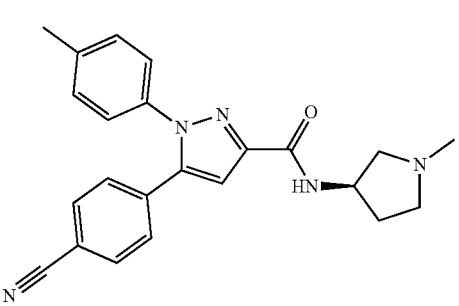 [SMILES: Cc1ccc(-n2nc(C(=O)N[C@@H]3CCN(C)C3)cc2-c2ccc(C#N)cc2)cc1] |
| 110 | 5-(4-cyano-3-fluorophenyl)-1-(2-fluoro-4-(pyrrolidine-1-yl)phenyl)-N-methyl-N-(piperidine-3-yl)-1H-pyrazole-3-carboximide | 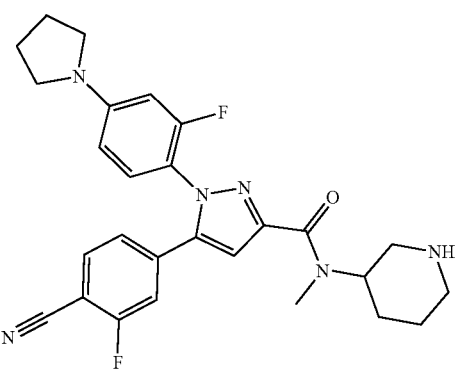 |

TABLE 1-continued

| Example | Name | Structure |
|---|---|---|
| 111 | (S)-5-(4-cyano-3-fluorophenyl)-1-(2-fluoro-4-(pyrrolidine-1-yl)phenyl)-N-methyl-N-(piperidine-3-yl)-1H-pyrazole-3-carboximide | 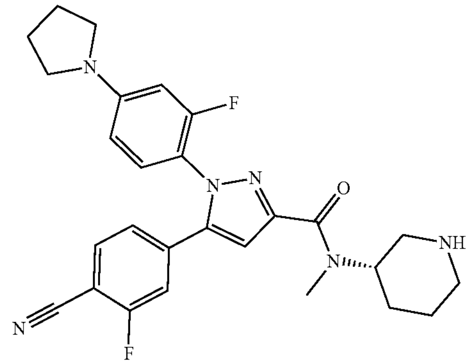 [SMILES: CN(C(=O)c1cc(-c2ccc(C#N)c(F)c2)n(-c2ccc(N3CCCC3)cc2F)n1)C1CCCNC1] |
| 112 | (R)-5-(4-cyano-3-fluorophenyl)-1-(2-fluoro-4-(pyrrolidine-1-yl)phenyl)-N-methyl-N-(piperidine-3-yl)-1H-pyrazole-3-carboximide | 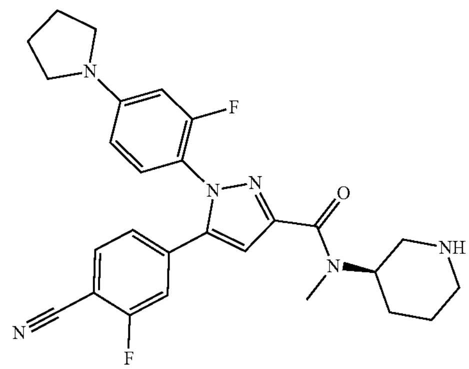 [SMILES: CN(C(=O)c1cc(-c2ccc(C#N)c(F)c2)n(-c2ccc(N3CCCC3)cc2F)n1)[C@@H]1CCCNC1] |
| 113 | (R)-4-(3-(3-aminopiperidine-1-carbonyl)-1-(4-cyclopropyl-2-fluorophenyl)-4-methyl-1H-pyrazole-5-yl)benzonitrile | 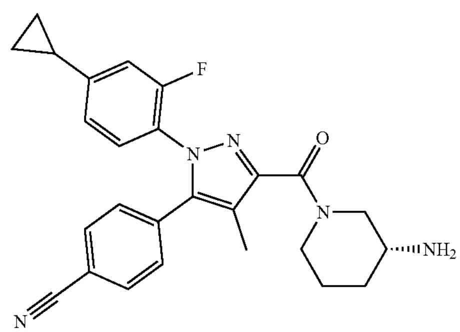 [SMILES: Cc1c(C(=O)N2CCC[C@@H](N)C2)nn(-c2ccc(C3CC3)cc2F)c1-c1ccc(C#N)cc1] |

The compounds prepare in the Examples were subjected to bioassay as follows.

Experimental Example 1: Biochemical Analysis of LSD1 Histone Demethylase Inhibitor The biochemical inhibition activity of the synthesized compounds on LSD1 was measured. The activity measurement was performed using LSD1 fluorescence analysis kit (available from BPS Bioscience Co., Ltd., Catalog No: 50106). This analysis kit is designed to measure activity of LSD1 enzyme. $H_2O_2$ generated upon demethylation of Lys4 moiety of histone H3 by LSD1 is reacted with HRP/Amplex Red reagent to form fluorescent Resorufin, which is measured by this kit, thereby confirming demethylation.

Activity inhibition of the compounds on LSD1 are shown in Table 2. The results are expressed as an $IC_{50}$ value. As for a control, GSK2879552 (available from GlaxoSmithKline USA) was used.

TABLE 2

| Example | LSD1 $IC_{50}$ (nM) |
|---|---|
| Control | 311 |
| 1 | 57 |
| 2 | 29 |
| 3 | 46 |
| 4 | 38 |
| 5 | 21 |
| 6 | 21 |
| 7 | 49 |
| 8 | 28 |
| 9 | 234 |
| 10 | 34 |
| 12 | 70 |
| 17 | 248 |
| 18 | 231 |
| 20 | 195 |
| 21 | 100 |
| 22 | 952 |
| 30 | 374 |

TABLE 2-continued

| Example | LSD1 IC$_{50}$ (nM) |
|---|---|
| 32 | 710 |
| 33 | 46 |
| 34 | 47 |
| 36 | 67 |
| 37 | 36 |
| 38 | 61 |
| 39 | 33 |
| 40 | 36 |
| 41 | 34 |
| 42 | 36 |
| 43 | 21 |
| 44 | 23 |
| 45 | 162 |
| 47 | 229 |
| 48 | 149 |
| 49 | 364 |
| 50 | 379 |
| 51 | 35 |
| 52 | 231 |
| 53 | 44 |
| 54 | 42 |
| 55 | 56 |
| 56 | 40 |
| 57 | 21 |
| 58 | 28 |
| 59 | 56 |
| 60 | 46 |
| 61 | 35 |
| 62 | 41 |
| 63 | 55 |
| 65 | 53 |
| 66 | 34 |
| 67 | 41 |
| 68 | 22 |
| 69 | 26 |
| 70 | 28 |
| 74 | 48 |
| 77 | 20 |
| 78 | 26 |
| 79 | 38 |
| 84 | 30 |
| 85 | 125 |
| 86 | 222 |
| 87 | 46 |
| 89 | 28 |
| 90 | 164 |
| 91 | 568 |
| 93 | 376 |
| 96 | 531 |
| 98 | 163 |
| 99 | 427 |
| 101 | 185 |
| 102 | 87 |
| 103 | 33 |

Experimental Example 2: Cell Growth Suppression Test

Cell growth suppression effects of the synthesized compounds on NCI-H1417 cells were identified. The cells were treated with the synthesized compounds for 10 days. Then, in order to test the cell growth suppression, CellTiter-Glo Luminescent Cell Viability Assay (available from Promega, USA) was used. This test is to measure emission signals proportional to the number of ATPs based on a fixed amount of ATPs, which represents the presence of metabolically active cells, thereby determining the number of viable cells. 50%-suppression of the compounds on NCI-H1417 cells are shown in Table 3. The results are expressed as a GI$_{50}$ value. As for a control, GSK2879552 (available from GlaxoSmithKline USA) was used.

TABLE 3

| Example | NCI-H1417 GI$_{50}$ (nM) |
|---|---|
| Control | 591 |
| 1 | 94 |
| 2 | 120 |
| 3 | 49 |
| 4 | 24 |
| 5 | 48 |
| 6 | 48 |
| 8 | 101 |
| 10 | 108 |
| 35 | 145 |
| 36 | 91 |
| 37 | 215 |
| 38 | 79 |
| 39 | 139 |
| 40 | 226 |
| 41 | 126 |
| 42 | 226 |
| 43 | 69 |
| 44 | 133 |
| 53 | 102 |
| 54 | 84 |
| 57 | 45 |
| 58 | 24 |
| 59 | 9.7 |
| 60 | 53 |
| 61 | 82 |
| 63 | 33 |
| 64 | 19 |
| 65 | 58 |
| 66 | 16 |
| 67 | 30 |
| 68 | 6.8 |
| 69 | 38 |
| 70 | 18 |
| 71 | 10 |
| 72 | 38 |
| 73 | 39 |
| 74 | 8.8 |
| 75 | 52 |
| 76 | 43 |
| 77 | 67 |
| 78 | 34 |
| 82 | 119 |
| 83 | 71 |
| 84 | 84 |
| 87 | 142 |
| 88 | 173 |
| 89 | 71 |

The invention claimed is:
1. A compound of the following Formula 4, an optical isomer, or a tautomer, or a pharmaceutically acceptable salt thereof:

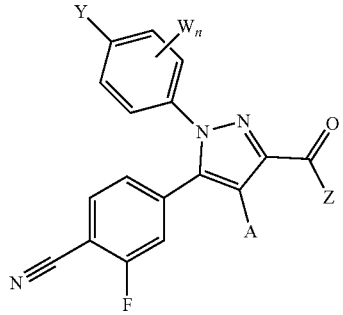

Formula 4 wherein, in Formula 4,
A is hydrogen or a C$_1$-C$_4$ alkyl group,
W(s) are each independently a halogen,
n is a natural number from 1 to 4, Y is a substituted or unsubstituted $C_3$-$C_6$ cycloalkyl group, a substituted or unsubstituted N-linked pyrrolidinyl group, or a substituted or unsubstituted N-linked piperidinyl group, wherein the substituted $C_3$-$C_6$ cycloalkyl group is a $C_3$-$C_6$ cycloalkyl group in which at least one hydrogen is substituted with a functional group each independently selected from halogen and a hydroxy group, and the substituted N-linked pyrrolidinyl group and the substituted N-linked piperidinyl group are each a N-linked pyrrolidinyl group and a N-linked piperidinyl group, respectively, in which at least one ring hydrogen atom is substituted with a functional group each independently selected from a $C_1$-$C_4$ alkyl group, halogen, a $C_1$-$C_4$ alkoxy group, a hydroxy group, and a $C_1$-$C_{10}$ heterocyclic group, and Z is a substituted or unsubstituted N-linked pyrrolidinyl group, a substituted or unsubstituted N-linked piperidinyl group, or a substituted or unsubstituted N-linked azepanyl group, wherein at least one substituent of the substituted N-linked pyrrolidinyl group, the substituted N-linked piperidinyl group, or the substituted N-linked azepanyl group is selected from an amino group, a $C_1$-$C_4$ alkylamino group, a $C_1$-$C_4$ alkyl group, a halogen, a $C_1$-$C_4$ alkoxy group, and a $C_1$-$C_{10}$ heterocyclic group.

2. The compound of claim 1, an optical isomer, or a tautomer, or a pharmaceutically acceptable salt thereof, wherein A is hydrogen, W(s) are fluorine, n is a natural number of 1, Y is a substituted or unsubstituted N-linked pyrrolidinyl group or a substituted or unsubstituted N-linked piperidinyl group, wherein the substituted N-linked pyrrolidinyl group and the substituted N-linked piperidinyl group are each a N-linked pyrrolidinyl group and a N-linked piperidinyl group, respectively, in which at least one ring hydrogen atom is substituted with a functional group each independently selected from a $C_1$-$C_4$ alkyl group, a halogen, a $C_1$-$C_4$ alkoxy group, and a hydroxy group, and Z is a substituted N-linked piperidinyl group or a unsubstituted piperidinyl group in which at least one substituent is substituted with a functional group selected from an amino group, a $C_1$-$C_4$ alkylamino group, a $C_1$-$C_4$ alkyl group, a halogen, and a $C_1$-$C_4$ alkoxy group.

3. A compound selected from Compounds 1) to 113), an optical isomer, a tautomer, or a pharmaceutically acceptable salt thereof:

1) (R)-4-(3-(3-aminopiperidine-1-carbonyl)-1-(4-cyclopropylphenyl)-1H-pyrazole-5-yl)benzonitrile
2) (R)-4-(1-(4-cyclopropylphenyl)-3-(3-methylaminopiperidine-1-carbonyl)-1H-pyrazole-5-yl)benzonitrile
3) (R)-4-(3-(3-aminopiperidine-1-carbonyl)-1-(4-cyclopropyl-2-fluorophenyl)-1H-pyrazole-5-yl)benzonitrile
4) (R)-4-(1-(4-cyclopropyl-2-fluorophenyl)-3-(3-(methylamino)piperidine-1-carbonyl)-1H-pyrazole-5-yl)benzonitrile
5) (R)-4-(3-(3-aminopiperidine-1-carbonyl)-1-(4-cyclopropyl-2-fluorophenyl)-1H-pyrazole-5-yl)-2-fluorobenzonitrile
6) (R)-4-(1-(4-cyclopropyl-2-fluorophenyl)-3-(3-(methylamino)piperidine-1-carbonyl)-1H-pyrazole-5-yl)-2-fluorobenzonitrile
7) (R)-4-(3-(3-aminoazepane-1-carbonyl)-1-(4-(cyclopropylphenyl)-1H-pyrazole-5-yl)benzonitrile
8) (R)-4-(3-(3-aminoazepane-1-carbonyl)-1-(4-cyclopropyl-2-fluorophenyl)-1H-pyrazole-5-yl)-2-fluorobenzonitrile
9) 4-(3-((3R,5R)-3-amino-5-methylpiperidine-1-carbonyl)-1-(4-cyclopropyl-2-fluorophenyl)-1H-pyrazole-5-yl)-2-fluorobenzonitrile
10) (R)-4-(3-(3-aminopiperidine-1-carbonyl)-1-(4-cyclopropyl-2,6-difluorophenyl)-1H-pyrazole-5-yl)-2-fluorobenzonitrile
11) (R)-4-(3-(3-aminoazepane-1-carbonyl)-1-(4-cyclopropyl-2,6-difluorophenyl)-1H-pyrazole-5-yl)-2-fluorobenzonitrile
12) (R)-4-(3-(3-aminopiperidine-1-carbonyl)-1-(2-chloro-4-cyclopropylphenyl)-1H-pyrazole-5-yl)-2-fluorobenzonitrile
13) (R)-4-(3-(3-aminoazepane-1-carbonyl)-1-(2-chloro-4-cyclopropylphenyl)-1H-pyrazole-5-yl)-2-fluorobenzonitrile
14) (R)-4-(3-(3-aminopiperidine-1-carbonyl)-1-phenyl-1H-pyrazole-5-yl)benzonitrile
15) (R)-4-(3-(3-aminopiperidine-1-carbonyl)-1-(pyridine-2-yl)-1H-pyrazole-5-yl)benzonitrile
16) (R)-4-(3-(3-aminopiperidine-1-carbonyl)-1-(4-fluorophenyl)-1H-pyrazole-5-yl)benzonitrile
17) (R)-4-(3-(3-aminopiperidine-1-carbonyl)-1-(4-chlorophenyl)-1H-pyrazole-5-yl)benzonitrile
18) (R)-4-(1-(4-chlorophenyl)-3-(3-(methylamino)piperidine-1-carbonyl)-1H-pyrazole-5-yl)benzonitrile
19) (R)-4-(3-(3-aminopiperidine-1-carbonyl)-1-(3-chlorophenyl)-1H-pyrazole-5-yl)benzonitrile
20) (R)-4-(3-(3-aminopiperidine-1-carbonyl)-1-(4-bromophenyl)-1H-pyrazole-5-yl)benzonitrile
21) (R)-4-(1-(4-bromophenyl)-3-(3-(methylamino)piperidine-1-carbonyl)-1H-pyrazole-5-yl)benzonitrile
22) (S)-4-(3-(3-aminopyrrolidine-1-carbonyl)-1-(p-tolyl)-1H-pyrazole-5-yl)benzonitrile
23) (S)-4-(3-(3-(methylamino)pyrrolidine-1-carbonyl)-1-(p-tolyl)-1H-pyrazole-5-yl)benzonitrile
24) (S)-4-(3-(3-(dimethylamino)pyrrolidine-1-carbonyl)-1-(p-tolyl)-1H-pyrazole-5-yl)benzonitrile
25) (R)-4-(3-(3-(dimethylamino)pyrrolidine-1-carbonyl)-1-(p-tolyl)-1H-pyrazole-5-yl)benzonitrile
26) (R)-4-(3-(3-(methylamino)pyrrolidine-1-carbonyl)-1-(p-tolyl)-1H-pyrazole-5-yl)benzonitrile
27) (R)-4-(3-(3-aminopyrrolidine-1-carbonyl)-1-(p-tolyl)-1H-pyrazole-5-yl)benzonitrile
28) (R)-4-(3-(3-aminopiperidine-1-carbonyl)-1-(p-tolyl)-1H-pyrazole-5-yl)benzonitrile
29) (R)-4-(3-(3-(methylamino)piperidine-1-carbonyl)-1-(p-tolyl)-1H-pyrazole-5-yl)benzonitrile
30) (R)-4-(3-(3-(dimethylamino)piperidine-1-carbonyl)-1-(p-tolyl)-1H-pyrazole-5-yl)benzonitrile
31) (R)-4-(3-(3-aminopiperidine-1-carbonyl)-1-(m-tolyl)-1H-pyrazole-5-yl)benzonitrile
32) (R)-4-(3-(3-aminopiperidine-1-carbonyl)-1-(o-tolyl)-1H-pyrazole-5-yl)benzonitrile
33) (R)-4-(3-(3-aminopiperidine-1-carbonyl)-1-(4-ethylphenyl)-1H-pyrazole-5-yl)benzonitrile
34) (R)-4-(1-(4-ethylphenyl)-3-(3-(methylamino)piperidine-1-carbonyl)-1H-pyrazole-5-yl)benzonitrile
35) (R)-4-(3-(3-aminopiperidine-1-carbonyl)-1-(4-isopropylphenyl)-1H-pyrazole-5-yl)benzonitrile
36) (R)-4-(1-(4-isopropylphenyl)-3-(3-(methylamino)piperidine-1-carbonyl)-1H-pyrazole-5-yl)benzonitrile 37) (R)-4-(3-(3-aminopiperidine-1-carbonyl)-1-(2-fluoro-4-isopropylphenyl)-1H-pyrazole-5-yl)benzonitrile
38) (R)-4-(3-(3-aminopiperidine-1-carbonyl)-1-(2-fluoro-4-isopropylphenyl)-1H-pyrazole-5-yl)-2-fluorobenzonitrile
39) (R)-4-(3-(3-aminoazepane-1-carbonyl)-1-(2-fluoro-4-isopropylphenyl)-1H-pyrazole-5-yl)-2-fluorobenzonitrile
40) (R)-4-(3-(3-aminopiperidine-1-carbonyl)-1-(4-(tert-butyl)phenyl)-1H-pyrazole-5-yl)benzonitrile
41) (R)-4-(1-(4-(tert-butyl)phenyl-3-(3-methylaminopiperidine-1-carbonyl)-1H-pyrazole-5-yl)benzonitrile
42) (R)-4-(3-(3-aminopiperidine-1-carbonyl)-1-(4-(tert-butyl)-2-fluorophenyl)-1H-pyrazole-5-yl)benzonitrile
43) (R)-4-(3-(3-aminopiperidine-1-carbonyl)-1-(4-(tert-butyl-2-fluorophenyl)-1H-pyrazole-5-yl)-2-fluorobenzonitrile
44) (R)-4-(3-(3-aminoazepane-1-carbonyl)-1-(4-(tert-butyl-2-fluorophenyl)-1H-pyrazole-5-yl)-2-fluorobenzonitrile
45) (R)-4-(3-(3-aminopiperidine-1-carbonyl)-1-(4-(trifluoromethoxy)phenyl)-1H-pyrazole-5-yl)benzonitrile
46) (R)-4-(3-(3-aminopiperidine-1-carbonyl)-1-(4-(methylsulfonyl)phenyl)-1H-pyrazole-5-yl)benzonitrile
47) (R)-4-(3-(3-aminopiperidine-1-carbonyl)-1-(4-(trifluoromethyl)phenyl)-1H-pyrazole-5-yl)benzonitrile
48) (R)-4-(3-(3-aminopiperidine-1-carbonyl)-1-(2-fluoro-4-methylphenyl)-1H-pyrazole-5-yl)benzonitrile
49) (R)-4-(3-(3-aminopiperidine-1-carbonyl)-1-(3-fluoro-4-methoxyphenyl)-1H-pyrazole-5-yl)benzonitrile
50) (R)-4,4'-(3-(3-aminopiperidine-1-carbonyl)-1H-pyrazole-1,5-diyl)dibenzonitrile
51) (R)-4-(1-(4-(dimethylamino)phenyl)-3-(3-(methylamino)piperidine-1-carbonyl)-1H-pyrazole-5-yl)benzonitrile
52) (R)-4-(3-(3-aminopiperidine-1-carbonyl)-1-(4-((2-(dimethylamino)ethyl)(methyl)amino)phenyl)-1H-pyrazole-5-yl)benzonitrile
53) ((R)-4-(3-(3-aminopiperidine-1-carbonyl)-1-(4-(dimethylamino)phenyl)-1H-pyrazole-5-yl)benzonitrile
54) (R)-4-(3-(3-aminopiperidine-1-carbonyl)-1-(4-(dimethylamino)-2-fluorophenyl)-1H-pyrazole-5-yl)benzonitrile
55) (R)-4-(3-(3-aminopiperidine-1-carbonyl)-1-(4-(diethylamino)-2-fluorophenyl)-1H-pyrazole-5-yl)benzonitrile
56) (R)-4-(3-(3-aminopiperidine-1-carbonyl)-1-(4-(azetidine-1-yl)-2-fluorophenyl)-1H-pyrazole-5-yl)benzonitrile
57) (R)-4-(3-(3-aminopiperidine-1-carbonyl)-1-(2-fluoro-4-(pyrrolidine-1-yl)phenyl)-1H-pyrazole-5-yl)benzonitrile
58) (R)-4-(3-(3-aminopiperidine-1-carbonyl)-1-(2-fluoro-4-(pyrrolidine-1-yl)phenyl)-1H-pyrazole-5-yl)-2-fluorobenzonitrile
59) (R)-2-fluoro-4-(1-(2-fluoro-4-(pyrrolidine-1-yl)phenyl)-3-(3-(methylamino)piperidine-1-carbonyl)-1H-pyrazole-5-yl)benzonitrile
60) (R)-4-(3-(3-aminoazepane-1-carbonyl)-1-(2-fluoro-4-(pyrrolidine-1-yl)phenyl)-1H-pyrazole-5-yl)-2-fluorobenzonitrile
61) 4-(3-((R)-3-aminopiperidine-1-carbonyl)-1-(2-fluoro-4-((R)-3-fluoropyrrolidine-1-yl)phenyl)-1H-pyrazole-5-yl)-2-fluorobenzonitrile
62) 4-(3-((R)-3-aminopiperidine-1-carbonyl)-1-(2-fluoro-4-((S)-3-fluoropyrrolidine-1-yl)phenyl)-1H-pyrazole-5-yl)-2-fluorobenzonitrile
63) (R)-4-(3-(3-aminopiperidine-1-carbonyl)-1-(4-(3,3-difluoropyrrolidine-1-yl)-2-fluorophenyl)-1H-pyrazole-5-yl)-2-fluorobenzonitrile
64) (R)-4-(1-(4-(3,3-difluoropyrrolidine-1-yl)-2-fluorophenyl)-3-(3-(methylamino)piperidine-1-carbonyl)-1H-pyrazole-5-yl)-2-fluorobenzonitrile
65) 4-(3-((R)-3-aminopiperidine-1-carbonyl)-1-(2-fluoro-4-(3-methoxypyrrolidin-1-yl)phenyl)-1H-pyrazol-5-yl)-2-fluorobenzonitrile
66) 2-fluoro-4-(1-(2-fluoro-4-(3-methoxypyrrolidine-1-yl)phenyl)-3-((R)-3-(methylamino)piperidine-1-carbonyl)-1H-pyrazole-5-yl)benzonitrile
67) 4-(3-((R)-3-aminopiperidine-1-carbonyl)-1-(2-fluoro-4-((S)-3-methoxypyrrolidine-1-yl)phenyl)-1H-pyrazole-5-yl)-2-fluorobenzonitrile
68) 2-fluoro-4-(1-(2-fluoro-4-((S)-3-methoxypyrrolidine-1-yl)phenyl)-3-((R)-3-(methylamino)piperidine-1-carbonyl)-1H-pyrazole-5-yl)benzonitrile
69) 4-(3-((R)-3-aminopiperidine-1-carbonyl)-1-(2-fluoro-4-((R)-3-methoxypyrrolidine-1-yl)phenyl)-1H-pyrazole-5-yl)-2-fluorobenzonitrile
70) 2-fluoro-4-(1-(2-fluoro-4-((R)-3-methoxypyrrolidine-1-yl)phenyl)-3-((R)-3-(methylamino)piperidine-1-carbonyl)-1H-pyrazole-5-yl)benzonitrile
71) 2-fluoro-4-(1-(2-fluoro-4-((S)-3-ethoxypyrrolidine-1-yl)phenyl)-3-((R)-3-(methylamino)piperidine-1-carbonyl)-1H-pyrazole-5-yl)benzonitrile
72) 4-(3-((R)-3-aminopiperidine-1-carbonyl)-1-(2-fluoro-4-(3-hydroxypyrrolidine-1-yl)phenyl)-1H-pyrazole-5-yl)-2-fluorobenzonitrile
73) 2-fluoro-4-(1-(2-fluoro-4-((S)-3-chloropyrrolidine-1-yl)phenyl)-3-((R)-3-(methylamino)piperidine-1-carbonyl)-1H-pyrazole-5-yl)benzonitrile
74) (R)-4-(3-(3-aminopiperidine-1-carbonyl)-1-(2,6-difluoro-4-(pyrrolidine-1-yl)phenyl)-1H-pyrazole-5-yl)-2-fluorobenzonitrile
75) (R)-4-(3-(3-aminopiperidine-1-carbonyl)-1-(2-chloro-4-(pyrrolidine-1-yl)phenyl)-1H-pyrazole-5-yl)-2-fluorobenzonitrile
76) (R)-4-(3-(3-aminopiperidine-1-carbonyl)-1-(2-methoxy-4-(pyrrolidine-1-yl)phenyl)-1H-pyrazole-5-yl)-2-fluorobenzonitrile
77) (R)-4-(3-(3-aminopiperidine-1-carbonyl)-1-(2-fluoro-4-(piperidine-1-yl)phenyl)-1H-pyrazole-5-yl)benzonitrile
78) (R)-4-(3-(3-aminopiperidine-1-carbonyl)-1-(2-fluoro-4-(piperidine-1-yl)phenyl)-1H-pyrazole-5-yl)-2-fluorobenzonitrile
79) (R)-2-fluoro-4-(1-(2-fluoro-4-(piperidine-1-yl)phenyl)-3-(3-(methylamino)piperidine-1-carbonyl)-1H-pyrazole-5-yl)benzonitrile
80) 4-(3-((R)-3-aminopiperidine-1-carbonyl)-1-(2-fluoro-4-(3-methylpiperidine-1-yl)phenyl)-1H-pyrazole-5-yl)-2-fluorobenzonitrile
81) (R)-4-(3-(3-aminopiperidine-1-carbonyl)-1-(2-fluoro-4-(4-methylpiperidine-1-yl)phenyl)-1H-pyrazole-5-yl)-2-fluorobenzonitrile
82) 4-(3-((R)-3-aminopiperidine-1-carbonyl)-1-(4-(3,5-dimethylpiperidine-1-yl)-2-fluorophenyl)-1H-pyrazole-5-yl)-2-fluorobenzonitrile
83) (R)-4-(1-(4-([1,4'-bipiperidine]-1'-yl)-2-fluorophenyl)-3-(3-aminopiperidine-1-carbonyl)-1H-pyrazole-5-yl)-2-fluorobenzonitrile 84) (R)-4-(3-(3-aminoazepane-1-carbonyl)-1-(2-fluoro-4-(piperidine-1-yl)phenyl)-1H-pyrazole-5-yl)-2-fluorobenzonitrile
85) (R)-4-(3-(3-aminopiperidine-1-carbonyl)-1-(1-methyl-1H-indazole-6-yl)-1H-pyrazole-5-yl)benzonitrile
86) (R)-4-(3-(3-aminopiperidine-1-carbonyl)-1-(2-methylbenzo[d]thiazole-5-yl)-1H-pyrazole-5-yl)benzonitrile
87) (R)-4-(3-(3-aminopiperidine-1-carbonyl)-1-(2,3-dihydro-1H-indane-5-yl)-1H-pyrazole-5-yl)benzonitrile
88) (R)-4-(3-(3-aminopiperidine-1-carbonyl)-1-(2,3-dihydro-1H-inden-5-yl)-1H-pyrazole-5-yl)-2-fluorobenzonitrile
89) (R)-4-(1-(2,3-dihydro-1H-inden-5-yl)-3-(3-(methylamino)piperidine-1-carbonyl)-1H-pyrazole-5-yl)benzonitrile
90) (R)-4-(3-(3-aminopiperidine-1-carbonyl)-1-(2,3-dihydrobenzo[b][1,4]dioxin-6-yl)-1H-pyrazole-5-yl)benzonitrile
91) (R)-4-(3-(3-aminopiperidine-1-carbonyl)-1-(quinoline-6-yl)-1H-pyrazole-5-yl)benzonitrile
92) (R)-4-(3-(3-aminopiperidine-1-carbonyl)-1-(quinoline-3-yl)-1H-pyrazole-5-yl)benzonitrile
93) (R)-4-(3-(3-aminopiperidine-1-carbonyl)-1-(1-methyl-1H-pyrrolo[2,3-b]pyridine-5-yl)-1H-pyrazole-5-yl)benzonitrile
94) (R)-4-(3-(3-aminopiperidine-1-carbonyl)-1-(2-fluoro-4-(2-hydroxy-2-methylpropyl)phenyl)-1H-pyrazole-5-yl)-2-fluorobenzonitrile
95) 4-(3-(piperazine-1-carbonyl)-1-(p-tolyl)-1H-pyrazole-5-yl)benzonitrile
96) 4-(3-(3-(aminomethyl)piperazine-1-carbonyl)-1-(p-tolyl)-1H-pyrazole-5-yl)benzonitrile
97) (S)-5-(4-cyanophenyl)-N-(1-(methylsulfonyl)piperidine-3-yl)-1-(p-tolyl)-1H-pyrazole-3-carboxamide
98) 4-(3-(2,7-diazaspiro[3.5]nonane-7-carbonyl)-1-(p-tolyl)-1H-pyrazole-5-yl)benzonitrile
99) 4-(3-(2,8-diazaspiro[4.5]decane-8-carbonyl)-1-(p-tolyl)-1H-pyrazole-5-yl)benzonitrile
100) 4-(3-(octahydro-1H-pyrrolo[2,3-c]pyridine-6-carbonyl)-1-(p-tolyl)-1H-pyrazole-5-yl)benzonitrile
101) 4-(3-(3,7-diazabicyclo[3.3.1]nonane-3-carbonyl)-1-(2-fluoro-4-isopropylphenyl)-1H-pyrazole-5-yl)-2-fluorobenzonitrile
102) 4-(3-(3-amino-8-azabicyclo[3.2.1]octane-8-carbonyl)-1-(2-fluoro-4-isopropylphenyl)-1H-pyrazole-5-yl)-2-fluorobenzonitrile
103) 4-(3-(3-amino-8-azabicyclo[3.2.1]octane-8-carbonyl)-1-(2-fluoro-4-pyrrolidine-1-yl)phenyl)-1H-pyrazole-5-yl)-2-fluorobenzonitrile
104) 4-(3-(3,7-diazabicyclo[3.3.1]nonane-3-carbonyl)-1-(p-tolyl)-1H-pyrazole-5-yl) benzonitrile
105) 5-(4-cyanophenyl)-N-(piperidine-4-yl)-1-(p-tolyl)-1H-pyrazole-3-carboximide
106) 5-(4-cyanophenyl)-N-(1-methylpiperidine-4-yl)-1-(p-tolyl)-1H-pyrazole-3-carboximide
107) (R)-5-(4-cyanophenyl)-N-(1-methylpiperidine-3-yl)-1-(p-tolyl)-1H-pyrazole-3-carboximide
108) (S)-5-(4-cyanophenyl)-N-(1-methylpiperidine-3-yl)-1-(p-tolyl)-1H-pyrazole-3-carboximide
109) (R)-5-(4-cyanophenyl)-N-(1-methylpyrrolidine-3-yl)-1-(p-tolyl)-1H-pyrazole-3-carboximide
110) 5-(4-cyano-3-fluorophenyl)-1-(2-fluoro-4-(pyrrolidine-1-yl)phenyl)-N-methyl-N-(piperidine-3-yl)-1H-pyrazole-3-carboximide
111) (S)-5-(4-cyano-3-fluorophenyl)-1-(2-fluoro-4-(pyrrolidine-1-yl)phenyl)-N-methyl-N-(piperidine-3-yl)-1H-pyrazole-3-carboximide
112) (R)-5-(4-cyano-3-fluorophenyl)-1-(2-fluoro-4-(pyrrolidine-1-yl)phenyl)-N-methyl-N-(piperidine-3-yl)-1H-pyrazole-3-carboximide
113) (R)-4-(3-(3-aminopiperidine-1-carbonyl)-1-(4-cyclopropyl-2-fluorophenyl)-4-methyl-1H-pyrazole-5-yl)benzonitrile.

4. The compound of claim 3, which is selected from Compounds 5), 6), 8) to 13), 58) to 75), and 78) to 84), an optical isomer, a tautomer, or a pharmaceutically acceptable salt thereof.

5. A pharmaceutical composition comprising: the compound according to claim 1, an optical isomer, a tautomer, or a pharmaceutically acceptable salt thereof, as an active ingredient; and a pharmaceutically acceptable carrier.

6. The pharmaceutical composition of claim 5 formulated in a pharmaceutically acceptable form comprising a tablet, a pill, powder, a capsule, syrup, emulsion, and microemulsion.

* * * * *